United States Patent
Esteves

(10) Patent No.: US 11,401,531 B2
(45) Date of Patent: Aug. 2, 2022

(54) AAV VECTORS ENCODING NF1 AND USES THEREOF

(71) Applicant: University of Massachusetts, Boston, MA (US)

(72) Inventor: Miguel Sena Esteves, Westford, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 17/483,115

(22) Filed: Sep. 23, 2021

(65) Prior Publication Data

US 2022/0090135 A1    Mar. 24, 2022

Related U.S. Application Data

(60) Provisional application No. 63/082,513, filed on Sep. 24, 2020.

(51) Int. Cl.
| | |
|---|---|
| C12N 15/86 | (2006.01) |
| A61P 35/00 | (2006.01) |
| C07K 14/47 | (2006.01) |
| A61K 48/00 | (2006.01) |

(52) U.S. Cl.
CPC ............... *C12N 15/86* (2013.01); *A61P 35/00* (2018.01); *C07K 14/4705* (2013.01); *A61K 48/00* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2003/0138772 A1 | 7/2003 | Gao et al. |
| 2008/0250514 A1 | 10/2008 | Tsunoda et al. |
| 2010/0092965 A1 | 4/2010 | Seshagiri et al. |
| 2010/0210830 A1 | 8/2010 | Massie et al. |
| 2015/0252432 A1 | 9/2015 | Lee et al. |
| 2019/0153050 A1 | 5/2019 | Boye et al. |

FOREIGN PATENT DOCUMENTS

WO    WO-2008061213 A2 *  5/2008  ........... C12Q 1/6886

OTHER PUBLICATIONS

Bai, et al. (May 24, 2019) "Feasibility of using NF1-GRD and AAV for gene replacement therapy in NF1-associated tumors", Gene Therapy, 26: 277-286. (Year: 2019).*
Keng, et al. (2012) "Conditional Inactivation of Pten with EGFR Overexpression in Schwann Cells Models Sporadic MPNST", Sarcoma, vol. 2012, Article ID 620834, 12 pages long. (Year: 2012).*
Hoyng, et al. (2015) "Gene delivery to rat and human Schwann cells and nerve segments: a comparison of AAV1-9 and lentiviral vectors", Gene Therapy, 22: 767-80. (Year: 2015).*

International Search Report and Written Opinion for Application No. PCT/US2021/051667, dated Dec. 27, 2021.
[No Author Listed], *Arabidopsis thaliana* transmembrane protein, putative (DUF707) (AT1G13000), mRNA. NCBI Ref Sequence No. NM_001035957.3. Feb. 14, 2019. 3 pages.
[No Author Listed], *Homo sapiens* neurofibromin 1 (NF1), transcript variant 1, mRNA. Feb. 13, 2022. NCBI Ref Sequence No. NM_001042492.3. 11 pages.
Bai et al., Feasibility of using NF1-GRD and AAV for gene replacement therapy in NF1-associated tumors. Gene Ther. Jun. 2019;26(6):277-286. doi: 10.1038/s41434-019-0080-9. Epub May 24, 2019.
Baudou et al., Can the Cognitive Phenotype in Neurofibromatosis Type 1 (NF1) Be Explained by Neuroimaging? A Review. Front Neurol. Jan. 14, 2020;10:1373. doi: 10.3389/fneur.2019.01373.
Cooper et al., The Human Gene Mutation Database. The Institute of Medical Genetics in Cardiff. Accessed on Mar. 2, 2022 at http://www.hgmd.cf.ac.uk/ac/index.php. 2007. 2 pages.
D'Angelo et al., A novel bipartite phospholipid-binding module in the neurofibromatosis type 1 protein. EMBO Rep. Feb. 2006;7(2):174-9. doi: 10.1038/sj.embor.7400602.
De Luca et al., Deletions of NF1 gene and exons detected by multiplex ligation-dependent probe amplification. J Med Genet. Dec. 2007;44(12):800-8. doi: 10.1136/jmg.2007.053785.
Hiatt et al., Neurofibromin GTPase-activating protein-related domains restore normal growth in Nf1-/- cells. J Biol Chem. Mar. 9, 2001;276(10):7240-5. doi: 10.1074/jbc.M009202200. Epub Nov. 15, 2000.
Johnson et al., Neurofibromin can inhibit Ras-dependent growth by a mechanism independent of its GTPase-accelerating function. Mol Cell Biol. Jan. 1994;14(1):641-5. doi: 10.1128/mcb.14.1.641-645.1994.
Li et al., Somatic mutations in the neurofibromatosis 1 gene in human tumors. Cell. Apr. 17, 1992;69(2):275-81. doi: 10.1016/0092-8674(92)90408-5.
Martin et al., The GAP-related domain of the neurofibromatosis type 1 gene product interacts with ras p21. Cell. Nov. 16, 1990;63(4):843-9. doi: 10.1016/0092-8674(90)90150-d.
Plantier et al., A factor VIII minigene comprising the truncated intron I of factor IX highly improves the in vitro production of factor VIII. Thromb Haemost. Aug. 2001;86(2):596-603.
Singh et al., 733. Approaches for Gene Therapy of Neurofibromatosis Type 1 (NF1) Using Mini-NF1 and Trans Splicing Dual Adeno-Associated Virus (AAV) Vectors. Mol Ther. Apr. 28, 2020:28(4S1):322-323.

(Continued)

*Primary Examiner* — Robert M Kelly
(74) *Attorney, Agent, or Firm* — Wolf, Greenfield & Sacks, P.C.

(57) ABSTRACT

Aspects of the disclosure relate to compositions and methods of treating certain genetic disease (e.g., Neurofibromatosis type I) by delivering functional neurofibromin 1 (NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

29 Claims, 13 Drawing Sheets

Specification includes a Sequence Listing.

(56) References Cited

OTHER PUBLICATIONS

Singh et al., 733. Approaches for Gene Therapy of Neurofibromatosis Type 1 (NF1) Using Mini-NF1 and Trans Splicing Dual Adeno-Associated Virus (AAV) Vectors. Poster Presentation. Am Soc Gene Cell Ther. No date. 4 pages.

Thomas et al., Reconstitution of the NF1 GAP-related domain in NF1-deficient human Schwann cells. Biochem Biophys Res Commun. Sep. 29, 2006;348(3):971-80. doi: 10.1016/j.bbrc.2006.07.159. Epub Aug. 2, 2006.

Welti et al., The sec14 homology module of neurofibromin binds cellular glycerophospholipids: mass spectrometry and structure of a lipid complex. J Mol Biol. Feb. 16, 2007;366(2):551-62. doi: 10.1016/j.jmb.2006.11.055. Epub Nov. 18, 2006.

Wu-Chou et al., Genetic diagnosis of neurofibromatosis type 1: targeted next-generation sequencing with Multiple Ligation-Dependent Probe Amplification analysis. J Biomed Sci. Oct. 5, 2018;25(1):72. doi: 10.1186/s12929-018-0474-9.

Xiao et al., Rescue of the albino phenotype by introducing a functional tyrosinase minigene into Kunming albino mice. World J Gastroenterol. Jan. 14, 2007;13(2):244-9. doi: 10.3748/wjg.v13.i2.244.

Yang et al., The investigation for potential modifier genes in patients with neurofibromatosis type 1 based on next-generation sequencing. Onco Targets Ther. Feb. 21, 2018;11:919-932. doi: 10.2147/OTT.S156998.

\* cited by examiner

AAV VECTORS ENCODING NF1 AND USES THEREOF

RELATED APPLICATIONS

This application claims the benefit under 35 U.S.C. 119(e) of the filing date of U.S. provisional application Ser. No. 63/082,513, filed Sep. 24, 2020, the entire contents of which are incorporated herein by reference.

REFERENCE TO A SEQUENCE LISTING SUBMITTED AS A TEXT FILE VIA EFS-WEB

The instant application contains a sequence listing which has been submitted in ASCII format via EFS-web and is hereby incorporated by reference in its entirety. The ASCII file, created on Sep. 23, 2021 is named U012070146US01-SEQ-SXT and is 230,444 bytes in size.

BACKGROUND OF INVENTION

Neurofibromatosis type I (NF1) is caused by sporadic or inherited germline mutations in the NF1 gene. Sporadic loss of the remaining wild-type allele is associated with skin lesions and benign neurofibromas, which develop along peripheral nerves. Malignant complications include optic pathway gliomas and malignant peripheral nerve sheath tumors (MPNST). In addition, NF1 haploinsufficiency can cause cognitive deficits and NF1 deficiency plays an important supporting role in tumor formation. However, the NF1 coding sequence is 8,540 bp, far exceeding the packaging capacity of recombinant AAV vectors, rendering gene therapy to correct NF1 gene mutation difficult.

SUMMARY OF INVENTION

The present disclosure relates to compositions and methods of treating certain genetic disease (e.g., Neurofibromatosis type I) by delivering functional neurofibromin 1 (NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

In some aspects, the present disclosure provides an isolated nucleic acid comprising a transgene, wherein the transgene comprises a nucleotide sequence encoding a mini-neurofibromin (mini-NF1) protein.

In some embodiments, the transgene further comprises a promoter operably linked to the nucleotide sequence encoding the mini-NF1 protein. In some embodiments, the promoter is a constitutive promoter, an inducible promoter, or a minimal promoter. In some embodiments, the promoter is a chicken β-actin (CBA) promoter, or a CAG promoter. In some embodiments, the minimal promoter is a short Mecp2 promoter, a mini-CMV promoter, or a Jet promoter.

In some embodiments, the mini-NF1 protein comprises a GTPase-activating protein (GAP)-related domain (GRD). In some embodiments, the nucleotide sequence encoding the mini-NF is codon optimized. In some embodiments, the mini-NF comprises the amino acid sequence of SEQ ID NO: 1. In some embodiments, the nucleotide sequence encoding the mini-NF comprises a nucleotide sequence at least 80% identical to SEQ ID NO: 2.

In some embodiments, the mini-NF1 comprises a GTPase-activating protein (GAP)-related domain (GRD) and a CRAL-TRIO domain. In some embodiments, the mini-NF comprises the amino acid sequence of SEQ ID NO: 3. In some embodiments, the nucleotide sequence encoding the mini-NF is codon optimized. In some embodiments, the nucleotide sequence encoding the mini-NF comprises a nucleotide sequence at least 80% identical to SEQ ID NO: 4.

In some embodiments, the mini-NF1 comprises a GTPase-activating protein (GAP)-related domain (GRD), a CRAL-TRIO domain and a bipartite phospholipid binding domain. In some embodiments, the mini-NF comprises the amino acid sequence of SEQ ID NO: 5. In some embodiments, the nucleotide sequence encoding the mini-NF is codon optimized. In some embodiments, the nucleotide sequence encoding the mini-NF comprises a nucleotide sequence at least 80% identical to SEQ ID NO: 6.

In some embodiments, the transgene further comprises a nucleotide sequence encoding a tag operably linked to the promoter. In some embodiments, the tag is a hemagglutinin (HA) tag.

In some embodiments, the transgene is flanked by adeno-associated virus (AAV) inverted terminal repeats (ITRs). In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the transgene further comprises a polyadenylation signal.

In some aspects, the present disclosure provides an 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, and a nucleotide sequence encoding a splice donor of an intron.

In some embodiments, the nucleotide sequence encoding the first portion of NF1 protein comprises exons 1-31 of an NF1 gene. In some embodiments, the nucleotide sequence encoding the first portion of NF1 protein comprises the nucleotide sequence of SEQ ID NO: 11.

In some embodiments, the promoter is a constitutive promoter, an inducible promoter, or a minimal promoter. In some embodiments, the promoter is a chicken β-actin (CBA) promoter, or a CAG promoter. In some embodiments, the minimal promoter is a short Mecp2 promoter, a mini-CMV promoter, or a Jet promoter.

In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the intron is a human dysferlin intron. In some embodiments, the nucleotide sequence encoding the splicing donor comprises the nucleotide sequence of SEQ ID NO: 18.

In some aspects, the present disclosure also provides an 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, and a nucleotide sequence encoding a second portion of NF1 protein. In some embodiments, the isolated nucleic acid further comprises a polyadenylation signal positioned between the nucleotide sequence encoding second portion of NF1 protein and the 3' ITR. In some embodiments, the polyadenylation signal is an SV40 polyadenylation signal.

In some embodiments, the nucleotide sequence encoding the second portion of NF1 protein comprises exons 32-61 of an NF1 gene. In some embodiments, the nucleotide sequence encoding the second portion of NF1 protein comprises the nucleotide sequence of SEQ ID NO: 14.

In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the intron is a human dysferlin intron. In some embodiments, the nucleotide sequence encoding the splicing acceptor comprises the nucleotide sequence of SEQ ID NO: 19.

In some aspects, the present disclosure also provides a vector comprising the isolated nucleic acid, the 5' isolated nucleic acid, or the 3' isolated nucleic acid as described herein. In some embodiments, the vector is a plasmid DNA, or closed-ended DNA, or lipid/DNA nanoparticle, or a viral vector. In some embodiments, the viral vector is an adeno-associated virus (AAV) vector, adenoviral (Ad) vector, lentiviral vector, retroviral vector, or Baculovirus vector. In some embodiments, the vector comprises a nucleic acid sequence of any one of SEQ ID NO: 7-19, 12, or 15.

In some aspects, the present disclosure provides a recombinant adeno-associated virus (rAAV) comprising: (i) the isolated nucleic acid encoding any of the mini-NF1 protein; and (ii) an AAV capsid protein.

In some aspects, the present disclosure also provides a 5' recombinant adeno-associated virus (rAAV) comprising: (i) the 5' isolated nucleic acid encoding the first portion of full-length NF1 protein; and (ii) an AAV capsid protein.

In some aspects, the present disclosure also provides a 3' recombinant adeno-associated virus (rAAV) comprising: (i) the 3' isolated nucleic acid encoding the second portion of full-length NF1 protein; and (ii) an AAV capsid protein.

In some embodiments, the capsid protein is of a serotype selected from AAV1, AAV2, AAV3, AAV4, AAV5, AAV6, AAV7, AAV8, AAV9 and a variant thereof. In some embodiments, the capsid protein is AAV9, AAV-DJ, AAV-Anc80, AAV-PHP.B, or AAV. PHP.eB, or AAVrh10.

In some embodiments, the capsid protein has tropism for Schwann cells, peripheral neurons, optic nerve glioma cells, or cells in the central nervous system.

In some aspects, the present disclosure provides a neurofibromin (NF1) expression system comprising: the 5'rAAV; and the 3' rAAV as described herein for delivering a full-length NF1 protein to a target cell.

In some aspects, the present disclosure provides a host cell comprising the isolated nucleic acid, the 5' isolated nucleic acid, the 3' isolated nucleic acid, the vector, the rAAV, the 5' rAAV, the 3' rAAV, or the NF1 expression system as described herein.

In some aspects, the present disclosure provides a pharmaceutical composition comprising the isolated nucleic acid, the 5' isolated nucleic acid, the 3' isolated nucleic acid, the vector, the rAAV, the 5' rAAV, the 3' rAAV, the NF1 expression system, or the host cell as described herein. In some embodiments, the pharmaceutical composition further comprises a pharmaceutically acceptable carrier.

In some aspects, the present disclosure also provides a method for inhibiting Ras activity in a cell, the method comprising delivering to the cell the isolated nucleic acid, the rAAV, the NF1 expression system, or the pharmaceutical composition as described herein.

In some aspects, the present disclosure also provides a method for inhibiting Ras activity in a subject in need thereof, the method comprising administering to the subject the isolated nucleic acid, the rAAV, the NF1 expression system, or the pharmaceutical composition as described herein.

In some aspects, the present disclosure also provides a method for preventing or treating an NF1-associated disease in a subject in need thereof, the method comprising administering to the subject the isolated nucleic acid, the rAAV, the NF1 expression system, or the pharmaceutical composition as described herein.

In some aspects, the present disclosure also provides a method for preventing or treating an Neurofibromatosis type I in a subject in need thereof, the method comprising administering to the subject the isolated nucleic acid, the rAAV, the NF1 expression system, or the pharmaceutical composition as described herein.

In some aspects, the present disclosure also provides a method for preventing or treating a cognitive dysfunction associated with NF1 in a subject in need thereof, the method comprising administering to the subject the isolated nucleic acid, the rAAV, the NF1 expression system, or the pharmaceutical composition as described herein.

In some embodiments, the subject comprises one or more mutation in NF1 gene. In some embodiments, the NF1-associated disease or Neurofibromatosis type I comprises skin lesions, benign tumor, malignant tumor, and/or cognitive impairment. In some embodiments, the benign tumor is a benign neurofibroma. In some embodiments, the malignant tumor is optic pathway gliomas or malignant peripheral nerve sheath tumors (MPNST).

In some embodiments, the subject is a human. In some embodiments, the subject is a non-human mammal. In some embodiments, the non-human mammal is mouse, rat, cat, dog, sheep, rabbit, horse, cow, goat, pig, guinea pig, hamster, chicken, turkey, or a non-human primate. In some embodiments, the administration is systemic administration or local administration. In some embodiments, the systemic administration is intravenous injection, intramuscular injection, or subcutaneous injection. In some embodiments, the local administration is intratumoral injection, intracranial injection, nerve injection, cerebral spinal fluid (CSF) injection via cerebral lateral ventricles, cisterna magna (CM) injection, intrathecal (IT) injection, or intracerebroventricular injection. In some embodiments, the local administration is intrathecal (IT) injection. In some embodiments, the local administration is intracerebroventricular injection. In some embodiments, the administration results in delivery of a neurofibromin (NF1) protein in Schwann cells, peripheral nerve cells, or optic nerve cells. In some embodiments, the administration results in delivery of a neurofibromin (NF1) protein in any cells or areas in the CNS that is appropriate for the isolated nucleic acids and methods disclosed herein.

In some embodiments, the present disclosure provides a dual vector system. In some embodiments, the dual vector system comprises a 5' recombinant adeno-associated virus (rAAV) comprising a 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, a nucleotide sequence encoding a splice donor of an intron, and an AAV capsid protein. In some embodiments, the dual vector system comprises a 3' rAAV comprising a 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, a nucleotide sequence encoding a second portion of NF1 protein and an AAV capsid protein.

In some embodiments, the administration of the isolated nucleic acid, the rAAV, the NF1 expression system, or the pharmaceutical composition as described herein results in reduction of tumor burden.

BRIEF DESCRIPTION OF DRAWINGS

FIG. 1A shows schematic illustrations of full-length NF1 genes and mini-NF1 genes. Full length NF1 with some domains identified for comparison with the mini-NF1 genes NF1-GAP_M, NF1-GAP_MCT and NF1-GAP_MLB. FIG. 1B shows AAV vector backbone with cytomegalovirus enhancer/chicken beta actin promoter (CMV enhancer/CB promoter) driving expression of mini-NF1 genes fused to an HA tag at the C-terminus. FIG. 1C is the rAAV vector map encoding mini-NF1 having the GRD (SEQ ID NO: 7). FIG. 1D is the rAAV vector map encoding mini-NF1 having the GRD and CRAL-TRIO domain (SEQ ID NO: 8). FIG. 1E is the rAAV vector map encoding mini-NF1 having the GRD, CRAL-TRIO domain, and the bipartite phospholipid binding domain (SEQ ID NO: 9). FIG. 1F shows western blot analysis of mini-NF1 protein expression at 72 hours post-infection of HEK293T cells at $3\times10^5$ vg/cell.

FIG. 2A shows the dual AAV-NF1 vector system: The AAV-MeCP2p-5'NF1-intron vector carries NF1 exons 1-31 under the mouse Mecp2 229-bp promoter followed by a splice donor (SD) and part of an intron; The AAV-intron.3NF1 carries part of an intron with a splice acceptor (SA) followed by NF1 exons 32-61 and an SV40 polyadenylation signal (pA). All cassettes flanked by AAV2 inverted terminal repeats (ITR). FIG. 2B is a schematic illustration that shows, upon dual infection of target cells, full length NF1 mRNA will be generated by trans-splicing across ITR elements in concatemerized AAV genomes. FIG. 2C shows trans-splicing dual AAV vector constructs. In 5' AAV vector consists of a small ubiquitous promoter, 5' sequence of NF1 cDNA and splice donor (SD) signal from NF1 intronic sequences. The 3' AAV vector consists of splice acceptor (SA) also from NF1 intronic sequences, 3' sequence of NF1 cDNA and HA-tag before the ploy A signal from SV40. Two parts of the transgene are delivered to the same cell and concatemerization of the right side ITR of the 5' vector and left side ITR of the 3' vector reconstitutes the full-length gene. After transcription, splicing leads to the removal of the ITR structure formed at the middle, which in-turn restores the mature RNA of the transgene. FIG. 2D shows the 5' AAV vector map encoding the first portion of NF1 protein. FIG. 2E shows the 3' AAV vector map encoding the first portion of NF1 protein. FIG. 2F shows western blot analysis of HA-tagged full length NF1 expression in HEK293T cells at 72 hrs post-transduction with each AAV vector alone, or in combination at $3\times10^5$ vg/cell.

FIG. 3A shows human ST267 and ST642 were transduced with increasing doses of AAV-DJ.GFP-NLS vector and GFP expression analyzed at 72 hours post-transduction. FIG. 3B shows western blot analysis of NF1 expression and impact on Ras pathway activity indirectly assessed by changes in pERK1/2 levels. Cells were transduced at $3\times10^5$ vg/cell and protein expression analyzed at 72 hours post-transduction. Antigens detected in each blot are shown on the left size. The approximate size of the detected bands is shown in KDa on the right side of the blots. The identity of samples 1-6 is shown on the bottom. FIG. 3C shows cell proliferation assays conducted in MPNST cells (STS26T and S462) treated with different AAV vectors encoding mini-NF1 genes, trans-splicing dual AAV vectors and GFP-NLS packaged with DJ capsid.

FIG. 4A shows MRIs of mice before and after intrathecal injection of AAV-mini NF1 vector. Mouse No. 613 was a male mouse and mouse No. 003 was a female mouse that were treated with $1\times10^{12}$ vg AAV-PHP.eB-GAP_MLB-HA (mini-NF1). FIG. 4B shows MRIs of mice before and after intrathecal injection of dual-AAV-NF1 vectors. Both mice No. 001 and No. 002 were female mice that were treated with $1\times10^{12}$ vg dual-AAV (5'NF1+3'NF1-HA).

DETAILED DESCRIPTION OF INVENTION

Figure 1A:
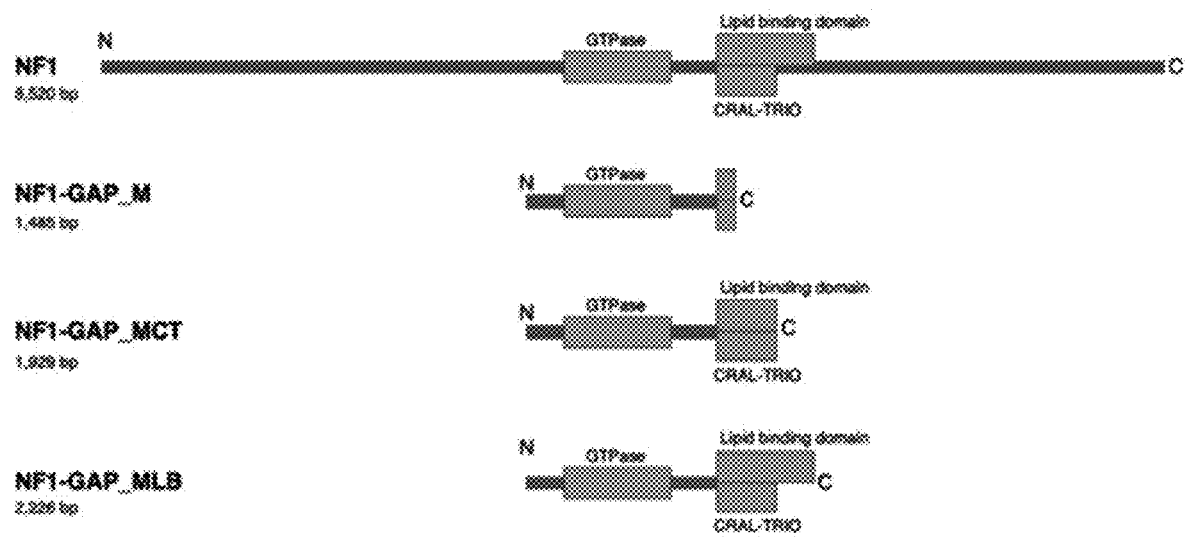
FIGS. 1A-1F show AAV vector system for mini-NF1 expression.

The present disclosure relates to compositions and methods of treating certain genetic disease (e.g., Neurofibromatosis type I) by delivering functional neurofibromin 1 (NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

Isolated Nucleic Acid

In some aspects, the disclosure relates to compositions and methods useful for treating certain genetic diseases, for example Neurofibromatosis type I and/or conditions associated thereof. Neurofibromatosis type I is caused by sporadic or inherited germline mutations in the Neurofibromin 1 gene (NF1 gene). Sporadic loss of the remaining wild-type NF1 allele is associated with skin lesions and benign neurofibromas, which develop along peripheral nerves. Malignant complications include conditions such as optic pathway gliomas and malignant peripheral nerve sheath tumors (MPNST). In addition, NF1 haploinsufficiency can cause cognitive deficits in Neurofibromatosis type I patients. NF1 deficiency plays an important supporting role in tumor formation. The NF1 protein is a GTPase-activating protein (GAP) that inactivates Ras through activation of GTP to GDP hydrolysis. Loss of NF1 GAP function leaves Ras in the activated state (Ras-GTP) with resulting over-activation of this signaling pathway (RAF-MEK-ERK) (see, e.g., Johnson et al., Neurofibromin 1 inhibits Ras-dependent growth by a mechanism independent of its GTPase-accelerating function, *Mol Cell Biol.* 1994 January; 14(1): 641-645). Ras activation stimulates cell growth and formation of benign tumors which may progress to malignancies (e.g., MPNSTs and optic gliomas). NF1 patients may also show cognitive deficits, suggesting that NF1 plays an important role in normal neuronal function. Reconstitution of normal NF1 function (e.g., by rAAV mediated gene therapy) is capable of repressing RAS over-activation and treating Neurofibromatosis type I and associated conditions. However, the NF1 coding sequence is 8,540 bp, far exceeding the packaging capacity of recombinant AAV vectors. In some embodiments, an NF1 protein coding sequence comprises the nucleic acid sequence set forth in NCBI Reference Sequence Accession Number NM_001042492.3 (SEQ ID NO: 16), or splice variants thereof generated by incorporation of exons 9a, 23a, or 48a. In some embodiments, an NF1 gene encodes a protein having the amino acid sequence set forth in NCBI Reference Sequence Accession Number NP_001035957.1 (SEQ ID NO: 17), or protein isoforms with additional amino acids resulting from incorporation of exons 9a, 23a, and 48a in the NF1 mRNA. In some embodiments, a wild-type full-length NF1 coding sequence comprises 61 exons.

Accordingly, the disclosure is based, in part, on isolated nucleic acids and gene therapy vectors, such as viral (e.g., rAAV) vectors, comprising a transgene, which comprises one or more nucleotide sequence encoding a therapeutic gene product, such as a functional neurofibromin 1 (NF1) protein (e.g., mini-NF1 protein and/or full-length NF1 protein). In some embodiment, the nucleotide sequence encoding the mini-NF1 protein is within the packaging capacity of recombinant AAV vectors. In some embodiments, the full-length NF1 protein is delivered by a dual AAV vector system.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

(i) NF1 Minigenes

In some aspects, the disclosure relates to isolated nucleic acids comprising a transgene (e.g., a minigene) encoding a functional NF1 protein, such as a mini-NF1 protein (e.g., a gene product expressed from a NF1 gene or a portion thereof, such as an NF1 minigene). As used herein, "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example dystrophin, dysferlin, Factor VIII, Amyloid precursor protein (APP), Tyrosinase (Tyr), NF1, etc. Minigenes are known in the art and are described, for example by Karpati and Acsadi (1994) Clin Invest Med 17(5):499-509; Plantier et al. (2001) Thromb Haemost. 86(2):596-603; and Xiao et al. (2007) World J. Gastroenterol. 13(2):244-9. In some embodiments, a minigene does not comprise the sequence of the corresponding naturally-occurring peptide or protein.

Generally, an isolated nucleic acid encoding a minigene (e.g., a therapeutic minigene, such as an NF1 minigene) is between about 10% and about 99% (e.g., about 10%, about 15%, about 20%, about 25%, about 30%, about 40% about 50%, about 60%, about 70%, about 75%, about 80%, about 90%, about 99%, etc.) truncated with respect to a nucleic acid sequence encoding the corresponding naturally-occurring wild-type NF1 protein (e.g., SEQ ID NO: 17). The truncations may be continuous (e.g., single, continuous truncation of amino acid residues) or discontinuous (e.g., two or more truncations of amino acids, for example truncation of two or more domains, that are separated by one or more peptides). For example, in some embodiments, a minigene encoding a mini-NF1 protein is truncated (e.g., comprises about less than 95%, less than 90%, less than 80%, less than 70%, less than 60%, less than 50%, less than 40%, less than 30%, less than 20%, or less than 10% of the wild type nucleic acid sequence encoding NF1) compared to a wild-type NF1 coding sequence (e.g., SEQ ID NO: 16). In some embodiments, a nucleotide sequence encoding a mini-NF1 protein (e.g., a mini-NF1 protein) comprises a start codon (e.g., the nucleic acid sequence ATG) prior to the nucleic acid sequence encoding the mini-NF1 protein. In some embodiments, the nucleic acid encoding any of the NF1-minigene described herein are codon optimized for expression in a target cell (e.g., human cell).

In some embodiments, an NF1 minigene comprises a GTPase-activating protein (GAP)-related domain (GRD) of the wildtype NF1 protein. The GRD of NF1 protein has been shown to be responsible for GAP activity and represents a functionally defined segment of NF1 protein (see, e.g., Li, Y. et al. (1992) Somatic mutations in the neurofibromatosis 1 gene in human tumors. Cell, 69, 275-281). In some embodiments, the mini-NF1 comprising the GRD domain of NF1 protein is capable of acting as a GTPase activating protein (GAP) on Ras. In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 1 or 20.

An exemplary amino acid sequence of a mini-NF1 protein comprising a GRD domain is set forth in SEQ ID NO: 1:

MEAKSQLFLKYFTLFMNLLNDCSEVEDESAQTGGRKRGMSRRLASLRHCTV

LAMSNLLNANVDSGLMHSIGLGYHKDLQTRATFMEVLTKILQQGTEFDTLA

ETVLADRFERLVELVTMMGDQGELPIAMALANVVPCSQWDELARVLVTLFD

SRHLLYQLLWNMFSKEVELADSMQTLFRGNSLASKIMTFCFKVYGATYLQK

LLDPLLRIVITSSDWQHVSFEVDPTRLEPSESLEENQRNLLQMTEKFFHAI

ISSSSEFPPQLRSVCHCLYQATCHSLLNKATVKEKKENKKSVVSQRFPQNS

IGAVGSAMFLRFINPAIVSPYEAGILDKKPPPRIERGLKLMSKILQSIANH

VLFTKEEHMRPFNDFVKSNFDAARRFFLDIASDCPTSDAVNHSLSFISDGN

VLALHRLLWNNQEKIGQYLSSNRDHKAVGRRPFDKMATLLAYLGPPEHKPV

ADTHWSSLNLTSSKFEEFMTRHQVHEKEEFKALKTL

An exemplary amino acid sequence of a mini-NF1 protein comprising a GRD domain with an HA tag (bold) is set forth in SEQ ID NO: 20:

```
MEAKSQLFLKYFTLFMNLLNDCSEVEDESAQTGGR
KRGMSRRLASLRHCTVLAMSNLLNANVDSGLMHSI
GLGYHKDLQTRATFMEVLTKILQQGTEFDTLAETV
LADRFERLVELVTMMGDQGELPIAMALANVVPCSQ
WDELARVLVTLFDSRHLLYQLLWNMFSKEVELADS
MQTLFRGNSLASKIMTFCFKVYGATYLQKLLDPLL
RIVITSSDWQHVSFEVDPTRLEPSESLEENQRNLL
QMTEKFFHAIISSSSEFPPQLRSVCHCLYQATCHS
LLNKATVKEKKENKKSVVSQRFPQNSIGAVGSAMF
LRFINPAIVSPYEAGILDKKPPPRIERGLKLMSKI
LQSIANHVLFTKEEHMRPFNDFVKSNFDAARRFFL
DIASDCPTSDAVNHSLSFISDGNVLALHRLLWNNQ
EKIGQYLSSNRDHKAVGRRPFDKMATLLAYLGPPE
HKPVADTHWSSLNLTSSKFEEFMTRHQVHEKEEFK
ALKTLYPYDVPDYA
```

In some embodiments, the nucleotide sequence encoding the mini-NF1 protein (e.g., mini-NF1 protein having the GRD domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 2 or 21.

An exemplary nucleotide sequence encoding a mini-NF1 having an NF1 GRD is set forth in SEQ ID NO: 2:

```
ATGGAAGCCAAGAGCCAGCTGTTTCTGAAATACTT
TACCCTGTTTATGAATCTGCTGAACGACTGTAGTG
AGGTGGAGGACGAGAGTGCCCAGACCGGCGGCAGG
AAGAGAGGCATGTCTAGGAGACTGGCCAGCCTGAG
GCACTGCACAGTGCTGGCCATGTCCAACCTGCTGA
ACGCCAATGTGGACTCCGGCCTGATGCACTCTATC
GGCCTGGGCTACCACAAGGATCTGCAGACCCGCGC
CACATTCATGGAGGTGCTGACCAAGATCCTGCAGC
AGGGCACCGAGTTTGACACACTGGCCGAGACCGTG
CTGGCAGATAGGTTCGAGCGCCTGGTGGAGCTGGT
GACAATGATGGGCGACCAGGGAGAGCTGCCTATCG
CAATGGCACTGGCCAACGTGGTGCCATGCAGCCAG
TGGGACGAGCTGGCCAGGGTGCTGGTGACCCTGTT
TGATTCCAGACACCTGCTGTACCAGCTGCTGTGGA
ACATGTTCTCTAAGGAGGTGGAGCTGGCCGACAGC
ATGCAGACACTGTTTAGGGGCAATTCCCTGGCCTC
TAAGATCATGACCTTCTGTTTTAAGGTGTACGGCG
CCACATATCTGCAGAAGCTGCTGGATCCACTGCTG
AGAATCGTGATCACCAGCTCCGACTGGCAGCACGT
GTCCTTCGAGGTGGATCCTACACGGCTGGAGCCAA
GCGAGTCCCTGGAGGAGAACCAGCGCAATCTGCTG
CAGATGACCGAGAAGTTCTTTCACGCCATCATCTC
TAGCTCCTCTGAGTTTCCCCCTCAGCTGCGGTCCG
TGTGCCACTGTCTGTACCAGGCCACCTGCCACTCT
CTGCTGAACAAGGCCACAGTGAAGGAGAAGAAGGA
GAATAAGAAGAGCGTGGTGTCCCAGAGGTTCCCAC
AGAACAGCATCGGAGCAGTGGGATCCGCCATGTTC
CTGAGGTTCATCAATCCCGCCATCGTGAGCCCTTA
TGAGGCCGGCATCCTGGACAAGAAGCCACCCCCTA
GGATCGAGAGAGGCCTGAAGCTGATGAGCAAGATC
CTGCAGTCCATCGCCAACCACGTGCTGTTCACCAA
GGAGGAGCACATGCGCCCCTTCAACGACTTTGTGA
AGTCTAATTTTGATGCCGCCCGGCGCTTCTTTCTG
GACATCGCCTCTGATTGTCCTACAAGCGACGCCGT
GAACCACTCTCTGAGCTTCATCAGCGATGGCAATG
TGCTGGCCCTGCACCGGCTGCTGTGGAACAATCAG
GAGAAGATCGGCCAGTACCTGAGCTCCAACAGGGA
CCACAAGGCAGTGGGCAGGAGACCTTTTGATAAGA
TGGCCACCCTGCTGGCATATCTGGGACCACCAGAG
CACAAGCCAGTGGCAGACACCCACTGGTCTAGCCT
GAATCTGACATCCTCTAAGTTCGAGGAGTTTATGA
CCCGGCACCAGGTGCACGAGAAGGAGGAGTTTAAG
GCCCTGAAGACCCTG
```

An exemplary nucleotide sequence encoding a mini-NF1 having an NF1 GRD with a HA tag is set forth in SEQ ID NO: 21:

```
ATGGAAGCCAAGAGCCAGCTGTTTCTGAAATACTT
TACCCTGTTTATGAATCTGCTGAACGACTGTAGTG
AGGTGGAGGACGAGAGTGCCCAGACCGGCGGCAGG
AAGAGAGGCATGTCTAGGAGACTGGCCAGCCTGAG
GCACTGCACAGTGCTGGCCATGTCCAACCTGCTGA
ACGCCAATGTGGACTCCGGCCTGATGCACTCTATC
GGCCTGGGCTACCACAAGGATCTGCAGACCCGCGC
CACATTCATGGAGGTGCTGACCAAGATCCTGCAGC
AGGGCACCGAGTTTGACACACTGGCCGAGACCGTG
CTGGCAGATAGGTTCGAGCGCCTGGTGGAGCTGGT
```

```
GACAATGATGGGCGACCAGGGAGAGCTGCCTATCG

CAATGGCACTGGCCAACGTGGTGCCATGCAGCCAG

TGGGACGAGCTGGCCAGGGTGCTGGTGACCCTGTT

TGATTCCAGACACCTGCTGTACCAGCTGCTGTGGA

ACATGTTCTCTAAGGAGGTGGAGCTGGCCGACAGC

ATGCAGACACTGTTTAGGGGCAATTCCCTGGCCTC

TAAGATCATGACCTTCTGTTTTAAGGTGTACGGCG

CCACATATCTGCAGAAGCTGCTGGATCCACTGCTG

AGAATCGTGATCACCAGCTCCGACTGGCAGCACGT

GTCCTTCGAGGTGGATCCTACACGGCTGGAGCCAA

GCGAGTCCCTGGAGGAGAACCAGCGCAATCTGCTG

CAGATGACCGAGAAGTTCTTTCACGCCATCATCTC

TAGCTCCTCTGAGTTTCCCCCTCAGCTGCGGTCCG

TGTGCCACTGTCTGTACCAGGCCACCTGCCACTCT

CTGCTGAACAAGGCCACAGTGAAGGAGAAGAAGGA

GAATAAGAAGAGCGTGGTGTCCCAGAGGTTCCCAC

AGAACAGCATCGGAGCAGTGGGATCCGCCATGTTC

CTGAGGTTCATCAATCCCGCCATCGTGAGCCCTTA

TGAGGCCGGCATCCTGGACAAGAAGCCACCCCCTA

GGATCGAGAGAGGCCTGAAGCTGATGAGCAAGATC

CTGCAGTCCATCGCCAACCACGTGCTGTTCACCAA

GGAGGAGCACATGCGCCCCTTCAACGACTTTGTGA

AGTCTAATTTTGATGCCGCCCGGCGCTTCTTTCTG

GACATCGCCTCTGATTGTCCTACAAGCGACGCCGT

GAACCACTCTCTGAGCTTCATCAGCGATGGCAATG

TGCTGGCCCTGCACCGGCTGCTGTGGAACAATCAG

GAGAAGATCGGCCAGTACCTGAGCTCCAACAGGGA

CCACAAGGCAGTGGGCAGGAGACCTTTTGATAAGA

TGGCCACCCTGCTGGCATATCTGGGACCACCAGAG

CACAAGCCAGTGGCAGACACCCACTGGTCTAGCCT

GAATCTGACATCCTCTAAGTTCGAGGAGTTTATGA

CCCGGCACCAGGTGCACGAGAAGGAGGAGTTTAAG

GCCCTGAAGACCCTGTATCCGTATGATGTGCCGGA

TTATGCG
```

In some embodiments, an NF1 minigene comprises a GTPase-activating protein (GAP)-related domain (GRD) and a CRAL-TRIO domain of the wildtype NF1 protein. The CRAL-TRIO domain of NF1 protein can serve as a regulatory scaffold that binds to GRD, GTPase, and Ras to facilitate Ras suppression. In some embodiments, the mini-NF1 comprising the GRD domain and the CRAL-TRIO domain of NF1 protein is capable of acting as a GTPase activating protein (GAP) on Ras. In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 3 and 22.

An exemplary amino acid sequence of a mini-NF1 protein comprising a GRD and a CRAL-TRIO domain is set forth in SEQ ID NO: 3:

```
MEAKSQLFLKYFTLFMNLLNDCSEVEDESAQTGGR

KRGMSRRLASLRHCTVLAMSNLLNANVDSGLMHSI

GLGYHKDLQTRATFMEVLTKILQQGTEFDTLAETV

LADRFERLVELVTMMGDQGELPIAMALANVVPCSQ

WDELARVLVTLFDSRHLLYQLLWNMFSKEVELADS

MQTLFRGNSLASKIMTFCFKVYGATYLQKLLDPLL

RIVITSSDWQHVSFEVDPTRLEPSESLEENQRNLL

QMTEKFFHAIISSSSEFPPQLRSVCHCLYQATCHS

LLNKATVKEKKENKKSVVSQRFPQNSIGAVGSAMF

LRFINPAIVSPYEAGILDKKPPPRIERGLKLMSKI

LQSIANHVLFTKEEHMRPFNDFVKSNFDAARRFFL

DIASDCPTSDAVNHSLSFISDGNVLALHRLLWNNQ

EKIGQYLSSNRDHKAVGRRPFDKMATLLAYLGPPE

HKPVADTHWSSLNLTSSKFEEFMTRHQVHEKEEFK

ALKTLSIFYQAGTSKAGNPIFYYVARRFKTGQING

DLLIYHVLLTLKPYYAKPYEIVVDLTHTGPSNRFK

TDFLSKWFVVFPGFAYDNVSAVYIYNCNSWVREYT

KYHERLLTGLKGSKRLVFIDCPGKLAEHIEHEQQK

LPAATLALEEDLK
```

An exemplary amino acid sequence of a mini-NF1 protein comprising a GRD and a CRAL-TRIO domain with a HA tag (bold) is set forth in SEQ ID NO: 22:

```
MEAKSQLFLKYFTLFMNLLNDCSEVEDESAQTGGR

KRGMSRRLASLRHCTVLAMSNLLNANVDSGLMHSI

GLGYHKDLQTRATFMEVLTKILQQGTEFDTLAETV

LADRFERLVELVTMMGDQGELPIAMALANVVPCSQ

WDELARVLVTLFDSRHLLYQLLWNMFSKEVELADS

MQTLFRGNSLASKIMTFCFKVYGATYLQKLLDPLL

RIVITSSDWQHVSFEVDPTRLEPSESLEENQRNLL

QMTEKFFHAIISSSSEFPPQLRSVCHCLYQATCHS

LLNKATVKEKKENKKSVVSQRFPQNSIGAVGSAMF

LRFINPAIVSPYEAGILDKKPPPRIERGLKLMSKI

LQSIANHVLFTKEEHMRPFNDFVKSNFDAARRFFL

DIASDCPTSDAVNHSLSFISDGNVLALHRLLWNNQ

EKIGQYLSSNRDHKAVGRRPFDKMATLLAYLGPPE

HKPVADTHWSSLNLTSSKFEEFMTRHQVHEKEEFK

ALKTLSIFYQAGTSKAGNPIFYYVARRFKTGQING
```

-continued

DLLIYHVLLTLKPYYAKPYEIVVDLTHTGPSNRFK

TDFLSKWFVVFPGFAYDNVSAVYIYNCNSWVREYT

KYHERLLTGLKGSKRLVFIDCPGKLAEHIEHEQQK

LPAATLALEEDLKYPYDVPDYA

In some embodiments, the nucleotide sequence encoding the mini-NF1 protein (e.g., mini-NF1 protein having the GRD and the CRAL-TRIO domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 4 and 23.

An exemplary nucleotide sequence encoding a mini-NF1 having an NF1 GRD and the CRAL-TRIO is set forth in SEQ ID NO: 4:

```
ATGGAAGCCAAGAGCCAGCTGTTTCTGAAATACTT

TACCCTGTTTATGAATCTGCTGAACGACTGTAGTG

AGGTGGAGGACGAGAGTGCCCAGACCGGCGGCAGG

AAGAGAGGCATGTCTAGGAGACTGGCCAGCCTGAG

GCACTGCACAGTGCTGGCCATGTCCAACCTGCTGA

ACGCCAATGTGGACTCCGGCCTGATGCACTCTATC

GGCCTGGGCTACCACAAGGATCTGCAGACCCGCGC

CACATTCATGGAGGTGCTGACCAAGATCCTGCAGC

AGGGCACCGAGTTTGACACACTGGCCGAGACCGTG

CTGGCAGATAGGTTCGAGCGCCTGGTGGAGCTGGT

GACAATGATGGGCGACCAGGGAGAGCTGCCTATCG

CAATGGCACTGGCCAACGTGGTGCCATGCAGCCAG

TGGGACGAGCTGGCCAGGGTGCTGGTGACCCTGTT

TGATTCCAGACACCTGCTGTACCAGCTGCTGTGGA

ACATGTTCTCTAAGGAGGTGGAGCTGGCCGACAGC

ATGCAGACACTGTTTAGGGGCAATTCCCTGGCCTC

TAAGATCATGACCTTCTGTTTTAAGGTGTACGGCG

CCACATATCTGCAGAAGCTGCTGGATCCACTGCTG

AGAATCGTGATCACCAGCTCCGACTGGCAGCACGT

GTCCTTCGAGGTGGATCCTACACGGCTGGAGCCAA

GCGAGTCCCTGGAGGAGAACCAGCGCAATCTGCTG

CAGATGACCGAGAAGTTCTTTCACGCCATCATCTC

TAGCTCCTCTGAGTTTCCCCCTCAGCTGCGGTCCG

TGTGCCACTGTCTGTACCAGGCCACCTGCCACTCT

CTGCTGAACAAGGCCACAGTGAAGGAGAAGAAGGA

GAATAAGAAGAGCGTGGTGTCCCAGAGGTTCCCAC

AGAACAGCATCGGAGCAGTGGGATCCGCCATGTTC

CTGAGGTTCATCAATCCCGCCATCGTGAGCCCTTA
```

-continued

```
TGAGGCCGGCATCCTGGACAAGAAGCCACCCCCTA

GGATCGAGAGAGGCCTGAAGCTGATGAGCAAGATC

CTGCAGTCCATCGCCAACCACGTGCTGTTCACCAA

GGAGGAGCACATGCGCCCCTTCAACGACTTTGTGA

AGTCTAATTTTGATGCCGCCCGGCGCTTCTTTCTG

GACATCGCCTCTGATTGTCCTACAAGCGACGCCGT

GAACCACTCTCTGAGCTTCATCAGCGATGGCAATG

TGCTGGCCCTGCACCGGCTGCTGTGGAACAATCAG

GAGAAGATCGGCCAGTACCTGAGCTCCAACAGGGA

CCACAAGGCAGTGGGCAGGAGACCATTTGATAAGA

TGGCCACACTGCTGGCCTATCTGGGACCACCAGAG

CACAAGCCAGTGGCAGACACACACTGGTCTAGCCT

GAATCTGACCTCCTCTAAGTTCGAGGAGTTTATGA

CCCGGCACCAGGTGCACGAGAAGGAGGAGTTTAAG

GCCCTGAAGACACTGTCTATCTTCTACCAGGCAGG

CACCAGCAAGGCAGGAAACCCAATCTTTTACTATG

TGGCCCGGCGCTTCAAGACAGGCCAGATCAATGGC

GATCTGCTGATCTACCACGTGCTGCTGACCCTGAA

GCCATACTATGCCAAGCCCTATGAGATCGTGGTGG

ACCTGACCCACACAGGCCCCTCCAACAGGTTTAAG

ACCGATTTCCTGTCTAAGTGGTTCGTGGTGTTTCC

TGGCTTCGCCTATGACAATGTGAGCGCCGTGTACA

TCTATAACTGCAATTCCTGGGTGCGGGAGTACACA

AAGTATCACGAGCGCCTGCTGACCGGCCTGAAGGG

ATCCAAGAGACTGGTGTTCATCGATTGTCCCGGCA

AGCTGGCCGAGCACATTGAACACGAACAGCAGAAA

CTGCCCGCCGCAACCCTGGCCCTGGAAGAGGACCT

GAAG
```

An exemplary nucleotide sequence encoding a mini-NF1 having an NF1 GRD and the CRAL-TRIO with a HA tag is set forth in SEQ ID NO: 23:

```
ATGGAAGCCAAGAGCCAGCTGTTTCTGAAATACTT

TACCCTGTTTATGAATCTGCTGAACGACTGTAGTG

AGGTGGAGGACGAGAGTGCCCAGACCGGCGGCAGG

AAGAGAGGCATGTCTAGGAGACTGGCCAGCCTGAG

GCACTGCACAGTGCTGGCCATGTCCAACCTGCTGA

ACGCCAATGTGGACTCCGGCCTGATGCACTCTATC

GGCCTGGGCTACCACAAGGATCTGCAGACCCGCGC

CACATTCATGGAGGTGCTGACCAAGATCCTGCAGC

AGGGCACCGAGTTTGACACACTGGCCGAGACCGTG

CTGGCAGATAGGTTCGAGCGCCTGGTGGAGCTGGT
```

```
GACAATGATGGGCGACCAGGGAGAGCTGCCTATCG

CAATGGCACTGGCCAACGTGGTGCCATGCAGCCAG

TGGGACGAGCTGGCCAGGGTGCTGGTGACCCTGTT

TGATTCCAGACACCTGCTGTACCAGCTGCTGTGGA

ACATGTTCTCTAAGGAGGTGGAGCTGGCCGACAGC

ATGCAGACACTGTTTAGGGGCAATTCCCTGGCCTC

TAAGATCATGACCTTCTGTTTTAAGGTGTACGGCG

CCACATATCTGCAGAAGCTGCTGGATCCACTGCTG

AGAATCGTGATCACCAGCTCCGACTGGCAGCACGT

GTCCTTCGAGGTGGATCCTACACGGCTGGAGCCAA

GCGAGTCCCTGGAGGAGAACCAGCGCAATCTGCTG

CAGATGACCGAGAAGTTCTTTCACGCCATCATCTC

TAGCTCCTCTGAGTTTCCCCCTCAGCTGCGGTCCG

TGTGCCACTGTCTGTACCAGGCCACCTGCCACTCT

CTGCTGAACAAGGCCACAGTGAAGGAGAAGAAGGA

GAATAAGAAGAGCGTGGTGTCCCAGAGGTTCCCAC

AGAACAGCATCGGAGCAGTGGGATCCGCCATGTTC

CTGAGGTTCATCAATCCCGCCATCGTGAGCCCTTA

TGAGGCCGGCATCCTGGACAAGAAGCCACCCCCTA

GGATCGAGAGAGGCCTGAAGCTGATGAGCAAGATC

CTGCAGTCCATCGCCAACCACGTGCTGTTCACCAA

GGAGGAGCACATGCGCCCCTTCAACGACTTTGTGA

AGTCTAATTTTGATGCCGCCCGGCGCTTCTTTCTG

GACATCGCCTCTGATTGTCCTACAAGCGACGCCGT

GAACCACTCTCTGAGCTTCATCAGCGATGGCAATG

TGCTGGCCCTGCACCGGCTGCTGTGGAACAATCAG

GAGAAGATCGGCCAGTACCTGAGCTCCAACAGGGA

CCACAAGGCAGTGGGCAGGAGACCATTTGATAAGA

TGGCCACACTGCTGGCCTATCTGGGACCACCAGAG

CACAAGCCAGTGGCAGACACACACTGGTCTAGCCT

GAATCTGACCTCCTCTAAGTTCGAGGAGTTTATGA

CCCGGCACCAGGTGCACGAGAAGGAGGAGTTTAAG

GCCCTGAAGACACTGTCTATCTTCTACCAGGCAGG

CACCAGCAAGGCAGGAAACCCAATCTTTTACTATG

TGGCCCGGCGCTTCAAGACAGGCCAGATCAATGGC

GATCTGCTGATCTACCACGTGCTGCTGACCCTGAA

GCCATACTATGCCAAGCCCTATGAGATCGTGGTGG

ACCTGACCCACACAGGCCCCTCCAACAGGTTTAAG

ACCGATTTCCTGTCTAAGTGGTTCGTGGTGTTTCC

TGGCTTCGCCTATGACAATGTGAGCGCCGTGTACA

TCTATAACTGCAATTCCTGGGTGCGGGAGTACACA

AAGTATCACGAGCGCCTGCTGACCGGCCTGAAGGG

ATCCAAGAGACTGGTGTTCATCGATTGTCCCGGCA

AGCTGGCCGAGCACATTGAACACGAACAGCAGAAA

CTGCCCGCCGCAACCCTGGCCCTGGAAGAGGACCT

GAAGTATCCGTATGATGTGCCGGATTATGCG
```

In some embodiments, an NF1 minigene comprises a GTPase-activating protein (GAP)-related domain (GRD), a CRAL-TRIO domain and a bipartite phospholipid binding domain of the wildtype NF1 protein. The bipartite phospholipid binding domain includes a Sec14p homologous segment and a pleckstrin homology (PH)-like domain. The lipid binding/interacting domains (CRAL-TRIO and bipartite Sec-PH) were included in this mini-NF1 gene to enhance interaction with Ras occurs at the cell membrane and lipid binding may be important for that interaction (see, e.g., Bai et al., Feasibility of using NF1-GRD and AAV for gene replacement therapy, Gene Therapy volume 26, pages 277-286(2019)). In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 5 and 24.

An exemplary amino acid sequence of a mini-NF1 protein comprising a GRD, a CRAL-TRIO domain and a bipartite phospholipid binding domain is set forth in SEQ ID NO: 5:

```
MEAKSQLFLKYFTLFMNLLNDCSEVEDESAQTGGR

KRGMSRRLASLRHCTVLAMSNLLNANVDSGLMHSI

GLGYHKDLQTRATFMEVLTKILQQGTEFDTLAETV

LADRFERLVELVTMMGDQGELPIAMALANVVPCSQ

WDELARVLVTLFDSRHLLYQLLWNMFSKEVELADS

MQTLFRGNSLASKIMTFCFKVYGATYLQKLLDPLL

RIVITSSDWQHVSFEVDPTRLEPSESLEENQRNLL

QMTEKFFHAIISSSSEFPPQLRSVCHCLYQATCHS

LLNKATVKEKKENKKSVVSQRFPQNSIGAVGSAMF

LRFINPAIVSPYEAGILDKKPPPRIERGLKLMSKI

LQSIANHVLFTKEEHMRPFNDFVKSNFDAARRFFL

DIASDCPTSDAVNHSLSFISDGNVLALHRLLWNNQ

EKIGQYLSSNRDHKAVGRRPFDKMATLLAYLGPPE

HKPVADTHWSSLNLTSSKFEEFMTRHQVHEKEEFK

ALKTLSIFYQAGTSKAGNPIFYYVARRFKTGQING

DLLIYHVLLTLKPYYAKPYEIVVDLTHTGPSNRFK

TDFLSKWFVVFPGFAYDNVSAVYIYNCNSWVREYT

KYHERLLTGLKGSKRLVFIDCPGKLAEHIEHEQQK

LPAATLALEEDLKVFHNALKLAHKDTKVSIKVGST

AVQVTSAERTKVLGQSVFLNDIYYASEIEEICLVD
```

ENQFTLTIANQGTPLTFMHQECEAIVQSIIHIRTR

WELSQPD

An exemplary amino acid sequence of a mini-NF1 protein comprising a GRD, a CRAL-TRIO domain and a bipartite phospholipid binding domain with an HA tag (bold) is set forth in SEQ ID NO: 24:

MEAKSQLFLKYFTLFMNLLNDCSEVEDESAQTGGR

KRGMSRRLASLRHCTVLAMSNLLNANVDSGLMHSI

GLGYHKDLQTRATFMEVLTKILQQGTEFDTLAETV

LADRFERLVELVTMMGDQGELPIAMALANVVPCSQ

WDELARVLVTLFDSRHLLYQLLWNMFSKEVELADS

MQTLFRGNSLASKIMTFCFKVYGATYLQKLLDPLL

RIVITSSDWQHVSFEVDPTRLEPSESLEENQRNLL

QMTEKFFHAIISSSSEFPPQLRSVCHCLYQATCHS

LLNKATVKEKKENKKSVVSQRFPQNSIGAVGSAMF

LRFINPAIVSPYEAGILDKKPPPRIERGLKLMSKI

LQSIANHVLFTKEEHMRPFNDFVKSNFDAARRFFL

DIASDCPTSDAVNHSLSFISDGNVLALHRLLWNNQ

EKIGQYLSSNRDHKAVGRRPFDKMATLLAYLGPPE

HKPVADTHWSSLNLTSSKFEEFMTRHQVHEKEEFK

ALKTLSIFYQAGTSKAGNPIFYYVARRFKTGQING

DLLIYHVLLTLKPYYAKPYEIVVDLTHTGPSNRFK

TDFLSKWFVVFPGFAYDNVSAVYIYNCNSWVREYT

KYHERLLTGLKGSKRLVFIDCPGKLAEHIEHEQQK

LPAATLALEEDLKVFHNALKLAHKDTKVSIKVGST

AVQVTSAERTKVLGQSVFLNDIYYASEIEEICLVD

ENQFTLTIANQGTPLTFMHQECEAIVQSIIHIRTR

WELSQPDYPYDVPDY

In some embodiments, the nucleotide sequence encoding the mini-NF1 protein (e.g., mini-NF1 protein having the GRD, the CRAL-TRIO domain and the bipartite phospholipid binding domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 6 and 25.

An exemplary nucleotide sequence encoding a mini-NF1 having an NF1 GRD, the CRAL-TRIO domain and the bipartite phospholipid binding domain is set forth in SEQ ID NO: 6:

ATGGAAGCCAAGAGCCAGCTGTTTCTGAAATACTT

TACCCTGTTTATGAATCTGCTGAACGACTGTAGTG

AGGTGGAGGACGAGAGTGCCCAGACCGGCGGCAGG

AAGAGAGGCATGTCTAGGAGACTGGCCAGCCTGAG

GCACTGCACAGTGCTGGCCATGTCCAACCTGCTGA

ACGCCAATGTGGACTCCGGCCTGATGCACTCTATC

GGCCTGGGCTACCACAAGGATCTGCAGACCCGCGC

CACATTCATGGAGGTGCTGACCAAGATCCTGCAGC

AGGGCACCGAGTTTGACACACTGGCCGAGACCGTG

CTGGCAGATAGGTTCGAGCGCCTGGTGGAGCTGGT

GACAATGATGGGCGACCAGGGAGAGCTGCCTATCG

CAATGGCACTGGCCAACGTGGTGCCATGCAGCCAG

TGGGACGAGCTGGCCAGGGTGCTGGTGACCCTGTT

TGATTCCAGACACCTGCTGTACCAGCTGCTGTGGA

ACATGTTCTCTAAGGAGGTGGAGCTGGCCGACAGC

ATGCAGACACTGTTTAGGGGCAATTCCCTGGCCTC

TAAGATCATGACCTTCTGTTTTAAGGTGTACGGCG

CCACATATCTGCAGAAGCTGCTGGATCCACTGCTG

AGAATCGTGATCACCAGCTCCGACTGGCAGCACGT

GTCCTTCGAGGTGGATCCTACACGGCTGGAGCCAA

GCGAGTCCCTGGAGGAGAACCAGCGCAATCTGCTG

CAGATGACCGAGAAGTTCTTTCACGCCATCATCTC

TAGCTCCTCTGAGTTTCCCCCTCAGCTGCGGTCCG

TGTGCCACTGTCTGTACCAGGCCACCTGCCACTCT

CTGCTGAACAAGGCCACAGTGAAGGAGAAGAAGGA

GAATAAGAAGAGCGTGGTGTCCCAGAGGTTCCCAC

AGAACAGCATCGGAGCAGTGGGATCCGCCATGTTC

CTGAGGTTCATCAATCCCGCCATCGTGAGCCCTTA

TGAGGCCGGCATCCTGGACAAGAAGCCACCCCCTA

GGATCGAGAGAGGCCTGAAGCTGATGAGCAAGATC

CTGCAGTCCATCGCCAACCACGTGCTGTTCACCAA

GGAGGAGCACATGCGCCCCTTCAACGACTTTGTGA

AGTCTAATTTTGATGCCGCCCGGCGCTTCTTTCTG

GACATCGCCTCTGATTGTCCTACAAGCGACGCCGT

GAACCACTCTCTGAGCTTCATCAGCGATGGCAATG

TGCTGGCCCTGCACCGGCTGCTGTGGAACAATCAG

GAGAAGATCGGCCAGTACCTGAGCTCCAACAGGGA

CCACAAGGCAGTGGGCAGGAGACCTTTTGATAAGA

TGGCCACCCTGCTGGCATATCTGGGACCACCAGAG

CACAAGCCAGTGGCAGACACCCACTGGTCTAGCCT

GAATCTGACATCCTCTAAGTTCGAGGAGTTTATGA

CCCGGCACCAGGTGCACGAGAAGGAGGAGTTTAAG

GCCCTGAAGACCCTGTCCATCTTCTACCAGGCCGG

CACATCTAAGGCCGGCAACCCTATCTTTTACTATG

```
TGGCCCGGCGCTTCAAGACCGGCCAGATCAATGGC
GATCTGCTGATCTACCACGTGCTGCTGACACTGAA
GCCATACTATGCCAAGCCCTATGAGATCGTGGTGG
ACCTGACCCACACAGGCCCAAGCAACAGGTTTAAG
ACCGATTTCCTGTCCAAGTGGTTCGTGGTGTTTCC
CGGCTTCGCCTATGACAACGTGAGCGCCGTGTACA
TCTATAACTGCAATAGCTGGGTGCGGGAGTACACC
AAGTATCACGAGCGCCTGCTGACAGGCCTGAAGGG
CAGCAAGAGACTGGTGTTCATCGATTGTCCCGGCA
AGCTGGCCGAGCACATCGAGCACGAGCAGCAGAAG
CTGCCTGCAGCCACCCTGGCCCTGGAGGAGGACCT
GAAGGTGTTTCACAACGCCCTGAAGCTGGCCCACA
AGGATACAAAGGTGTCCATCAAGGTCGGCTCTACA
GCCGTGCAGGTGACCTCCGCCGAGAGAACAAAGGT
GCTGGGCCAGAGCGTGTTCCTGAATGACATCTACT
ATGCCAGCGAGATCGAGGAGATCTGCCTGGTGGAT
GAGAACCAGTTTACCCTGACAATCGCCAATCAGGG
CACCCCCCTGACATTCATGCACCAGGAGTGTGAAG
CAATCGTCCAGAGCATTATTCACATTCGCACTCGG
TGGGAACTGAGCCAGCCTGAC
```

An exemplary nucleotide sequence encoding a mini-NF1 having an NF1 GRD, the CRAL-TRIO domain and the bipartite phospholipid binding domain with a HA tag is set forth in SEQ ID NO: 25:

ATGGAAGCCAAGAGCCAGCTGTTTCTGAAATACTT

TACCCTGTTTATGAATCTGCTGAACGACTGTAGTG

AGGTGGAGGACGAGAGTGCCCAGACCGGCGGCAGG

AAGAGAGGCATGTCTAGGAGACTGGCCAGCCTGAG

GCACTGCACAGTGCTGGCCATGTCCAACCTGCTGA

ACGCCAATGTGGACTCCGGCCTGATGCACTCTATC

GGCCTGGGCTACCACAAGGATCTGCAGACCCGCGC

CACATTCATGGAGGTGCTGACCAAGATCCTGCAGC

AGGGCACCGAGTTTGACACACTGGCCGAGACCGTG

CTGGCAGATAGGTTCGAGCGCCTGGTGGAGCTGGT

GACAATGATGGGCGACCAGGGAGAGCTGCCTATCG

CAATGGCACTGGCCAACGTGGTGCCATGCAGCCAG

TGGGACGAGCTGGCCAGGGTGCTGGTGACCCTGTT

TGATTCCAGACACCTGCTGTACCAGCTGCTGTGGA

ACATGTTCTCTAAGGAGGTGGAGCTGGCCGACAGC

ATGCAGACACTGTTTAGGGGCAATTCCCTGGCCTC

TAAGATCATGACCTTCTGTTTTAAGGTGTACGGCG

-continued

CCACATATCTGCAGAAGCTGCTGGATCCACTGCTG

AGAATCGTGATCACCAGCTCCGACTGGCAGCACGT

GTCCTTCGAGGTGGATCCTACACGGCTGGAGCCAA

GCGAGTCCCTGGAGGAGAACCAGCGCAATCTGCTG

CAGATGACCGAGAAGTTCTTTCACGCCATCATCTC

TAGCTCCTCTGAGTTTCCCCCTCAGCTGCGGTCCG

TGTGCCACTGTCTGTACCAGGCCACCTGCCACTCT

CTGCTGAACAAGGCCACAGTGAAGGAGAAGAAGGA

GAATAAGAAGAGCGTGGTGTCCCAGAGGTTCCCAC

AGAACAGCATCGGAGCAGTGGGATCCGCCATGTTC

CTGAGGTTCATCAATCCCGCCATCGTGAGCCCTTA

TGAGGCCGGCATCCTGGACAAGAAGCCACCCCCTA

GGATCGAGAGAGGCCTGAAGCTGATGAGCAAGATC

CTGCAGTCCATCGCCAACCACGTGCTGTTCACCAA

GGAGGAGCACATGCGCCCCTTCAACGACTTTGTGA

AGTCTAATTTTGATGCCGCCCGGCGCTTCTTTCTG

GACATCGCCTCTGATTGTCCTACAAGCGACGCCGT

GAACCACTCTCTGAGCTTCATCAGCGATGGCAATG

TGCTGGCCCTGCACCGGCTGCTGTGGAACAATCAG

GAGAAGATCGGCCAGTACCTGAGCTCCAACAGGGA

CCACAAGGCAGTGGGCAGGAGACCTTTTGATAAGA

TGGCCACCCTGCTGGCATATCTGGGACCACCAGAG

CACAAGCCAGTGGCAGACACCCACTGGTCTAGCCT

GAATCTGACATCCTCTAAGTTCGAGGAGTTTATGA

CCCGGCACCAGGTGCACGAGAAGGAGGAGTTTAAG

GCCCTGAAGACCCTGTCCATCTTCTACCAGGCCGG

CACATCTAAGGCCGGCAACCCTATCTTTTACTATG

TGGCCCGGCGCTTCAAGACCGGCCAGATCAATGGC

GATCTGCTGATCTACCACGTGCTGCTGACACTGAA

GCCATACTATGCCAAGCCCTATGAGATCGTGGTGG

ACCTGACCCACACAGGCCCAAGCAACAGGTTTAAG

ACCGATTTCCTGTCCAAGTGGTTCGTGGTGTTTCC

CGGCTTCGCCTATGACAACGTGAGCGCCGTGTACA

TCTATAACTGCAATAGCTGGGTGCGGGAGTACACC

AAGTATCACGAGCGCCTGCTGACAGGCCTGAAGGG

CAGCAAGAGACTGGTGTTCATCGATTGTCCCGGCA

AGCTGGCCGAGCACATCGAGCACGAGCAGCAGAAG

CTGCCTGCAGCCACCCTGGCCCTGGAGGAGGACCT

GAAGGTGTTTCACAACGCCCTGAAGCTGGCCCACA

AGGATACAAAGGTGTCCATCAAGGTCGGCTCTACA

GCCGTGCAGGTGACCTCCGCCGAGAGAACAAAGGT

-continued

```
GCTGGGCCAGAGCGTGTTCCTGAATGACATCTACT

ATGCCAGCGAGATCGAGGAGATCTGCCTGGTGGAT

GAGAACCAGTTTACCCTGACAATCGCCAATCAGGG

CACCCCCCTGACATTCATGCACCAGGAGTGTGAAG

CAATCGTCCAGAGCATTATTCACATTCGCACTCGG

TGGGAACTGAGCCAGCCTGACTATCCGTATGATGT

GCCGGATTATGC
```

In some embodiments, an NF1 minigene comprises (or consists of) the nucleic acid sequence set forth in any one of SEQ ID NOs: 2, 4, or 6. In some embodiments, an NF1 minigene encodes a protein (referred to as a mini-NF1 protein) that comprises (or consists of) an amino acid sequence set forth in any one of SEQ ID NOs: 1, 3, or 5.

In some embodiments, the transgene encoding the mini-NF1 proteins further comprises a nucleotide sequence encoding a polypeptide tag. A polypeptide tag, as used herein, refers to polypeptide sequences that are attached to proteins to facilitate easy detection and purification of expressed proteins. In addition, they can also be used to identify potential binding partners for the protein of interest. Non-limiting examples of a polypeptide tag includes a human influenza hemagglutinin (HA) tag, a FLAG tag, a Myc tag, a Maltose-binding protein (MBP) tag, a Calmodulin Binding Protein (CBP) tag, Poly-Histidine tag (His) tag, or a Glutathione-S transferase (GST) tag. In some embodiments, the polypeptide tag is an HA tag. In some embodiments, the HA tag is position at the N-terminal of the protein it is attached to (e.g., an mini-NF1 protein). In some embodiments, the polypeptide tag is an HA tag. In some embodiments, the HA tag is position at the C-terminal of the protein it is attached to (e.g., an mini-NF1 protein). In some embodiments, the transgene encoding the mini-NF protein does not comprise a nucleotide sequence encoding a polypeptide tag.

(ii) Dual-AAV Vector System Encoding Full-Length NF1

In some aspects, the present disclosure provides a set of isolated nucleic acids (e.g., a 5' isolated nucleic acid and/or a 3' isolated nucleic acid) each encoding a different portion of a protein (e.g., a portion of NF1 protein). The delivery of both isolated nucleic acids (e.g., by recombinant adeno-associated virus (rAAV) to the same cell results in delivery of a full-length protein (e.g., full-length NF1 protein to the cell).

In some embodiments, a 5' isolated nucleic acid, as used herein, refers to an isolated nucleic acid comprising nucleotide sequence encoding a first portion (e.g., N-terminal portion) of a protein (e.g., full-length NF1 protein. In some embodiments, the 5' isolated nucleic acid, which is flanked by adeno-associated virus (AAV) inverted terminal repeats (ITRs), comprises, from 5' to 3', a promoter operably linked to a nucleotide sequence encoding a first portion of NF1 protein, a nucleotide sequence encoding a splice donor, and a first portion of an intron.

In some embodiments, a 3' isolated nucleic acid, as used herein, refers to an isolated nucleic acid comprising nucleotide sequence encoding a second portion (e.g., C-terminal portion) of a protein (e.g., full-length NF1 protein. In some embodiments, the 3' isolated nucleic acid, which is flanked by adeno-associated virus (AAV) inverted terminal repeats (ITRs), comprises, from 5' to 3', a second portion of an intron, a nucleotide sequence encoding a splice acceptor, a nucleotide sequence encoding a second portion of NF1 protein. In some embodiments, the 3' and a polyadenylation signal positioned between the nucleotide sequence encoding a second portion of NF1 protein and the 3' ITR of the 3' isolated nucleic acid.

In some embodiments, the 5' isolated nucleic acid comprises a nucleotide sequence of exon 1 of the NF1 coding sequence, and one or more exons from exons 2-61 of the wild-type NF1 coding sequence (e.g., exons 1-25, exons 1-26, exons 1-27, exons 1-28, exons 1-29, exons 1-30, exons 1-31, exons 1-32, exons 1-33, exons 1-34, exons 1-35, exons 1-36, exons 1-37, exons 1-38, exons 1-39, exons 1-40, exons 1-41, exons 1-42, exons 1-43, exons 1-44, exons 1-45, exons 1-46, exons 1-47, exons 1-48, exons 1-49, exons 1-50, exons 1-51, exons 1-52, exons 1-53, exons 1-54, exons 1-55, exons 1-56, exons 1-57, exons 1-58, exons 1-59, or exons 1-60). In some embodiments, the 3' isolated nucleic acid comprises a nucleotide sequence of exon 61 of the NF1 coding sequence, and one or more exons from exons 1-60 of the wild-type NF1 coding sequence (e.g., exons 2-61, exons 3-61, exons 4-61, exons 5-61, exons 6-61, exons 7-61, exons 8-61, exons 9-61, exons 10-61, exons 11-61, exons 12-61, exons 13-61, exons 14-61, exons 15-61, exons 16-61, exons 17-61, exons 18-61, exons 19-61, exons 20-61, exons 21-61, exons 22-61, exons 23-61, exons 24-61, exons 25-61, exons 26-61, exons 27-61, exons 28-61, exons 29-61, exons 30-61, exons 31-61, exons 32-61, exons 33-61, exons 34-61, exons 35-61, or exons 36-61). In some embodiments, the 5' isolated nucleic acid comprises a nucleotide sequence of exon 1-31 of the NF1 coding sequence, and the 3' isolated nucleic acid comprises a nucleotide sequence of exon 32-61 of the NF1 coding sequence. In some embodiments, the 5' isolated nucleic acid comprises a nucleotide sequence of exon 1 of the NF1 coding sequence, and the 3' isolated nucleic acid comprises a nucleotide sequence of exons 2-61 of the NF1 coding sequence. In some embodiments, the 5' isolated nucleic acid comprises a nucleotide sequence of exons 1-2 of the NF1 coding sequence, and the 3' isolated nucleic acid comprises a nucleotide sequence of exons 3-61 of the NF1 coding sequence. In some embodiments, the 5' isolated nucleic acid comprises a nucleotide sequence of exons 1-3 of the NF1 coding sequence, and the 3' isolated nucleic acid comprises a nucleotide sequence of exons 4-61 of the NF1 coding sequence. In some embodiments, the 5' isolated nucleic acid comprises a nucleotide sequence of exons 1-4 of the NF1 coding sequence, and the 3' isolated nucleic acid comprises a nucleotide sequence of exons 5-61 of the NF1 coding sequence. In some embodiments, the 5' isolated nucleic acid comprises a nucleotide sequence of exons 1-5 of the NF1 coding sequence, and the 3' isolated nucleic acid comprises a nucleotide sequence of exons 6-61 of the NF1 coding sequence. In some embodiments, the 5' isolated nucleic acid comprises a nucleotide sequence of exons 1-6 of the NF1 coding sequence, and the 3' isolated nucleic acid comprises a nucleotide sequence of exons 7-61 of the NF1 coding sequence. In some embodiments, the 5' isolated nucleic acid comprises a nucleotide sequence of exons 1-7 of the NF1 coding sequence, and the 3' isolated nucleic acid comprises a nucleotide sequence of exons 8-61 of the NF1 coding sequence. In some embodiments, the 5' isolated nucleic acid comprises a nucleotide sequence of exons 1-8 of the NF1 coding sequence, and the 3' isolated nucleic acid comprises a nucleotide sequence of exons 9-61 of the NF1 coding sequence. In some embodiments, the 5' isolated nucleic acid comprises a nucleotide sequence of exons 1-9 of the NF1 coding sequence, and the 3' isolated nucleic acid comprises a nucleotide sequence of exons 10-61 of the NF1 coding sequence. In some embodiments, the 5' isolated nucleic acid comprises a nucleotide sequence of exons 1-10 of the NF1 coding sequence, and the 3' isolated nucleic acid comprises a nucleotide sequence of exons 11-61 of the NF1 coding sequence. In some embodiments, the 5' isolated nucleic acid comprises a nucleotide sequence of exons 1-11 of the NF1 coding sequence, and the 3' isolated nucleic acid comprises a nucleotide sequence of exons 12-61 of the NF1 coding sequence. In some embodiments, the 5' isolated nucleic acid comprises a nucleotide sequence of exons 1-12 of the NF1 coding sequence, and the 3' isolated nucleic acid comprises a nucleotide sequence of exons 13-61 of the NF1 coding sequence. In some embodiments, the 5' isolated nucleic acid comprises a nucleotide sequence of exons 1-13 of the NF1 coding sequence, and the 3' isolated nucleic acid comprises a nucleotide sequence of exons 14-61 of the NF1 coding sequence. In some embodiments, the 5' isolated nucleic acid comprises a nucleotide sequence of exons 1-14 of the NF1 coding sequence, and the 3' isolated nucleic acid comprises a nucleotide sequence of exons 15-61 of the NF1 coding sequence. In some embodiments, the 5' isolated nucleic acid comprises a nucleotide sequence of exons 1-15 of the NF1 coding sequence, and the 3' isolated nucleic acid comprises a nucleotide sequence of exons 16-61 of the NF1 coding sequence. In some embodiments, the 5' isolated nucleic acid comprises a nucleotide sequence of exons 1-16 of the NF1 coding sequence, and the 3' isolated nucleic acid comprises a nucleotide sequence of exons 17-61 of the NF1 coding sequence. In some embodiments, the 5' isolated nucleic acid comprises a nucleotide sequence of exons 1-17 of the NF1 coding sequence, and the 3' isolated nucleic acid comprises a nucleotide sequence of exons 18-61 of the NF1 coding sequence. In some embodiments, the 5' isolated nucleic acid comprises a nucleotide sequence of exons 1-18 of the NF1 coding sequence, and the 3' isolated nucleic acid comprises a nucleotide sequence of exons 19-61 of the NF1 coding sequence. In some embodiments, the 5' isolated nucleic acid comprises a nucleotide sequence of exons 1-19 of the NF1 coding sequence, and the 3' isolated nucleic acid comprises a nucleotide sequence of exons 20-61 of the NF1 coding sequence. In some embodiments, the 5' isolated nucleic acid comprises a nucleotide sequence of exons 1-20 of the NF1 coding sequence, and the 3' isolated nucleic acid comprises a nucleotide sequence of exons 21-61 of the NF1 coding sequence. In some embodiments, the 5' isolated nucleic acid comprises a nucleotide sequence of exons 1-21 of the NF1 coding sequence, and the 3' isolated nucleic acid comprises a nucleotide sequence of exons 22-61 of the NF1 coding sequence. In some embodiments, the 5' isolated nucleic acid comprises a nucleotide sequence of exons 1-22 of the NF1 coding sequence, and the 3' isolated nucleic acid comprises a nucleotide sequence of exons 23-61 of the NF1 coding sequence. In some embodiments, the 5' isolated nucleic acid comprises a nucleotide sequence of exons 1-23 of the NF1 coding sequence, and the 3' isolated nucleic acid comprises a nucleotide sequence of exons 24-61 of the NF1 coding sequence. In some embodiments, the 5' isolated nucleic acid comprises a nucleotide sequence of exons 1-24 of the NF1 coding sequence, and the 3' isolated nucleic acid comprises a nucleotide sequence of exons 25-61 of the NF1 coding sequence. In some embodiments, the 5' isolated nucleic acid comprises a nucleotide sequence of exons 1-25 of the NF1 coding sequence, and the 3' isolated nucleic acid comprises a nucleotide sequence of exons 25-61 of the NF1 coding sequence. In some embodiments, the 5' isolated nucleic acid comprises a nucleotide sequence of exons 1-26 of the NF1 coding sequence, and the 3' isolated nucleic acid comprises a nucleotide sequence of exons 27-61 of the NF1 coding sequence. In some embodiments, the 5' isolated nucleic acid comprises a nucleotide sequence of exons 1-28 of the NF1 coding sequence, and the 3' isolated nucleic acid comprises a nucleotide sequence of exons 29-61 of the NF1 coding sequence. In some embodiments, the 5' isolated nucleic acid comprises a nucleotide sequence of exons 1-30 of the NF1 coding sequence, and the 3' isolated nucleic acid comprises a nucleotide sequence of exons 31-61 of the NF1 coding sequence. In some embodiments, the 5' isolated nucleic acid comprises a nucleotide sequence of exons 1-32 of the NF1 coding sequence, and the 3' isolated nucleic acid comprises a nucleotide sequence of exons 33-61 of the NF1 coding sequence. In some embodiments, the 5' isolated nucleic acid comprises a nucleotide sequence of exons 1-33 of the NF1 coding sequence, and the 3' isolated nucleic acid comprises a nucleotide sequence of exons 34-61 of the NF1 coding sequence. In some embodiments, the 5' isolated nucleic acid comprises a nucleotide sequence of exons 1-34 of the NF1 coding sequence, and the 3' isolated nucleic acid comprises a nucleotide sequence of exons 35-61 of the NF1 coding sequence. In some embodiments, the 5' isolated nucleic acid comprises a nucleotide sequence of exons 1-35 of the NF1 coding sequence, and the 3' isolated nucleic acid comprises a nucleotide sequence of exons 36-61 of the NF1 coding sequence. In some embodiments, the 5' isolated nucleic acid comprises a nucleotide sequence of exons 1-36 of the NF1 coding sequence, and the 3' isolated nucleic acid comprises a nucleotide sequence of exons 37-61 of the NF1 coding sequence. In some embodiments, the 5' isolated nucleic acid comprises a nucleotide sequence of exons 1-37 of the NF1 coding sequence, and the 3' isolated nucleic acid comprises a nucleotide sequence of exons 38-61 of the NF1 coding sequence. In some embodiments, the 5' isolated nucleic acid comprises a nucleotide sequence of exons 1-38 of the NF1 coding sequence, and the 3' isolated nucleic acid comprises a nucleotide sequence of exons 39-61 of the NF1 coding sequence. In some embodiments, the 5' isolated nucleic acid comprises a nucleotide sequence of exons 1-39 of the NF1 coding sequence, and the 3' isolated nucleic acid comprises a nucleotide sequence of exons 40-61 of the NF1 coding sequence. In some embodiments, the 5' isolated nucleic acid comprises a nucleotide sequence of exons 1-40 of the NF1 coding sequence, and the 3' isolated nucleic acid comprises a nucleotide sequence of exons 41-61 of the NF1 coding sequence. In some embodiments, the 5' isolated nucleic acid comprises a nucleotide sequence of exons 1-41 of the NF1 coding sequence, and the 3' isolated nucleic acid comprises a nucleotide sequence of exons 42-61 of the NF1 coding sequence. In some embodiments, the 5' isolated nucleic acid comprises a nucleotide sequence of exons 1-42 of the NF1 coding sequence, and the 3' isolated nucleic acid comprises a nucleotide sequence of exons 43-61 of the NF1 coding sequence. In some embodiments, the 5' isolated nucleic acid comprises a nucleotide sequence of exons 1-43 of the NF1 coding sequence, and the 3' isolated nucleic acid comprises a nucleotide sequence of exons 44-61 of the NF1 coding sequence. In some embodiments, the 5' isolated nucleic acid comprises a nucleotide sequence of exons 1-44 of the NF1 coding sequence, and the 3' isolated nucleic acid comprises a nucleotide sequence of exons 45-61 of the NF1 coding sequence. In some embodiments, the 5' isolated nucleic acid comprises a nucleotide sequence of exons 1-46 of the NF1 coding sequence, and the 3' isolated nucleic acid comprises a nucleotide sequence of exons 47-61 of the NF1 coding sequence. In some embodiments, the 5' isolated nucleic acid comprises a nucleotide sequence of exons 1-47 of the NF1 coding sequence, and the 3' isolated nucleic acid comprises a nucleotide sequence of exons 48-61 of the NF1 coding sequence. In some embodiments, the 5' isolated nucleic acid comprises a nucleotide sequence of exons 1-48 of the NF1 coding sequence, and the 3' isolated nucleic acid comprises a nucleotide sequence of exons 49-61 of the NF1 coding sequence. In some embodiments, the 5' isolated nucleic acid comprises a nucleotide sequence of exons 1-49 of the NF1 coding sequence, and the 3' isolated nucleic acid comprises a nucleotide sequence of exons 50-61 of the NF1 coding sequence. In some embodiments, the 5' isolated nucleic acid comprises a nucleotide sequence of exons 1-50 of the NF1 coding sequence, and the 3' isolated nucleic acid comprises a nucleotide sequence of exons 51-61 of the NF1 coding sequence. In some embodiments, the 5' isolated nucleic acid comprises a nucleotide sequence of exons 1-51 of the NF1 coding sequence, and the 3' isolated nucleic acid comprises a nucleotide sequence of exons 52-61 of the NF1 coding sequence. In some embodiments, the 5' isolated nucleic acid comprises a nucleotide sequence of exons 1-52 of the NF1 coding sequence, and the 3' isolated nucleic acid comprises a nucleotide sequence of exons 53-61 of the NF1 coding sequence. In some embodiments, the 5' isolated nucleic acid comprises a nucleotide sequence of exons 1-53 of the NF1 coding sequence, and the 3' isolated nucleic acid comprises a nucleotide sequence of exons 54-61 of the NF1 coding sequence. In some embodiments, the 5' isolated nucleic acid comprises a nucleotide sequence of exons 1-54 of the NF1 coding sequence, and the 3' isolated nucleic acid comprises a nucleotide sequence of exons 55-61 of the NF1 coding sequence. In some embodiments, the 5' isolated nucleic acid comprises a nucleotide sequence of exons 1-55 of the NF1 coding sequence, and the 3' isolated nucleic acid comprises a nucleotide sequence of exons 56-61 of the NF1 coding sequence. In some embodiments, the 5' isolated nucleic acid comprises a nucleotide sequence of exons 1-56 of the NF1 coding sequence, and the 3' isolated nucleic acid comprises a nucleotide sequence of exons 57-61 of the NF1 coding sequence. In some embodiments, the 5' isolated nucleic acid comprises a nucleotide sequence of exons 1-57 of the NF1 coding sequence, and the 3' isolated nucleic acid comprises a nucleotide sequence of exons 58-61 of the NF1 coding sequence. In some embodiments, the 5' isolated nucleic acid comprises a nucleotide sequence of exons 1-59 of the NF1 coding sequence, and the 3' isolated nucleic acid comprises a nucleotide sequence of exons 60-61 of the NF1 coding sequence. In some embodiments, the 5' isolated nucleic acid comprises a nucleotide sequence of exons 1-60 of the NF1 coding sequence, and the 3' isolated nucleic acid comprises a nucleotide sequence of exon 61 of the NF1 coding sequence.

In some embodiments, the nucleotide sequence encoding a first portion of the NF1 protein comprises exons 1-31 of the wild-type NF1 coding sequence. In some embodiments, the first portion of the NF1 protein comprises an amino acid sequence at least 80%, at least 85%, at least 90%, at least 91%, at least 92%, at least 93%, at least 94%, at least 95%, at least 96%, at least 97%, at least 98%, at least 99%, or 100% identical to SEQ ID NO: 10. An exemplary amino acid sequence of the first portion of the NF1 protein is set forth in SEQ ID NO: 10:

```
MAAHRPVEWVQAVVSRFDEQLPIKTGQQNTHTKVS

TEHNKECLINISKYKFSLVISGLTTILKNVNNMRI
```

-continued
```
FGEAAEKNLYLSQLIILDTLEKCLAGQPKDTMRLD

ETMLVKQLLPEICHFLHTCREGNQHAAELRNSASG

VLFSLSCNNFNAVFSRISTRLQELTVCSEDNVDVH

DIELLQYINVDCAKLKRLLKETAFKFKALKKVAQL

AVINSLEKAFWNWVENYPDEFTKLYQIPQTDMAEC

AEKLFDLVDGFAESTKRKAAVWPLQIILLILCPEI

IQDISKDVVDENNMNKKLFLDSLRKALAGHGGSRQ

LTESAAIACVKLCKASTYINWEDNSVIFLLVQSMV

VDLKNLLFNPSKPFSRGSQPADVDLMIDCLVSCFR

ISPHNNQHFKICLAQNSPSTFHYVLVNSLHRIITN

SALDWWPKIDAVYCHSVELRNMFGETLHKAVQGCG

AHPAIRMAPSLTFKEKVTSLKFKEKPTDLETRSYK

YLLLSMVKLIHADPKLLLCNPRKQGPETQGSTAEL

ITGLVQLVPQSHMPEIAQEAMEALLVLHQLDSIDL

WNPDAPVETFWEISSQMLFYICKKLTSHQMLSSTE

ILKWLREILICRNKFLLKNKQADRSSCHFLLFYGV

GCDIPSSGNTSQMSMDHEELLRTPGASLRKGKGNS

SMDSAAGCSGTPPICRQAQTKLEVALYMFLWNPDT

EAVLVAMSCFRHLCEEADIRCGVDEVSVHNLLPNY

NTFMEFASVSNMMSTGRAALQKRVMALLRRIEHPT

AGNTEAWEDTHAKWEQATKLILNYPKAKMEDGQAA

ESLHKTIVKRRMSHVSGGGSIDLSDTDSLQEWINM

TGFLCALGGVCLQQRSNSGLATYSPPMGPVSERKG

SMISVMSSEGNADTPVSKFMDRLLSLMVCNHEKVG

LQIRTNVKDLVGLELSPALYPMLFNKLKNTISKFF

DSQGQVLLTDTNTQFVEQTIAIMKNLLDNHTEGSS

EHLGQASIETMMLNLVRYVRVLGNMVHAIQIKTKL

CQLVEVMMARRDDLSFCQEMKFRNKMVEYLTDWVM

GTSNQAADDDVKCLTRDLDQASMEAVVSLLAGLPL

QPEEGDGVELMEAKSQLFLKYFTLFMNLLNDCSEV

EDESAQTGGRKRGMSRRLASLRHCTVLAMSNLLNA

NVDSGLMHSIGLGYHKDLQTRATFMEVLTKILQQG

TEFDTLAETVLADRFERLVELVTMMGDQGELPIAM

ALANVVPCSQWDELARVLVTLFDSRHLLYQLLWNM

FSKEVELADSMQTLFRGNSLASKIMTFCFKVYGAT

YLQKLLDPLLRIVITSSDWQHVSFEVDPTRLEPSE

SLEENQRNLLQMTEKFFHAIISSSSEFPPQLRSVC

HCLYQATCHSLLNKATVKEKKENKKS
```

In some embodiments, the nucleotide sequence encoding the first portion of the NF1 protein (e.g., exons 1-31) is at least at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 11. A nucleotide sequence encoding the first portion of the NF1 protein is set forth in SEQ ID NO: 11.

```
ATGGCCGCGCACAGGCCGGTGGAATGGGTCCAGGC

CGTGGTCAGCCGCTTCGACGAGCAGCTTCCAATAA

AAACAGGACAGCAGAACACACATACCAAAGTCAGT

ACTGAGCACAACAAGGAATGTCTAATCAATATTTC

CAAATACAAGTTTTCTTTGGTTATAAGCGGCCTCA

CTACTATTTTAAAGAATGTTAACAATATGAGAATA

TTTGGAGAAGCTGCTGAAAAAAATTTATATCTCTC

TCAGTTGATTATATTGGATACACTGGAAAAATGTC

TTGCTGGGCAACCAAAGGACACAATGAGATTAGAT

GAAACGATGCTGGTCAAACAGTTGCTGCCAGAAAT

CTGCCATTTTCTTCACACCTGTCGTGAAGGAAACC

AGCATGCAGCTGAACTTCGGAATTCTGCCTCTGGG

GTTTTATTTTCTCTCAGCTGCAACAACTTCAATGC

AGTCTTTAGTCGCATTTCTACCAGGTTACAGGAAT

TAACTGTTTGTTCAGAAGACAATGTTGATGTTCAT

GATATAGAATTGTTACAGTATATCAATGTGGATTG

TGCAAAATTAAAACGACTCCTGAAGGAAACAGCAT

TTAAATTTAAAGCCCTAAAGAAGGTTGCGCAGTTA

GCAGTTATAAATAGCCTGGAAAAGGCATTTTGGAA

CTGGGTAGAAAATTATCCAGATGAATTTACAAAAC

TGTACCAGATCCCACAGACTGATATGGCTGAATGT

GCAGAAAAGCTATTTGACTTGGTGGATGGTTTTGC

TGAAAGCACCAAACGTAAAGCAGCAGTTTGGCCAC

TACAAATCATTCTCCTTATCTTGTGCCCAGAAATA

ATCCAGGATATATCCAAAGACGTGGTTGATGAAAA

CAACATGAATAAGAAGTTATTTCTGGACAGTCTAC

GAAAAGCTCTTGCTGGCCATGGAGGAAGTAGGCAG

CTGACAGAAAGTGCTGCAATTGCCTGTGTCAAACT

GTGTAAAGCAAGTACTTACATCAATTGGGAAGATA

ACTCTGTCATTTTCCTACTTGTTCAGTCCATGGTG

GTTGATCTTAAGAACCTGCTTTTTAATCCAAGTAA

GCCATTCTCAAGAGGCAGTCAGCCTGCAGATGTGG

ATCTAATGATTGACTGCCTTGTTTCTTGCTTTCGT

ATAAGCCCTCACAACAACCAACACTTTAAGATCTG

CCTGGCTCAGAATTCACCTTCTACATTTCACTATG

TGCTGGTAAATTCACTCCATCGAATCATCACCAAT

TCCGCATTGGATTGGTGGCCTAAGATTGATGCTGT

GTATTGTCACTCGGTTGAACTTCGAAATATGTTTG

GTGAAACACTTCATAAAGCAGTGCAAGGTTGTGGA

GCACACCCAGCAATACGAATGGCACCGAGTCTTAC

ATTTAAAGAAAAAGTAACAAGCCTTAAATTTAAAG

AAAAACCTACAGACCTGGAGACAAGAAGCTATAAG

TATCTTCTCTTGTCCATGGTGAAACTAATTCATGC

AGATCCAAAGCTCTTGCTTTGTAATCCAAGAAAAC

AGGGGCCCGAAACCCAAGGCAGTACAGCAGAATTA

ATTACAGGGCTCGTCCAACTGGTCCCTCAGTCACA

CATGCCAGAGATTGCTCAGGAAGCAATGGAGGCTC

TGCTGGTTCTTCATCAGTTAGATAGCATTGATTTG

TGGAATCCTGATGCTCCTGTAGAAACATTTTGGGA

GATTAGCTCACAAATGCTTTTTTACATCTGCAAGA

AATTAACTAGTCATCAAATGCTTAGTAGCACAGAA

ATTCTCAAGTGGTTGCGGGAAATATTGATCTGCAG

GAATAAATTTCTTCTTAAAAATAAGCAGGCAGATA

GAAGTTCCTGTCACTTTCTCCTTTTTTACGGGGTA

GGATGTGATATTCCTTCTAGTGGAAATACCAGTCA

AATGTCCATGGATCATGAAGAATTACTACGTACTC

CTGGAGCCTCTCTCCGGAAGGGAAAAGGGAACTCC

TCTATGGATAGTGCAGCAGGATGCAGCGGAACCCC

CCCAATTTGCCGACAAGCCCAGACCAAACTAGAAG

TGGCCCTGTACATGTTTCTGTGGAACCCTGACACT

GAAGCTGTTCTGGTTGCCATGTCCTGTTTCCGCCA

CCTCTGTGAGGAAGCAGATATCCGGTGTGGGGTGG

ATGAAGTGTCAGTGCATAACCTCTTGCCCAACTAT

AACACATTCATGGAGTTTGCCTCTGTCAGCAATAT

GATGTCAACAGGAAGAGCAGCACTTCAGAAAAGAG

TGATGGCACTGCTGAGGCGCATTGAGCATCCCACT

GCAGGAAACACTGAGGCTTGGGAAGATACACATGC

AAAATGGGAACAAGCAACAAAGCTAATCCTTAACT

ATCCAAAAGCCAAAATGGAAGATGGCCAGGCTGCT

GAAAGCCTTCACAAGACCATTGTTAAGAGGCGAAT

GTCCCATGTGAGTGGAGGAGGATCCATAGATTTGT

CTGACACAGACTCCCTACAGGAATGGATCAACATG

ACTGGCTTCCTTTGTGCCCTTGGGGAGTGTGCCT

CCAGCAGAGAAGCAATTCTGGCCTGGCAACCTATA

GCCCACCCATGGGTCCAGTCAGTGAACGTAAGGGT

TCTATGATTTCAGTGATGTCTTCAGAGGGAAACGC

AGATACACCTGTCAGCAAATTTATGGATCGGCTGT

TGTCCTTAATGGTGTGTAACCATGAGAAAGTGGGA
```

```
CTTCAAATACGGACCAATGTTAAGGATCTGGTGGG
TCTAGAATTGAGTCCTGCTCTGTATCCAATGCTAT
TTAACAAATTGAAGAATACCATCAGCAAGTTTTTT
GACTCCCAAGGACAGGTTTTATTGACTGATACCAA
TACTCAATTTGTAGAACAAACCATAGCTATAATGA
AGAACTTGCTAGATAATCATACTGAAGGCAGCTCT
GAACATCTAGGGCAAGCTAGCATTGAAACAATGAT
GTTAAATCTGGTCAGGTATGTTCGTGTGCTTGGGA
ATATGGTCCATGCAATTCAAATAAAAACGAAACTG
TGTCAATTAGTTGAAGTAATGATGGCAAGGAGAGA
TGACCTCTCATTTTGCCAAGAGATGAAATTTAGGA
ATAAGATGGTAGAATACCTGACAGACTGGGTTATG
GGAACATCAAACCAAGCAGCAGATGATGATGTAAA
ATGTCTTACAAGAGATTTGGACCAGGCAAGCATGG
AAGCAGTAGTTTCACTTCTAGCTGGTCTCCCTCTG
CAGCCTGAAGAAGGAGATGGTGTGGAATTGATGGA
AGCCAAATCACAGTTATTTCTTAAATACTTCACAT
TATTTATGAACCTTTTGAATGACTGCAGTGAAGTT
GAAGATGAAAGTGCGCAAACAGGTGGCAGGAAACG
TGGCATGTCTCGGAGGCTGGCATCACTGAGGCACT
GTACGTCCTTGCAATGTCAAACTTACTCAATGCC
AACGTAGACAGTGGTCTCATGCACTCCATAGGCTT
AGGTTACCACAAGGATCTCCAGACAAGAGCTACAT
TTATGGAAGTTCTGACAAAAATCCTTCAACAAGGC
ACAGAATTTGACACACTTGCAGAAACAGTATTGGC
TGATCGGTTTGAGAGATTGGTGGAACTGGTCACAA
TGATGGGTGATCAAGGAGAACTCCCTATAGCGATG
GCTCTGGCCAATGTGGTTCCTTGTTCTCAGTGGGA
TGAACTAGCTCGAGTTCTGGTTACTCTGTTTGATT
CTCGGCATTTACTCTACCAACTGCTCTGGAACATG
TTTTCTAAAGAAGTAGAATTGGCAGACTCCATGCA
GACTCTCTTCCGAGGCAACAGCTTGGCCAGTAAAA
TAATGACATTCTGTTTCAAGGTATATGGTGCTACC
TATCTACAAAAACTCCTGGATCCTTTATTACGAAT
TGTGATCACATCCTCTGATTGGCAACATGTTAGCT
TTGAAGTGGATCCTACCAGGTTAGAACCATCAGAG
AGCCTTGAGGAAAACCAGCGGAACCTCCTTCAGAT
GACTGAAAAGTTCTTCCATGCCATCATCAGTTCCT
CCTCAGAATTCCCCCCTCAACTTCGAAGTGTGTGC
CACTGTTTATACCAGGCAACTTGCCACTCCCTACT
```

```
GAATAAAGCTACAGTAAAAGAAAAAAAGGAAAACA
AAAAATCA
```

In some embodiments, the nucleotide sequence encoding a second portion of the NF1 protein comprises exons 32-61 of the wild-type NF1 coding sequence. In some embodiments, the second portion of the NF1 protein comprises an amino acid sequence at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 13 or 26.

An exemplary amino acid sequence of the second portion of the NF1 protein is set forth in SEQ ID NO: 13:

```
MVSQRFPQNSIGAVGSAMFLRFINPAIVSPYEAGI
LDKKPPPRIERGLKLMSKILQSIANHVLFTKEEHM
RPFNDFVKSNFDAARRFFLDIASDCPTSDAVNHSL
SFISDGNVLALHRLLWNNQEKIGQYLSSNRDHKAV
GRRPFDKMATLLAYLGPPEHKPVADTHWSSLNLTS
SKFEEFMTRHQVHEKEEFKALKTLSIFYQAGTSKA
GNPIFYYVARRFKTGQINGDLLIYHVLLTLKPYYA
KPYEIVVDLTHTGPSNRFKTDFLSKWFVVFPGFAY
DNVSMVYIYNCNSWVREYTKYHERLLTGLKGSKRL
VFIDCPGKLAEHIEHEQQKLPAATLALEEDLKVFH
NALKLAHKDTKVSIKVGSTAVQVTSAERTKVLGQS
VFLNDIYYASEIEEICLVDENQFTLTIANQGTPLT
FMHQECEAIVQSIIHIRTRWELSQPDSIPQHTKIR
PKDVPGTLLNIALLNLGSSDPSLRSAAYNLLCALT
CTFNLKIEGQLLETSGLCIPANNTLFIVSISKTLA
ANEPHLTLEFLEECISGFSKSSIELKHLCLEYMTP
WLSNLVRFCKHNDDAKRQRVTAILDKLITMTINEK
QMYPSIQAKIWGSLGQITDLLDVVLDSFIKTSATG
GLGSIKAEVMADTAVALASGNVKLVSSKVIGRMCK
IIDKTCLSPTPTLEQHLMWDDIAILARYMLMLSFN
NSLDVAAHLPYLFHVVTFLVATGPLSLRASTHGLV
INIIHSLCTCSQLHFSEETKQVLRLSLTEFSLPKF
YLLFGISKVKSAAVIAFRSSYRDRSFSPGSYERET
FALTSLETVTEALLEIMEACMRDIPTCKWLDQWTE
LAQRFAFQYNPSLQPRALVVFGCISKRVSHGQIKQ
IIRILSKALESCLKGPDTYNSQVLIEATVIALTKL
QPLLNKDSPLHKALFWVAVAVLQLDEVNLYSAGTA
LLEQNLHTLDSLRIFNDKSPEEVFMAIRNPLEWHC
KQMDHFVGLNFNSNFNFALVGHLLKGYRHPSPAIV
ARTVRILHTLLTLVNKHRNCDKFEVNTQSVAYLAA
LLTVSEEVRSRCSLKHRKSLLLTDISMENVPMDTY
```

```
PIHHGDPSYRTLKETQPWSSPKGSEGYLAATYPTV

GQTSPRARKSMSLDMGQPSQANTKKLLGTRKSFDH

LISDTKAPKRQEMESGITTPPKMRRVAETDYEMET

QRISSSQQHPHLRKVSVSESNVLLDEEVLTDPKIQ

ALLLTVLATLVKYTTDEFDQRILYEYLAEASVVFP

KVFPVVHNLLDSKINTLLSLCQDPNLLNPIHGIVQ

SVVYHEESPPQYQTSYLQSFGFNGLWRFAGPFSKQ

TQIPDYAELIVKFLDALIDTYLPGIDEETSEESLL

TPTSPYPPALQSQLSITANLNLSNSMTSLATSQHS

PGIDKENVELSPTTGHCNSGRTRHGSASQVQKQRS

AGSFKRNSIKKIV
```

An exemplary amino acid sequence of the second portion of the NF1 protein with a HA tag (bold) is set forth in SEQ ID NO: 26:

```
MVSQRFPQNSIGAVGSAMFLRFINPAIVSPYEAGI

LDKKPPPRIERGLKLMSKILQSIANHVLFTKEEHM

RPFNDFVKSNFDAARRFFLDIASDCPTSDAVNHSL

SFISDGNVLALHRLLWNNQEKIGQYLSSNRDHKAV

GRRPFDKMATLLAYLGPPEHKPVADTHWSSLNLTS

SKFEEFMTRHQVHEKEEFKALKTLSIFYQAGTSKA

GNPIFYYVARRFKTGQINGDLLIYHVLLTLKPYYA

KPYEIVVDLTHTGPSNRFKTDFLSKWFVVFPGFAY

DNVSMVYIYNCNSWVREYTKYHERLLTGLKGSKRL

VFIDCPGKLAEHIEHEQQKLPAATLALEEDLKVFH

NALKLAHKDTKVSIKVGSTAVQVTSAERTKVLGQS

VFLNDIYYASEIEEICLVDENQFTLTIANQGTPLT

FMHQECEAIVQSIIHIRTRWELSQPDSIPQHTKIR

PKDVPGTLLNIALLNLGSSDPSLRSAAYNLLCALT

CTFNLKIEGQLLETSGLCIPANNTLFIVSISKTLA

ANEPHLTLEFLEECISGFSKSSIELKHLCLEYMTP

WLSNLVRFCKHNDDAKRQRVTAILDKLITMTINEK

QMYPSIQAKIWGSLGQITDLLDVVLDSFIKTSATG

GLGSIKAEVMADTAVALASGNVKLVSSKVIGRMCK

IIDKTCLSPTPTLEQHLMWDDIAILARYMLMLSFN

NSLDVAAHLPYLFHVVTFLVATGPLSLRASTHGLV

INIIHSLCTCSQLHFSEETKQVLRLSLTEFSLPKF

YLLFGISKVKSAAVIAFRSSYRDRSFSPGSYERET

FALTSLETVTEALLEIMEACMRDIPTCKWLDQWTE

LAQRFAFQYNPSLQPRALVVFGCISKRVSHGQIKQ

IIRILSKALESCLKGPDTYNSQVLIEATVIALTKL

QPLLNKDSPLHKALFWVAVAVLQLDEVNLYSAGTA

LLEQNLHTLDSLRIFNDKSPEEVFMAIRNPLEWHC

KQMDHFVGLNFNSNFNFALVGHLLKGYRHPSPAIV

ARTVRILHTLLTLVNKHRNCDKFEVNTQSVAYLAA

LLTVSEEVRSRCSLKHRKSLLLTDISMENVPMDTY

PIHHGDPSYRTLKETQPWSSPKGSEGYLAATYPTV

GQTSPRARKSMSLDMGQPSQANTKKLLGTRKSFDH

LISDTKAPKRQEMESGITTPPKMRRVAETDYEMET

QRISSSQQHPHLRKVSVSESNVLLDEEVLTDPKIQ

ALLLTVLATLVKYTTDEFDQRILYEYLAEASVVFP

KVFPVVHNLLDSKINTLLSLCQDPNLLNPIHGIVQ

SVVYHEESPPQYQTSYLQSFGFNGLWRFAGPFSKQ

TQIPDYAELIVKFLDALIDTYLPGIDEETSEESLL

TPTSPYPPALQSQLSITANLNLSNSMTSLATSQHS

PGIDKENVELSPTTGHCNSGRTRHGSASQVQKQRS

AGSFKRNSIKKIVYPYDVPDYA
```

In some embodiments, the nucleotide sequence encoding the second portion of the NF1 protein (e.g., exons 32-61) is at least at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 14 or 27.

A nucleotide sequence encoding the second portion of the NF1 protein is set forth in SEQ ID NO: 14:

```
GTGGTTAGCCAGCGTTTCCCTCAGAACAGCATCGGTGCAGTAGGAAGTGC

CATGTTCCTCAGATTTATCAATCCTGCCATTGTCTCACCGTATGAAGCAG

GGATTTTAGATAAAAAGCCACCACCTAGAATCGAAAGGGGCTTGAAGTTA

ATGTCAAAGATACTTCAGAGTATTGCCAATCATGTTCTCTTCACAAAAGA

AGAACATATGCGGCCTTTCAATGATTTTGTGAAAAGCAACTTTGATGCAG

CACGCAGGTTTTTCCTTGATATAGCATCTGATTGTCCTACAAGTGATGCA

GTAAATCATAGTCTTTCCTTCATAAGTGACGGCAATGTGCTTGCTTTACA

TCGTCTACTCTGGAACAATCAGGAGAAAATTGGGCAGTATCTTTCCAGCA

ACAGGGATCATAAAGCTGTTGGAAGACGACCTTTTGATAAGATGGCAACA

CTTCTTGCATACCTGGGTCCTCCAGAGCACAAACCTGTGGCAGATACACA

CTGGTCCAGCCTTAACCTTACCAGTTCAAAGTTTGAGGAATTTATGACTA

GGCATCAGGTACATGAAAAAGAAGAATTCAAGGCTTTGAAAACGTTAAGT

ATTTTCTACCAAGCTGGGACTTCCAAAGCTGGGAATCCTATTTTTTATTA

TGTTGCACGGAGGTTCAAAACTGGTCAAATCAATGGTGATTTGCTGATAT

ACCATGTCTTACTGACTTTAAAGCCATATTATGCAAAGCCATATGAAATT

GTAGTGGACCTTACCCATACCGGGCCTAGCAATCGCTTTAAAACAGACTT

TCTCTCTAAGTGGTTTGTTGTTTTCCTGGCTTTGCTTACGACAACGTCT

CCGCAGTCTATATCTATAACTGTAACTCCTGGGTCAGGGAGTACACCAAG
```

-continued

```
TATCATGAGCGGCTGCTGACTGGCCTCAAAGGTAGCAAAAGGCTTGTTTT
CATAGACTGTCCTGGGAAACTGGCTGAGCACATAGAGCATGAACAACAGA
AACTACCTGCTGCCACCTTGGCTTTAGAAGAGGACCTGAAGGTATTCCAC
AATGCTCTCAAGCTAGCTCACAAAGACACCAAAGTTTCTATTAAAGTTGG
TTCTACTGCTGTCCAAGTAACTTCAGCAGAGCGAACAAAAGTCCTAGGGC
AATCAGTCTTTCTAAATGACATTTATTATGCTTCGGAAATTGAAGAAATC
TGCCTAGTAGATGAGAACCAGTTCACCTTAACCATTGCAAACCAGGGCAC
GCCGCTCACCTTCATGCACCAGGAGTGTGAAGCCATTGTCCAGTCTATCA
TTCATATCCGGACCCGCTGGGAACTGTCACAGCCCGACTCTATCCCCCAA
CACACCAAGATTCGGCCAAAAGATGTCCCTGGGACACTGCTCAATATCGC
ATTACTTAATTTAGGCAGTTCTGACCCGAGTTTACGGTCAGCTGCCTATA
ATCTTCTGTGTGCCTTAACTTGTACCTTTAATTTAAAAATCGAGGGCCAG
TTACTAGAGACATCAGGTTTATGTATCCCTGCCAACAACACCCTCTTTAT
TGTCTCTATTAGTAAGACACTGGCAGCCAATGAGCCACACCTCACGTTAG
AATTTTTGGAAGAGTGTATTTCTGGATTTAGCAAATCTAGTATTGAATTG
AAACACCTTTGTTTGGAATACATGACTCCATGGCTGTCAAATCTAGTTCG
TTTTTGCAAGCATAATGATGATGCCAAACGACAAAGAGTTACTGCTATTC
TTGACAAGCTGATAACAATGACCATCAATGAAAAACAGATGTACCCATCT
ATTCAAGCAAAAATATGGGGAAGCCTTGGGCAGATTACAGATCTGCTTGA
TGTTGTACTAGACAGTTTCATCAAAACCAGTGCAACAGGTGGCTTGGGAT
CAATAAAAGCTGAGGTGATGGCAGATACTGCTGTAGCTTTGGCTTCTGGA
AATGTGAAATTGGTTTCAAGCAAGGTTATTGGAAGGATGTGCAAAATAAT
TGACAAGACATGCTTATCTCCAACTCCTACTTTAGAACAACATCTTATGT
GGGATGATATTGCTATTTTAGCACGCTACATGCTGATGCTGTCCTTCAAC
AATTCCCTTGATGTGGCAGCTCATCTTCCCTACCTCTTCCACGTTGTTAC
TTTCTTAGTAGCCACAGGTCCGCTCTCCCTTAGAGCTTCCACACATGGAC
TGGTCATTAATATCATTCACTCTCTGTGTACTTGTTCACAGCTTCATTTT
AGTGAAGAGACCAAGCAAGTTTTGAGACTCAGTCTGACAGAGTTCTCATT
ACCCAAATTTTACTTGCTGTTTGGCATTAGCAAAGTCAAGTCAGCTGCTG
TCATTGCCTTCCGTTCCAGTTACCGGGACAGGTCATTCTCTCCTGGCTCC
TATGAGAGAGACTTTTGCTTTGACATCCTTGGAAACAGTCACAGAAGC
TTTGTTGGAGATCATGGAGGCATGCATGAGAGATATTCCAACGTGCAAGT
GGCTGGACCAGTGGACAGAACTAGCTCAAAGATTTGCATTCCAATATAAT
CCATCCCTGCAACCAAGAGCTCTTGTTGTCTTTGGGTGTATTAGCAAACG
AGTGTCTCATGGGCAGATAAAGCAGATAATCCGTATTCTTAGCAAGGCAC
TTGAGAGTTGCTTAAAAGGACCTGACACTTACAACAGTCAAGTTCTGATA
GAAGCTACAGTAATAGCACTAACCAAATTACAGCCACTTCTTAATAAGGA
CTCGCCTCTGCACAAAGCCCTCTTTTGGGTAGCTGTGGCTGTGCTGCAGC
TTGATGAGGTCAACTTGTATTCAGCAGGTACCGCACTTCTTGAACAAAAC
CTGCATACTTTAGATAGTCTCCGTATATTCAATGACAAGAGTCCAGAGGA
AGTATTTATGGCAATCCGGAATCCTCTGGAGTGGCACTGCAAGCAAATGG
```

-continued

```
ATCATTTTGTTGGACTCAATTTCAACTCTAACTTTAACTTTGCATTGGTT
GGACACCTTTTAAAAGGGTACAGGCATCCTTCACCTGCTATTGTTGCAAG
AACAGTCAGAATTTTACATACACTACTAACTCTGGTTAACAAACACAGAA
ATTGTGACAAATTTGAAGTGAATACACAGAGCGTGGCCTACTTAGCAGCT
TTACTTACAGTGTCTGAAGAAGTTCGAAGTCGCTGCAGCCTAAAACATAG
AAAGTCACTTCTTCTTACTGATATTTCAATGGAAAATGTTCCTATGGATA
CATATCCCATTCATCATGGTGACCCTTCCTATAGGACACTAAAGGAGACT
CAGCCATGGTCCTCTCCCAAAGGTTCTGAAGGATACCTTGCAGCCACCTA
TCCAACTGTCGGCCAGACCAGTCCCCGAGCCAGGAAATCCATGAGCCTGG
ACATGGGGCAACCTTCTCAGGCCAACACTAAGAAGTTGCTTGGAACAAGG
AAAAGTTTTGATCACTTGATATCAGACACAAAGGCTCCTAAAAGGCAAGA
AATGGAATCAGGGATCACAACACCCCCAAAATGAGGAGAGTAGCAGAAA
CTGATTATGAAATGGAAACTCAGAGGATTTCCTCATCACAACAGCACCCA
CATTTACGTAAAGTTTCAGTGTCTGAATCAAATGTTCTCTTGGATGAAGA
AGTACTTACTGATCCGAAGATCCAGGCGCTGCTTCTTACTGTTCTAGCTA
CACTGGTAAAATATACCACAGATGAGTTTGATCAACGAATTCTTTATGAA
TACTTAGCAGAGGCCAGTGTTGTGTTTCCCAAAGTCTTTCCTGTTGTGCA
TAATTTGTTGGACTCTAAGATCAACACCCTGTTATCATTGTGCCAAGATC
CAAATTTGTTAAATCCAATCCATGGAATTGTGCAGAGTGTGGTGTACCAT
GAAGAATCCCCACCACAATACCAAACATCTTACCTGCAAAGTTTTGGTTT
TAATGGCTTGTGGCGGTTTGCAGGACCGTTTTCAAAGCAAACACAAATTC
CAGACTATGCTGAGCTTATTGTTAAGTTTCTTGATGCCTTGATTGACACG
TACCTGCCTGGAATTGATGAAGAAACCAGTGAAGAATCCCTCCTGACTCC
CACATCTCCTTACCCTCCTGCACTGCAGAGCCAGCTTAGTATCACTGCCA
ACCTTAACCTTTCTAATTCCATGACCTCACTTGCAACTTCCCAGCATTCC
CCAGGAATCGACAAGGAGAACGTTGAACTCTCCCCTACCACTGGCCACTG
TAACAGTGGACGAACTCGCCACGGATCCGCAAGCCAAGTGCAGAAGCAAA
GAAGCGCTGGCAGTTTCAAACGTAATAGCATTAAGAAGATCGTG
```

A nucleotide sequence encoding the second portion of the NF1 protein with a HA tag is set forth in SEQ ID NO: 27:

```
GTGGTTAGCCAGCGTTTCCCTCAGAACAGCATCGGTGCAGTAGGAAGTGC
CATGTTCCTCAGATTTATCAATCCTGCCATTGTCTCACCGTATGAAGCAG
GGATTTTAGATAAAAAGCCACCACCTAGAATCGAAAGGGGCTTGAAGTTA
ATGTCAAAGATACTTCAGAGTATTGCCAATCATGTTCTCTTCACAAAAGA
AGAACATATGCGGCCTTTCAATGATTTTGTGAAAAGCAACTTTGATGCAG
CACGCAGGTTTTTCCTTGATATAGCATCTGATTGTCCTACAAGTGATGCA
GTAAATCATAGTCTTTCCTTCATAAGTGACGGCAATGTGCTTGCTTTACA
TCGTCTACTCTGGAACAATCAGGAGAAAATTGGGCAGTATCTTTCCAGCA
ACAGGGATCATAAAGCTGTTGGAAGACGACCTTTTGATAAGATGGCAACA
CTTCTTGCATACCTGGGTCCTCCAGAGCACAAACCTGTGGCAGATACACA
```

-continued

CTGGTCCAGCCTTAACCTTACCAGTTCAAAGTTTGAGGAATTTATGACTA

GGCATCAGGTACATGAAAAAGAAGAATTCAAGGCTTTGAAAACGTTAAGT

ATTTTCTACCAAGCTGGGACTTCCAAAGCTGGGAATCCTATTTTTTATTA

TGTTGCACGGAGGTTCAAAACTGGTCAAATCAATGGTGATTTGCTGATAT

ACCATGTCTTACTGACTTTAAAGCCATATTATGCAAAGCCATATGAAATT

GTAGTGGACCTTACCCATACCGGGCCTAGCAATCGCTTTAAAACAGACTT

TCTCTCTAAGTGGTTTGTTGTTTTTCCTGGCTTTGCTTACGACAACGTCT

CCGCAGTCTATATCTATAACTGTAACTCCTGGGTCAGGGAGTACACCAAG

TATCATGAGCGGCTGCTGACTGGCCTCAAAGGTAGCAAAAGGCTTGTTTT

CATAGACTGTCCTGGGAAACTGGCTGAGCACATAGAGCATGAACAACAGA

AACTACCTGCTGCCACCTTGGCTTTAGAAGAGGACCTGAAGGTATTCCAC

AATGCTCTCAAGCTAGCTCACAAAGACACCAAAGTTTCTATTAAAGTTGG

TTCTACTGCTGTCCAAGTAACTTCAGCAGAGCGAACAAAAGTCCTAGGGC

AATCAGTCTTTCTAAATGACATTTATTATGCTTCGGAAATTGAAGAAATC

TGCCTAGTAGATGAGAACCAGTTCACCTTAACCATTGCAAACCAGGGCAC

GCCGCTCACCTTCATGCACCAGGAGTGTGAAGCCATTGTCCAGTCTATCA

TTCATATCCGGACCCGCTGGGAACTGTCACAGCCCGACTCTATCCCCCAA

CACACCAAGATTCGGCCAAAAGATGTCCCTGGGACACTGCTCAATATCGC

ATTACTTAATTTAGGCAGTTCTGACCCGAGTTTACGGTCAGCTGCCTATA

ATCTTCTGTGTGCCTTAACTTGTACCTTTAATTTAAAAATCGAGGGCCAG

TTACTAGAGACATCAGGTTTATGTATCCCTGCCAACAACACCCTCTTTAT

TGTCTCTATTAGTAAGACACTGGCAGCCAATGAGCCACACCTCACGTTAG

AATTTTTGGAAGAGTGTATTTCTGGATTTAGCAAATCTAGTATTGAATTG

AAACACCTTTGTTTGGAATACATGACTCCATGGCTGTCAAATCTAGTTCG

TTTTTGCAAGCATAATGATGATGCCAAACGACAAAGAGTTACTGCTATTC

TTGACAAGCTGATAACAATGACCATCAATGAAAAACAGATGTACCCATCT

ATTCAAGCAAAAATATGGGAAGCCTTGGGCAGATTACAGATCTGCTTGA

TGTTGTACTAGACAGTTTCATCAAAACCAGTGCAACAGGTGGCTTGGGAT

CAATAAAAGCTGAGGTGATGGCAGATACTGCTGTAGCTTTGGCTTCTGGA

AATGTGAAATTGGTTTCAAGCAAGGTTATTGGAAGGATGTGCAAAATAAT

TGACAAGACATGCTTATCTCCAACTCCTACTTTAGAACAACATCTTATGT

GGGATGATATTGCTATTTTAGCACGCTACATGCTGATGCTGTCCTTCAAC

AATTCCCTTGATGTGGCAGCTCATCTTCCCTACCTCTTCCACGTTGTTAC

TTTCTTAGTAGCCACAGGTCCGCTCTCCCTTAGAGCTTCCACACATGGAC

TGGTCATTAATATCATTCACTCTCTGTGTACTTGTTCACAGCTTCATTTT

AGTGAAGAGACCAAGCAAGTTTTGAGACTCAGTCTGACAGAGTTCTCATT

ACCCAAATTTTACTTGCTGTTTGGCATTAGCAAAGTCAAGTCAGCTGCTG

TCATTGCCTTCCGTTCCAGTTACCGGGACAGGTCATTCTCTCCTGGCTCC

TATGAGAGAGAGACTTTTGCTTTGACATCCTTGGAAACAGTCACAGAAGC

TTTGTTGGAGATCATGGAGGCATGCATGAGAGATATTCCAACGTGCAAGT

GGCTGGACCAGTGGACAGAACTAGCTCAAAGATTTGCATTCCAATATAAT

CCATCCCTGCAACCAAGAGCTCTTGTTGTCTTTGGGTGTATTAGCAAACG

AGTGTCTCATGGGCAGATAAAGCAGATAATCCGTATTCTTAGCAAGGCAC

TTGAGAGTTGCTTAAAAGGACCTGACACTTACAACAGTCAAGTTCTGATA

GAAGCTACAGTAATAGCACTAACCAAATTACAGCCACTTCTTAATAAGGA

CTCGCCTCTGCACAAAGCCCTCTTTTGGGTAGCTGTGGCTGTGCTGCAGC

TTGATGAGGTCAACTTGTATTCAGCAGGTACCGCACTTCTTGAACAAAAC

CTGCATACTTTAGATAGTCTCCGTATATTCAATGACAAGAGTCCAGAGGA

AGTATTTATGGCAATCCGGAATCCTCTGGAGTGGCACTGCAAGCAAATGG

ATCATTTTGTTGGACTCAATTTCAACTCTAACTTTAACTTTGCATTGGTT

GGACACCTTTTAAAAGGGTACAGGCATCCTTCACCTGCTATTGTTGCAAG

AACAGTCAGAATTTTACATACACTACTAACTCTGGTTAACAAACACAGAA

ATTGTGACAAATTTGAAGTGAATACACAGAGCGTGGCCTACTTAGCAGCT

TTACTTACAGTGTCTGAAGAAGTTCGAAGTCGCTGCAGCCTAAAACATAG

AAAGTCACTTCTTCTTACTGATATTTCAATGGAAAATGTTCCTATGGATA

CATATCCCATTCATCATGGTGACCCTTCCTATAGGACACTAAAGGAGACT

CAGCCATGGTCCTCTCCCAAAGGTTCTGAAGGATACCTTGCAGCCACCTA

TCCAACTGTCGGCCAGACCAGTCCCCGAGCCAGGAAATCCATGAGCCTGG

ACATGGGGCAACCTTCTCAGGCCAACACTAAGAAGTTGCTTGGAACAAGG

AAAAGTTTTGATCACTTGATATCAGACACAAAGGCTCCTAAAAGGCAAGA

AATGGAATCAGGGATCACAACACCCCCAAAATGAGGAGAGTAGCAGAAA

CTGATTATGAAATGGAAACTCAGAGGATTTCCTCATCACAACAGCACCCA

CATTTACGTAAAGTTTCAGTGTCTGAATCAAATGTTCTCTTGGATGAAGA

AGTACTTACTGATCCGAAGATCCAGGCGCTGCTTCTTACTGTTCTAGCTA

CACTGGTAAAATATACCACAGATGAGTTTGATCAACGAATTCTTTATGAA

TACTTAGCAGAGGCCAGTGTTGTGTTTCCCAAAGTCTTTCCTGTTGTGCA

TAATTTGTTGGACTCTAAGATCAACACCCTGTTATCATTGTGCCAAGATC

CAAATTTGTTAAATCCAATCCATGGAATTGTGCAGAGTGTGGTGTACCAT

GAAGAATCCCCACCACAATACCAAACATCTTACCTGCAAAGTTTTGGTTT

TAATGGCTTGTGGCGGTTTGCAGGACCGTTTTCAAAGCAAACACAAATTC

CAGACTATGCTGAGCTTATTGTTAAGTTTCTTGATGCCTTGATTGACACG

TACCTGCCTGGAATTGATGAAGAAACCAGTGAAGAATCCCTCCTGACTCC

CACATCTCCTTACCCTCCTGCACTGCAGAGCCAGCTTAGTATCACTGCCA

ACCTTAACCTTTCTAATTCCATGACCTCACTTGCAACTTCCCAGCATTCC

CCAGGAATCGACAAGGAGAACGTTGAACTCTCCCCTACCACTGGCCACTG

TAACAGTGGACGAACTCGCCACGGATCCGCAAGCCAAGTGCAGAAGCAAA

GAAGCGCTGGCAGTTTCAAACGTAATAGCATTAAGAAGATCGTGTATCCG

TATGATGTGCCGGATTATGCGT

In some embodiments, the 3' isolated nucleic acid further comprises a polyadenylation signal positioned between the nucleotide sequence encoding a second portion of NF1 protein and the 3' ITR. Any of the polyadenylation signal described herein can be used in the 3' isolated nucleic. In some embodiments, the polyadenylation signal is an SV40 polyadenylation signal.

In some embodiments, the 3' isolated nucleic acid further comprises a nucleotide sequence encoding a polypeptide tag. Non-limiting examples of a polypeptide tag includes a human influenza hemagglutinin (HA) tag, a FLAG tag, a Myc tag, a Maltose-binding protein (MBP) tag, a Calmodulin Binding Protein (CBP) tag, Poly-Histidine tag (His) tag, or a Glutathione-S transferase (GST) tag. In some embodiments, the polypeptide tag is a HA tag. In some embodiments, the HA tag is position at the C-terminal of the protein it is attached to (e.g., the second portion of the full-length NF1 protein). In some embodiments, the 3' isolated nucleic acid does not comprise a nucleotide sequence encoding a polypeptide tag.

In some embodiments, the 5' isolated nucleic acid further comprises nucleotide sequence encoding a splice donor located of an intron between the nucleotide sequence encoding the first portion of a protein (e.g., NF1 protein) and the 3' ITR. In addition, the 3' isolated nucleic acid comprises a nucleotide sequence encoding a splice acceptor of an intron between the 5' ITR and the nucleotide sequence encoding the second portion of a protein (e.g., NF1 protein). In some embodiments, the splice donor in the 5' isolated nucleic acid and the splice acceptor in the 3' isolated nucleic acid are derived from the same intron. Any intronic splice donor/ splice acceptor sequence can be used in the 5' and 5' isolated nucleic acid described herein. In some embodiments, the intron is a human dysferlin intron.

In some embodiments, the nucleotide sequence encoding the splicing donor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 18. An exemplary nucleotide sequence of a splicing donor is set forth in SEQ ID NO: 18.

GTGGGCAGCATGTGGAACCTGGCGAGCCCCATCCCCGGCAAGCTCTCAAG

CCATGCTGGTGGGGACGACTGAATGCCAGGGCCCTTCACTGGGCTATTTC

ACCCAGGGACGCTTCTTGAAGGCACCCCCCACTCCAAGCTCAATTGAA

In some embodiments, the nucleotide sequence encoding the splicing acceptor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 19. An exemplary nucleotide sequence of a splicing donor is set forth in SEQ ID NO: 19.

GCAAATTAGGACCGAGAGTCAGTGGCCGCTCAAGAGTCTGTGACCATGCC

CCAAATTCAGAGATGGTCCCAGGAGAGATGGGGGGAACTGCCAAGCAATG

AGTGACCGGTTCCCCCTCCCCCAG

As disclosed herein, "identity" of sequences refers to the measurement or calculation of the percent of identical matches between two or more sequences with gap alignments addressed by a mathematical model, algorithm, or computer program that is known to one of ordinary skill in the art. The percent identity of two sequences (e.g., nucleic acid or amino acid sequences) may, for example, be determined using Basic Local Alignment Search Tool (BLAST®) such as NBLAST® and XBLAST® programs (version 2.0). Alignment technique such as Clustal Omega may be used for multiple sequence alignments. Other algorithms or alignment methods may include but are not limited to the Smith-Waterman algorithm, the Needleman-Wunsch algorithm, or Fast Optimal Global Sequence Alignment Algorithm (FOGSAA).

In some embodiments, the present disclosure provides a 5' isolated nucleic acid encoding a first portion of a protein (e.g., NF1 protein) and a 3' isolated nucleic acid encoding a second portion of a protein (e.g., NF1 protein) in a way (e.g., delivered to the same target cell by a 5' rAAV comprising the 5' isolated nucleic acid and an 3' rAAV comprising the 3' isolated nucleic acid) that the two isolated nucleic acids form a full length (e.g., NF1 protein) mRNA in a target cell after transcription and trans-splicing. Once the 5' isolated nucleic acid and the 3' isolated nucleic acid are delivered to a target cell (e.g., by rAAVs), the two isolated nucleic acid would go through head to tail concatemerization from 3' ITR of the 5' isolated nucleic acid and 5' ITR of the 3' isolated nucleic acid such that the two isolated nucleic acids are combined in one single AAV genome. After transcription, the mRNA comprises the NF1 first portion mRNA, splicing sites including the splicing donor, concactemerized ITR, and splicing acceptor, and NF1 second portion mRNA. Trans-splicing, as used herein, refers to a special form of RNA processing where exons from two different primary RNA transcripts are joined end to end and ligated. It is usually found in eukaryotes and mediated by the spliceosome. In eukaryotic cells, mRNA splicing occurs at intronic sites. A splice donor (e.g., 5' end of the intron) and a splice acceptor (e.g., 3' end of the intron) are required for splicing. Accordingly, as part of the RNA splicing mechanism, the spliceosome in the cell will then splice out the splicing sites, thereby stitching the NF1 first portion mRNA and NF1 second portion mRNA to form a complete mRNA encoding a full-length NF1.

An isolated nucleic acid sequence described herein (e.g., the isolated nucleic acid comprising a transgene which encodes a mini-NF1 protein or the 5' isolated nucleic acid in the dual AAV vector system) may further comprise a promoter operably linked to the coding sequences (e.g., NF1 minigenes, or the nucleotide sequence encoding the first portion of the NF1 protein). A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. A promoter may be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter comprises a chicken beta-actin (CBA) promoter. In some embodiments, a promoter is an enhanced chicken β-actin promoter. In some embodiments, a promoter is a U6 promoter. In some embodiments, a promoter is a chicken beta-actin (CBA) promoter. In some embodiments, the promoter is a minimal promoter. In some embodiments, the promoter is a mini-CMV promoter. In some embodiments, the promoter is a jet promoter. In some embodiments, the promoter is a short Mecp2 promoter. In some embodiments, the transgene encoding the mini-NF1 proteins comprises a CBA promoter. In some embodiments, the 5' isolated nucleic acid described herein comprises a short Mecp2 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is a neuron-specific promoter.

In some embodiments, a promoter is a RNA polymerase III (pol III) promoter. Non-limiting examples of pol III promoters include U6 and H1 promoter sequences. In some embodiments, a promoter is a RNA polymerase II (pol II) promoter. Non-limiting examples of pol II promoters include T7, T3, SP6, RSV, and cytomegalovirus promoter sequences.

Aspects of the disclosure relate to gene therapy vectors comprising an isolated nucleic acid as described herein. A gene therapy vector may be a viral vector (e.g., a lentiviral vector, an adeno-associated virus vector, an adenoviral (Ad) vector, etc.), a plasmid, a closed-ended DNA (e.g., ceDNA), a lipid/DNA nanoparticle, etc. In some embodiments, a gene therapy vector is a viral vector. In some embodiments, a transgene (e.g., a minigene) encoding a mini protein (e.g., mini-NF1 protein) is flanked by one or more viral replication sequences, for example lentiviral long terminal repeats (LTRs) or adeno-associated virus (AAV) inverted terminal repeats (ITRs). In some embodiments, a viral vector is a Baculovirus vector. In some embodiments, the 5' isolated nucleic acid and the 3' isolated nucleic acid for expressing full-length NF1 protein are flanked by one or more viral replication sequences, for example lentiviral long terminal repeats (LTRs) or adeno-associated virus (AAV) inverted terminal repeats (ITRs). In some embodiments, a viral vector is a Baculovirus vector.

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The isolated nucleic acids may comprise, as disclosed elsewhere herein, one or more regions that encode one or more proteins (e.g., mini-NF1 protein, or a portion of NF1 protein). The isolated nucleic acids may also comprise a region encoding, for example, a miRNA binding site, and/or an expression control sequence (e.g., a poly-A tail).

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second AAV ITR is an AAV2 ITR. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR, or ΔITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

An isolated nucleic acid described herein may also contain an intron, desirably located between the promoter/enhancer sequence and the transgene. In some embodiments, an intron is a synthetic or artificial (e.g., heterologous) intron. Examples of synthetic introns include an intron sequence derived from SV-40 (referred to as the SV-40 T intron sequence) and intron sequences derived from chicken beta-actin gene. In some embodiments, a transgene described by the disclosure comprises one or more (1, 2, 3, 4, 5, or more) artificial introns. In some embodiments, the one or more artificial introns are positioned between a promoter and a nucleotide sequence encoding a transgene.

In some embodiments, the rAAV vector described herein comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE).

In some embodiments, the vector further comprises conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

A polyadenylation sequence generally is inserted following the coding sequences and optionally before a 3' AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional, and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989].

In some embodiments, the rAAV vector encoding the mini-NF1 proteins comprises a nucleic acid as set forth in SEQ ID NOs: 7-9 or 28-30.

An exemplary AAV vector sequence encoding a mini-NF1 having an NF1 GRD is set forth in SEQ ID NO: 7:

```
CCTGCAGGCAGCTGCGCGCTCGCTCGCTCACTGAGGCCGCCCGGGCAAAG
CCCGGGCGTCGGGCGACCTTTGGTCGCCCGGCCTCAGTGAGCGAGCGAGC
GCGCAGAGAGGGAGTGGCCAACTCCATCACTAGGGGTTCCTGCGGCCAGA
TCTTCAATATTGGCCATTAGCCATATTATTCATTGGTTATATAGCATAAA
TCAATATTGGCTATTGGCCATTGCATACGTTGTATCTATATCATAATATG
TACATTTATATTGGCTCATGTCCAATATGACCGCCATGTTGGCATTGATT
ATTGACTAGTTATTAATAGTAATCAATTACGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGAGTATT
TACGGTAAACTGCCCACTTGGCAGTACATCAAGTGTATCATATGCCAAGT
CCGCCCCCTATTGACGTCAATGACGGTAAATGGCCCGCCTGGCATTATGC
CCAGTACATGACCTTACGGGACTTTCCTACTTGGCAGTACATCTACGTAT
TAGTCATCGCTATTACCATGGTCGAGGTGAGCCCCACGTTCTGCTTCACT
CTCCCCATCTCCCCCCCCTCCCCACCCCCAATTTTGTATTTATTTATTTT
TTAATTATTTTGTGCAGCGATGGGGCGGGGGGGGGGGGGGGCGCGCGC
CAGGCGGGGCGGGGCGGGGCGAGGGGCGGGGCGGGGCGAGGCGGAGAGGT
GCGGCGGCAGCCAATCAGAGCGGCGCGCTCCGAAAGTTTCCTTTTATGGC
GAGGCGGCGGCGGCGGCGGCCCTATAAAAAGCGAAGCGCGCGGCGGGCGG
GAGTCGCTGCGCGCTGCCTTCGCCCCGTGCCCCGCTCCGCCGCCGCCTCG
CGCCGCCCGCCCCGGCTCTGACTGACCGCGTTACTCCCACAGGTGAGCGG
GCGGGACGGCCCTTCTCCTCCGGGCTGTAATTAGCGCTTGGTTTAATGAC
GGCTTGTTTCTTTTCTGTGGCTGCGTGAAAGCCTTGAGGGGCTCCGGGAG
GGCCCTTTGTGCGGGGGGAGCGGCTCGGGGGGTGCGTGCGTGTGTGTGTG
CGTGGGGAGCGCCGCGTGCGGCTCCGCGCTGCCCGGCGGCTGTGAGCGCT
GCGGGCGCGGCGCGGGGCTTTGTGCGCTCCGCAGTGTGCGCGAGGGGAGC
GCGGCCGGGGCGGTGCCCCGCGGTGCGGGGGGGCTGCGAGGGGAACAA
AGGCTGCGTGCGGGGTGTGTGCGTGGGGGGGTGAGCAGGGGGTGTGGGCG
CGTCGGTCGGGCTGCAACCCCCCCTGCACCCCCCTCCCCGAGTTGCTGAG
CACGGCCCGGCTTCGGGTGCGGGGCTCCGTACGGGGCGTGGCGCGGGGCT
CGCCGTGCCGGGCGGGGGGTGGCGGCAGGTGGGGGTGCCGGGCGGGGCGG
GGCCGCCTCGGGCCGGGAGGGCTCGGGGAGGGGCGCGGCGGCCCCGG
AGCGCCGGCGGCTGTCGAGGCGCGGCGAGCCGCAGCCATTGCCTTTTATG
GTAATCGTGCGAGAGGGCGCAGGGACTTCCTTTGTCCCAAATCTGTGCGG
AGCCGAAATCTGGGAGGCGCCGCCGCACCCCCTCTAGCGGGCGCGGGGCG
AAGCGGTGCGGCGCCGGCAGGAAGGAAATGGGCGGGAGGGCCTTCGTGC
GTCGCCGCGCCGCCGTCCCCTTCTCCCTCTCCAGCCTCGGGGCTGTCCGC
GGGGGGACGGCTGCCTTCGGGGGGACGGGGCAGGGCGGGGTTCGGCTTC
TGGCGTGTGACCGGCGGCTCTAGAGCCTCTGCTAACCATGTTCATGCCTT
```

CTTCTTTTTCCTACAGCTCCTGGGCAACGTGCTGGTTATTGTGCTGTCTC

ATCATTTTGGCAAAGAATTCGATATCAAGCTTGCCACCATGGAAGCCAAG

AGCCAGCTGTTTCTGAAATACTTTACCCTGTTTATGAATCTGCTGAACGA

CTGTAGTGAGGTGGAGGACGAGAGTGCCCAGACCGGCGGCAGGAAGAGAG

GCATGTCTAGGAGACTGGCCAGCCTGAGGCACTGCACAGTGCTGGCCATG

TCCAACCTGCTGAACGCCAATGTGGACTCCGGCCTGATGCACTCTATCGG

CCTGGGCTACCACAAGGATCTGCAGACCCGCGCCACATTCATGGAGGTGC

TGACCAAGATCCTGCAGCAGGGCACCGAGTTTGACACACTGGCCGAGACC

GTGCTGGCAGATAGGTTCGAGCGCCTGGTGGAGCTGGTGACAATGATGGG

CGACCAGGGAGAGCTGCCTATCGCAATGGCACTGGCCAACGTGGTGCCAT

GCAGCCAGTGGGACGAGCTGGCCAGGGTGCTGGTGACCCTGTTTGATTCC

AGACACCTGCTGTACCAGCTGCTGTGGAACATGTTCTCTAAGGAGGTGGA

GCTGGCCGACAGCATGCAGACACTGTTTAGGGGCAATTCCCTGGCCTCTA

AGATCATGACCTTCTGTTTTAAGGTGTACGGCGCCACATATCTGCAGAAG

CTGCTGGATCCACTGCTGAGAATCGTGATCACCAGCTCCGACTGGCAGCA

CGTGTCCTTCGAGGTGGATCCTACACGGCTGGAGCCAAGCGAGTCCCTGG

AGGAGAACCAGCGCAATCTGCTGCAGATGACCGAGAAGTTCTTTCACGCC

ATCATCTCTAGCTCCTCTGAGTTTCCCCCTCAGCTGCGGTCCGTGTGCCA

CTGTCTGTACCAGGCCACCTGCCACTCTCTGCTGAACAAGGCCACAGTGA

AGGAGAAGAAGGAGAATAAGAAGAGCGTGGTGTCCCAGAGGTTCCCACAG

AACAGCATCGGAGCAGTGGGATCCGCCATGTTCCTGAGGTTCATCAATCC

CGCCATCGTGAGCCCTTATGAGGCCGGCATCCTGGACAAGAAGCCACCCC

CTAGGATCGAGAGAGGCCTGAAGCTGATGAGCAAGATCCTGCAGTCCATC

GCCAACCACGTGCTGTTCACCAAGGAGGAGCACATGCGCCCCTTCAACGA

CTTTGTGAAGTCTAATTTTGATGCCGCCCGGCGCTTCTTTCTGGACATCG

CCTCTGATTGTCCTACAAGCGACGCCGTGAACCACTCTCTGAGCTTCATC

AGCGATGGCAATGTGCTGGCCCTGCACCGGCTGCTGTGGAACAATCAGGA

GAAGATCGGCCAGTACCTGAGCTCCAACAGGGACCACAAGGCAGTGGGCA

GGAGACCTTTTGATAAGATGGCCACCCTGCTGGCATATCTGGGACCACCA

GAGCACAAGCCAGTGGCAGACACCCACTGGTCTAGCCTGAATCTGACATC

CTCTAAGTTCGAGGAGTTTATGACCCGGCACCAGGTGCACGAGAAGGAGG

AGTTTAAGGCCCTGAAGACCCTGGATGACTCGAGTTTTTTTTGCGGCCG

CTTCGAGCAGACATGATAAGATACATTGATGAGTTTGGACAAACCACAAC

TAGAATGCAGTGAAAAAAATGCTTTATTTGTGAAATTTGTGATGCTATTG

CTTTATTTGTAACCATTATAAGCTGCAATAAACAAGTTAACAACAACAAT

TGCATTCATTTTATGTTTCAGGTTCAGGGGGAGATGTGGGAGGTTTTTTA

AAGCAAGTAAAACCTCTACAAATGTGGTAAAATCGATAGGCCGCAGGAAC

CCCTAGTGATGGAGTTGGCCACTCCCTCTCTGCGCGCTCGCTCGCTCACT

GAGGCCGGGCGACCAAAGGTCGCCCGACGCCCGGGCGGCCTCAGTGAGCG

AGCGAGCGCGCAGCTGCCTGCAGGACATGTGAGCAAAAGGCCAGCAAAAG

GCCAGGAACCGTAAAAAGGCCGCGTTGCTGGCGTTTTTCCATAGGCTCCG

CCCCCCTGACGAGCATCACAAAAATCGACGCTCAAGTCAGAGGTGGCGAA

ACCCGACAGGACTATAAAGATACCAGGCGTTTCCCCCTGGAAGCTCCCTC

GTGCGCTCTCCTGTTCCGACCCTGCCGCTTACCGGATACCTGTCCGCCTT

TCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTC

CAACCCGGTAAGACACGACTTATCGCCACTGGCAGCAGCCACTGGTAACA

GGATTAGCAGAGCGAGGTATGTAGGCGGTGCTACAGAGTTCTTGAAGTGG

TGGCCTAACTACGGCTACACTAGAAGAACAGTATTTGGTATCTGCGCTCT

GCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATT

ACGCGCAGAAAAAAAGGATCTCAAGAAGATCCTTTGATCTTTTCTACGGG

GTCTGACGCTCAGTGGAACGAAAACTCACGTTAAGGGATTTTGGTCATGA

GATTATCAAAAAGGATCTTCACCTAGATCCTTTTAAATTAAAAATGAAGT

TTTAAATCAATCTAAAGTATATATGAGTAAACTTGGTCTGACAGTTACCA

ATGCTTAATCAGTGAGGCACCTATCTCAGCGATCTGTCTATTTCGTTCAT

CCATAGTTGCCTGACTCCCCGTCGTGTAGATAACTACGATACGGGAGGGC

TTACCATCTGGCCCCAGTGCTGCAATGATACCGCGAGACCCACGCTCACC

GGCTCCAGATTTATCAGCAATAAACCAGCCAGCCGGAAGGGCCGAGCGCA

GAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGT

TGCCATTGCTACAGGCATCGTGGTGTCACGCTCGTCGTTTGGTATGGCTT

CATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATT

CTCTTACTGTCATGCCATCCGTAAGATGCTTTTCTGTGACTGGTGAGTAC

TCAACCAAGTCATTCTGAGAATAGTGTATGCGGCGACCGAGTTGCTCTTG

CCCGGCGTCAATACGGGATAATACCGCGCCACATAGCAGAACTTTAAAAG

TGCTCATCATTGGAAAACGTTCTTCGGGGCGAAAACTCTCAAGGATCTTA

CCGCTGTTGAGATCCAGTTCGATGTAACCCACTCGTGCACCCAACTGATC

TTCAGCATCTTTTACTTTCACCAGCGTTTCTGGGTGAGCAAAAACAGGAA

GGCAAAATGCCGCAAAAAAGGGAATAAGGGCGACACGGAAATGTTGAATA

CTCATACTCTTCCTTTTTCAATATTATTGAAGCATTTATCAGGGTTATTG

TCTCATGAGCGGATACATATTTGAATGTATTTAGAAAAATAAACAAATAG

GGGTTCCGCGCACATTTCCCCGAAAAGTGCCACCTGACGTCTAAGAAACC

ATTATTATCATGACATTAACCTATAAAAATAGGCGTATCACGAGGCCCTT

TCGTCTCGCGCGTTTCGGTGATGACGGTGAAAACCTCTGACACATGCAGC

TCCCGGAGACGGTCACAGCTTGTCTGTAAGCGGATGCCGGGAGCAGACAA

GCCCGTCAGGGCGCGTCAGCGGGTGTTGGCGGGTGTCGGGGCTGGCTTAA

CTATGCGGCATCAGAGCAGATTGTACTGAGAGTGCACCATAAAATTGTAA

```
ACGTTAATATTTTGTTAAAATTCGCGTTAAATTTTTGTTAAATCAGCTCA

TTTTTTAACCAATAGGCCGAAATCGGCAAAATCCCTTATAAATCAAAAGA

ATAGCCCGAGATAGGGTTGAGTGTTGTTCCAGTTTGGAACAAGAGTCCAC

TATTAAAGAACGTGGACTCCAACGTCAAAGGGCGAAAAACCGTCTATCAG

GGCGATGGCCCACTACGTGAACCATCACCCAAATCAAGTTTTTTGGGGTC

GAGGTGCCGTAAAGCACTAAATCGGAACCCTAAAGGGAGCCCCCGATTTA

GAGCTTGACGGGGAAAGCCGGCGAACGTGGCGAGAAAGGAAGGGAAGAAA

GCGAAAGGAGCGGGCGCTAAGGCGCTGGCAAGTGTAGCGGTCACGCTGCG

CGTAACCACCACACCCGCCGCGCTTAATGCGCCGCTACAGGGCGCGTACT

ATGGTTGCTTTGACGTATGCGGTGTGAAATACCGCACAGATGCGTAAGGA

GAAAATACCGCATCAGGCGCC
```

An exemplary AAV vector sequence encoding a mini-NF1 having an NF1 GRD, and the CRAL-TRIO domain is set forth in SEQ ID NO: 8:

```
CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTAATTATTTTGTGCAGC

GATGGGGGCGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGTGCGTGCGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGCTGCGAGGG

GAACAAAGGCTGCGTGCGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA
```

-continued

```
AGAGCCAGCTGTTTCTGAAATACTTTACCCTGTTTATGAATCTGCTGAACGACTGTAGTGAGGT
GGAGGACGAGAGTGCCCAGACCGGCGGCAGGAAGAGAGGCATGTCTAGGAGACTGGCCAGCCTG
AGGCACTGCACAGTGCTGGCCATGTCCAACCTGCTGAACGCCAATGTGGACTCCGGCCTGATGC
ACTCTATCGGCCTGGGCTACCACAAGGATCTGCAGACCCGCGCCACATTCATGGAGGTGCTGAC
CAAGATCCTGCAGCAGGGCACCGAGTTTGACACACTGGCCGAGACCGTGCTGGCAGATAGGTTC
GAGCGCCTGGTGGAGCTGGTGACAATGATGGGCGACCAGGGAGAGCTGCCTATCGCAATGGCAC
TGGCCAACGTGGTGCCATGCAGCCAGTGGGACGAGCTGGCCAGGGTGCTGGTGACCCTGTTTGA
TTCCAGACACCTGCTGTACCAGCTGCTGTGGAACATGTTCTCTAAGGAGGTGGAGCTGGCCGAC
AGCATGCAGACACTGTTTAGGGGCAATTCCCTGGCCTCTAAGATCATGACCTTCTGTTTTAAGG
TGTACGGCGCCACATATCTGCAGAAGCTGCTGGATCCACTGCTGAGAATCGTGATCACCAGCTC
CGACTGGCAGCACGTGTCCTTCGAGGTGGATCCTACACGGCTGGAGCCAAGCGAGTCCCTGGAG
GAGAACCAGCGCAATCTGCTGCAGATGACCGAGAAGTTCTTTCACGCCATCATCTCTAGCTCCT
CTGAGTTTCCCCCTCAGCTGCGGTCCGTGTGCCACTGTCTGTACCAGGCCACCTGCCACTCTCT
GCTGAACAAGGCCACAGTGAAGGAGAAGAAGGAGAATAAGAAGAGCGTGGTGTCCCAGAGGTTC
CCACAGAACAGCATCGGAGCAGTGGGATCCGCCATGTTCCTGAGGTTCATCAATCCCGCCATCG
TGAGCCCTTATGAGGCCGGCATCCTGGACAAGAAGCCACCCCCTAGGATCGAGAGAGGCCTGAA
GCTGATGAGCAAGATCCTGCAGTCCATCGCCAACCACGTGCTGTTCACCAAGGAGGAGCACATG
CGCCCCTTCAACGACTTTGTGAAGTCTAATTTTGATGCCGCCCGGCGCTTCTTTCTGGACATCG
CCTCTGATTGTCCTACAAGCGACGCCGTGAACCACTCTCTGAGCTTCATCAGCGATGGCAATGT
GCTGGCCCTGCACCGGCTGCTGTGGAACAATCAGGAGAAGATCGGCCAGTACCTGAGCTCCAAC
AGGGACCACAAGGCAGTGGGCAGGAGACCATTTGATAAGATGGCCACACTGCTGGCCTATCTGG
GACCACCAGAGCACAAGCCAGTGGCAGACACACACTGGTCTAGCCTGAATCTGACCTCCTCTAA
GTTCGAGGAGTTTATGACCCGGCACCAGGTGCACGAGAAGGAGGAGTTTAAGGCCCTGAAGACA
CTGTCTATCTTCTACCAGGCAGGCACCAGCAAGGCAGGAAACCCAATCTTTTACTATGTGGCCC
GGCGCTTCAAGACAGGCCAGATCAATGGCGATCTGCTGATCTACCACGTGCTGCTGACCCTGAA
GCCATACTATGCCAAGCCCTATGAGATCGTGGTGGACCTGACCCACACAGGCCCCTCCAACAGG
TTTAAGACCGATTTCCTGTCTAAGTGGTTCGTGGTGTTTCCTGGCTTCGCCTATGACAATGTGA
GCGCCGTGTACATCTATAACTGCAATTCCTGGGTGCGGGAGTACACAAAGTATCACGAGCGCCT
GCTGACCGGCCTGAAGGGATCCAAGAGACTGGTGTTCATCGATTGTCCCGGCAAGCTGGCCGAG
CACATTGAACACGAACAGCAGAAACTGCCCGCCGCAACCCTGGCCCTGGAAGAGGACCTGAAGG
ATGACTCGAGTTTTTTTTTGCGGCCGCTTCGAGCAGACATGATAAGATACATTGATGAGTTTGG
ACAAACCACAACTAGAATGCAGTGAAAAAAATGCTTTATTTGTGAAATTTGTGATGCTATTGCT
TTATTTGTAACCATTATAAGCTGCAATAAACAAGTTAACAACAACAATTGCATTCATTTTATGT
TTCAGGTTCAGGGGGAGATGTGGGAGGTTTTTTAAAGCAAGTAAAACCTCTACAAATGTGGTAA
AATCGATAGGCCGCAGGAACCCCTAGTGATGGAGTTGGCCACTCCCTCTCTGCGCGCTCGCTCG
CTCACTGAGGCCGGGCGACCAAAGGTCGCCCGACGCCCGGCGGCCTCAGTGAGCGAGCGAGCG
CGCAGCTGCCTGCAGGACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCCAA
```

```
GCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCTACAC
TAGAAGAACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGT
GCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGG
ATCTTACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAAAAGGG
AATAAGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACAAATAG
GGGTTCCGCGCACATTTCCCCGAAAAGTGCCACCTGACGTCTAAGAAACCATTATTATCATGAC
ATTAACCTATAAAAATAGGCGTATCACGAGGCCCTTTCGTCTCGCGCGTTTCGGTGATGACGGT
GAAAACCTCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTTAACTATGC
GGCATCAGAGCAGATTGTACTGAGAGTGCACCATAAAATTGTAAACGTTAATATTTTGTTAAAA
TTCGCGTTAAATTTTTGTTAAATCAGCTCATTTTTTAACCAATAGGCCGAAATCGGCAAAATCC
CTTATAAATCAAAAGAATAGCCCGAGATAGGGTTGAGTGTTGTTCCAGTTTGGAACAAGAGTCC
ACTATTAAAGAACGTGGACTCCAACGTCAAAGGGCGAAAAACCGTCTATCAGGGCGATGGCCCA
CTACGTGAACCATCACCCAAATCAAGTTTTTTGGGGTCGAGGTGCCGTAAAGCACTAAATCGGA
ACCCTAAAGGGAGCCCCCGATTTAGAGCTTGACGGGGAAAGCCGGCGAACGTGGCGAGAAAGGA
AGGGAAGAAAGCGAAAGGAGCGGGCGCTAAGGCGCTGGCAAGTGTAGCGGTCACGCTGCGCGTA
ACCACCACACCCGCCGCGCTTAATGCGCCGCTACAGGGCGCGTACTATGGTTGCTTTGACGTAT
GCGGTGTGAAATACCGCACAGATGCGTAAGGAGAAAATACCGCATCAGGCGCC
```

An exemplary AAV vector sequence encoding a mini-NF1 having an NF1 GRD, the CRAL-TRIO domain and the bipartite phospholipid binding domain is set forth in SEQ ID NO: 9:

CCTGCAGGCAGCTGCGCGCTCGCTCGCTCACTGAGGCCGCCCGGGCAAAG
CCCGGGCGTCGGGCGACCTTTGGTCGCCCGGCCTCAGTGAGCGAGCGAGC
GCGCAGAGAGGGAGTGGCCAACTCCATCACTAGGGGTTCCTGCGGCCAGA
TCTTCAATATTGGCCATTAGCCATATTATTCATTGGTTATATAGCATAAA
TCAATATTGGCTATTGGCCATTGCATACGTTGTATCTATATCATAATATG
TACATTTATATTGGCTCATGTCCAATATGACCGCCATGTTGGCATTGATT
ATTGACTAGTTATTAATAGTAATCAATTACGGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGAGTATT
TACGGTAAACTGCCCACTTGGCAGTACATCAAGTGTATCATATGCCAAGT
CCGCCCCCTATTGACGTCAATGACGGTAAATGGCCCGCCTGGCATTATGC
CCAGTACATGACCTTACGGGACTTTCCTACTTGGCAGTACATCTACGTAT
TAGTCATCGCTATTACCATGGTCGAGGTGAGCCCCACGTTCTGCTTCACT
CTCCCCATCTCCCCCCCCTCCCCACCCCCAATTTTGTATTTATTTATTTT
TTAATTATTTTGTGCAGCGATGGGGGCGGGGGGGGGGGGGGCGCGCGC
CAGGCGGGGCGGGGCGGGGCGAGGGGCGGGGCGGGGCGAGGCGGAGAGGT
GCGGCGGCAGCCAATCAGAGCGGCGCGCTCCGAAAGTTTCCTTTTATGGC
GAGGCGGCGGCGGCGGCGGCCCTATAAAAAGCGAAGCGCGCGGCGGGCGG
GAGTCGCTGCGCGCTGCCTTCGCCCCGTGCCCGCTCCGCCGCCGCTCG
CGCCGCCCGCCCCGGCTCTGACTGACCGCGTTACTCCCACAGGTGAGCGG
GCGGGACGGCCCTTCTCCTCCGGGCTGTAATTAGCGCTTGGTTTAATGAC
GGCTTGTTTCTTTTCTGTGGCTGCGTGAAAGCCTTGAGGGGCTCCGGGAG
GGCCCTTTGTGCGGGGGAGCGGCTCGGGGGGTGCGTGCGTGTGTGTGTG
CGTGGGAGCGCCGCGTGCGGCTCCGCGCTGCCCGGCGGCTGTGAGCGCT
GCGGGCGCGGCGCGGGCTTTGTGCGCTCCGCAGTGTGCGCGAGGGGAGC
GCGGCCGGGGCGGTGCCCCGCGGTGCGGGGGGGCTGCGAGGGGAACAA
AGGCTGCGTGCGGGTGTGTGCGTGGGGGGTGAGCAGGGGGTGTGGGCG
CGTCGGTCGGGCTGCAACCCCCCCTGCACCCCCCTCCCCGAGTTGCTGAG
CACGGCCCGGCTTCGGGTGCGGGGCTCCGTACGGGGCGTGGCGCGGGCT
CGCCGTGCCGGGCGGGGGTGGCGGCAGGTGGGGTGCCGGGCGGGGCGG
GGCCGCCTCGGGCCGGGGAGGGCTCGGGGGGAGGGGCGCGGCGGCCCCGG
AGCGCCGGCGGCTGTCGAGGCGCGGCGAGCCGCAGCCATTGCCTTTTATG
GTAATCGTGCGAGAGGGCGCAGGGACTTCCTTTGTCCCAAATCTGTGCGG
AGCCGAAATCTGGGAGGCGCCGCCGCACCCCCTCTAGCGGGCGCGGGGCG
AAGCGGTGCGGCGCCGGCAGGAAGGAAATGGGCGGGAGGGCCTTCGTGC
GTCGCCGCGCCGCCGTCCCCTTCTCCCTCTCCAGCCTCGGGGCTGTCCGC
GGGGGGACGGCTGCCTTCGGGGGGGACGGGGCAGGGCGGGGTTCGGCTTC

TGGCGTGTGACCGGCGGCTCTAGAGCCTCTGCTAACCATGTTCATGCCTT
CTTCTTTTTCCTACAGCTCCTGGGCAACGTGCTGGTTATTGTGCTGTCTC
ATCATTTTGGCAAAGAATTCGATATCAAGCTTGCCACCATGGAAGCCAAG
AGCCAGCTGTTTCTGAAATACTTTACCCTGTTTATGAATCTGCTGAACGA
CTGTAGTGAGGTGGAGGACGAGAGTGCCCAGACCGGCGGCAGGAAGAGAG
GCATGTCTAGGAGACTGGCCAGCCTGAGGCACTGCACAGTGCTGGCCATG
TCCAACCTGCTGAACGCCAATGTGGACTCCGGCCTGATGCACTCTATCGG
CCTGGGCTACCACAAGGATCTGCAGACCCGCGCCACATTCATGGAGGTGC
TGACCAAGATCCTGCAGCAGGGCACCGAGTTTGACACACTGGCCGAGACC
GTGCTGGCAGATAGGTTCGAGCGCCTGGTGGAGCTGGTGACAATGATGGG
CGACCAGGGAGAGCTGCCTATCGCAATGGCACTGGCCAACGTGGTGCCAT
GCAGCCAGTGGGACGAGCTGGCCAGGGTGCTGGTGACCCTGTTTGATTCC
AGACACCTGCTGTACCAGCTGCTGTGGAACATGTTCTCTAAGGAGGTGGA
GCTGGCCGACAGCATGCAGACACTGTTTAGGGGCAATTCCCTGGCCTCTA
AGATCATGACCTTCTGTTTTAAGGTGTACGGCGCCACATATCTGCAGAAG
CTGCTGGATCCACTGCTGAGAATCGTGATCACCAGCTCCGACTGGCAGCA
CGTGTCCTTCGAGGTGGATCCTACACGGCTGGAGCCAAGCGAGTCCCTGG
AGGAGAACCAGCGCAATCTGCTGCAGATGACCGAGAAGTTCTTTCACGCC
ATCATCTCTAGCTCCTCTGAGTTTCCCCCTCAGCTGCGGTCCGTGTGCCA
CTGTCTGTACCAGGCCACCTGCCACTCTCTGCTGAACAAGGCCACAGTGA
AGGAGAAGAAGGAGAATAAGAAGAGCGTGGTGTCCCAGAGGTTCCCACAG
AACAGCATCGGAGCAGTGGGATCCGCCATGTTCCTGAGGTTCATCAATCC
CGCCATCGTGAGCCCTTATGAGGCCGGCATCCTGGACAAGAAGCCACCCC
CTAGGATCGAGAGAGGCCTGAAGCTGATGAGCAAGATCCTGCAGTCCATC
GCCAACCACGTGCTGTTCACCAAGGAGGAGCACATGCGCCCCTTCAACGA
CTTTGTGAAGTCTAATTTTGATGCCGCCCGGCGCTTCTTTCTGGACATCG
CCTCTGATTGTCCTACAAGCGACGCCGTGAACCACTCTCTGAGCTTCATC
AGCGATGGCAATGTGCTGGCCCTGCACCGGCTGCTGTGGAACAATCAGGA
GAAGATCGGCCAGTACCTGAGCTCCAACAGGGACCACAAGGCAGTGGGCA
GGAGACCTTTTGATAAGATGGCCACCCTGCTGGCATATCTGGGACCACCA
GAGCACAAGCCAGTGGCAGACACCCACTGGTCTAGCCTGAATCTGACATC
CTCTAAGTTCGAGGAGTTTATGACCCGGCACCAGGTGCACGAGAAGGAGG
AGTTTAAGGCCCTGAAGACCCTGTCCATCTTCTACCAGGCCGGCACATCT
AAGGCCGGCAACCCTATCTTTTACTATGTGGCCCGGCGCTTCAAGACCGG
CCAGATCAATGGCGATCTGCTGATCTACCACGTGCTGCTGACACTGAAGC
CATACTATGCCAAGCCCTATGAGATCGTGGTGGACCTGACCCACACAGGC
CCAAGCAACAGGTTTAAGACCGATTTCCTGTCCAAGTGGTTCGTGGTGTT
TCCCGGCTTCGCCTATGACAACGTGAGCGCCGTGTACATCTATAACTGCA
ATAGCTGGGTGCGGGAGTACACCAAGTATCACGAGCGCCTGCTGACAGGC
CTGAAGGGCAGCAAGAGACTGGTGTTCATCGATTGTCCCGGCAAGCTGGC

```
CGAGCACATCGAGCACGAGCAGCAGAAGCTGCCTGCAGCCACCCTGGCCC
TGGAGGAGGACCTGAAGGTGTTTCACAACGCCCTGAAGCTGGCCCACAAG
GATACAAAGGTGTCCATCAAGGTCGGCTCTACAGCCGTGCAGGTGACCTC
CGCCGAGAGAACAAAGGTGCTGGGCCAGAGCGTGTTCCTGAATGACATCT
ACTATGCCAGCGAGATCGAGGAGATCTGCCTGGTGGATGAGAACCAGTTT
ACCCTGACAATCGCCAATCAGGGCACCCCCCTGACATTCATGCACCAGGA
GTGTGAAGCAATCGTCCAGAGCATTATTCACATTCGCACTCGGTGGGAAC
TGAGCCAGCCTGACGATGACTCGAGTTTTTTTTTGCGGCCGCTTCGAGCA
GACATGATAAGATACATTGATGAGTTTGGACAAACCACAACTAGAATGCA
GTGAAAAAAATGCTTTATTTGTGAAATTTGTGATGCTATTGCTTTATTTG
TAACCATTATAAGCTGCAATAAACAAGTTAACAACAACAATTGCATTCAT
TTTATGTTTCAGGTTCAGGGGAGATGTGGGAGGTTTTTTAAAGCAAGTA
AAACCTCTACAAATGTGGTAAAATCGATAGGCCGCAGGAACCCCTAGTGA
TGGAGTTGGCCACTCCCTCTCTGCGCGCTCGCTCGCTCACTGAGGCCGGG
CGACCAAAGGTCGCCCGACGCCCGGGCGGCCTCAGTGAGCGAGCGAGCGC
GCAGCTGCCTGCAGGACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCT
CCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGAGTACTCAACCAAG
TCATTCTGAGAATAGTGTATGCGGCGACCGAGTTGCTCTTGCCCGGCGTC
AATACGGGATAATACCGCGCCACATAGCAGAACTTTAAAAGTGCTCATCA
TTGGAAAACGTTCTTCGGGGCGAAAACTCTCAAGGATCTTACCGCTGTTG
AGATCCAGTTCGATGTAACCCACTCGTGCACCCAACTGATCTTCAGCATC
TTTTACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCATGAG
CGGATACATATTTGAATGTATTTAGAAAAATAAACAAATAGGGGTTCCGC
GCACATTTCCCCGAAAAGTGCCACCTGACGTCTAAGAAACCATTATTATC
ATGACATTAACCTATAAAAATAGGCGTATCACGAGGCCCTTTCGTCTCGC
GCGTTTCGGTGATGACGGTGAAAACCTCTGACACATGCAGCTCCCGGAGA
CGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGC
ATCAGAGCAGATTGTACTGAGAGTGCACCATAAAATTGTAAACGTTAATA
TTTTGTTAAAATTCGCGTTAAATTTTTGTTAAATCAGCTCATTTTTTAAC
CAATAGGCCGAAATCGGCAAAATCCCTTATAAATCAAAAGAATAGCCCGA
GATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGC
CCACTACGTGAACCATCACCCAAATCAAGTTTTTTGGGGTCGAGGTGCCG
TAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGA
GCGGGCGCTAAGGCGCTGGCAAGTGTAGCGGTCACGCTGCGCGTAACCAC
CACACCCGCCGCGCTTAATGCGCCGCTACAGGGCGCGTACTATGGTTGCT
TTGACGTATGCGGTGTGAAATACCGCACAGATGCGTAAGGAGAAAATACC
GCATCAGGCGCC
```

An exemplary AAV vector sequence encoding a mini-NF1 having an NF1 GRD with a HA tag is set forth in SEQ ID NO: 28:

```
CCTGCAGGCAGCTGCGCGCTCGCTCGCTCACTGAGGCCGCCCGGGCAAAG
CCCGGGCGTCGGGCGACCTTTGGTCGCCCGGCCTCAGTGAGCGAGCGAGC
GCGCAGAGAGGGAGTGGCCAACTCCATCACTAGGGGTTCCTGCGGCCAGA
TCTTCAATATTGGCCATTAGCCATATTATTCATTGGTTATATAGCATAAA
TCAATATTGGCTATTGGCCATTGCATACGTTGTATCTATATCATAATATG
TACATTTATATTGGCTCATGTCCAATATGACCGCCATGTTGGCATTGATT
ATTGACTAGTTATTAATAGTAATCAATTACGGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGAGTATT
```

TACGGTAAACTGCCCACTTGGCAGTACATCAAGTGTATCATATGCCAAGT
CCGCCCCCTATTGACGTCAATGACGGTAAATGGCCCGCCTGGCATTATGC
CCAGTACATGACCTTACGGGACTTTCCTACTTGGCAGTACATCTACGTAT
TAGTCATCGCTATTACCATGGTCGAGGTGAGCCCCACGTTCTGCTTCACT
CTCCCCATCTCCCCCCCCTCCCCACCCCCAATTTTGTATTTATTTATTTT
TTAATTATTTTGTGCAGCGATGGGGGCGGGGGGGGGGGGGGGCGCGCG
CAGGCGGGGCGGGGCGGGGCGAGGGGCGGGGCGGGGCGAGGCGGAGAGGT
GCGGCGGCAGCCAATCAGAGCGGCGCGCTCCGAAAGTTTCCTTTTATGGC
GAGGCGGCGGCGGCGGCGGCCCTATAAAAAGCGAAGCGCGCGGCGGGCGG
GAGTCGCTGCGCGCTGCCTTCGCCCCGTGCCCCGCTCCGCCGCCGCCTCG
CGCCGCCCGCCCCGGCTCTGACTGACCGCGTTACTCCCACAGGTGAGCGG
GCGGGACGGCCCTTCTCCTCCGGGCTGTAATTAGCGCTTGGTTTAATGAC
GGCTTGTTTCTTTTCTGTGGCTGCGTGAAAGCCTTGAGGGGCTCCGGAG
GGCCCTTTGTGCGGGGGGAGCGGCTCGGGGGGTGCGTGCGTGTGTGTG
CGTGGGGAGCGCCGCGTGCGGCTCCGCGCTGCCCGGCGGCTGTGAGCGCT
GCGGGCGCGGCGCGGGGCTTTGTGCGCTCCGCAGTGTGCGCGAGGGGAGC
GCGGCCGGGGCGGTGCCCCGCGGTGCGGGGGGGCTGCGAGGGGAACAA
AGGCTGCGTGCGGGGTGTGTGCGTGGGGGGGTGAGCAGGGGTGTGGGCG
CGTCGGTCGGGCTGCAACCCCCCTGCACCCCCCTCCCCGAGTTGCTGAG
CACGGCCCGGCTTCGGGTGCGGGGCTCCGTACGGGGCGTGGCGCGGGCT
CGCCGTGCCGGGCGGGGGTGGCGGCAGGTGGGGGTGCCGGGCGGGGCGG
GGCCGCCTCGGGCCGGGGAGGGCTCGGGGAGGGGCGCGGCGGCCCCCGG
AGCGCCGGCGGCTGTCGAGGCGCGGCGAGCCGCAGCCATTGCCTTTTATG
GTAATCGTGCGAGAGGGCGCAGGGACTTCCTTTGTCCCAAATCTGTGCGG
AGCCGAAATCTGGGAGGCGCCGCCGCACCCCCTCTAGCGGGCGCGGGGCG
AAGCGGTGCGGCGCCGGCAGGAAGGAAATGGGCGGGGAGGGCCTTCGTGC
GTCGCCGCGCCGCCGTCCCCTTCTCCCTCTCCAGCCTCGGGGCTGTCCGC
GGGGGGACGGCTGCCTTCGGGGGGGACGGGGCAGGGCGGGGTTCGGCTTC
TGGCGTGTGACCGGCGGCTCTAGAGCCTCTGCTAACCATGTTCATGCCTT
CTTCTTTTTCCTACAGCTCCTGGGCAACGTGCTGGTTATTGTGCTGTCTC
ATCATTTTGGCAAAGAATTCGATATCAAGCTTGCCACCATGGAAGCCAAG
AGCCAGCTGTTTCTGAAATACTTTACCCTGTTTATGAATCTGCTGAACGA
CTGTAGTGAGGTGGAGGACGAGAGTGCCCAGACCGGCGGCAGGAAGAGAG
GCATGTCTAGGAGACTGGCCAGCCTGAGGCACTGCACAGTGCTGGCCATG
TCCAACCTGCTGAACGCCAATGTGGACTCCGGCCTGATGCACTCTATCGG
CCTGGGCTACCACAAGGATCTGCAGACCCGCGCCACATTCATGGAGGTGC
TGACCAAGATCCTGCAGCAGGGCACCGAGTTTGACACACTGGCCGAGACC
GTGCTGGCAGATAGGTTCGAGCGCCTGGTGGAGCTGGTGACAATGATGGG
CGACCAGGGAGAGCTGCCTATCGCAATGGCACTGGCCAACGTGGTGCCAT
GCAGCCAGTGGGACGAGCTGGCCAGGGTGCTGGTGACCCTGTTTGATTCC
AGACACCTGCTGTACCAGCTGCTGTGGAACATGTTCTCTAAGGAGGTGGA
GCTGGCCGACAGCATGCAGACACTGTTTAGGGGCAATTCCCTGGCCTCTA
AGATCATGACCTTCTGTTTTAAGGTGTACGGCGCCACATATCTGCAGAAG
CTGCTGGATCCACTGCTGAGAATCGTGATCACCAGCTCCGACTGGCAGCA
CGTGTCCTTCGAGGTGGATCCTACACGGCTGGAGCCAAGCGAGTCCCTGG
AGGAGAACCAGCGCAATCTGCTGCAGATGACCGAGAAGTTCTTTCACGCC
ATCATCTCTAGCTCCTCTGAGTTTCCCCCTCAGCTGCGGTCCGTGTGCCA
CTGTCTGTACCAGGCCACCTGCCACTCTCTGCTGAACAAGGCCACAGTGA
AGGAGAAGAAGGAGAATAAGAAGAGCGTGGTGTCCCAGAGGTTCCCACAG
AACAGCATCGGAGCAGTGGGATCCGCCATGTTCCTGAGGTTCATCAATCC
CGCCATCGTGAGCCCTTATGAGGCCGGCATCCTGGACAAGAAGCCACCCC
CTAGGATCGAGAGAGGCCTGAAGCTGATGAGCAAGATCCTGCAGTCCATC
GCCAACCACGTGCTGTTCACCAAGGAGGAGCACATGCGCCCCTTCAACGA
CTTTGTGAAGTCTAATTTTGATGCCGCCCGGCGCTTCTTTCTGGACATCG
CCTCTGATTGTCCTACAAGCGACGCCGTGAACCACTCTCTGAGCTTCATC
AGCGATGGCAATGTGCTGGCCCTGCACCGGCTGCTGTGGAACAATCAGGA
GAAGATCGGCCAGTACCTGAGCTCCAACAGGGACCACAAGGCAGTGGGCA
GGAGACCTTTTGATAAGATGGCCACCCTGCTGGCATATCTGGGACCACCA
GAGCACAAGCCAGTGGCAGACACCCACTGGTCTAGCCTGAATCTGACATC
CTCTAAGTTCGAGGAGTTTATGACCCGGCACCAGGTGCACGAGAAGGAGG
AGTTTAAGGCCCTGAAGACCCTG

TATCCGTATGATGTGCCGGATTATGCGT

GATGACTCGAGTTTTTTTTTGCGGCCGCTTCGAGCAGACATGATAAGATA
CATTGATGAGTTTGGACAAACCACAACTAGAATGCAGTGAAAAAAATGCT
TTATTTGTGAAATTTGTGATGCTATTGCTTTATTTGTAACCATTATAAGC
TGCAATAAACAAGTTAACAACAACAATTGCATTCATTTTATGTTTCAGGT
TCAGGGGGAGATGTGGGAGGTTTTTTAAAGCAAGTAAAACCTCTACAAAT
GTGGTAAAATCGATAGGCCGCAGGAACCCCTAGTGATGGAGTTGGCCACT
CCCTCTCTGCGCGCTCGCTCGCTCACTGAGGCCGGGCGACCAAAGGTCGC
CCGACGCCCGGGCGGCCTCAGTGAGCGAGCGAGCGCGCAGCTGCCTGCAG
GACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAA
ATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGC
CTTATCCGGTAACTATCGTCTTGAGTCCAACCCGGTAAGACACGACTTAT
CGCCACTGGCAGCAGCCACTGGTAACAGGATTAGCAGAGCGAGGTATGTA
GGCGGTGCTACAGAGTTCTTGAAGTGGTGGCCTAACTACGGCTACACTAG
AAGAACAGTATTTGGTATCTGCGCTCTGCTGAAGCCAGTTACCTTCGGAA

```
AAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAA
ACTCACGTTAAGGGATTTTGGTCATGAGATTATCAAAAAGGATCTTCACC
TAGATCCTTTTAAATTAAAAATGAAGTTTTAAATCAATCTAAAGTATATA
TGAGTAAACTTGGTCTGACAGTTACCAATGCTTAATCAGTGAGGCACCTA
TCTCAGCGATCTGTCTATTTCGTTCATCCATAGTTGCCTGACTCCCCGTC
GTGTAGATAACTACGATACGGGAGGGCTTACCATCTGGCCCCAGTGCTGC
AATGATACCGCGAGACCCACGCTCACCGGCTCCAGATTTATCAGCAATAA
ACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACCGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAATGCCGCAAAAAAGGGA
ATAAGGGCGACACGGAAATGTTGAATACTCATACTCTTCCTTTTTCAATA
TTATTGAAGCATTTATCAGGGTTATTGTCTCATGAGCGGATACATATTTG
AATGTATTTAGAAAAATAAACAAATAGGGGTTCCGCGCACATTTCCCCGA
AAAGTGCCACCTGACGTCTAAGAAACCATTATTATCATGACATTAACCTA
TAAAAATAGGCGTATCACGAGGCCCTTTCGTCTCGCGCGTTTCGGTGATG
ACGGTGAAAACCTCTGACACATGCAGCTCCCGGAGACGGTCACAGCTTGT
CTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTG
TACTGAGAGTGCACCATAAAATTGTAAACGTTAATATTTTGTTAAAATTC
GCGTTAAATTTTTGTTAAATCAGCTCATTTTTTAACCAATAGGCCGAAAT
CGGCAAAATCCCTTATAAATCAAAAGAATAGCCCGAGATAGGGTTGAGTG
TTGTTCCAGTTTGGAACAAGAGTCCACTATTAAAGAACGTGGACTCCAAC
GTCAAAGGGCGAAAAACCGTCTATCAGGGCGATGGCCCACTACGTGAACC
ATCACCCAAATCAAGTTTTTTGGGGTCGAGGTGCCGTAAAGCACTAAATC
GGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAAGGC
GCTGGCAAGTGTAGCGGTCACGCTGCGCGTAACCACCACACCCGCCGCGC
TTAATGCGCCGCTACAGGGCGCGTACTATGGTTGCTTTGACGTATGCGGT
GTGAAATACCGCACAGATGCGTAAGGAGAAAATACCGCATCAGGCGCC
```

An exemplary AAV vector sequence encoding a mini-NF1 having an NF1 GRD, and the CRAL-TRIO domain with a HA tag is set forth in SEQ ID NO: 29:

```
CCTGCAGGCAGCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCCATC
ACTAGGGGTTCCTGCGGCCAGATCTTCAATATTGGCCATTAGCCATATTATTCATTGGTTATAT
AGCATAAATCAATATTGGCTATTGGCCATTGCATACGTTGTATCTATATCATAATATGTACATT
TATATTGGCTCATGTCCAATATGACCGCCATGTTGGCATTGATTATTGACTAGTTATTAATAGT
AATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACGGTAAACTG
CCCACTTGGCAGTACATCAAGTGTATCATATGCCAAGTCCGCCCCCTATTGACGTCAATGACGG
TAAATGGCCCGCCTGGCATTATGCCCAGTACATGACCTTACGGGACTTTCCTACTTGGCAGTAC
ATCTACGTATTAGTCATCGCTATTACCATGGTCGAGGTGAGCCCCACGTTCTGCTTCACTCTCC
CCATCTCCCCCCCCTCCCCACCCCCAATTTTGTATTTATTTATTTTTAATTATTTTGTGCAGC
GATGGGGGCGGGGGGGGGGGGGGGCGCGCGCCAGGCGGGGCGGGGCGGGGCGAGGGGCGGGGC
GGGGCGAGGCGGAGAGGTGCGGCGGCAGCCAATCAGAGCGGCGCGCTCCGAAAGTTTCCTTTTA
TGGCGAGGCGGCGGCGGCGGCGGCCCTATAAAAAGCGAAGCGCGCGGCGGGCGGGAGTCGCTGC
GCGCTGCCTTCGCCCCGTGCCCCGCTCCGCCGCCGCCTCGCGCCGCCCGCCCCGGCTCTGACTG
ACCGCGTTACTCCCACAGGTGAGCGGGCGGGACGGCCCTTCTCCTCCGGGCTGTAATTAGCGCT
TGGTTTAATGACGGCTTGTTTCTTTTCTGTGGCTGCGTGAAAGCCTTGAGGGGCTCCGGGAGGG
```

```
CCCTTTGTGCGGGGGGAGCGGCTCGGGGGGTGCGTGCGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGCTGCGAGGG

GAACAAAGGCTGCGTGCGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCATTTGATAAGATGGCCACACTGCTGGCCTATCTGG

GACCACCAGAGCACAAGCCAGTGGCAGACACACACTGGTCTAGCCTGAATCTGACCTCCTCTAA

GTTCGAGGAGTTTATGACCCGGCACCAGGTGCACGAGAAGGAGGAGTTTAAGGCCCTGAAGACA

CTGTCTATCTTCTACCAGGCAGGCACCAGCAAGGCAGGAAACCCAATCTTTTACTATGTGGCCC

GGCGCTTCAAGACAGGCCAGATCAATGGCGATCTGCTGATCTACCACGTGCTGCTGACCCTGAA

GCCATACTATGCCAAGCCCTATGAGATCGTGGTGGACCTGACCCACACAGGCCCCTCCAACAGG
```

```
TTTAAGACCGATTTCCTGTCTAAGTGGTTCGTGGTGTTTCCTGGCTTCGCCTATGACAATGTGA

GCGCCGTGTACATCTATAACTGCAATTCCTGGGTGCGGGAGTACACAAAGTATCACGAGCGCCT

GCTGACCGGCCTGAAGGGATCCAAGAGACTGGTGTTCATCGATTGTCCCGGCAAGCTGGCCGAG

CACATTGAACACGAACAGCAGAAACTGCCCGCCGCAACCCTGGCCCTGGAAGAGGACCTGAAG**T

ATCCGTATGATGTGCCGGATTATGCGT**GATGACTCGAGTTTTTTTTGCGGCCGCTTCGAGCAG

ACATGATAAGATACATTGATGAGTTTGGACAAACCACAACTAGAATGCAGTGAAAAAAATGCTT

TATTTGTGAAATTTGTGATGCTATTGCTTTATTTGTAACCATTATAAGCTGCAATAAACAAGTT

AACAACAACAATTGCATTCATTTTATGTTTCAGGTTCAGGGGGAGATGTGGGAGGTTTTTTAAA

GCAAGTAAAACCTCTACAAATGTGGTAAAATCGATAGGCCGCAGGAACCCCTAGTGATGGAGTT

GGCCACTCCCTCTCTGCGCGCTCGCTCGCTCACTGAGGCCGGGCGACCAAAGGTCGCCCGACGC

CCGGGCGGCCTCAGTGAGCGAGCGAGCGCGCAGCTGCCTGCAGGACATGTGAGCAAAAGGCCAG

CAAAAGGCCAGGAACCGTAAAAAGGCCGCGTTGCTGGCGTTTTTCCATAGGCTCCGCCCCCCTG

ACGAGCATCACAAAAATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCCTGCCGCTTACCGGA

TACCTGTCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTCAGCCCGA

CCGCTGCGCCTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCTACAGAGTTCT

TGAAGTGGTGGCCTAACTACGGCTACACTAGAAGAACAGTATTTGGTATCTGCGCTCTGCTGAA

GCCAGTTACCTTCGGAAAAAGAGTTGGTAGCTCTTGATCCGGCAAACAAACCACCGCTGGTAGC

GGTGGTTTTTTTGTTTGCAAGCAGCAGATTACGCGCAGAAAAAAAGGATCTCAAGAAGATCCTT

TGATCTTTTCTACGGGGTCTGACGCTCAGTGGAACGAAAACTCACGTTAAGGGATTTTGGTCAT

GAGATTATCAAAAAGGATCTTCACCTAGATCCTTTTAAATTAAAAATGAAGTTTTAAATCAATC

TAAAGTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTACGAT

ACGGGAGGGCTTACCATCTGGCCCCAGTGCTGCAATGATACCGCGAGACCCACGCTCACCGGCT

CCAGATTTATCAGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGTGTTATCACT

CATGGTTATGGCAGCACTGCATAATTCTCTTACTGTCATGCCATCCGTAAGATGCTTTTCTGTG

ACTGGTGAGTACTCAACCAAGTCATTCTGAGAATAGTGTATGCGGCGACCGAGTTGCTCTTGCC

CGGCGTCAATACGGGATAATACCGCGCCACATAGCAGAACTTTAAAAGTGCTCATCATTGGAAA

ACGTTCTTCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAGCAAAAA

CAGGAAGGCAAAATGCCGCAAAAAAGGGAATAAGGGCGACACGGAAATGTTGAATACTCATACT

CTTCCTTTTTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAAGTGCCACCTG

ACGTCTAAGAAACCATTATTATCATGACATTAACCTATAAAAATAGGCGTATCACGAGGCCCTT

TCGTCTCGCGCGTTTCGGTGATGACGGTGAAAACCTCTGACACATGCAGCTCCCGGAGACGGTC
```

-continued

```
ACAGCTTGTCTGTAAGCGGATGCCGGGAGCAGACAAGCCCGTCAGGGCGCGTCAGCGGGTGTTG

GCGGGTGTCGGGGCTGGCTTAACTATGCGGCATCAGAGCAGATTGTACTGAGAGTGCACCATAA

AATTGTAAACGTTAATATTTTGTTAAAATTCGCGTTAAATTTTTGTTAAATCAGCTCATTTTTT

AACCAATAGGCCGAAATCGGCAAAATCCCTTATAAATCAAAAGAATAGCCCGAGATAGGGTTGA

GTGTTGTTCCAGTTTGGAACAAGAGTCCACTATTAAAGAACGTGGACTCCAACGTCAAAGGGCG

AAAAACCGTCTATCAGGGCGATGGCCCACTACGTGAACCATCACCCAAATCAAGTTTTTTGGGG

TCGAGGTGCCGTAAAGCACTAAATCGGAACCCTAAAGGGAGCCCCCGATTTAGAGCTTGACGGG

GAAAGCCGGCGAACGTGGCGAGAAAGGAAGGGAAGAAAGCGAAAGGAGCGGGCGCTAAGGCGCT

GGCAAGTGTAGCGGTCACGCTGCGCGTAACCACCACACCCGCCGCGCTTAATGCGCCGCTACAG

GGCGCGTACTATGGTTGCTTTGACGTATGCGGTGTGAAATACCGCACAGATGCGTAAGGAGAAA

ATACCGCATCAGGCGCC
```

An exemplary AAV vector sequence encoding a mini-NF1 having an NF1 GRD, the CRAL-TRIO domain and the bipartite phospholipid binding domain with a HA tag is set forth in SEQ ID NO: 30:

```
CCTGCAGGCAGCTGCGCGCTCGCTCGCTCACTGAGGCCGCCCGGGCAAAG

CCCGGGCGTCGGGCGACCTTTGGTCGCCCGGCCTCAGTGAGCGAGCGAGC

GCGCAGAGAGGGAGTGGCCAACTCCATCACTAGGGGTTCCTGCGGCAGA

TCTTCAATATTGGCCATTAGCCATATTATTCATTGGTTATATAGCATAAA

TCAATATTGGCTATTGGCCATTGCATACGTTGTATCTATATCATAATATG

TACATTTATATTGGCTCATGTCCAATATGACCGCCATGTTGGCATTGATT

ATTGACTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGAGTATT

TACGGTAAACTGCCCACTTGGCAGTACATCAAGTGTATCATATGCCAAGT

CCGCCCCCTATTGACGTCAATGACGGTAAATGGCCCGCCTGGCATTATGC

CCAGTACATGACCTTACGGGACTTTCCTACTTGGCAGTACATCTACGTAT

TAGTCATCGCTATTACCATGGTCGAGGTGAGCCCCACGTTCTGCTTCACT

CTCCCCATCTCCCCCCCCTCCCCACCCCCAATTTTGTATTTATTTATTTT

TTAATTATTTTGTGCAGCGATGGGGCGGGGGGGGGGGGGGGCGCGCGC

CAGGCGGGGCGGGGCGGGCGAGGGGCGGGCGGGCGAGGCGGAGAGGT

GCGGCGGCAGCCAATCAGAGCGGCGCGCTCCGAAAGTTTCCTTTTATGGC

GAGGCGGCGGCGGCGGCCCTATAAAAAGCGAAGCGCGCGGCGGGCGG

GAGTCGCTGCGCGCTGCCTTCGCCCCGTGCCCCGCTCCGCCGCCGCCTCG

CGCCGCCCGCCCCGGCTCTGACTGACCGCGTTACTCCCACAGGTGAGCGG

GCGGGACGGCCCTTCTCCTCCGGGCTGTAATTAGCGCTTGGTTTAATGAC

GGCTTGTTTCTTTTCTGTGGCTGCGTGAAAGCCTTGAGGGGCTCCGGGAG

GGCCCTTTGTGCGGGGGAGCGGCTCGGGGGGTGCGTGCGTGTGTGTGTG

CGTGGGGAGCGCCGCGTGCGGCTCCGCGCTGCCCGGCGGCTGTGAGCGCT

GCGGGCGCGGCGCGGGGCTTTGTGCGCTCCGCAGTGTGCGCGAGGGGAGC

GCGGCCGGGGCGGTGCCCCGCGGTGCGGGGGGGCTGCGAGGGGAACAA

AGGCTGCGTGCGGGGTGTGTGCGTGGGGGGTGAGCAGGGGGTGTGGGCG

CGTCGGTCGGGCTGCAACCCCCCTGCACCCCCCTCCCCGAGTTGCTGAG

CACGGCCCGGCTTCGGGTGCGGGGCTCCGTACGGGGCGTGGCGCGGGGCT

CGCCGTGCCGGGCGGGGGTGGCGGCAGGTGGGGGTGCCGGGCGGGGCGG

GGCCGCCTCGGGCCGGGGAGGGCTCGGGGGAGGGGCGCGGCGGCCCCGG

AGCGCCGGCGGCTGTCGAGGCGCGGCGAGCCGCAGCCATTGCCTTTTATG

GTAATCGTGCGAGAGGGCGCAGGGACTTCCTTTGTCCCAAATCTGTGCGG

AGCCGAAATCTGGGAGGCGCCGCCGCACCCCCTCTAGCGGGCGCGGGGCG

AAGCGGTGCGGCGCCGGCAGGAAGGAAATGGGCGGGGAGGGCCTTCGTGC

GTCGCCGCGCCGCCGTCCCCTTCTCCCTCTCCAGCCTCGGGGCTGTCCGC

GGGGGGACGGCTGCCTTCGGGGGGGACGGGGCAGGGCGGGGTTCGGCTTC

TGGCGTGTGACCGGCGGCTCTAGAGCCTCTGCTAACCATGTTCATGCCTT

CTTCTTTTTCCTACAGCTCCTGGGCAACGTGCTGGTTATTGTGCTGTCTC

ATCATTTTGGCAAAGAATTCGATATCAAGCTTGCCACCATGGAAGCCAAG

AGCCAGCTGTTTCTGAAATACTTTACCCTGTTTATGAATCTGCTGAACGA

CTGTAGTGAGGTGGAGGACGAGAGTGCCCAGACCGGCGGCAGGAAGAGAG

GCATGTCTAGGAGACTGGCCAGCCTGAGGCACTGCACAGTGCTGGCCATG

TCCAACCTGCTGAACGCCAATGTGGACTCCGGCCTGATGCACTCTATCGG

CCTGGGCTACCACAAGGATCTGCAGACCCGCGCCACATTCATGGAGGTGC

TGACCAAGATCCTGCAGCAGGGCACCGAGTTTGACACACTGGCCGAGACC

GTGCTGGCAGATAGGTTCGAGCGCCTGGTGGAGCTGGTGACAATGATGGG

CGACCAGGGAGAGCTGCCTATCGCAATGGCACTGGCCAACGTGGTGCCAT

GCAGCCAGTGGGACGAGCTGGCCAGGGTGCTGGTGACCCTGTTTGATTCC

AGACACCTGCTGTACCAGCTGCTGTGGAACATGTTCTCTAAGGAGGTGGA

GCTGGCCGACAGCATGCAGACACTGTTTAGGGGCAATTCCCTGGCCTCTA
```

-continued

AGATCATGACCTTCTGTTTTAAGGTGTACGGCGCCACATATCTGCAGAAG
CTGCTGGATCCACTGCTGAGAATCGTGATCACCAGCTCCGACTGGCAGCA
CGTGTCCTTCGAGGTGGATCCTACACGGCTGGAGCCAAGCGAGTCCCTGG
AGGAGAACCAGCGCAATCTGCTGCAGATGACCGAGAAGTTCTTTCACGCC
ATCATCTCTAGCTCCTCTGAGTTTCCCCCTCAGCTGCGGTCCGTGTGCCA
CTGTCTGTACCAGGCCACCTGCCACTCTCTGCTGAACAAGGCCACAGTGA
AGGAGAAGAAGGAGAATAAGAAGAGCGTGGTGTCCCAGAGGTTCCCACAG
AACAGCATCGGAGCAGTGGGATCCGCCATGTTCCTGAGGTTCATCAATCC
CGCCATCGTGAGCCCTTATGAGGCCGGCATCCTGGACAAGAAGCCACCCC
CTAGGATCGAGAGAGGCCTGAAGCTGATGAGCAAGATCCTGCAGTCCATC
GCCAACCACGTGCTGTTCACCAAGGAGGAGCACATGCGCCCCTTCAACGA
CTTTGTGAAGTCTAATTTTGATGCCGCCCGGCGCTTCTTTCTGGACATCG
CCTCTGATTGTCCTACAAGCGACGCCGTGAACCACTCTCTGAGCTTCATC
AGCGATGGCAATGTGCTGGCCCTGCACCGGCTGCTGTGGAACAATCAGGA
GAAGATCGGCCAGTACCTGAGCTCCAACAGGGACCACAAGGCAGTGGGCA
GGAGACCTTTTGATAAGATGGCCACCCTGCTGGCATATCTGGGACCACCA
GAGCACAAGCCAGTGGCAGACACCCACTGGTCTAGCCTGAATCTGACATC
CTCTAAGTTCGAGGAGTTTATGACCCGGCACCAGGTGCACGAGAAGGAGG
AGTTTAAGGCCCTGAAGACCCTGTCCATCTTCTACCAGGCCGGCACATCT
AAGGCCGGCAACCCTATCTTTTACTATGTGGCCCGGCGCTTCAAGACCGG
CCAGATCAATGGCGATCTGCTGATCTACCACGTGCTGCTGACACTGAAGC
CATACTATGCCAAGCCCTATGAGATCGTGGTGGACCTGACCCACACAGGC
CCAAGCAACAGGTTTAAGACCGATTTCCTGTCCAAGTGGTTCGTGGTGTT
TCCCGGCTTCGCCTATGACAACGTGAGCGCCGTGTACATCTATAACTGCA
ATAGCTGGGTGCGGGAGTACACCAAGTATCACGAGCGCCTGCTGACAGGC
CTGAAGGGCAGCAAGAGACTGGTGTTCATCGATTGTCCCGGCAAGCTGGC
CGAGCACATCGAGCACGAGCAGCAGAAGCTGCCTGCAGCCACCCTGGCCC
TGGAGGAGGACCTGAAGGTGTTTCACAACGCCCTGAAGCTGGCCCACAAG
GATACAAAGGTGTCCATCAAGGTCGGCTCTACAGCCGTGCAGGTGACCTC
CGCCGAGAGAACAAAGGTGCTGGGCCAGAGCGTGTTCCTGAATGACATCT
ACTATGCCAGCGAGATCGAGGAGATCTGCCTGGTGGATGAGAACCAGTTT
ACCCTGACAATCGCCAATCAGGGCACCCCCCTGACATTCATGCACCAGGA
GTGTGAAGCAATCGTCCAGAGCATTATTCACATTCGCACTCGGTGGGAAC
TGAGCCAGCCTGAC
TATCCGTATGATGTGCCGGATTATGCGT
GATGACTCGAGTTTTTTTTGCGGCCGCTTCGAGCAGACATGATAAGATA
CATTGATGAGTTTGGACAAACCACAACTAGAATGCAGTGAAAAAAATGCT
TTATTTGTGAAATTTGTGATGCTATTGCTTTATTTGTAACCATTATAAGC
TGCAATAAACAAGTTAACAACAACAATTGCATTCATTTTATGTTTCAGGT
TCAGGGGAGATGTGGGAGGTTTTTTAAAGCAAGTAAAACCTCTACAAAT
GTGGTAAAATCGATAGGCCGCAGGAACCCCTAGTGATGGAGTTGGCCACT

-continued

CCCTCTCTGCGCGCTCGCTCGCTCACTGAGGCCGGGCGACCAAAGGTCGC
CCGACGCCCGGCGGCCTCAGTGAGCGAGCGAGCGCGCAGCTGCCTGCAG
GACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAA
ATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGC
CTTATCCGGTAACTATCGTCTTGAGTCCAACCCGGTAAGACACGACTTAT
CGCCACTGGCAGCAGCCACTGGTAACAGGATTAGCAGAGCGAGGTATGTA
GGCGGTGCTACAGAGTTCTTGAAGTGGTGGCCTAACTACGGCTACACTAG
AAGAACAGTATTTGGTATCTGCGCTCTGCTGAAGCCAGTTACCTTCGGAA
AAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAA
ACTCACGTTAAGGGATTTTGGTCATGAGATTATCAAAAAGGATCTTCACC
TAGATCCTTTTAAATTAAAAATGAAGTTTTAAATCAATCTAAAGTATATA
TGAGTAAACTTGGTCTGACAGTTACCAATGCTTAATCAGTGAGGCACCTA
TCTCAGCGATCTGTCTATTTCGTTCATCCATAGTTGCCTGACTCCCCGTC
GTGTAGATAACTACGATACGGGAGGGCTTACCATCTGGCCCCAGTGCTGC
AATGATACCGCGAGACCCACGCTCACCGGCTCCAGATTTATCAGCAATAA
ACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACCGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAAATGCCGCAAAAAAGGGA
ATAAGGGCGACACGGAAATGTTGAATACTCATACTCTTCCTTTTTCAATA
TTATTGAAGCATTTATCAGGGTTATTGTCTCATGAGCGGATACATATTTG
AATGTATTTAGAAAAATAAACAATAGGGGTTCCGCGCACATTTCCCCGA
AAAGTGCCACCTGACGTCTAAGAAACCATTATTATCATGACATTAACCTA
TAAAAATAGGCGTATCACGAGGCCCTTTCGTCTCGCGCGTTTCGGTGATG

```
ACGGTGAAAACCTCTGACACATGCAGCTCCCGGAGACGGTCACAGCTTGT

CTGTAAGCGGATGCCGGGAGCAGACAAGCCCGTCAGGGCGCGTCAGCGGG

TGTTGGCGGGTGTCGGGGCTGGCTTAACTATGCGGCATCAGAGCAGATTG

TACTGAGAGTGCACCATAAAATTGTAAACGTTAATATTTTGTTAAAATTC

GCGTTAAATTTTTGTTAAATCAGCTCATTTTTTAACCAATAGGCCGAAAT

CGGCAAAATCCCTTATAAATCAAAAGAATAGCCCGAGATAGGGTTGAGTG

TTGTTCCAGTTTGGAACAAGAGTCCACTATTAAAGAACGTGGACTCCAAC

GTCAAAGGGCGAAAAACCGTCTATCAGGGCGATGGCCCACTACGTGAACC

ATCACCCAAATCAAGTTTTTTGGGGTCGAGGTGCCGTAAAGCACTAAATC

GGAACCCTAAAGGGAGCCCCCGATTTAGAGCTTGACGGGGAAAGCCGGCG

AACGTGGCGAGAAAGGAAGGGAAGAAAGCGAAAGGAGCGGGCGCTAAGGC

GCTGGCAAGTGTAGCGGTCACGCTGCGCGTAACCACCACACCCGCCGCGC

TTAATGCGCCGCTACAGGGCGCGTACTATGGTTGCTTTGACGTATGCGGT

GTGAAATACCGCACAGATGCGTAAGGAGAAAATACCGCATCAGGCGCC
```

In some embodiments, the 5' AAV vector and the 3' AAV vector encoding the full-length NF1 proteins comprises a nucleic acid as set forth in SEQ ID NOs: 12 and 15 or 31.

An exemplary 5' AAV vector sequence comprising the 5' isolated nucleic acid of the dual AAV vector system encoding full-length NF1 protein is set forth in SEQ ID NO: 12:

```
CCTGCAGGCAGCTGCGCGCTCGCTCGCTCACTGAG

GCCGCCCGGGCAAAGCCCGGGCGTCGGGCGACCTT

TGGTCGCCCGGCCTCAGTGAGCGAGCGAGCGCGCA

GAGAGGGAGTGGCCAACTCCATCACTAGGGGTTCC

TGCGGCCAGATCTGTCGACAATTGAGGGCGTCACC

GCTAAGGCTCCGCCCCAGCCTGGGCTCCACAACCA

ATGAAGGGTAATCTCGACAAAGAGCAAGGGGTGGG

GCGCGGGCGCGCAGGTGCAGCAGCACACAGGCTGG

TCGGGAGGGCGGGGCGCGACGTCTGCCGTGCGGGG

TCCCGGCATCGGTTGCGCGCGCGCTCCCTCCTCTC

GGAGAGAGGGCTGTGGTAAAACCCGTCCGGAAAAC

TAGTGCCACCATGGCCGCGCACAGGCCGGTGGAAT

GGGTCCAGGCCGTGGTCAGCCGCTTCGACGAGCAG

CTTCCAATAAAAACAGGACAGCAGAACACACATAC

CAAAGTCAGTACTGAGCACAACAAGGAATGTCTAA

TCAATATTTCCAAATACAAGTTTTCTTTGGTTATA

AGCGGCCTCACTACTATTTTAAAGAATGTTAACAA

TATGAGAATATTTGGAGAAGCTGCTGAAAAAAATT

TATATCTCTCTCAGTTGATTATATTGGATACACTG

GAAAAATGTCTTGCTGGGCAACCAAAGGACACAAT

GAGATTAGATGAAACGATGCTGGTCAAACAGTTGC

TGCCAGAAATCTGCCATTTTCTTCACACCTGTCGT

GAAGGAAACCAGCATGCAGCTGAACTTCGGAATTC

TGCCTCTGGGGTTTTATTTTCTCTCAGCTGCAACA

ACTTCAATGCAGTCTTTAGTCGCATTTCTACCAGG

TTACAGGAATTAACTGTTTGTTCAGAAGACAATGT

TGATGTTCATGATATAGAATTGTTACAGTATATCA

ATGTGGATTGTGCAAAATTAAAACGACTCCTGAAG

GAAACAGCATTTAAATTTAAAGCCCTAAAGAAGGT

TGCGCAGTTAGCAGTTATAAATAGCCTGGAAAAGG

CATTTTGGAACTGGGTAGAAAATTATCCAGATGAA

TTTACAAAACTGTACCAGATCCCACAGACTGATAT

GGCTGAATGTGCAGAAAAGCTATTTGACTTGGTGG

ATGGTTTTGCTGAAAGCACCAAACGTAAAGCAGCA

GTTTGGCCACTACAAATCATTCTCCTTATCTTGTG

CCCAGAAATAATCCAGGATATATCCAAAGACGTGG

TTGATGAAAACAACATGAATAAGAAGTTATTTCTG

GACAGTCTACGAAAAGCTCTTGCTGGCCATGGAGG

AAGTAGGCAGCTGACAGAAAGTGCTGCAATTGCCT

GTGTCAAACTGTGTAAAGCAAGTACTTACATCAAT

TGGGAAGATAACTCTGTCATTTTCCTACTTGTTCA

GTCCATGGTGGTTGATCTTAAGAACCTGCTTTTTA

ATCCAAGTAAGCCATTCTCAAGAGGCAGTCAGCCT

GCAGATGTGGATCTAATGATTGACTGCCTTGTTTC

TTGCTTTCGTATAAGCCCTCACAACAACCAACACT

TTAAGATCTGCCTGGCTCAGAATTCACCTTCTACA

TTTCACTATGTGCTGGTAAATTCACTCCATCGAAT

CATCACCAATTCCGCATTGGATTGGTGGCCTAAGA

TTGATGCTGTGTATTGTCACTCGGTTGAACTTCGA

AATATGTTTGGTGAAACACTTCATAAAGCAGTGCA

AGGTTGTGGAGCACACCCAGCAATACGAATGGCAC

CGAGTCTTACATTTAAAGAAAAAGTAACAAGCCTT

AAATTTAAAGAAAAACCTACAGACCTGGAGACAAG

AAGCTATAAGTATCTTCTCTTGTCCATGGTGAAAC

TAATTCATGCAGATCCAAAGCTCTTGCTTTGTAAT

CCAAGAAAACAGGGGCCCGAAACCCAAGGCAGTAC

AGCAGAATTAATTACAGGGCTCGTCCAACTGGTCC

CTCAGTCACACATGCCAGAGATTGCTCAGGAAGCA

ATGGAGGCTCTGCTGGTTCTTCATCAGTTAGATAG

CATTGATTTGTGGAATCCTGATGCTCCTGTAGAAA

CATTTGGGAGATTAGCTCACAAATGCTTTTTTAC

ATCTGCAAGAATTAACTAGTCATCAAATGCTTAG
```

-continued
TAGCACAGAAATTCTCAAGTGGTTGCGGGAAATAT
TGATCTGCAGGAATAAATTTCTTCTTAAAAATAAG
CAGGCAGATAGAAGTTCCTGTCACTTTCTCCTTTT
TTACGGGGTAGGATGTGATATTCCTTCTAGTGGAA
ATACCAGTCAAATGTCCATGGATCATGAAGAATTA
CTACGTACTCCTGGAGCCTCTCTCCGGAAGGGAAA
AGGGAACTCCTCTATGGATAGTGCAGCAGGATGCA
GCGGAACCCCCCCAATTTGCCGACAAGCCCAGACC
AAACTAGAAGTGGCCCTGTACATGTTTCTGTGGAA
CCCTGACACTGAAGCTGTTCTGGTTGCCATGTCCT
GTTTCCGCCACCTCTGTGAGGAAGCAGATATCCGG
TGTGGGGTGGATGAAGTGTCAGTGCATAACCTCTT
GCCCAACTATAACACATTCATGGAGTTTGCCTCTG
TCAGCAATATGATGTCAACAGGAAGAGCAGCACTT
CAGAAAAGAGTGATGGCACTGCTGAGGCGCATTGA
GCATCCCACTGCAGGAAACACTGAGGCTTGGGAAG
ATACACATGCAAAATGGGAACAAGCAACAAAGCTA
ATCCTTAACTATCCAAAAGCCAAAATGGAAGATGG
CCAGGCTGCTGAAAGCCTTCACAAGACCATTGTTA
AGAGGCGAATGTCCCATGTGAGTGGAGGAGGATCC
ATAGATTTGTCTGACACAGACTCCCTACAGGAATG
GATCAACATGACTGGCTTCCTTTGTGCCCTTGGGG
GAGTGTGCCTCCAGCAGAGAAGCAATTCTGGCCTG
GCAACCTATAGCCCACCCATGGGTCCAGTCAGTGA
ACGTAAGGGTTCTATGATTTCAGTGATGTCTTCAG
AGGGAAACGCAGATACACCTGTCAGCAAATTTATG
GATCGGCTGTTGTCCTTAATGGTGTGTAACCATGA
GAAAGTGGGACTTCAAATACGGACCAATGTTAAGG
ATCTGGTGGGTCTAGAATTGAGTCCTGCTCTGTAT
CCAATGCTATTTAACAAATTGAAGAATACCATCAG
CAAGTTTTTTGACTCCCAAGGACAGGTTTTATTGA
CTGATACCAATACTCAATTTGTAGAACAAACCATA
GCTATAATGAAGAACTTGCTAGATAATCATACTGA
AGGCAGCTCTGAACATCTAGGGCAAGCTAGCATTG
AAACAATGATGTTAAATCTGGTCAGGTATGTTCGT
GTGCTTGGGAATATGGTCCATGCAATTCAAATAAA
AACGAAACTGTGTCAATTAGTTGAAGTAATGATGG
CAAGGAGAGATGACCTCTCATTTTGCCAAGAGATG
AAATTTAGGAATAAGATGGTAGAATACCTGACAGA
CTGGGTTATGGGAACATCAAACCAAGCAGCAGATG
ATGATGTAAAATGTCTTACAAGAGATTTGGACCAG -continued
GCAAGCATGGAAGCAGTAGTTTCACTTCTAGCTGG
TCTCCCTCTGCAGCCTGAAGAAGGAGATGGTGTGG
AATTGATGGAAGCCAAATCACAGTTATTTCTTAAA
TACTTCACATTATTTATGAACCTTTTGAATGACTG
CAGTGAAGTTGAAGATGAAAGTGCGCAAACAGGTG
GCAGGAAACGTGGCATGTCTCGGAGGCTGGCATCA
CTGAGGCACTGTACGGTCCTTGCAATGTCAAACTT
ACTCAATGCCAACGTAGACAGTGGTCTCATGCACT
CCATAGGCTTAGGTTACCACAAGGATCTCCAGACA
AGAGCTACATTTATGGAAGTTCTGACAAAAATCCT
TCAACAAGGCACAGAATTTGACACACTTGCAGAAA
CAGTATTGGCTGATCGGTTTGAGAGATTGGTGGAA
CTGGTCACAATGATGGGTGATCAAGGAGAACTCCC
TATAGCGATGGCTCTGGCCAATGTGGTTCCTTGTT
CTCAGTGGGATGAACTAGCTCGAGTTCTGGTTACT
CTGTTTGATTCTCGGCATTTACTCTACCAACTGCT
CTGGAACATGTTTTCTAAAGAAGTAGAATTGGCAG
ACTCCATGCAGACTCTCTTCCGAGGCAACAGCTTG
GCCAGTAAAATAATGACATTCTGTTTCAAGGTATA
TGGTGCTACCTATCTACAAAAACTCCTGGATCCTT
TATTACGAATTGTGATCACATCCTCTGATTGGCAA
CATGTTAGCTTTGAAGTGGATCCTACCAGGTTAGA
ACCATCAGAGAGCCTTGAGGAAAACCAGCGGAACC
TCCTTCAGATGACTGAAAAGTTCTTCCATGCCATC
ATCAGTTCCTCCTCAGAATTCCCCCCTCAACTTCG
AAGTGTGTGCCACTGTTTATACCAGGCAACTTGCC
ACTCCCTACTGAATAAAGCTACAGTAAAAGAAAAA
AAGGAAAACAAAAAATCAGTGGGCAGCATGTGGAA
CCTGGCGAGCCCATCCCCGGCAAGCTCTCAAGCC
ATGCTGGTGGGACGACTGAATGCCAGGGCCCTTC
ACTGGGCTATTTCACCCAGGGACGCTTCTTGAAGG
CACCCCCCACTCCAAGCTCAATTGAACTCGAGAAT
CGATAGGCCGCAGGAACCCCTAGTGATGGAGTTGG
CCACTCCCTCTCTGCGCGCTCGCTCGCTCACTGAG
GCCGGGCGACCAAAGGTCGCCCGACGCCCGGGCGG
CCTCAGTGAGCGAGCGAGCGCGCAGCTGCCTGCAG
GACATGTGAGCAAAAGGCCAGCAAAAGGCCAGGAA
CCGTAAAAAGGCCGCGTTGCTGGCGTTTTTCCATA
GGCTCCGCCCCCTGACGAGCATCACAAAAATCGA
CGCTCAAGTCAGAGGTGGCGAAACCCGACAGGACT

```
ATAAAGATACCAGGCGTTTCCCCCTGGAAGCTCCC
TCGTGCGCTCTCCTGTTCCGACCCTGCCGCTTACC
GGATACCTGTCCGCCTTTCTCCCTTCGGGAAGCGT
GGCGCTTTCTCATAGCTCACGCTGTAGGTATCTCA
GTTCGGTGTAGGTCGTTCGCTCCAAGCTGGGCTGT
GTGCACGAACCCCCCGTTCAGCCCGACCGCTGCGC
CTTATCCGGTAACTATCGTCTTGAGTCCAACCCGG
TAAGACACGACTTATCGCCACTGGCAGCAGCCACT
GGTAACAGGATTAGCAGAGCGAGGTATGTAGGCGG
TGCTACAGAGTTCTTGAAGTGGTGGCCTAACTACG
GCTACACTAGAAGAACAGTATTTGGTATCTGCGCT
CTGCTGAAGCCAGTTACCTTCGGAAAAAGAGTTGG
TAGCTCTTGATCCGGCAAACAAACCACCGCTGGTA
GCGGTGGTTTTTTGTTTGCAAGCAGCAGATTACG
CGCAGAAAAAAGGATCTCAAGAAGATCCTTTGAT
CTTTTCTACGGGGTCTGACGCTCAGTGGAACGAAA
ACTCACGTTAAGGGATTTTGGTCATGAGATTATCA
AAAAGGATCTTCACCTAGATCCTTTTAAATTAAAA
ATGAAGTTTTAAATCAATCTAAAGTATATATGAGT
AAACTTGGTCTGACAGTTACCAATGCTTAATCAGT
GAGGCACCTATCTCAGCGATCTGTCTATTTCGTTC
ATCCATAGTTGCCTGACTCCCCGTCGTGTAGATAA
CTACGATACGGGAGGGCTTACCATCTGGCCCCAGT
GCTGCAATGATACCGCGAGACCCACGCTCACCGGC
TCCAGATTTATCAGCAATAAACCAGCCAGCCGGAA
GGGCCGAGCGCAGAAGTGGTCCTGCAACTTTATCC
GCCTCCATCCAGTCTATTAATTGTTGCCGGGAAGC
TAGAGTAAGTAGTTCGCCAGTTAATAGTTTGCGCA
ACGTTGTTGCCATTGCTACAGGCATCGTGGTGTCA
CGCTCGTCGTTTGGTATGGCTTCATTCAGCTCCGG
TTCCCAACGATCAAGGCGAGTTACATGATCCCCCA
TGTTGTGCAAAAAAGCGGTTAGCTCCTTCGGTCCT
CCGATCGTTGTCAGAAGTAAGTTGGCCGCAGTGTT
ATCACTCATGGTTATGGCAGCACTGCATAATTCTC
TTACTGTCATGCCATCCGTAAGATGCTTTTCTGTG
ACTGGTGAGTACTCAACCAAGTCATTCTGAGAATA
GTGTATGCGGCGACCGAGTTGCTCTTGCCCGGCGT
CAATACGGGATAATACCGCGCCACATAGCAGAACT
TTAAAAGTGCTCATCATTGGAAAACGTTCTTCGGG
GCGAAAACTCTCAAGGATCTTACCGCTGTTGAGAT
CCAGTTCGATGTAACCCACTCGTGCACCCAACTGA
TCTTCAGCATCTTTTACTTTCACCAGCGTTTCTGG
GTGAGCAAAAACAGGAAGGCAAAATGCCGCAAAAA
AGGGAATAAGGGCGACACGGAAATGTTGAATACTC
ATACTCTTCCTTTTTCAATATTATTGAAGCATTTA
TCAGGGTTATTGTCTCATGAGCGGATACATATTTG
AATGTATTTAGAAAAATAAACAAATAGGGGTTCCG
CGCACATTTCCCCGAAAAGTGCCACCTGACGTCTA
AGAAACCATTATTATCATGACATTAACCTATAAAA
ATAGGCGTATCACGAGGCCCTTTCGTCTCGCGCGT
TTCGGTGATGACGGTGAAAACCTCTGACACATGCA
GCTCCCGGAGACGGTCACAGCTTGTCTGTAAGCGG
ATGCCGGGAGCAGACAAGCCCGTCAGGGCGCGTCA
GCGGGTGTTGGCGGGTGTCGGGGCTGGCTTAACTA
TGCGGCATCAGAGCAGATTGTACTGAGAGTGCACC
ATAAAATTGTAAACGTTAATATTTTGTTAAAATTC
GCGTTAAATTTTGTTAAATCAGCTCATTTTTTAA
CCAATAGGCCGAAATCGGCAAAATCCCTTATAAAT
CAAAAGAATAGCCCGAGATAGGGTTGAGTGTTGTT
CCAGTTTGGAACAAGAGTCCACTATTAAAGAACGT
GGACTCCAACGTCAAAGGGCGAAAAACCGTCTATC
AGGGCGATGGCCCACTACGTGAACCATCACCCAAA
TCAAGTTTTTTGGGGTCGAGGTGCCGTAAAGCACT
AAATCGGAACCCTAAAGGGAGCCCCCGATTTAGAG
CTTGACGGGGAAAGCCGGCGAACGTGGCGAGAAAG
GAAGGGAAGAAAGCGAAAGGAGCGGGCGCTAAGGC
GCTGGCAAGTGTAGCGGTCACGCTGCGCGTAACCA
CCACACCCGCCGCGCTTAATGCGCCGCTACAGGGC
GCGTACTATGGTTGCTTTGACGTATGCGGTGTGAA
ATACCGCACAGATGCGTAAGGAGAAAATACCGCAT
CAGGCGCC
```

An exemplary 3' AAV vector sequence comprising the 3' isolated nucleic acid of the dual AAV vector system encoding full-length NF1 protein is set forth in SEQ ID NO: 15:

```
CCTGCAGGCAGCTGCGCGCTCGCTCGCTCACTGAG
GCCGCCCGGGCAAAGCCCGGGCGTCGGGCGACCTT
TGGTCGCCCGGCCTCAGTGAGCGAGCGAGCGCGCA
GAGAGGGAGTGGCCAACTCCATCACTAGGGGTTCC
TGCGGCCAGATCTGCAAATTAGGACCGAGAGTCAG
TGGCCGCTCAAGAGTCTGTGACCATGCCCCAAATT
CAGAGATGGTCCCAGGAGAGATGGGGGGAACTGCC
```

-continued

AAGCAATGAGTGACCGGTTCCCCCTCCCCCAGGTG
GTTAGCCAGCGTTTCCCTCAGAACAGCATCGGTGC
AGTAGGAAGTGCCATGTTCCTCAGATTTATCAATC
CTGCCATTGTCTCACCGTATGAAGCAGGGATTTTA
GATAAAAAGCCACCACCTAGAATCGAAAGGGCTT
GAAGTTAATGTCAAAGATACTTCAGAGTATTGCCA
ATCATGTTCTCTTCACAAAAGAAGAACATATGCGG
CCTTTCAATGATTTTGTGAAAAGCAACTTTGATGC
AGCACGCAGGTTTTTCCTTGATATAGCATCTGATT
GTCCTACAAGTGATGCAGTAAATCATAGTCTTTCC
TTCATAAGTGACGGCAATGTGCTTGCTTTACATCG
TCTACTCTGGAACAATCAGGAGAAAATTGGGCAGT
ATCTTTCCAGCAACAGGGATCATAAAGCTGTTGGA
AGACGACCTTTTGATAAGATGGCAACACTTCTTGC
ATACCTGGGTCCTCCAGAGCACAAACCTGTGGCAG
ATACACACTGGTCCAGCCTTAACCTTACCAGTTCA
AAGTTTGAGGAATTTATGACTAGGCATCAGGTACA
TGAAAAGAAGAATTCAAGGCTTTGAAAACGTTAA
GTATTTCTACCAAGCTGGGACTTCCAAAGCTGGG
AATCCTATTTTTTATTATGTTGCACGGAGGTTCAA
AACTGGTCAAATCAATGGTGATTTGCTGATATACC
ATGTCTTACTGACTTTAAAGCCATATTATGCAAAG
CCATATGAAATTGTAGTGGACCTTACCCATACCGG
GCCTAGCAATCGCTTTAAAACAGACTTTCTCTCTA
AGTGGTTTGTTGTTTTCCTGGCTTTGCTTACGAC
AACGTCTCCGCAGTCTATATCTATAACTGTAACTC
CTGGGTCAGGGAGTACACCAAGTATCATGAGCGGC
TGCTGACTGGCCTCAAAGGTAGCAAAAGGCTTGTT
TTCATAGACTGTCCTGGGAAACTGGCTGAGCACAT
AGAGCATGAACAACAGAAACTACCTGCTGCCACCT
TGGCTTTAGAAGAGGACCTGAAGGTATTCCACAAT
GCTCTCAAGCTAGCTCACAAAGACACCAAAGTTTC
TATTAAAGTTGGTTCTACTGCTGTCCAAGTAACTT
CAGCAGAGCGAACAAAAGTCCTAGGGCAATCAGTC
TTTCTAAATGACATTTATTATGCTTCGGAAATTGA
AGAAATCTGCCTAGTAGATGAGAACCAGTTCACCT
TAACCATTGCAAACCAGGGCACGCCGCTCACCTTC
ATGCACCAGGAGTGTGAAGCCATTGTCCAGTCTAT
CATTCATATCCGGACCCGCTGGGAACTGTCACAGC
CCGACTCTATCCCCCAACACACCAAGATTCGGCCA
AAAGATGTCCCTGGGACACTGCTCAATATCGCATT

-continued

ACTTAATTTAGGCAGTTCTGACCCGAGTTTACGGT
CAGCTGCCTATAATCTTCTGTGTGCCTTAACTTGT
ACCTTTAATTTAAAAATCGAGGGCCAGTTACTAGA
GACATCAGGTTTATGTATCCCTGCCAACAACACCC
TCTTTATTGTCTCTATTAGTAAGACACTGGCAGCC
AATGAGCCACACCTCACGTTAGAATTTTTGGAAGA
GTGTATTTCTGGATTTAGCAAATCTAGTATTGAAT
TGAAACACCTTTGTTTGGAATACATGACTCCATGG
CTGTCAAATCTAGTTCGTTTTTGCAAGCATAATGA
TGATGCCAAACGACAAAGAGTTACTGCTATTCTTG
ACAAGCTGATAACAATGACCATCAATGAAAAACAG
ATGTACCCATCTATTCAAGCAAAATATGGGGAAG
CCTTGGGCAGATTACAGATCTGCTTGATGTTGTAC
TAGACAGTTTCATCAAAACCAGTGCAACAGGTGGC
TTGGGATCAATAAAAGCTGAGGTGATGGCAGATAC
TGCTGTAGCTTTGGCTTCTGGAAATGTGAAATTGG
TTTCAAGCAAGGTTATTGGAAGGATGTGCAAAATA
ATTGACAAGACATGCTTATCTCCAACTCCTACTTT
AGAACAACATCTTATGTGGGATGATATTGCTATTT
TAGCACGCTACATGCTGATGCTGTCCTTCAACAAT
TCCCTTGATGTGGCAGCTCATCTTCCCTACCTCTT
CCACGTTGTTACTTTCTTAGTAGCCACAGGTCCGC
TCTCCCTTAGAGCTTCCACACATGGACTGGTCATT
AATATCATTCACTCTCTGTGTACTTGTTCACAGCT
TCATTTTAGTGAAGAGACCAAGCAAGTTTTGAGAC
TCAGTCTGACAGAGTTCTCATTACCCAAATTTTAC
TTGCTGTTTGGCATTAGCAAAGTCAAGTCAGCTGC
TGTCATTGCCTTCCGTTCCAGTTACCGGGACAGGT
CATTCTCCTGGCTCCTATGAGAGAGAGACTTTT
GCTTTGACATCCTTGGAAACAGTCACAGAAGCTTT
GTTGGAGATCATGGAGGCATGCATGAGAGATATTC
CAACGTGCAAGTGGCTGGACCAGTGGACAGAACTA
GCTCAAAGATTTGCATTCCAATATAATCCATCCCT
GCAACCAAGAGCTCTTGTTGTCTTTGGGTGTATTA
GCAAACGAGTGTCTCATGGGCAGATAAAGCAGATA
ATCCGTATTCTTAGCAAGGCACTTGAGAGTTGCTT
AAAAGGACCTGACACTTACAACAGTCAAGTTCTGA
TAGAAGCTACAGTAATAGCACTAACCAAATTACAG
CCACTTCTTAATAAGGACTCGCCTCTGCACAAAGC
CCTCTTTTGGGTAGCTGTGGCTGTGCTGCAGCTTG

```
ATGAGGTCAACTTGTATTCAGCAGGTACCGCACTT
CTTGAACAAAACCTGCATACTTTAGATAGTCTCCG
TATATTCAATGACAAGAGTCCAGAGGAAGTATTTA
TGGCAATCCGGAATCCTCTGGAGTGGCACTGCAAG
CAAATGGATCATTTTGTTGGACTCAATTTCAACTC
TAACTTTAACTTTGCATTGGTTGGACACCTTTTAA
AAGGGTACAGGCATCCTTCACCTGCTATTGTTGCA
AGAACAGTCAGAATTTTACATACACTACTAACTCT
GGTTAACAAACACAGAAATTGTGACAAATTTGAAG
TGAATACACAGAGCGTGGCCTACTTAGCAGCTTTA
CTTACAGTGTCTGAAGAAGTTCGAAGTCGCTGCAG
CCTAAAACATAGAAAGTCACTTCTTCTTACTGATA
TTTCAATGGAAAATGTTCCTATGGATACATATCCC
ATTCATCATGGTGACCCTTCCTATAGGACACTAAA
GGAGACTCAGCCATGGTCCTCTCCCAAAGGTTCTG
AAGGATACCTTGCAGCCACCTATCCAACTGTCGGC
CAGACCAGTCCCCGAGCCAGGAAATCCATGAGCCT
GGACATGGGCAACCTTCTCAGGCCAACACTAAGA
AGTTGCTTGGAACAAGGAAAAGTTTTGATCACTTG
ATATCAGACACAAAGGCTCCTAAAAGGCAAGAAAT
GGAATCAGGGATCACAACACCCCCAAAATGAGGA
GAGTAGCAGAAACTGATTATGAAATGGAAACTCAG
AGGATTTCCTCATCACAACAGCACCCACATTTACG
TAAAGTTTCAGTGTCTGAATCAAATGTTCTCTTGG
ATGAAGAAGTACTTACTGATCCGAAGATCCAGGCG
CTGCTTCTTACTGTTCTAGCTACACTGGTAAAATA
TACCACAGATGAGTTTGATCAACGAATTCTTTATG
AATACTTAGCAGAGGCCAGTGTTGTGTTTCCCAAA
GTCTTTCCTGTTGTGCATAATTTGTTGGACTCTAA
GATCAACACCCTGTTATCATTGTGCCAAGATCCAA
ATTTGTTAAATCCAATCCATGGAATTGTGCAGAGT
GTGGTGTACCATGAAGAATCCCCACCACAATACCA
AACATCTTACCTGCAAAGTTTTGGTTTTAATGGCT
TGTGGCGGTTTGCAGGACCGTTTTCAAAGCAAACA
CAAATTCCAGACTATGCTGAGCTTATTGTTAAGTT
TCTTGATGCCTTGATTGACACGTACCTGCCTGGAA
TTGATGAAGAAACCAGTGAAGAATCCCTCCTGACT
CCCACATCTCCTTACCCTCCTGCACTGCAGAGCCA
GCTTAGTATCACTGCCAACCTTAACCTTTCTAATT
CCATGACCTCACTTGCAACTTCCCAGCATTCCCCA
GGAATCGACAAGGAGAACGTTGAACTCTCCCCTAC
CACTGGCCACTGTAACAGTGGACGAACTCGCCACG
GATCCGCAAGCCAAGTGCAGAAGCAAAGAAGCGCT
GGCAGTTTCAAACGTAATAGCATTAAGAAGATCGT
GGAGCGGCCGCTTCGAGCAGACATGATAAGATACA
TTGATGAGTTTGGACAAACCACAACTAGAATGCAG
TGAAAAAAATGCTTTATTTGTGAAATTTGTGATGC
TATTGCTTTATTTGTAACCATTATAAGCTGCAATA
AACAAGTTAACAACAACAATTGCATTCATTTTATG
TTTCAGGTTCAGGGGAGATGTGGGAGGTTTTTTA
AAGCAAGTAAAACCTCTACAAATGTGGTAAAATCG
ATAGGCCGCAGGAACCCCTAGTGATGGAGTTGGCC
ACTCCCTCTCTGCGCGCTCGCTCGCTCACTGAGGC
CGGGCGACCAAAGGTCGCCCGACGCCCGGGCGGCC
TCAGTGAGCGAGCGAGCGCGCAGCTGCCTGCAGGA
CATGTGAGCAAAAGGCCAGCAAAAGGCCAGGAACC
GTAAAAAGGCCGCGTTGCTGGCGTTTTTCCATAGG
CTCCGCCCCCCTGACGAGCATCACAAAAATCGACG
CTCAAGTCAGAGGTGGCGAAACCCGACAGGACTAT
AAAGATACCAGGCGTTTCCCCCTGGAAGCTCCCTC
GTGCGCTCTCCTGTTCCGACCCTGCCGCTTACCGG
ATACCTGTCCGCCTTTCTCCCTTCGGGAAGCGTGG
CGCTTTCTCATAGCTCACGCTGTAGGTATCTCAGT
TCGGTGTAGGTCGTTCGCTCCAAGCTGGGCTGTGT
GCACGAACCCCCGTTCAGCCCGACCGCTGCGCCT
TATCCGGTAACTATCGTCTTGAGTCCAACCCGGTA
AGACACGACTTATCGCCACTGGCAGCAGCCACTGG
TAACAGGATTAGCAGAGCGAGGTATGTAGGCGGTG
CTACAGAGTTCTTGAAGTGGTGGCCTAACTACGGC
TACACTAGAAGAACAGTATTTGGTATCTGCGCTCT
GCTGAAGCCAGTTACCTTCGGAAAAAGAGTTGGTA
GCTCTTGATCCGGCAAACAAACCACCGCTGGTAGC
GGTGGTTTTTTTGTTTGCAAGCAGCAGATTACGCG
CAGAAAAAAAGGATCTCAAGAAGATCCTTTGATCT
TTTCTACGGGGTCTGACGCTCAGTGGAACGAAAAC
TCACGTTAAGGGATTTTGGTCATGAGATTATCAAA
AAGGATCTTCACCTAGATCCTTTTAAATTAAAAAT
GAAGTTTTAAATCAATCTAAAGTATATATGAGTAA
ACTTGGTCTGACAGTTACCAATGCTTAATCAGTGA
GGCACCTATCTCAGCGATCTGTCTATTTCGTTCAT
CCATAGTTGCCTGACTCCCCGTCGTGTAGATAACT
```

```
ACGATACGGGAGGGCTTACCATCTGGCCCCAGTGC
TGCAATGATACCGCGAGACCCACGCTCACCGGCTC
CAGATTTATCAGCAATAAACCAGCCAGCCGGAAGG
GCCGAGCGCAGAAGTGGTCCTGCAACTTTATCCGC
CTCCATCCAGTCTATTAATTGTTGCCGGGAAGCTA
GAGTAAGTAGTTCGCCAGTTAATAGTTTGCGCAAC
GTTGTTGCCATTGCTACAGGCATCGTGGTGTCACG
CTCGTCGTTTGGTATGGCTTCATTCAGCTCCGGTT
CCCAACGATCAAGGCGAGTTACATGATCCCCCATG
TTGTGCAAAAAAGCGGTTAGCTCCTTCGGTCCTCC
GATCGTTGTCAGAAGTAAGTTGGCCGCAGTGTTAT
CACTCATGGTTATGGCAGCACTGCATAATTCTCTT
ACTGTCATGCCATCCGTAAGATGCTTTTCTGTGAC
TGGTGAGTACTCAACCAAGTCATTCTGAGAATAGT
GTATGCGGCGACCGAGTTGCTCTTGCCCGGCGTCA
ATACGGGATAATACCGCGCCACATAGCAGAACTTT
AAAAGTGCTCATCATTGGAAAACGTTCTTCGGGGC
GAAAACTCTCAAGGATCTTACCGCTGTTGAGATCC
AGTTCGATGTAACCCACTCGTGCACCCAACTGATC
TTCAGCATCTTTTACTTTCACCAGCGTTTCTGGGT
GAGCAAAAACAGGAAGGCAAAATGCCGCAAAAAG
GGAATAAGGGCGACACGGAAATGTTGAATACTCAT
ACTCTTCCTTTTTCAATATTATTGAAGCATTTATC
AGGGTTATTGTCTCATGAGCGGATACATATTTGAA
TGTATTTAGAAAAATAAACAAATAGGGGTTCCGCG
CACATTTCCCCGAAAAGTGCCACCTGACGTCTAAG
AAACCATTATTATCATGACATTAACCTATAAAAAT
AGGCGTATCACGAGGCCCTTTCGTCTCGCGCGTTT
CGGTGATGACGGTGAAAACCTCTGACACATGCAGC
TCCCGGAGACGGTCACAGCTTGTCTGTAAGCGGAT
GCCGGGAGCAGACAAGCCCGTCAGGGCGCGTCAGC
GGGTGTTGGCGGGTGTCGGGGCTGGCTTAACTATG
CGGCATCAGAGCAGATTGTACTGAGAGTGCACCAT
AAAATTGTAAACGTTAATATTTTGTTAAAATTCGC
GTTAAATTTTGTTAAATCAGCTCATTTTTTAACC
AATAGGCCGAAATCGGCAAAATCCCTTATAAATCA
AAAGAATAGCCCGAGATAGGGTTGAGTGTTGTTCC
AGTTTGGAACAAGAGTCCACTATTAAAGAACGTGG
ACTCCAACGTCAAAGGGCGAAAAACCGTCTATCAG
GGCGATGGCCCACTACGTGAACCATCACCCAAATC
AAGTTTTTTGGGGTCGAGGTGCCGTAAAGCACTAA
ATCGGAACCCTAAAGGGAGCCCCCGATTTAGAGCT
TGACGGGGAAAGCCGGCGAACGTGGCGAGAAAGGA
AGGGAAGAAAGCGAAAGGAGCGGGCGCTAAGGCGC
TGGCAAGTGTAGCGGTCACGCTGCGCGTAACCACC
ACACCCGCCGCGCTTAATGCGCCGCTACAGGGCGC
GTACTATGGTTGCTTTGACGTATGCGGTGTGAAAT
ACCGCACAGATGCGTAAGGAGAAAATACCGCATCA
GGCGCC
```

An exemplary 3' AAV vector sequence comprising the 3' isolated nucleic acid of the dual AAV vector system encoding full-length NF1 protein with a HA tag is set forth in SEQ ID NO:31:

```
CCTGCAGGCAGCTGCGCGCTCGCTCGCTCACTGAG
GCCGCCCGGGCAAAGCCCGGGCGTCGGGCGACCTT
TGGTCGCCCGGCCTCAGTGAGCGAGCGAGCGCGCA
GAGAGGGAGTGGCCAACTCCATCACTAGGGGTTCC
TGCGGCCAGATCTGCAAATTAGGACCGAGAGTCAG
TGGCCGCTCAAGAGTCTGTGACCATGCCCCAAATT
CAGAGATGGTCCCAGGAGAGATGGGGGGAACTGCC
AAGCAATGAGTGACCGGTTCCCCCTCCCCCAGGTG
GTTAGCCAGCGTTTCCCTCAGAACAGCATCGGTGC
AGTAGGAAGTGCCATGTTCCTCAGATTTATCAATC
CTGCCATTGTCTCACCGTATGAAGCAGGGATTTTA
GATAAAAAGCCACCACCTAGAATCGAAAGGGGCTT
GAAGTTAATGTCAAAGATACTTCAGAGTATTGCCA
ATCATGTTCTCTTCACAAAAGAAGAACATATGCGG
CCTTTCAATGATTTTGTGAAAAGCAACTTTGATGC
AGCACGCAGGTTTTTCCTTGATATAGCATCTGATT
GTCCTACAAGTGATGCAGTAAATCATAGTCTTTCC
TTCATAAGTGACGGCAATGTGCTTGCTTTACATCG
TCTACTCTGGAACAATCAGGAGAAAATTGGGCAGT
ATCTTTCCAGCAACAGGGATCATAAAGCTGTTGGA
AGACGACCTTTTGATAAGATGGCAACACTTCTTGC
ATACCTGGGTCCTCCAGAGCACAAACCTGTGGCAG
ATACACACTGGTCCAGCCTTAACCTTACCAGTTCA
AAGTTTGAGGAATTTATGACTAGGCATCAGGTACA
TGAAAAGAAGAATTCAAGGCTTTGAAAACGTTAA
GTATTTTCTACCAAGCTGGGACTTCAAAGCTGGG
AATCCTATTTTTTATTATGTTGCACGGAGGTTCAA
AACTGGTCAAATCAATGGTGATTTGCTGATATACC
ATGTCTTACTGACTTTAAAGCCATATTATGCAAAG
```

-continued

CCATATGAAATTGTAGTGGACCTTACCCATACCGG

GCCTAGCAATCGCTTTAAAACAGACTTTCTCTCTA

AGTGGTTTGTTGTTTTTCCTGGCTTTGCTTACGAC

AACGTCTCCGCAGTCTATATCTATAACTGTAACTC

CTGGGTCAGGGAGTACACCAAGTATCATGAGCGGC

TGCTGACTGGCCTCAAAGGTAGCAAAAGGCTTGTT

TTCATAGACTGTCCTGGGAAACTGGCTGAGCACAT

AGAGCATGAACAACAGAAACTACCTGCTGCCACCT

TGGCTTTAGAAGAGGACCTGAAGGTATTCCACAAT

GCTCTCAAGCTAGCTCACAAAGACACCAAAGTTTC

TATTAAAGTTGGTTCTACTGCTGTCCAAGTAACTT

CAGCAGAGCGAACAAAAGTCCTAGGGCAATCAGTC

TTTCTAAATGACATTTATTATGCTTCGGAAATTGA

AGAAATCTGCCTAGTAGATGAGAACCAGTTCACCT

TAACCATTGCAAACCAGGGCACGCCGCTCACCTTC

ATGCACCAGGAGTGTGAAGCCATTGTCCAGTCTAT

CATTCATATCCGGACCCGCTGGGAACTGTCACAGC

CCGACTCTATCCCCCAACACACCAAGATTCGGCCA

AAAGATGTCCCTGGGACACTGCTCAATATCGCATT

ACTTAATTTAGGCAGTTCTGACCCGAGTTTACGGT

CAGCTGCCTATAATCTTCTGTGTGCCTTAACTTGT

ACCTTTAATTTAAAAATCGAGGGCCAGTTACTAGA

GACATCAGGTTTATGTATCCCTGCCAACAACACCC

TCTTTATTGTCTCTATTAGTAAGACACTGGCAGCC

AATGAGCCACACCTCACGTTAGAATTTTTGGAAGA

GTGTATTTCTGGATTTAGCAAATCTAGTATTGAAT

TGAAACACCTTTGTTTGGAATACATGACTCCATGG

CTGTCAAATCTAGTTCGTTTTTGCAAGCATAATGA

TGATGCCAAACGACAAAGAGTTACTGCTATTCTTG

ACAAGCTGATAACAATGACCATCAATGAAAAACAG

ATGTACCCATCTATTCAAGCAAAAATATGGGGAAG

CCTTGGGCAGATTACAGATCTGCTTGATGTTGTAC

TAGACAGTTTCATCAAAACCAGTGCAACAGGTGGC

TTGGGATCAATAAAAGCTGAGGTGATGGCAGATAC

TGCTGTAGCTTTGGCTTCTGGAAATGTGAAATTGG

TTTCAAGCAAGGTTATTGGAAGGATGTGCAAAATA

ATTGACAAGACATGCTTATCTCCAACTCCTACTTT

AGAACAACATCTTATGTGGGATGATATTGCTATTT

TAGCACGCTACATGCTGATGCTGTCCTTCAACAAT

TCCCTTGATGTGGCAGCTCATCTTCCCTACCTCTT

-continued

CCACGTTGTTACTTTCTTAGTAGCCACAGGTCCGC

TCTCCCTTAGAGCTTCCACACATGGACTGGTCATT

AATATCATTCACTCTCTGTGTACTTGTTCACAGCT

TCATTTTAGTGAAGAGACCAAGCAAGTTTTGAGAC

TCAGTCTGACAGAGTTCTCATTACCCAAATTTTAC

TTGCTGTTTGGCATTAGCAAAGTCAAGTCAGCTGC

TGTCATTGCCTTCCGTTCCAGTTACCGGGACAGGT

CATTCTCTCCTGGCTCCTATGAGAGAGAGACTTTT

GCTTTGACATCCTTGGAAACAGTCACAGAAGCTTT

GTTGGAGATCATGGAGGCATGCATGAGAGATATTC

CAACGTGCAAGTGGCTGGACCAGTGGACAGAACTA

GCTCAAAGATTTGCATTCCAATATAATCCATCCCT

GCAACCAAGAGCTCTTGTTGTCTTTGGGTGTATTA

GCAAACGAGTGTCTCATGGGCAGATAAAGCAGATA

ATCCGTATTCTTAGCAAGGCACTTGAGAGTTGCTT

AAAAGGACCTGACACTTACAACAGTCAAGTTCTGA

TAGAAGCTACAGTAATAGCACTAACCAAATTACAG

CCACTTCTTAATAAGGACTCGCCTCTGCACAAAGC

CCTCTTTTGGGTAGCTGTGGCTGTGCTGCAGCTTG

ATGAGGTCAACTTGTATTCAGCAGGTACCGCACTT

CTTGAACAAAACCTGCATACTTTAGATAGTCTCCG

TATATTCAATGACAAGAGTCCAGAGGAAGTATTTA

TGGCAATCCGGAATCCTCTGGAGTGGCACTGCAAG

CAAATGGATCATTTGTTGGACTCAATTTCAACTC

TAACTTTAACTTTGCATTGGTTGGACACCTTTTAA

AAGGGTACAGGCATCCTTCACCTGCTATTGTTGCA

AGAACAGTCAGAATTTTACATACACTACTAACTCT

GGTTAACAAACACAGAAATTGTGACAAATTTGAAG

TGAATACACAGAGCGTGGCCTACTTAGCAGCTTTA

CTTACAGTGTCTGAAGAAGTTCGAAGTCGCTGCAG

CCTAAAACATAGAAAGTCACTTCTTCTTACTGATA

TTTCAATGGAAAATGTTCCTATGGATACATATCCC

ATTCATCATGGTGACCCTTCCTATAGGACACTAAA

GGAGACTCAGCCATGGTCCTCTCCCAAAGGTTCTG

AAGGATACCTTGCAGCCACCTATCCAACTGTCGGC

CAGACCAGTCCCCGAGCCAGGAAATCCATGAGCCT

GGACATGGGCAACCTTCTCAGGCCAACACTAAGA

AGTTGCTTGGAACAAGGAAAAGTTTTGATCACTTG

ATATCAGACACAAAGGCTCCTAAAAGGCAAGAAAT

GGAATCAGGGATCACAACACCCCCCAAAATGAGGA

GAGTAGCAGAAACTGATTATGAAATGGAAACTCAG

AGGATTTCCTCATCACAACAGCACCCACATTTACG
TAAAGTTTCAGTGTCTGAATCAAATGTTCTCTTGG
ATGAAGAAGTACTTACTGATCCGAAGATCCAGGCG
CTGCTTCTTACTGTTCTAGCTACACTGGTAAAATA
TACCACAGATGAGTTTGATCAACGAATTCTTTATG
AATACTTAGCAGAGGCCAGTGTTGTGTTTCCCAAA
GTCTTTCCTGTTGTGCATAATTTGTTGGACTCTAA
GATCAACACCCTGTTATCATTGTGCCAAGATCCAA
ATTTGTTAAATCCAATCCATGGAATTGTGCAGAGT
GTGGTGTACCATGAAGAATCCCCACCACAATACCA
AACATCTTACCTGCAAAGTTTTGGTTTTAATGGCT
TGTGGCGGTTTGCAGGACCGTTTTCAAAGCAAACA
CAAATTCCAGACTATGCTGAGCTTATTGTTAAGTT
TCTTGATGCCTTGATTGACACGTACCTGCCTGGAA
TTGATGAAGAAACCAGTGAAGAATCCCTCCTGACT
CCCACATCTCCTTACCCTCCTGCACTGCAGAGCCA
GCTTAGTATCACTGCCAACCTTAACCTTTCTAATT
CCATGACCTCACTTGCAACTTCCCAGCATTCCCCA
GGAATCGACAAGGAGAACGTTGAACTCTCCCCTAC
CACTGGCCACTGTAACAGTGGACGAACTCGCCACG
GATCCGCAAGCCAAGTGCAGAAGCAAAGAAGCGCT
GGCAGTTTCAAACGTAATAGCATTAAGAAGATCGT
GTATCCGTATGATGTGCCGGATTATGCGTGAGCGG
CCGCTTCGAGCAGACATGATAAGATACATTGATGA
GTTTGGACAAACCACAACTAGAATGCAGTGAAAAA
AATGCTTTATTTGTGAAATTTGTGATGCTATTGCT
TTATTTGTAACCATTATAAGCTGCAATAAACAAGT
TAACAACAACAATTGCATTCATTTTATGTTTCAGG
TTCAGGGGAGATGTGGGAGGTTTTTTAAAGCAAG
TAAAACCTCTACAAATGTGGTAAAATCGATAGGCC
GCAGGAACCCCTAGTGATGGAGTTGGCCACTCCCT
CTCTGCGCGCTCGCTCGCTCACTGAGGCCGGGCGA
CCAAAGGTCGCCCGACGCCCGGGCGGCCTCAGTGA
GCGAGCGAGCGCGCAGCTGCCTGCAGGACATGTGA
GCAAAAGGCCAGCAAAAGGCCAGGAACCGTAAAAA
GGCCGCGTTGCTGGCGTTTTTCCATAGGCTCCGCC
CCCCTGACGAGCATCACAAAAATCGACGCTCAAGT
CAGAGGTGGCGAAACCCGACAGGACTATAAAGATA
CCAGGCGTTTCCCCCTGGAAGCTCCCTCGTGCGCT
CTCCTGTTCCGACCCTGCCGCTTACCGGATACCTG

TCCGCCTTTCTCCCTTCGGGAAGCGTGGCGCTTTC
TCATAGCTCACGCTGTAGGTATCTCAGTTCGGTGT
AGGTCGTTCGCTCCAAGCTGGGCTGTGTGCACGAA
CCCCCCGTTCAGCCCGACCGCTGCGCCTTATCCGG
TAACTATCGTCTTGAGTCCAACCCGGTAAGACACG
ACTTATCGCCACTGGCAGCAGCCACTGGTAACAGG
ATTAGCAGAGCGAGGTATGTAGGCGGTGCTACAGA
GTTCTTGAAGTGGTGGCCTAACTACGGCTACACTA
GAAGAACAGTATTTGGTATCTGCGCTCTGCTGAAG
CCAGTTACCTTCGGAAAAAGAGTTGGTAGCTCTTG
ATCCGGCAAACAAACCACCGCTGGTAGCGGTGGTT
TTTTTGTTTGCAAGCAGCAGATTACGCGCAGAAAA
AAAGGATCTCAAGAAGATCCTTTGATCTTTTCTAC
GGGGTCTGACGCTCAGTGGAACGAAAACTCACGTT
AAGGGATTTTGGTCATGAGATTATCAAAAAGGATC
TTCACCTAGATCCTTTTAAATTAAAAATGAAGTTT
TAAATCAATCTAAAGTATATATGAGTAAACTTGGT
CTGACAGTTACCAATGCTTAATCAGTGAGGCACCT
ATCTCAGCGATCTGTCTATTTCGTTCATCCATAGT
TGCCTGACTCCCCGTCGTGTAGATAACTACGATAC
GGGAGGGCTTACCATCTGGCCCCAGTGCTGCAATG
ATACCGCGAGACCCACGCTCACCGGCTCCAGATTT
ATCAGCAATAAACCAGCCAGCCGGAAGGGCCGAGC
GCAGAAGTGGTCCTGCAACTTTATCCGCCTCCATC
CAGTCTATTAATTGTTGCCGGGAAGCTAGAGTAAG
TAGTTCGCCAGTTAATAGTTTGCGCAACGTTGTTG
CCATTGCTACAGGCATCGTGGTGTCACGCTCGTCG
TTTGGTATGGCTTCATTCAGCTCCGGTTCCCAACG
ATCAAGGCGAGTTACATGATCCCCCATGTTGTGCA
AAAAAGCGGTTAGCTCCTTCGGTCCTCCGATCGTT
GTCAGAAGTAAGTTGGCCGCAGTGTTATCACTCAT
GGTTATGGCAGCACTGCATAATTCTCTTACTGTCA
TGCCATCCGTAAGATGCTTTTCTGTGACTGGTGAG
TACTCAACCAAGTCATTCTGAGAATAGTGTATGCG
GCGACCGAGTTGCTCTTGCCCGGCGTCAATACGGG
ATAATACCGCGCCACATAGCAGAACTTTAAAAGTG
CTCATCATTGGAAAACGTTCTTCGGGGCGAAAACT
CTCAAGGATCTTACCGCTGTTGAGATCCAGTTCGA
TGTAACCCACTCGTGCACCCAACTGATCTTCAGCA
TCTTTTACTTTCACCAGCGTTTCTGGGTGAGCAAA
AACAGGAAGGCAAAATGCCGCAAAAAAGGGAATAA

```
GGGCGACACGGAAATGTTGAATACTCATACTCTTC

CTTTTTCAATATTATTGAAGCATTTATCAGGGTTA

TTGTCTCATGAGCGGATACATATTTGAATGTATTT

AGAAAAATAAACAAATAGGGGTTCCGCGCACATTT

CCCCGAAAAGTGCCACCTGACGTCTAAGAAACCAT

TATTATCATGACATTAACCTATAAAAATAGGCGTA

TCACGAGGCCCTTTCGTCTCGCGCGTTTCGGTGAT

GACGGTGAAAACCTCTGACACATGCAGCTCCCGGA

GACGGTCACAGCTTGTCTGTAAGCGGATGCCGGGA

GCAGACAAGCCCGTCAGGGCGCGTCAGCGGGTGTT

GGCGGGTGTCGGGGCTGGCTTAACTATGCGGCATC

AGAGCAGATTGTACTGAGAGTGCACCATAAAATTG

TAAACGTTAATATTTTGTTAAAATTCGCGTTAAAT

TTTTGTTAAATCAGCTCATTTTTTAACCAATAGGC

CGAAATCGGCAAAATCCCTTATAAATCAAAAGAAT

AGCCCGAGATAGGGTTGAGTGTTGTTCCAGTTTGG

AACAAGAGTCCACTATTAAAGAACGTGGACTCCAA

CGTCAAAGGGCGAAAAACCGTCTATCAGGGCGATG

GCCCACTACGTGAACCATCACCCAAATCAAGTTTT

TTGGGGTCGAGGTGCCGTAAAGCACTAAATCGGAA

CCCTAAAGGGAGCCCCCGATTTAGAGCTTGACGGG

GAAAGCCGGCGAACGTGGCGAGAAAGGAAGGGAAG

AAAGCGAAAGGAGCGGGCGCTAAGGCGCTGGCAAG

TGTAGCGGTCACGCTGCGCGTAACCACCACACCCG

CCGCGCTTAATGCGCCGCTACAGGGCGCGTACTAT

GGTTGCTTTGACGTATGCGGTGTGAAATACCGCAC

AGATGCGTAAGGAGAAAATACCGCATCAGGCGCC
```

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, and AAV10. In some embodiments, an AAV capsid protein is of a serotype derived from a non-human primate, for example AAVrh8 serotype. In some embodiments, the AAV capsid protein is of a serotype that has tropism for the CNS tissue of a subject, for example an AAV (e.g., AAV5, AAV6, AAV6.2, AAV7, AAV8, AAV9, AAVrh.8, AAVrh.10, AAV-Anc80, AAVrh.39 and AAVrh.43) that transduces neuron cells of a subject more efficiently than other AAV capsid proteins. In some embodiments, an AAV capsid protein is of an AAV9 serotype. In some embodiments, the AAV capsid is of AAV9.PHP.eB. In some embodiments, the AAV capsid is of AAV9.PHP.B. In some embodiments, an AAV capsid protein is a chimeric capsid protein. In some embodiments, the AAV capsid protein is AAV-DJ. In some embodiments, the AAV capsid protein is AAV-Anc80.

In some embodiments, the AAV capsid is of a serotype that has tropism to cells of the nervous system. In some embodiments, the AAV capsid is of a serotype that has tropism to cells of the central nervous system (CNS). In some embodiments, the AAV capsid is of a serotype that has tropism to cells of the peripheral nervous system. In some embodiments, the AAV capsid is of a serotype that has tropism for glial cells (e.g., satellite cells, Schwann cells). In some embodiments, the AAV capsid is of a serotype that has tropism for Schwann cells. In some embodiments, the AAV capsid is of a serotype that has tropism for neurons. In some embodiments, the AAV capsid is of a serotype that has tropism for benign neuron fibroma cells. In some embodiments, the AAV capsid is of a serotype that has tropism for optic glioma cells. In some embodiments, the AAV capsid is of a serotype that has tropism for malignant peripheral nerve sheath tumors cells.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence encoding a protein (e.g., a mini-NF1 protein). In some embodiments, the host cell is a mammalian cell (e.g., HEK293 cell, or MPNST cells) or an insect cell (e.g., SF9 cell). In some embodiments, the disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV plasmid (e.g., AAV vectors encoding mini-NF1 protein, or dual-AAV vectors encoding the full-length NF1 protein), an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

In some embodiments, the present disclosure provides a rAAV comprises the isolated nucleic acid encoding any of the mini-NF1 proteins; and an AAV capsid protein described herein. In some embodiments, the capsid protein is AAV-DJ capsid or AAV. PHP.eB In some embodiments, the present disclosure provides an A 5' recombinant adeno-associated virus (rAAV) comprising the 5' isolated nucleic acid encoding the first portion of an NF1 protein; and an AAV capsid protein. In some embodiments, the present disclosure provides an 3' recombinant adeno-associated virus (rAAV) comprising the 3' isolated nucleic acid encoding the second portion of an NF1 protein; and an AAV capsid protein. In some embodiments, the capsid protein is AAV-DJ capsid or AAV. PHP.eB.

Also provided herein, is a neurofibromin (NF1) expression system comprising: the 5' rAAV and the 3' rAAV as described herein. Upon co-infection of a target cell by both the 5' rAAV and the 3' rAAV, the two rAAV genomes would go through head to tail concatemerization from 3' ITR of the 5' isolated nucleic acid and 5' ITR of the 3' isolated nucleic acid such that the two isolated nucleic acids form one single AAV genome. After transcription, the mRNA comprises the NF1 first portion mRNA, splicing sites including the splicing donor, concactemerized ITR, and splicing acceptor, and NF1 second portion mRNA. The splicing sites can be removed by spliceosome via trans-splicing, thereby stitching the NF1 first portion mRNA and NF1 second portion mRNA to form a complete mRNA encoding a full-length NF1.

Methods

Methods for inhibiting Ras activity in a cell (e.g., MPNST cells) or in a subject in need thereof are provided herein. The methods typically involve administering to a subject in need thereof an effective amount of a rAAV comprising a nucleic acid for expressing a transgene (e.g., a mini-NF1 protein) in the subject. Alternatively, the methods involve administering to a subject in need thereof an effective amount of dual rAAVs comprising nucleic acids for expressing a full-length protein (e.g., full-length NF1 protein).

Methods for treating NF1 associated diseases in a subject are provided herein. The methods typically involve administering to a subject an amount (e.g., an effective amount) of a rAAV comprising a nucleic acid for expressing a transgene (e.g., a mini-NF1 protein) in the subject. Alternatively, the methods involve administering to a subject an amount (e.g., an effective amount) of dual rAAVs comprising nucleic acids for expressing a full-length protein (e.g., full-length NF1 protein). Non-limiting NF1 associated diseases include Neurofibromatosis Type I, Neurofibromatosis-Noonan Syndrome, juvenile myelomonocytic leukemia, or Watson syndrome. In some embodiments, the NF1-associated disease is Neurofibromatosis type I.

Methods for treating Neurofibromatosis type I in a subject are provided herein. The methods typically involve administering to a subject an amount (e.g., an effective amount) of a rAAV comprising a nucleic acid for expressing a transgene (e.g., a mini-NF1 protein) in the subject. Alternatively, the methods involve administering to a subject an amount (e.g., an effective amount) of dual rAAVs comprising nucleic acids for expressing a full-length protein (e.g., full-length NF1 protein). In some embodiments, the Neurofibromatosis type I includes skin lesions, bone deformities, benign neurofibroma, tumor on the optic nerve (e.g., optic glioma), malignant peripheral nerve sheath tumors (MPNST), and/or cognitive impairment.

Methods for preventing or treating cognitive impairment associated with NF1 are provided herein. Neurofibromatosis type 1 (NF1) is associated with cognitive dysfunctions in several domains such as executive functioning, language, visual perception, motor skills, social skills, memory and/or attention (see, e.g., Baudon et al., Can the Cognitive Phenotype in Neurofibromatosis Type 1 (NF1) Be Explained by Neuroimaging? A Review, Front. Neurol. 10:1373, which is incorporated herein by reference). The methods typical involve administering to a subject an amount (e.g., an effective amount) of a rAAV comprising a nucleic acid for expressing a transgene (e.g., a mini-NF1 protein) in the subject. Alternatively, the method involves administering to a subject an amount (e.g., an effective amount) of dual rAAVs comprising nucleic acids for expressing a full-length protein (e.g., full-length NF1 protein). In some embodiments, the administration results in the delivery of NF1 protein in the central nervous system (CNS). In some embodiments, the administration involves direct injection into the CNS (e.g., via intracranial injection, nerve injection, cerebral spinal fluid (CSF) injection via cerebral lateral ventricles, cisterna magna (CM) injection, intrathecal (IT) injection, or intracerebroventricular injection).

In some embodiments, the administration comprises direct injection into the CNS via intrathecal (IT) injection. In some embodiments, the administration comprises direct injection into the CNS via intracerebroventricular injection. In some embodiments, the administration comprises any methods that may be suitable for the method or the isolated nucleic acid disclosed herein.

An "effective amount" or "amount effective" of a rAAV is an amount sufficient to infect a sufficient number of cells of a target tissue in a subject. In some embodiments, a target tissue is nervous system (e.g., neuron cells having loss of function of NF1, etc.) tissue. In some embodiments, a transgene is delivered to neurons (e.g., peripheral neurons such as optic nerve).

An effective amount of a rAAV may be an amount sufficient to have a therapeutic benefit in a subject, e.g., to improve in the subject one or more symptoms of disease, e.g., a symptom of Neurofibromatosis type I (e.g., a disease associated with a mutation of NF1 gene). Examples of mutations in NF1 gene include those described by The Human Gene Mutation Database (HGMD, Institute of Medical Genetics, Cardiff, http://www.hgmd.org), by the Leiden Open Variation Database (LOVD), which are incorporated herein by reference. In some embodiments, the mutations in the NF1 gene include those described in Wu-Chou et al, Genetic diagnosis of neurofibromatosis type 1: targeted next-generation sequencing with Multiple Ligation-Dependent Probe Amplification analysis, Journal of Biomedical Science (2018) 25:72; Yang et al., The investigation for potential modifier genes in patients with neurofibromatosis type 1 based on next-generation sequencing, OncoTargets and Therapy 2018:11 919-932, which are incorporated herein by reference). The effective amount will depend on a variety of factors such as, for example, the species, age, weight, health of the subject, and the tissue to be targeted, and may thus vary among subject and tissue. An effective amount may also depend on the rAAV used.

In some embodiments, the administration results in reduction of tumor burden in a subject in need thereof by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control subject. In some embodiments, the control subject is a subject in need thereof who is not administered with the rAAV, the dual-AAV vector system, and/or the NF system. In some embodiments, the control subject is a healthy subject.

In some embodiments, the administration results in changes of molecular markers of NF1 signaling pathway. In some embodiments, the changes of the molecular markers of NF1 signaling pathway may reverse the pre-existing neurological deficits associated with NF1. In some embodiments, the changes of the molecular markers of NF1 signaling pathway may prevent neurological deficits associated with NF1. In some embodiments, the molecular markers of NF1 signaling pathway comprise at least pCREB, pSynapsinI, pERK1/2, pDARP32 and tyrosine hydroxylase (TH). In some embodiments, the administration results in an increase of pCREB. In some embodiments, the administration results in a decrease of pERK1/2. In some embodiments, the molecular markers of NF1 signaling pathway can comprise any biological markers that are known or unknown in the art.

In some embodiments, the administration results in changes of molecular markers of NF1 signaling pathway in a subject in need thereof by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a subject in need thereof who is not administered.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

Aspects of the disclosure relate to methods for treating Neurofibromatosis type I in a subject in need thereof. In some embodiments, a subject is a mammal, for example a human, mouse, rat, dog, cat, non-human primate, etc. In some embodiments, a subject is a human.

As used herein, the term "treating" refers to the application or administration of a composition (e.g., an isolated nucleic acid or rAAV as described herein) to a subject who exhibits one or more signs or symptoms of Neurofibromatosis type I (e.g., skin lesions, bone deformities, benign neurofibroma, tumor on the optic nerve (e.g., optic glioma), malignant peripheral nerve sheath tumors (MPNST), cognitive impairment, one or more mutations in an NF1 gene, etc.), with the purpose to cure, heal, alleviate, relieve, alter, remedy, ameliorate, improve, or affect the disorder, the symptom of the disease, or the predisposition toward Neurofibromatosis type I.

Alleviating Neurofibromatosis type I includes delaying the development or progression of the disease, or reducing disease severity. Alleviating the disease does not necessarily require curative results. As used therein, "delaying" the development of Neurofibromatosis type I means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

An effective amount may also depend on the mode of administration. For example, targeting a nervous tissue (e.g., peripheral neuron, etc.) tissue by intrastromal administration or subcutaneous injection may require different (e.g., higher or lower) doses, in some cases, than targeting a nervous tissue (e.g., peripheral neuron, etc.) by another method (e.g., systemic administration, topical administration). In some embodiments, intrastromal injection (IS) of rAAV having certain serotypes (e.g., AAV-DJ, AAV9, AAV1, AAVrh10, or AAV9.PHP.eB) mediates efficient transduction of a nervous tissue (e.g., peripheral neuron, etc.). Thus, in some embodiments, the injection is intrastromal injection (IS). In some embodiments, the administration is via injection, optionally via intratumoral injection, etc. In some embodiments, the injection is topical administration (e.g., topical administration to the skin lesion). In some cases, multiple doses of a rAAV are administered.

The rAAVs and/or the NF1 expression system may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs or the NF1 expression to a mammalian subject may be by, for example, local injection to the affected tissues (e.g., CNS, brain, skin, optical nerve, peripheral nerve tumor or optic glioma tissue). Combinations of administration methods (e.g., topical administration to the skin and injection to the optical nerve) can also be used.

The compositions of the disclosure may comprise administering a rAAV (e.g., a mini-NF1) alone, or in combination with one or more other viruses (e.g., a second rAAV encoding having one or more different transgenes, such as a transgene encoding a different mini-NF1 protein). In some embodiments, the method may comprise administering a NF1 expression system alone, or in combination with one or more other viruses (e.g., an additional rAAV encoding having one or more different transgenes, such as a transgene encoding a mini-NF1 protein). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline).

Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., nervous tissue, such as optical nerve, etc., tissue) and to provide sufficient levels of gene transfer and expression without undue adverse effects. Examples of pharmaceutically acceptable routes of administration include, but are not limited to, direct delivery to the selected organ (e.g., delivery to the optical nerve, skin or peripheral nerve tumors), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of a rAAV is an amount sufficient to target infect an animal, target a desired tissue. The effective amount will depend primarily on factors such as the species, age, weight, health of the subject, and the tissue to be targeted, and may thus vary among animal and tissue. For example, an effective amount of the rAAV is generally in the range of from about 1 mL to about 100 mL of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target diseased tissue (e.g., skin tissue). In some embodiments, a dose more concentrated than $10^9$ rAAV genome copies is toxic when administered to a subject. In some embodiments, an effective amount is produced by multiple doses of a rAAV.

In some embodiments, delivery of the NF1 expression system involves co-delivery of the 5' and the 3' rAAV such that the target cell can express a full-length NF1. In some embodiments, the effective amount of the NF1 expression system sufficient to infect a target cell may be higher than delivering a single rAAV. For example, an effective amount of the NF1 expression system may be in the range of from about 1 ml to about 100 ml of solution containing from about $10^{13}$ to $10^{16}$ genome copies for each of the 5' rAAV and the 3' rAAV. In some cases, a dosage between about $10^{11}$ to $10^{13}$ rAAV genome copies is appropriate. In some embodiments, an effective amount is produced by multiple doses of the 5' rAAV and the 3' rAAV.

In some embodiments, a dose of rAAV or the NF1 expression system is administered to a subject no more than once per calendar day (e.g., a 24-hour period). In some embodiments, a dose of rAAV or the NF1 expression system is administered to a subject no more than once per 2, 3, 4, 5, 6, or 7 calendar days. In some embodiments, a dose of rAAV or the NF1 expression system is administered to a subject no more than once per calendar week (e.g., 7 calendar days). In some embodiments, a dose of rAAV or the NF1 expression system is administered to a subject no more than bi-weekly (e.g., once in a two-calendar week period). In some embodiments, a dose of rAAV or the NF1 expression system is administered to a subject no more than once per calendar month (e.g., once in 30 calendar days). In some embodiments, a dose of rAAV or the NF1 expression system is administered to a subject no more than once per six calendar months. In some embodiments, a dose of rAAV or the NF1 expression system is administered to a subject no more than once per calendar year (e.g., 365 days or 366 days in a leap year).

In some embodiments, rAAV or the NF1 expression system compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

EXAMPLES

Example 1: Design and Testing of Gene Expression Constructs

Neurofibromatosis type I (NF1) is caused by sporadic or inherited germline mutations in the NF1 gene. Sporadic loss of the remaining wild-type allele is associated with skin lesions and benign neurofibromas, which develop along peripheral nerves. Malignant complications include optic pathway gliomas and malignant peripheral nerve sheath tumors (MPNST). In addition, NF1 haploinsufficiency can cause cognitive deficits and NF1 deficiency plays an important supporting role in tumor formation. Treatment options are limited. However, genetic interventions using recombinant adeno-associated virus (AAV) vectors and antisense oligonucleotide (ASO) drugs have begun to yield transformative outcomes in patients afflicted with other devastating inherited neurological diseases such as Spinal Muscular Atrophy. The NF1 protein is a GTPase-activating protein (GAP) that inactivates Ras through activation of GTP to GDP hydrolysis. Loss of NF1 GAP function leaves Ras in the activated state (Ras-GTP), which leads to over-activation of RAS signaling pathway (RAF-MEK-ERK). Ras activation stimulates cell growth and most often formation of benign tumors that often times progress to malignancies such as MPNSTs and optic gliomas. NF1 patients also show cognitive deficits, suggesting that NF1 plays an important role in normal neuronal function. The NF1 coding sequence is 8,540 bp, far exceeding the packaging capacity of recombinant AAV vectors. Two approaches were explored in order to restore normal NF1 function using AAV-mediated gene therapy. One is to develop a dual AAV vector system to restore full length NF1 expression through trans-splicing of genomes in transduced cells, and the other is to develop minimal NF1 proteins (mini-NF1) capable of regulating the Ras pathway, and at the same time, small enough to be packaged into a single AAV vector. The NF1 GAP-related domain (GRD) has been shown to be sufficient to restore normal growth of various $NF1^{-/-}$ cell types, including MPNSTs. It is possible that a mini-NF1 containing only the GRD domain and additional modifications is sufficient to restore regulation of Ras in MPNST cell lines (e.g., Bai et al., Feasibility of using NF1-GRD and AAV for gene replacement therapy, Gene Therapy volume 26, pages 277-286(2019)). In Bai et al, it was discovered that the most effective mini-NF1 was one where the GRD was fused to ten amino acids (GCMSCKCVLS (SEQ ID NO: 32)) from the H-Ras C-terminal. The present disclosure has taken a different approach to engineer a minimal NF1 gene by adding additional NF1 domains to the minimal GRD.

Figure 1B:
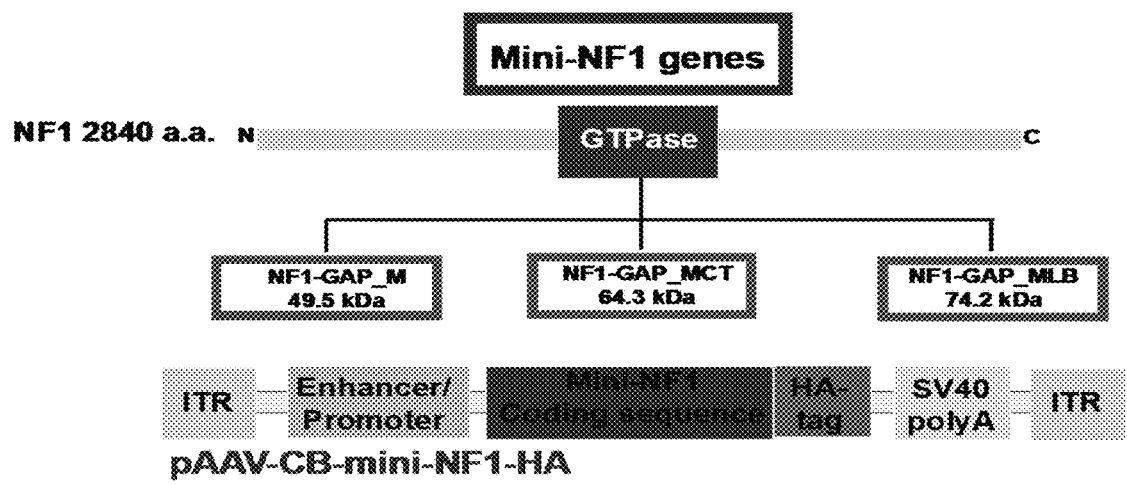
Figure 1C:
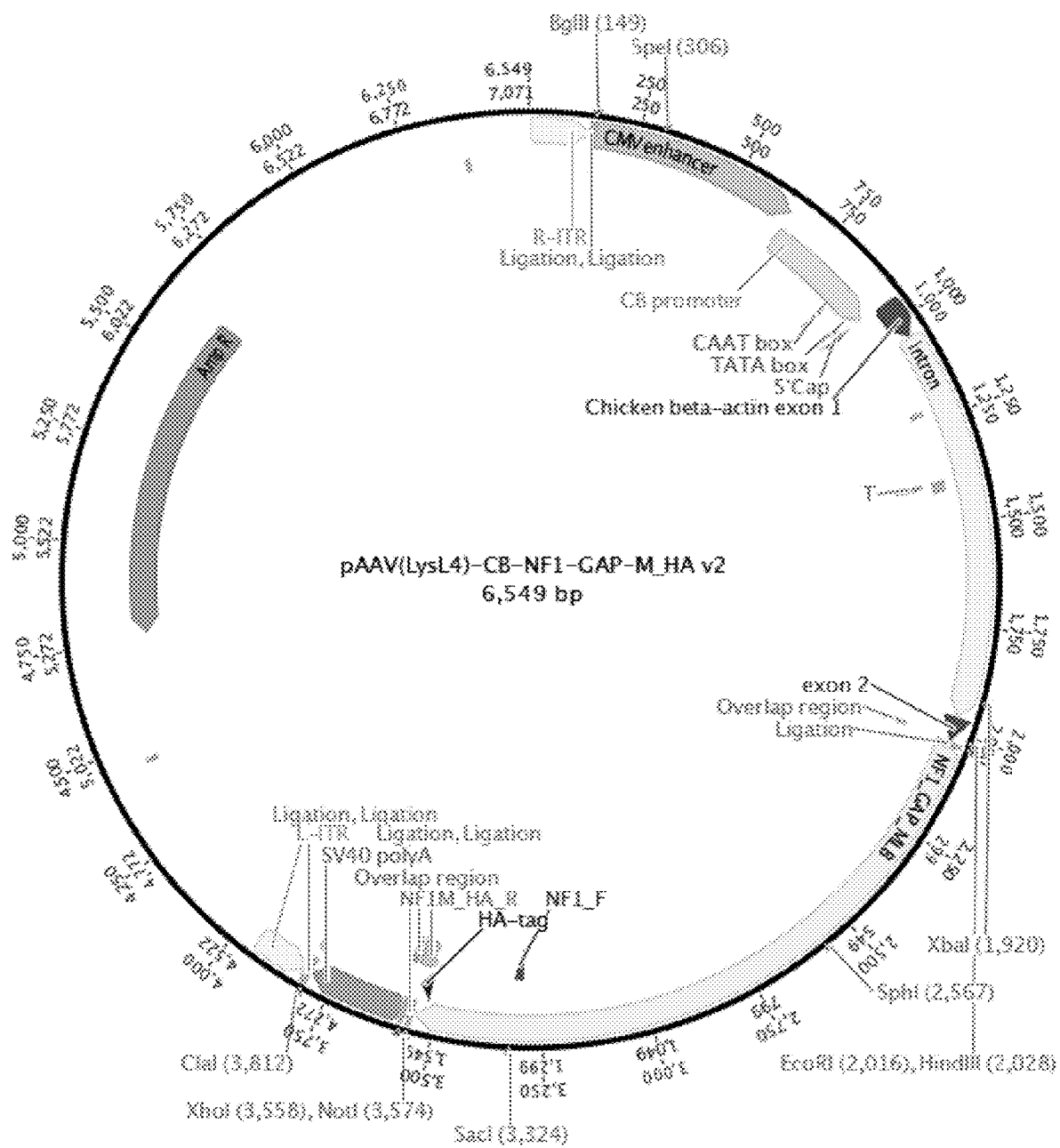
Figure 1D:
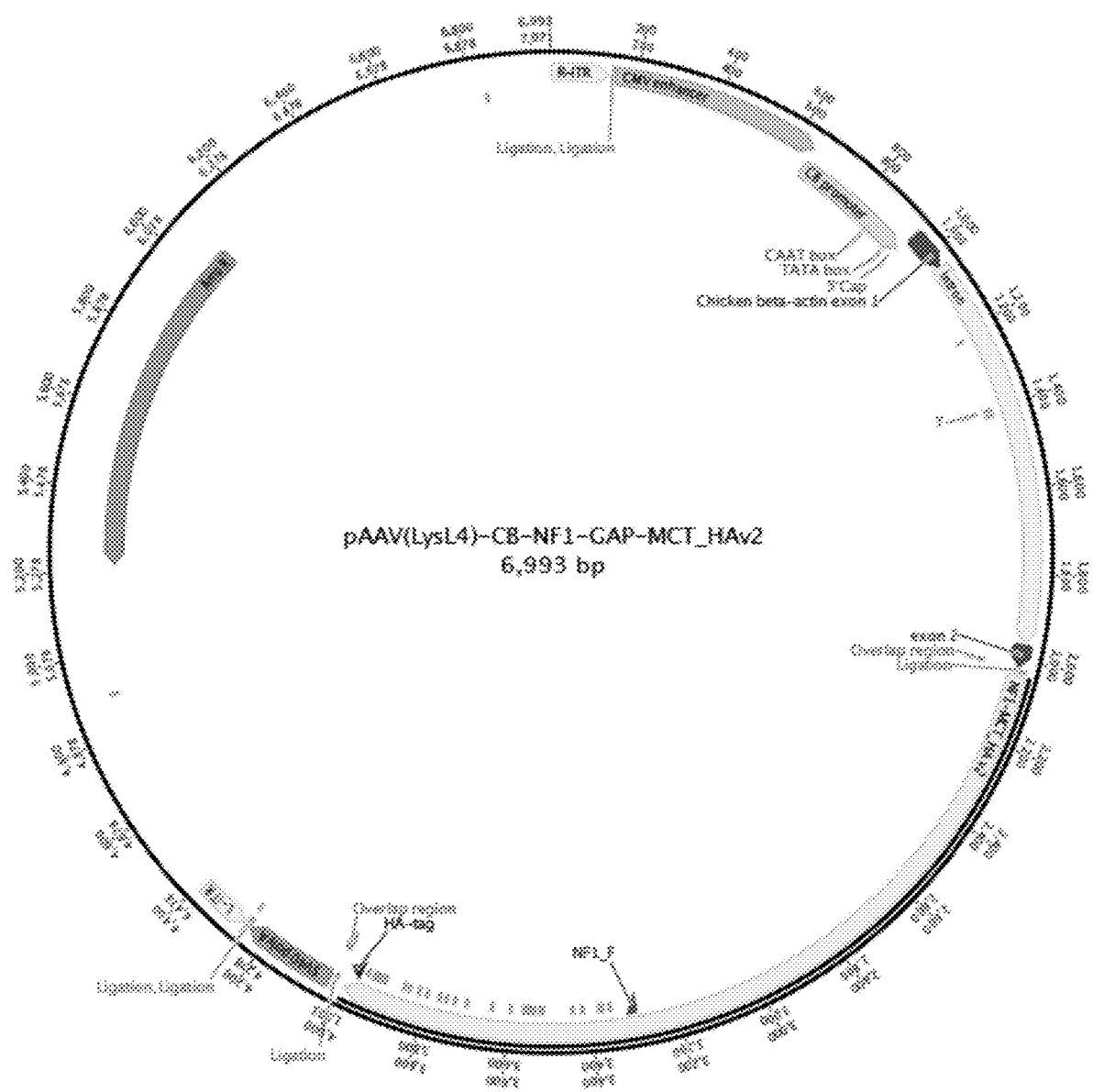
Figure 1E:
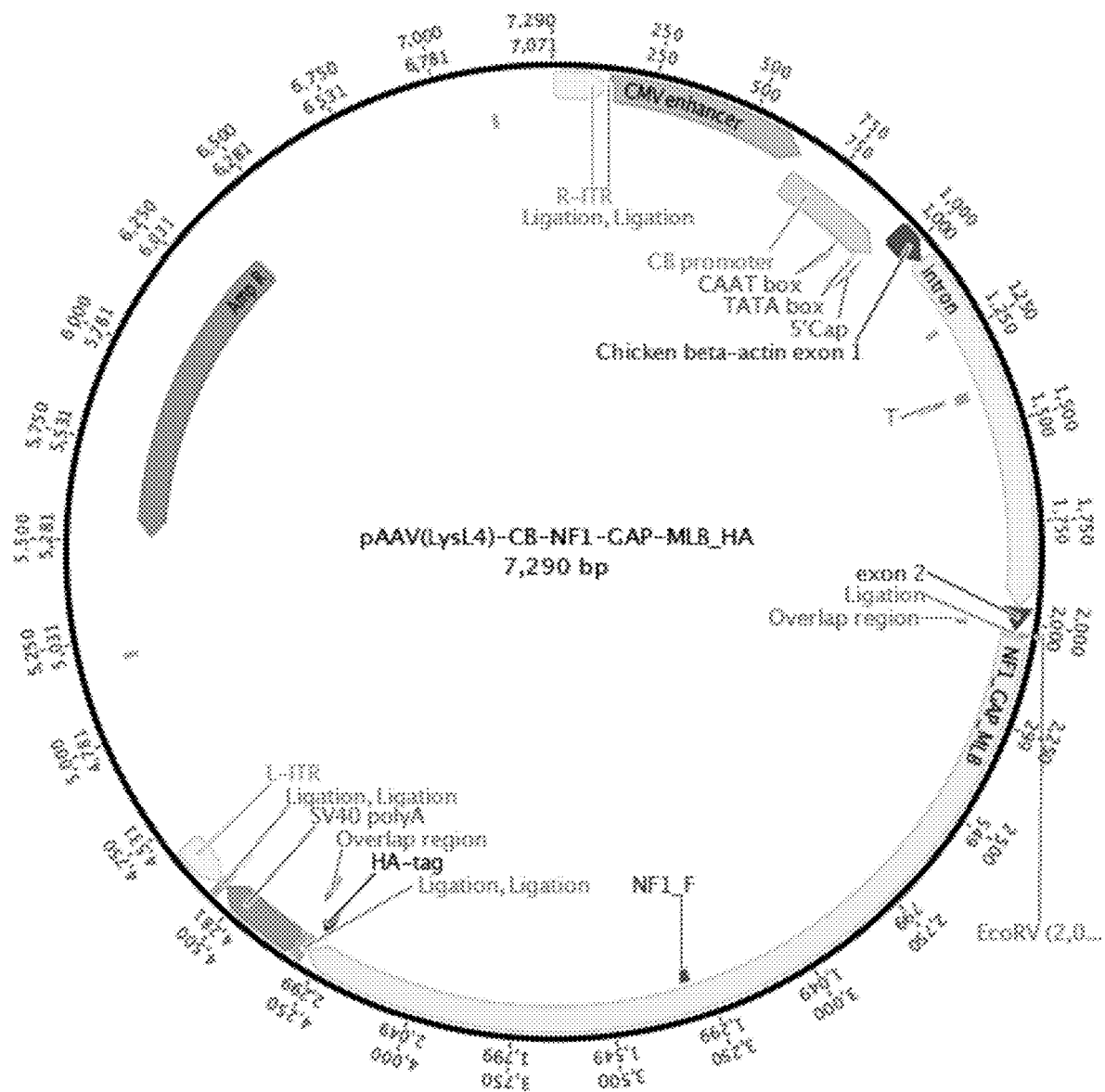
Figure 1F:
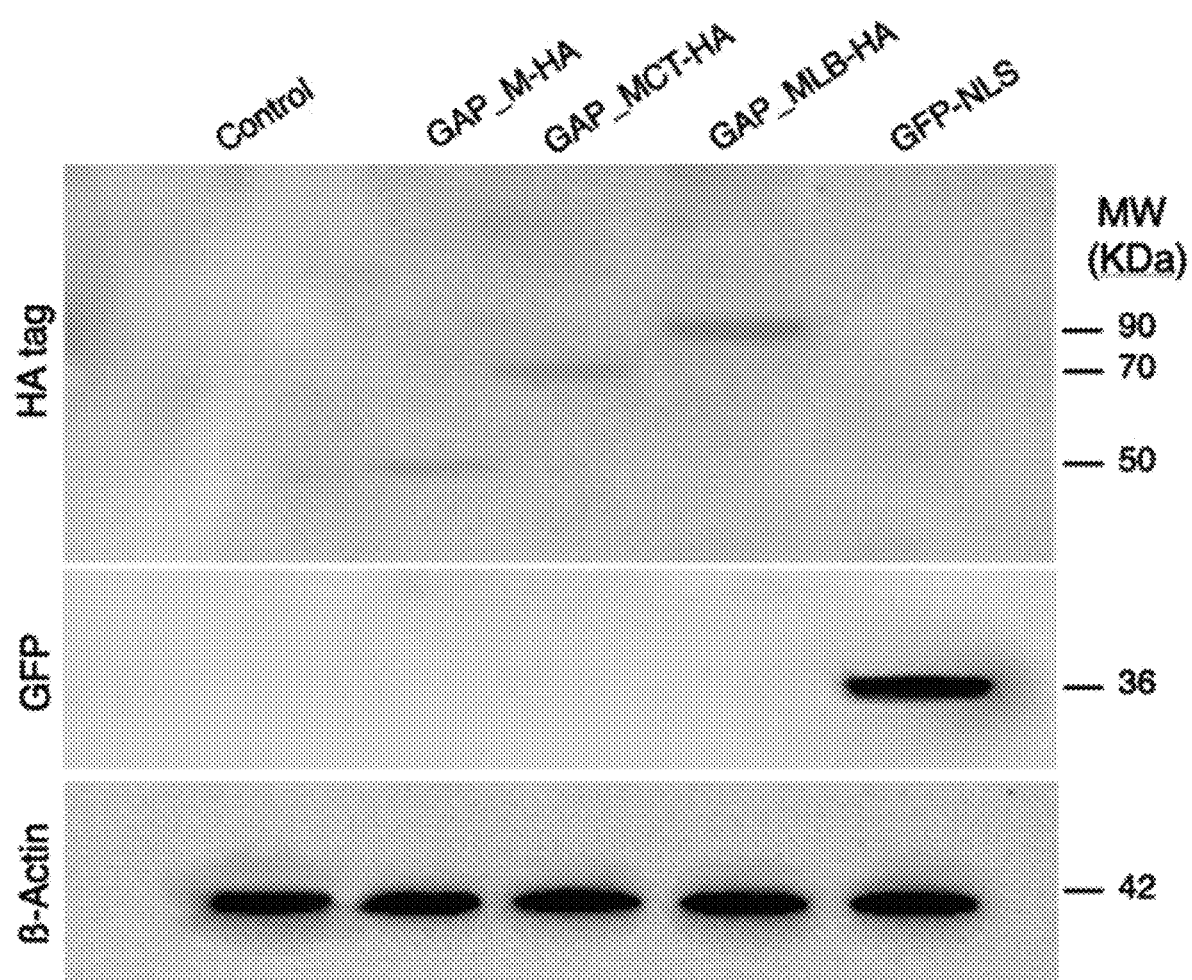

AAV vectors encoding three different mini-NF1 genes (FIG. 1A) were constructed: (i) a small version containing NF1-GRD only (NF1-GAP_M); (ii) a second version which extends the mini-NF1 coding sequence to the CRAL-TRIO domain (NF1-GAP_MCT); and (iii) a third version which extends the NF1 coding sequence to the end of the bipartite phospholipid binding domain (NF1-GAP_MLB), which is composed of a Sec14p homologous segment and a pleckstrin homology (PH)-like domain. All three mini-NF1 genes carry an HA-tag epitope fused to the C-terminus to allow detection by western blot and histologically. All three genes were codon optimized for expression in human cells, synthesized and cloned into a single stranded AAV vector genome driving gene expression from a CBA promoter, and an HA tag at the C-terminus (FIG. 1B). The lipid binding/interacting domains (CRAL-TRIO and bipartite Sec-PH) were included in the third mini-NF1 genes as interaction with Ras occurs at the cell membrane and lipid binding may be important for that interaction. AAV-DJ viron stocks were prepared and tested in HEK293T cells for protein expression. The rAAV vector maps encoding each of the mini-NF1 are show in FIGS. 1C-1E. As expected, 72 hours after infection, HEK293T cells transduced with AAV-DJ virons encoding HA-tagged NF1-GAP transgenes expressed HA-positive proteins of the expected sizes of ~50, 70 and 90 KDa. (FIG. 1F).

Figure 2A:
FIGS. 2A-2F show dual-AAV vector system for full-length NF1 expression.
Figure 2B:
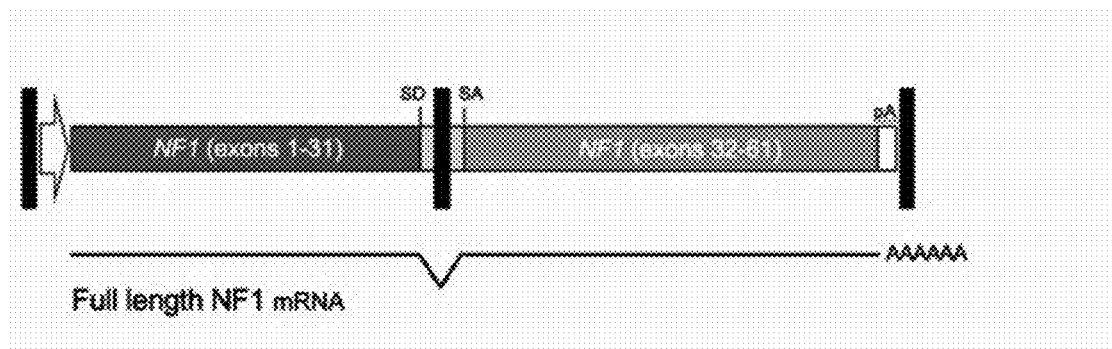
Figure 2C:
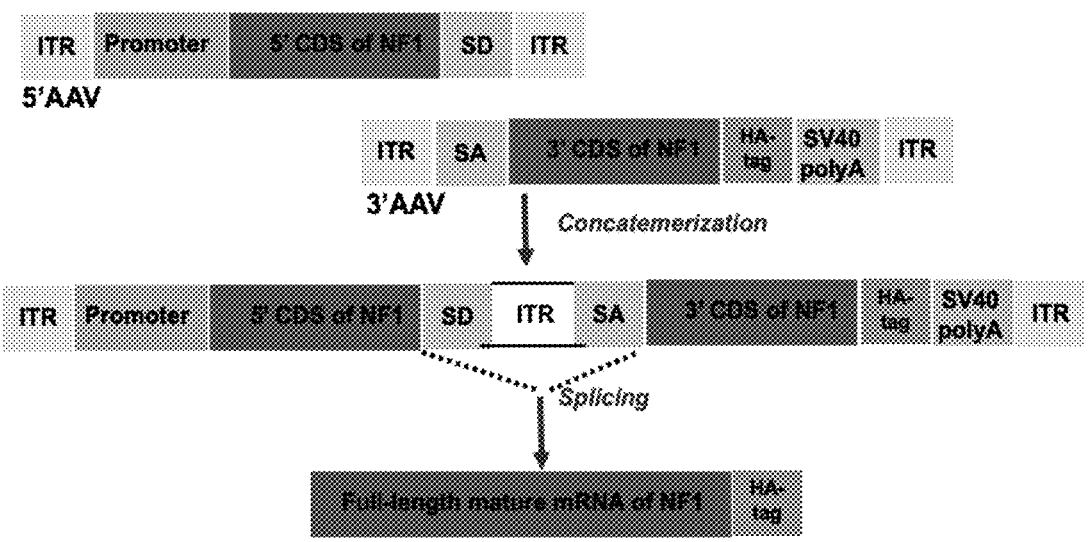
Figure 2D:
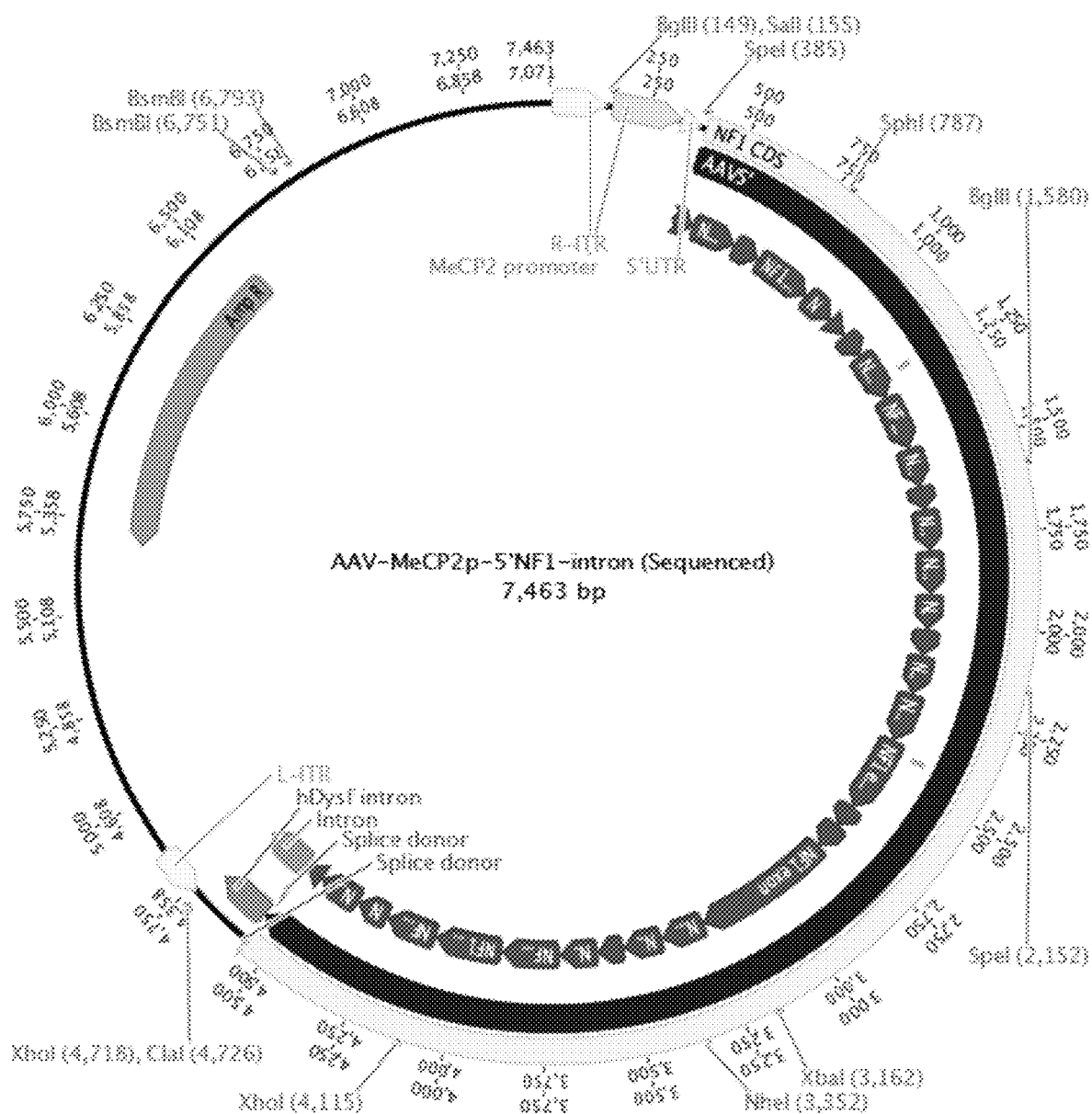
Figure 2E:
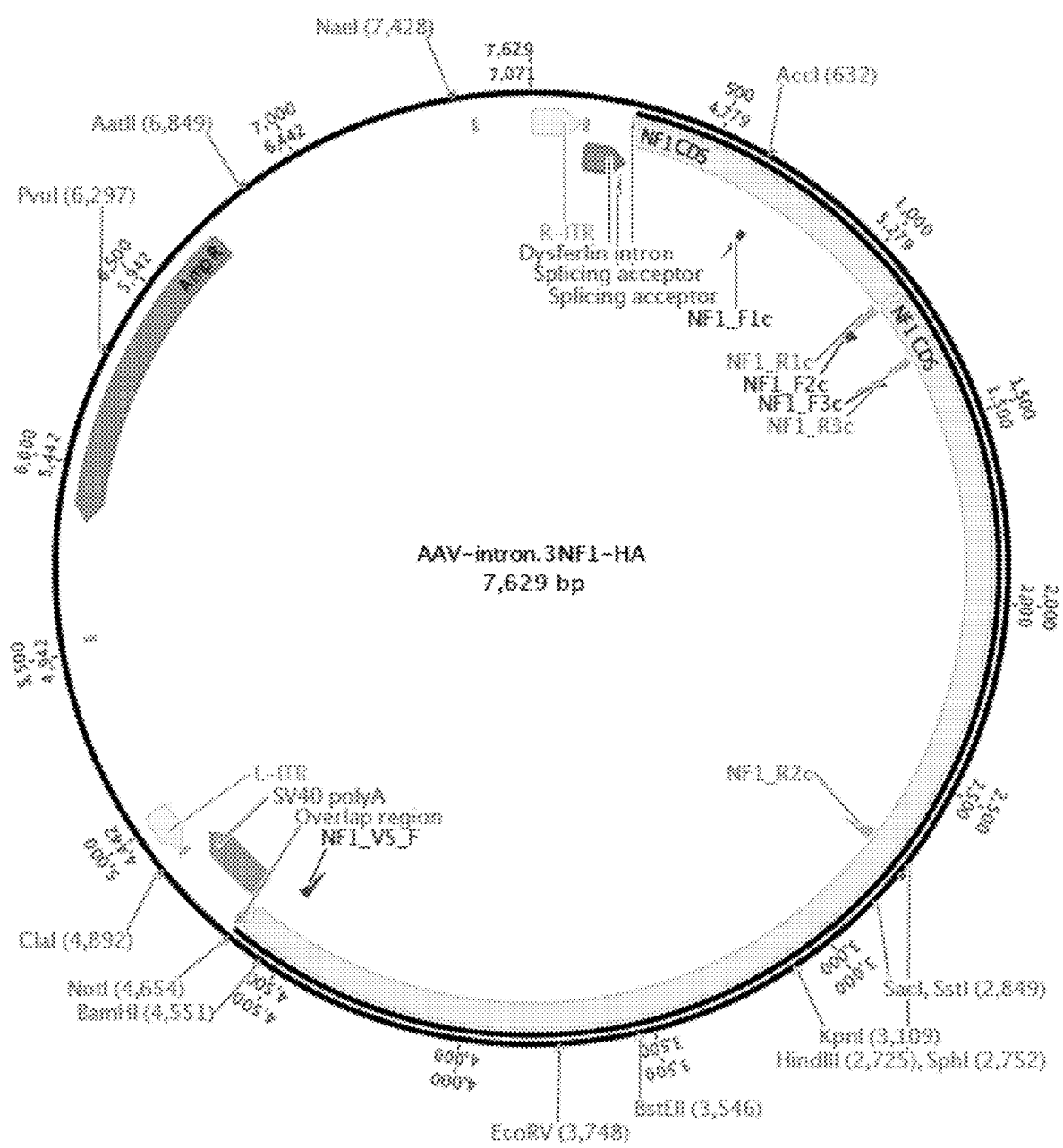
Figure 2F:
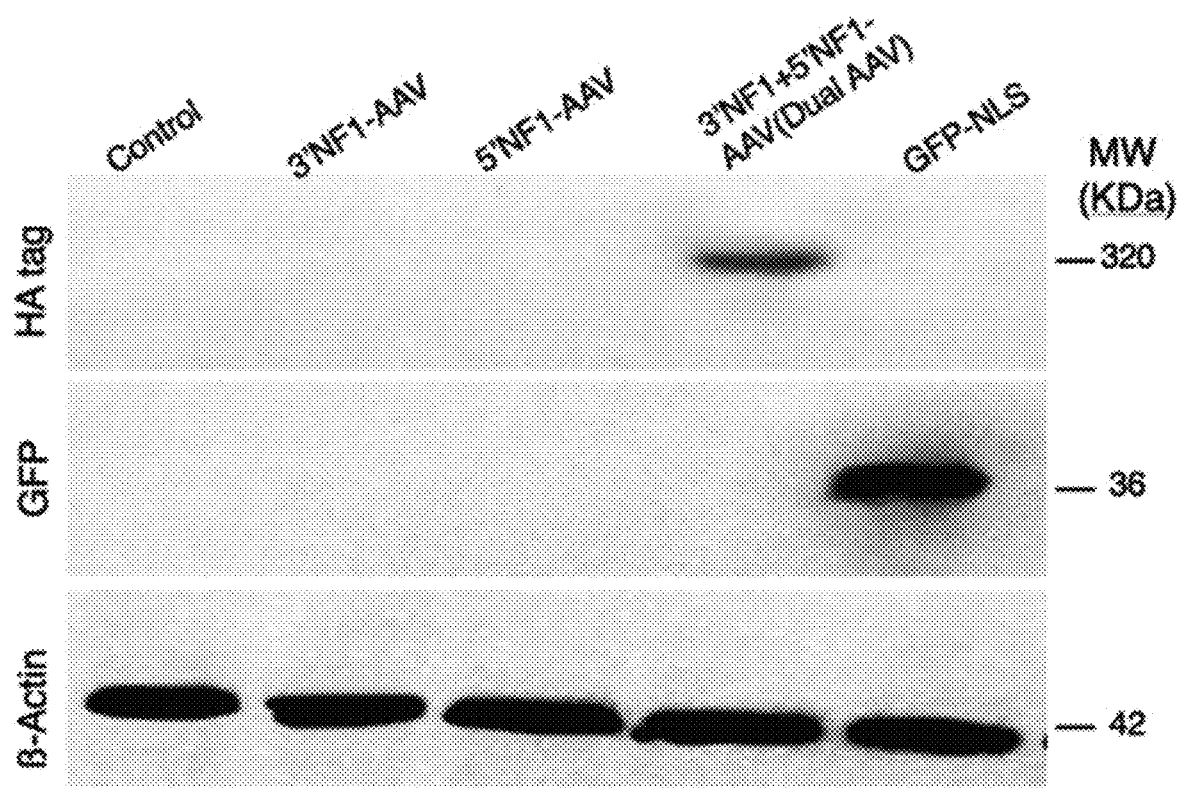

Alternatively, a dual AAV vector system comprised of AAV-MeCP2p-5'NF1-intron and AAV-intron.3'NF1 was designed, for expression of full length human NF1 after concatemerization in the nucleus of doubly infected target cells. As shown in FIG. 2A, in 5' AAV vector consists of a small ubiquitous promoter (e.g., short mouse Mecp2 promoter), 5' sequence of NF1 cDNA (e.g., exons 1-31 of NF1 gene) and a splice donor (SD) signal from NF1 intronic sequences (AAV-MeCP2p-5'NF1-intron vector). The 3' AAV vector consists of splice acceptor (SA) also from NF1 intronic sequences, 3' sequence of NF1 cDNA (e.g., exon 32-81 of NF1 gene) and HA-tag before the ployA signal from SV40 (AAV-intron.3NF1). After both rAAVs that encode each of the two parts of the transgenes are delivered to the same cell, concatemerization of the right side ITR of the 5' vector and left side ITR of the 3' vector reconstitutes the full-length NF1 gene. After transcription, trans-splicing leads to the removal of the ITR structure formed at the middle, which in-turn restores the mature RNA of the transgene (FIGS. 2B-2C). The rAAV vector maps encoding the first and the second portion of NF-1 protein are shown in FIGS. 2D-2E. AAV-DJ virons stocks were produced for each of the two vectors and were tested in HEK293T cells infected with each vector alone, or both vectors simultaneously. As anticipated, expression of a large ~320 KDa HA-positive protein was documented only in cells transduced with both AAV-DJ vectors (FIG. 2F).

Figure 3A:
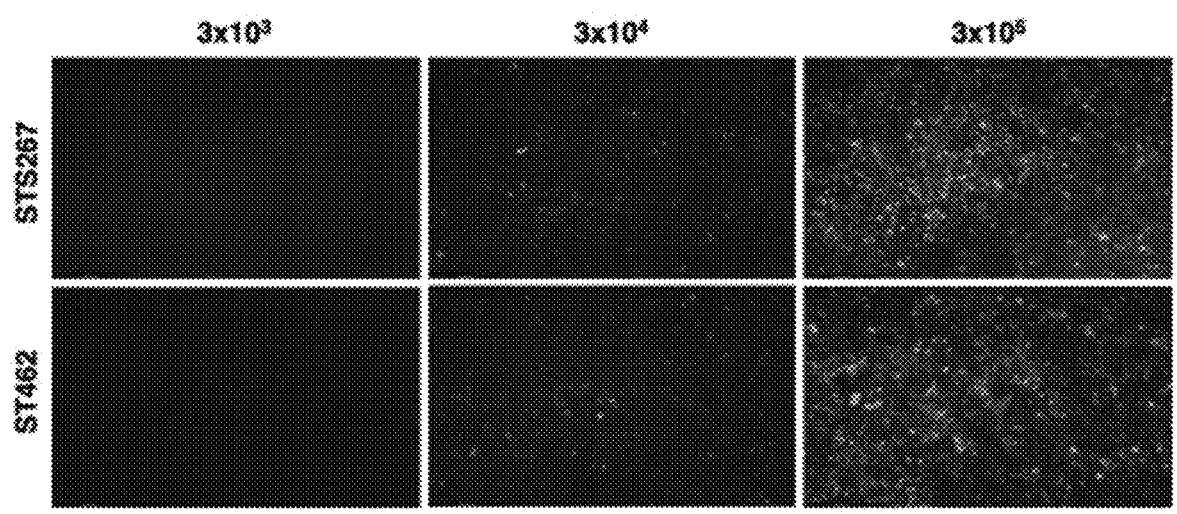
FIGS. 3A-3C are graphs showing that transduction of human MPNST cell lines (ST267 and ST642) with AAV-NF1 vectors reduced Ras pathway activity.
Figure 3B:
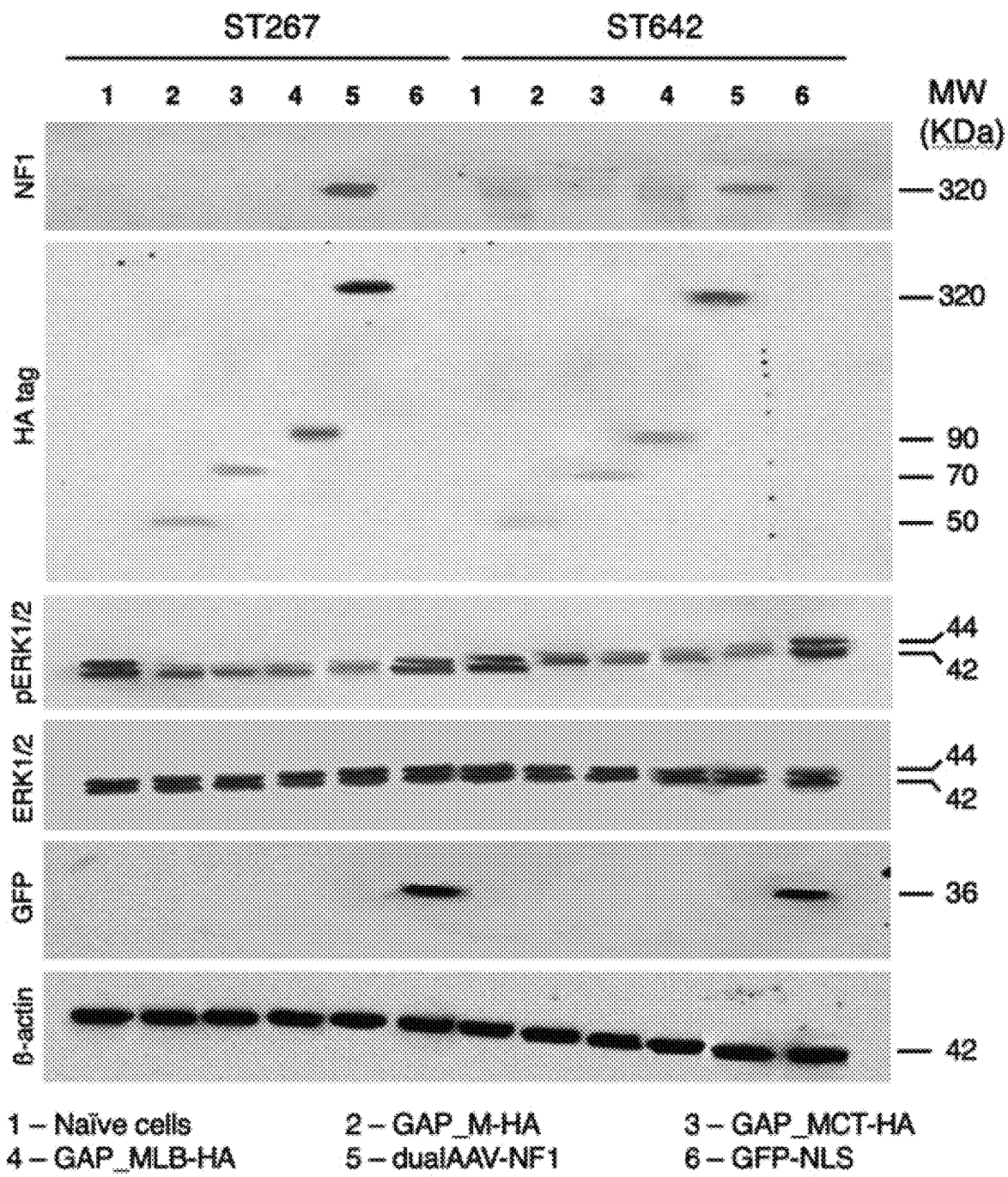
Figure 3C:
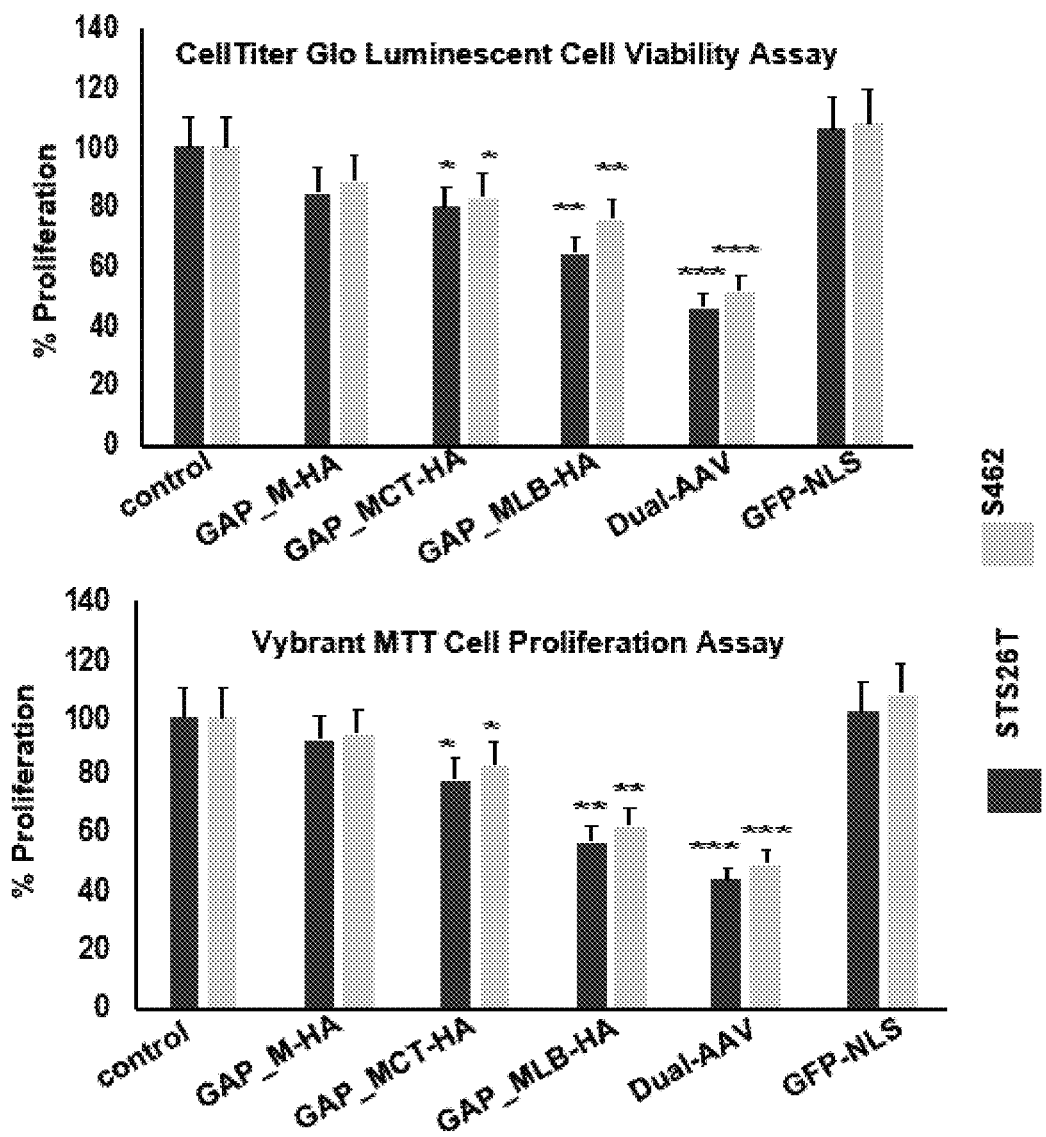

The functionality of the new mini-NF1 genes and the dual AAV-NF1 vector system was tested in human malignant peripheral nerve sheath tumor (MPNST) cell lines for their ability to decrease the activity of the Ras pathway. In the absence of NF1, the Ras pathway is overactive and several downstream signaling mediators are continually activated, through phosphorylation, as evidenced by phospho-ERK1/2 (pERK1/2). Two human MPNST cell lines, ST267 and ST642, were used to assess the ability of mini-NF1 proteins and the dual AAV-NF1 vector system to regulate the Ras pathway by indirectly measuring changes in pERK1/2 levels by western blot. A dose escalation study with a GFP-NLS encoding vector showed the transduction efficiency of AAV-DJ to be comparable for both ST267 and ST642 cell lines (FIG. 3A). Western blot analysis of ST267 and ST642 cells transduced with AAV-DJ vectors encoding mini-NFis, or dualAAV-NF1 vector system showed expression of appropriately sized HA-tagged proteins, and also full length NF1 protein (FIG. 3B). Detection with an anti-NF1 antibody was only possible for the full length NF1 protein because the antibody was raised against an epitope in the N-terminus of full length NF1, which is absent in the mini-NF1 proteins (FIG. 1A). Expression of mini-NF1 proteins and full length NF1 decreased the levels of p-ERK1/2 compared to controls (naïve cells and cells infected with AAV-DJ vector encoding GFP-NLS), while the total levels of ERK1/2 protein remained unchanged across experimental groups (FIG. 3B). In addition, over-activation of Ras signaling pathway also leads to cell proliferation. Expression of mini-NF1 proteins and full length NF1 decreased ST267 and ST642 cell proliferation rate compared to controls (naïve cells and cells infected with AAV-DJ vector encoding GFP-NLS) (FIG. 3C). These data indicate that AAV expressed mini-NF1 and full length NF1 are biologically active in regulating the Ras pathway. Further, in vivo studies are conducted in Nfl$^{-/-}$ mice to assess expression levels, spatial distribution and functionality of the mini-NF1 proteins, and dual AAV NF1 expression system after systemic delivery of AAV-PHP.eB-NF1 virons.

Example 2: Effects of AAV-NF1 Gene Therapy in Nf1$^{Arg681*}$: DhhCre Mice

To determine the effects of the AAV-NF1 gene therapy in vivo, Four Nf1$^{Arg681*}$. DhhCre mice (3 females numbered 001, 002, 003, and one male numbered 613) were used for conducting an assessment of the impact of AAV-NF1 gene therapy on tumor burden in these mice. Tumor burden in each Nf1$^{Arg6s1*}$; DhhCre mouse was assessed in the 3T MRI focusing on the spinal cord, particularly in the cervical and thoracic regions. T2-weighted images were collected which displayed the tumors as hyperintensities compared to the spinal cord.

One week after MRI, mice were injected intrathecally with AAV vectors. Two mice (mouse Nos. 003 and 613) were treated with 1×10$^{12}$ vg AAV-PHP.eB-GAP_MLB-HA (mini-NF1). The other two mice (mouse Nos. 001 and 002) were treated with 1×10$^{12}$ vg dual-AAVs (5'NF1 AAV+ 3'NF1-HA AAV). Tumor burden in these AAV treated Nf1$^{Arg681*}$; DhhCre mice was assessed again at one month after treatment. For volumetric analysis of pre-treated and post-treated tumors, the images were normalized relative to the normal part of the spine with no tumors. The thresholding was applied to isolate the tumors from the image. This thresholding was based on the normalized intensity which captures the proton relaxation or proton density. Anything greater than 1 mm was recognized as a tumor.

Figure 4A:
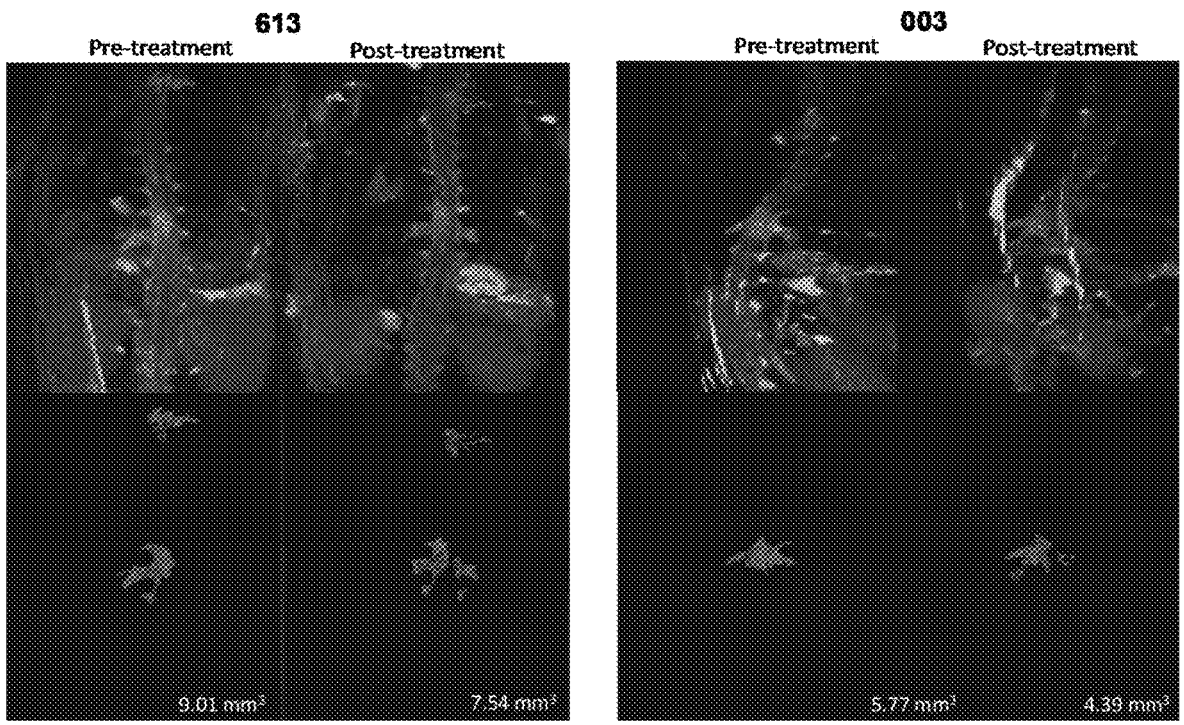
FIGS. 4A-4B show MRI detection of tumors in the spinal cord of $Nf^{Arg681*}$; DhhCre mice.
Figure 4B:
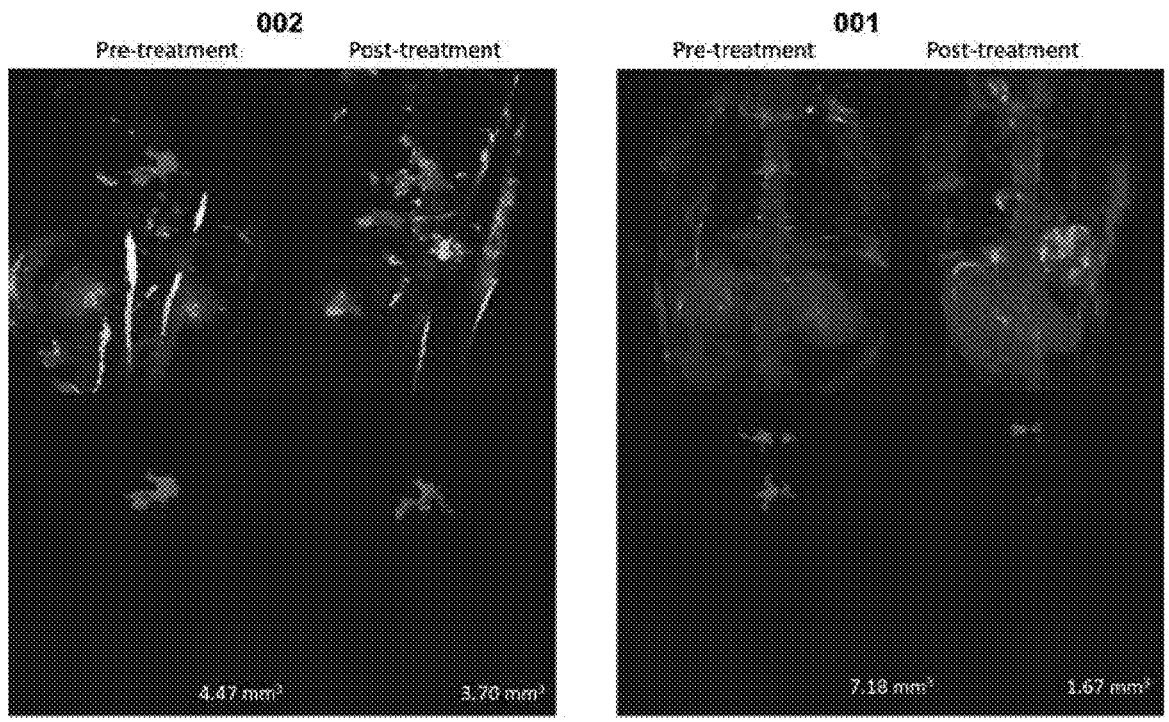

The scanned MRI image revealed a decrease of 16.3% and 23.9% in tumor burden in mice treated with mini-NF1 vector (mouse Nos. 613 and 003) (FIG. 4A). Interestingly, the scanned MRI image revealed a decrease of 17.22% and 76.7% in tumor burden in mice (mouse Nos. 002 and 001) treated with dual-AAV vectors (FIG. 4B). These mice remained alive even after untreated Nf1$^{Arg681*}$; DhhCre reached the humane endpoint (due to hindlimb paralysis) about 5 months of age.

Example 3: Determination of Molecular Markers of Neurobehavior Disease in Neurofibromatosis Type I (NF1)

To evaluate the expression of the potential molecular markers in vivo, Nf1$^{+/-}$ mice were treated with AAV-NF1 vectors at 6-8 weeks of age by systemic delivery (Table 2) and neonatal intracerebroventricular injection (Table 3). Behavioral tests will be conducted on Nf1$^{+/-}$ and wild type mice in the Morris water maze using a developed protocol.

TABLE 2

Nfl$^{+/-}$ male mice treated at 6-8 weeks
of age by systemic delivery of AAV-NF1 vectors

| | WT | Group A | Group B | Group C |
|---|---|---|---|---|
| No. of animals | 12 | 12 | 12 | 12 |

TABLE 3

Nfl$^{+/-}$ mice treated at post-natal day 1 by
intracerebroventricular injection of AAV-NF1 vectors

| | AAV Mini-NF1 (encoding NF1-GAP_MLB) | Dual-AAV-NF1 |
|---|---|---|
| No. of animals | 28 | 14 |

Upon completion of behavioral testing on the mice, various parameters in the CNS including western blot analysis of several proteins previously shown to be altered in the Nfl$^{+/-}$ mouse brain will be assessed. The western blot conditions for those proteins, which can be considered molecular markers of neurobehavior disease in NF1, were optimized.

Figure 5:
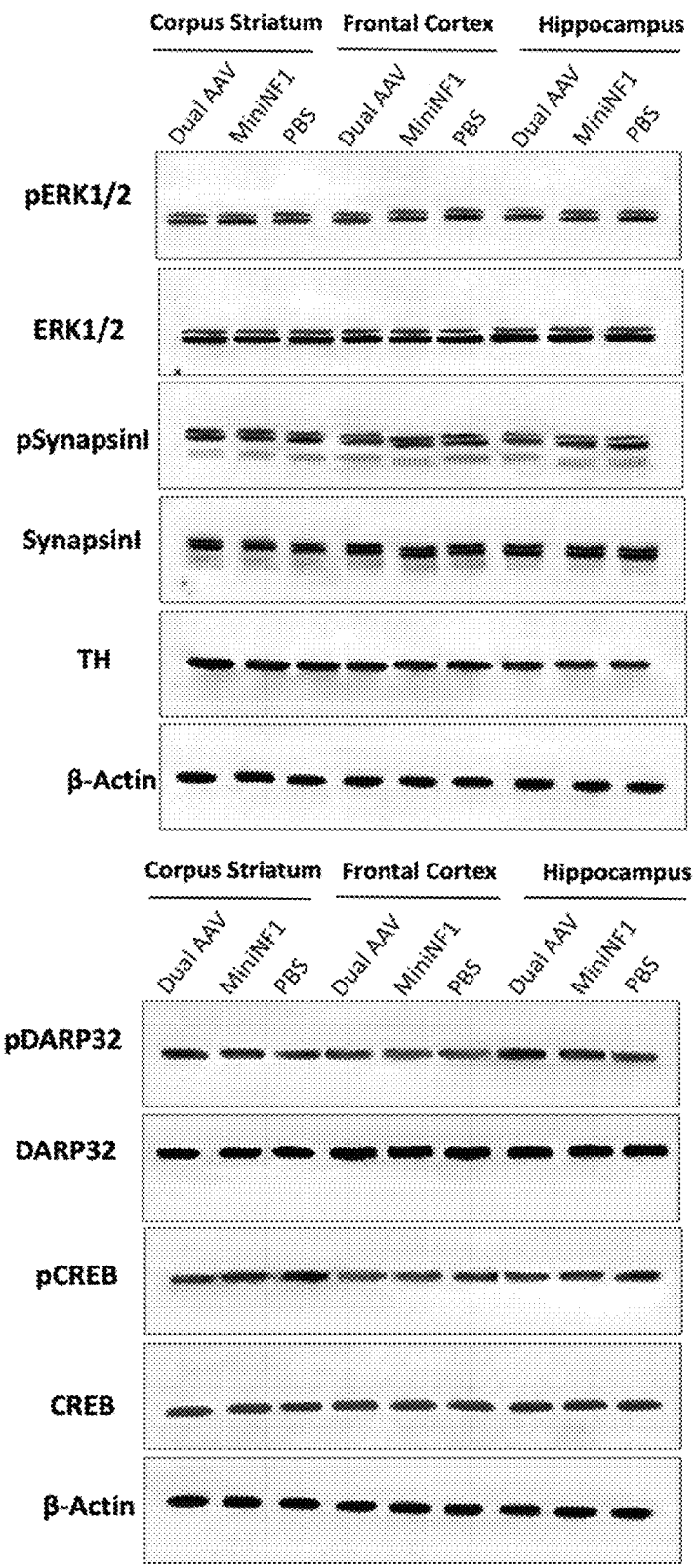
FIG. 5 shows western blot analysis of selected molecular markers of NF1 signaling in mice that were injected with PBS, $1\times10^{12}$ vg AAV-PHP.eB-GAP_MLB-HA, or $1\times10^{12}$ vg dual AAV (5'NF1+3'NF1-HA).

The lead candidates AAV-mini-NF1, encoding NF1-GAP_MLB, and the trans splicing dual-AAV-NF1 vector system, were previously tested in normal C57BL/6 for their ability to express NF1 in the CNS and peripheral tissues after systemic delivery as AAV-PHP.eB vectors. Mice received tail vein injections of vehicle (PBS; group 1), $1\times10^{12}$ vg AAV-PHP.eB-GAP_MLB-HA (group 2; Mini-NF1) or $1\times10^{12}$ vg dual-AAV (dual AAV; 5'NF1+3'NF1-HA) (group 3) vectors. Mice were euthanized at 4 weeks post-infusion and the following brain parts were collected: hippocampus, frontal cortex and corpus striatum, regions which are involved with cognition deficits and behavioral problems related to NF1 disease and tissue lysates were prepared for Western blot analysis. As these mice represented normal mice expressing normal levels of neurofibromin, expression of various neurobehavioral markers such as pERK1/2, pSynapsinI, pCREB, pDARP32 and tyrosine hydroxylase (TH) assessed (FIG. 5). The expression of phosphorylated proteins was normalized against the total protein using anti-ERK1/2, anti-SynapsinI, anti-CREB and anti-DARP32 antibodies. The anti-3-actin antibody was used as loading control throughout the validation process. Expression of all protein markers in the analyzed brain structures in animals from all three groups was observed. Changes in phosphorylated forms of various marker proteins expected after increased expression of NF1 (AAV treated groups) was observed, such as decrease in pERK1/2 and increase in pCREB in various structures with no changes in total protein. These encouraging results indicate that sufficient CNS transduction was obtained to change the levels of downstream NF1 signaling targets, especially ones that correlate with neurobehavior disease in NF1.

As part of the follow-up studies, Nfl$^{+/-}$ mice treated systemically with AAV-PHP.eB-NF1$^{dual}$ system for determining the efficacy of prevention, or reversal, of neurological deficits caused by NF1 gene mutations. Specifically, systemic delivery of high dose AAV-PHP.eB-NF1$^{dual}$ in Nfl$^{+/-}$, Nfl$^{+/-}$/p53$^{+/-}$ (cis); Nfl$^{+/-}$/p53$^{+/-}$/Suz12$^{+/-}$ (cis) mice at 4 weeks of age will be conducted. NF1 expression and cell signaling in CNS and peripheral nerve at 4, 8 and 12 months of age (or humane endpoint) will be assessed, and correlative neuropathologic evaluation will be conducted. Longitudinal assessment of neurological function and survival to 1 year of age will be conducted.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. The terms "about" and "substantially" preceding a numerical value represent ±10% of the recited numerical value.

What is claimed is:

1. A recombinant adeno-associated virus (rAAV) comprising:
   (i) an isolated nucleic acid comprising a transgene, wherein the transgene comprises a nucleotide sequence encoding a mini-neurofibromin (mini-NF1) protein, wherein the mini-NF1 protein comprises:
      (a) a GTPase-activating protein (GAP)-related domain (GRD) and a CRAL-TRIO domain; or
      (b) a GTPase-activating protein (GAP)-related domain (GRD) and a CRAL-TRIO domain and a bipartite phospholipid binding domain; and
   (ii) an AAV capsid protein.

2. The rAAV of claim 1, wherein the transgene further comprises a promoter operably linked to the nucleotide sequence encoding the mini-NF1 protein, optionally wherein the promoter is a constitutive promoter, an inducible promoter, or a minimal promoter.

3. The rAAV of claim 2, wherein the promoter is a chicken β-actin (CBA) promoter, or a CAG promoter, a short Mecp2 promoter, a mini-CMV promoter, or a jet promoter.

4. The rAAV of claim 1, wherein the mini-NF comprises the amino acid sequence of SEQ ID Nos: 3 or 5.

5. The rAAV of claim 2, wherein the transgene further comprises a nucleotide sequence encoding a tag operably linked to the promoter, optionally wherein the tag is an HA tag.

6. The rAAV of claim 1, wherein the nucleotide sequence encoding the mini-NF comprises a nucleotide sequence at least 80% identical to SEQ ID NOs: 4 or 6.

7. The rAAV of claim 1, wherein the transgene is flanked by adeno-associated virus (AAV) inverted terminal repeats (ITRs), optionally wherein the ITRs are adeno-associated virus ITRs of a serotype selected from the group consisting of AAV1 ITR, AAV2 ITR, AAV3 ITR, AAV4 ITR, AAV5 ITR, and AAV6 ITR.

8. The rAAV of claim 7, wherein the ITRs are AAV2 ITR.

9. The rAAV of claim 1, wherein the transgene further comprises a polyadenylation signal.

10. The rAAV of claim 1, wherein the capsid protein is of a serotype selected from AAV1, AAV2, AAV3, AAV4, AAV5, AAV6, AAV7, AAV8, AAV9 and a variant thereof, optionally wherein the capsid protein is AAV9, AAV-DJ, AAVrh10, AAV. PHP.B, Anc80, or AAV. PHP.eB.

11. The rAAV of claim 1, wherein the capsid protein has tropism for Schwann cells, peripheral neurons, optic nerve glioma cells, or cells in the central nervous system.

12. A method for preventing or treating an NF1-associated disease, an Neurofibromatosis type I, and/or a cognitive dysfunction associated with NF1 in a subject in need thereof, the method comprising administering to the subject the rAAV of claim 1.

13. The method of claim 12, wherein the NF1-associated disease or Neurofibromatosis type I comprises skin lesions, benign tumor, malignant tumor, and/or cognitive impairment, optionally wherein the benign tumor is a benign neurofibroma and/or the malignant tumor is optic gliomas or malignant peripheral nerve sheath tumors (MPNST).

14. The method of claim 12, wherein the subject is a human.

15. The method of claim 12, wherein the administration is systemic administration or local administration, optionally wherein the systemic administration is intravenous injection, intramuscular injection, or subcutaneous injection and the local administration is intratumoral injection, intracranial injection, nerve injection, cerebral spinal fluid (CSF) injection via cerebral lateral ventricles, cisterna magna (CM) injection, intrathecal (IT) injection, or intracerebroventricular injection, optionally wherein the administration is intrathecal (IT) injection and/or intracerebroventricular injection.

16. The method of claim 12, wherein the administration results in delivery of a neurofibromin (NF1) protein in Schwann cells, peripheral nerve cells, or optic nerve cells.

17. A 5' recombinant adeno-associated virus (rAAV) comprising:
   (i) a 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, and a nucleotide sequence encoding a splice donor of an intron; and
   (ii) an AAV capsid protein.

18. The 5' rAAV of claim 17, wherein the nucleotide sequence encoding the first portion of NF1 protein comprises exons 1-31 of an NF1 gene, optionally wherein the nucleotide sequence encoding the first portion of NF1 protein comprises a nucleotide sequence of SEQ ID NO: 11.

19. The 5' rAAV of claim 17, wherein the promoter is a chicken β-actin (CBA) promoter, or a CAG promoter, a short Mecp2 promoter, a mini-CMV promoter, or a jet promoter.

20. The 5' rAAV of claim 17, wherein the ITRs are adeno-associated virus ITRs of a serotype selected from the group consisting of AAV1 ITR, AAV2 ITR, AAV3 ITR, AAV4 ITR, AAV5 ITR, and AAV6 ITR, optionally wherein the ITRs are AAV2 ITR.

21. The 5' rAAV of claim 17, wherein the intron is a human dysferlin intron.

22. The 5' rAAV of claim 17, wherein the nucleotide sequence encoding the splicing donor comprises a nucleotide sequence of SEQ ID NO: 18.

23. A 3' recombinant adeno-associated virus (rAAV) comprising:
   (i) a 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, and a nucleotide sequence encoding a second portion of NF1 protein; and
   (ii) an AAV capsid protein.

24. The 3' rAAV of claim 23, wherein the 3' isolated nucleic acid further comprises a polyadenylation signal positioned between the nucleotide sequence encoding second portion of NF1 protein and the 3' ITR, optionally wherein the polyadenylation signal is an SV40 polyadenylation signal.

25. The 3' rAAV of claim 23, wherein the nucleotide sequence encoding the second portion of NF1 protein comprises exons 32-61 of an NF1 gene, optionally wherein the nucleotide sequence encoding the second portion of NF1 protein comprises a nucleotide sequence of SEQ ID NO: 14.

26. The 3' rAAV of claim 23, wherein the nucleotide sequence encoding the splicing acceptor comprises a nucleotide sequence of SEQ ID NO: 19.

27. The 3' rAAV of claim 23, wherein the ITRs are adeno-associated virus ITRs of a serotype selected from the group consisting of AAV1 ITR, AAV2 ITR, AAV3 ITR, AAV4 ITR, AAV5 ITR, and AAV6 ITR, optionally wherein the ITRs are AAV2 ITR.

28. The 3' rAAV of claim 23, wherein the intron is a human dysferlin intron.

29. A dual vector system comprising:
(i) a 5' rAAV comprising: (a) a 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, a nucleotide sequence encoding a splice donor of an intron; and (b) an AAV capsid protein; and
(ii) a 3' rAAV comprising: (a) a 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, and a nucleotide sequence encoding a second portion of NF1 protein; and (b) an AAV capsid protein.

* * * * *

```
                          SEQUENCE LISTING

<160> NUMBER OF SEQ ID NOS: 32

<210> SEQ ID NO 1
<211> LENGTH: 495
<212> TYPE: PRT
<213> ORGANISM: Artificial Sequence
<220> FEATURE:
<223> OTHER INFORMATION: Synthetic

<400> SEQUENCE: 1

Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205
```

```
Leu Leu Arg Ile Val Ile Thr Ser Ser Asp Trp Gln His Val Ser Phe
    210                 215                 220
Glu Val Asp Pro Thr Arg Leu Glu Pro Ser Glu Ser Leu Glu Asn
225                 230                 235                 240
Gln Arg Asn Leu Leu Gln Met Thr Glu Lys Phe Phe His Ala Ile Ile
                245                 250                 255
Ser Ser Ser Ser Glu Phe Pro Pro Gln Leu Arg Ser Val Cys His Cys
            260                 265                 270
Leu Tyr Gln Ala Thr Cys His Ser Leu Leu Asn Lys Ala Thr Val Lys
        275                 280                 285
Glu Lys Lys Glu Asn Lys Lys Ser Val Val Ser Gln Arg Phe Pro Gln
290                 295                 300
Asn Ser Ile Gly Ala Val Gly Ser Ala Met Phe Leu Arg Phe Ile Asn
305                 310                 315                 320
Pro Ala Ile Val Ser Pro Tyr Glu Ala Gly Ile Leu Asp Lys Lys Pro
                325                 330                 335
Pro Pro Arg Ile Glu Arg Gly Leu Lys Leu Met Ser Lys Ile Leu Gln
            340                 345                 350
Ser Ile Ala Asn His Val Leu Phe Thr Lys Glu Glu His Met Arg Pro
        355                 360                 365
Phe Asn Asp Phe Val Lys Ser Asn Phe Asp Ala Ala Arg Arg Phe Phe
370                 375                 380
Leu Asp Ile Ala Ser Asp Cys Pro Thr Ser Asp Ala Val Asn His Ser
385                 390                 395                 400
Leu Ser Phe Ile Ser Asp Gly Asn Val Leu Ala Leu His Arg Leu Leu
                405                 410                 415
Trp Asn Asn Gln Glu Lys Ile Gly Gln Tyr Leu Ser Ser Asn Arg Asp
            420                 425                 430
His Lys Ala Val Gly Arg Arg Pro Phe Asp Lys Met Ala Thr Leu Leu
        435                 440                 445
Ala Tyr Leu Gly Pro Pro Glu His Lys Pro Val Ala Asp Thr His Trp
        450                 455                 460
Ser Ser Leu Asn Leu Thr Ser Ser Lys Phe Glu Glu Phe Met Thr Arg
465                 470                 475                 480
His Gln Val His Glu Lys Glu Glu Phe Lys Ala Leu Lys Thr Leu
                485                 490                 495

<210> SEQ ID NO 2
<211> LENGTH: 1485
<212> TYPE: DNA
<213> ORGANISM: Artificial Sequence
<220> FEATURE:
<223> OTHER INFORMATION: Synthetic

<400> SEQUENCE: 2
atggaagcca agagccagct gttctgaaa actttaccc tgtttatgaa tctgctgaac     60
gactgtagtg aggtggagga cgagagtgcc cagaccggcg gcaggaagag aggcatgtct    120
aggagactgg ccagcctgag gcactgcaca gtgctggcca tgtccaacct gctgaacgcc    180
aatgtggact ccggcctgat gcactctatc ggcctgggct accacaagga tctgcagacc    240
cgcgccacat tcatggaggt gctgaccaag atcctgcagc agggcaccga gtttgacaca    300
ctggccgaga ccgtgctggc agataggttc gagcgcctgg tggagctggt gacaatgatg    360
ggcgaccagg gagagctgcc tatcgcaatg gcactggcca cgtggtgcc atgcagccag    420 tgggacgagc tggccagggt gctggtgacc ctgtttgatt ccagacacct gctgtaccag    480
```

```
ctgctgtgga acatgttctc taaggaggtg gagctggccg acagcatgca gacactgttt      540
aggggcaatt ccctggcctc taagatcatg accttctgtt ttaaggtgta cggcgccaca      600
tatctgcaga agctgctgga tccactgctg agaatcgtga tcaccagctc cgactggcag      660
cacgtgtcct tcgaggtgga tcctacacgg ctggagccaa gcgagtccct ggaggagaac      720
cagcgcaatc tgctgcagat gaccgagaag ttctttcacg ccatcatctc tagctcctct      780
gagtttcccc ctcagctgcg gtccgtgtgc cactgtctgt accaggccac ctgccactct      840
ctgctgaaca aggccacagt gaaggagaag aaggagaata agaagagcgt ggtgtcccag      900
aggttcccac agaacagcat cggagcagtg ggatccgcca tgttcctgag gttcatcaat      960
cccgccatcg tgagcccttt tgaggccggc atcctggaca agaagccacc ccctaggatc     1020
gagagaggcc tgaagctgat gagcaagatc ctgcagtcca tcgccaacca cgtgctgttc     1080
accaaggagg agcacatgcg ccccttcaac gactttgtga agtctaattt tgatgccgcc     1140
cggcgcttct ttctggacat cgcctctgat tgtcctacaa gcgacgccgt gaaccactct     1200
ctgagcttca tcagcgatgg caatgtgctg ccctgcacc ggctgctgtg gaacaatcag     1260
gagaagatcg gccagtacct gagctccaac agggaccaca aggcagtggg caggagacct     1320
tttgataaga tggccaccct gctggcatat ctgggaccac cagagcacaa gccagtggca     1380
gacacccact ggtctagcct gaatctgaca tcctctaagt tcgaggagtt tatgacccgg     1440
caccaggtgc acgagaagga ggagtttaag gccctgaaga ccctg                     1485
```

<210> SEQ ID NO 3
<211> LENGTH: 643
<212> TYPE: PRT
<213> ORGANISM: Artificial Sequence
<220> FEATURE:
<223> OTHER INFORMATION: Synthetic

<400> SEQUENCE: 3

```
Met Glu Ala Lys Ser Gln Leu Phe Leu Lys Tyr Phe Thr Leu Phe Met
 1               5                  10                  15

Asn Leu Leu Asn Asp Cys Ser Glu Val Glu Asp Glu Ser Ala Gln Thr
             20                  25                  30

Gly Gly Arg Lys Arg Gly Met Ser Arg Arg Leu Ala Ser Leu Arg His
         35                  40                  45

Cys Thr Val Leu Ala Met Ser Asn Leu Leu Asn Ala Asn Val Asp Ser
     50                  55                  60

Gly Leu Met His Ser Ile Gly Leu Gly Tyr His Lys Asp Leu Gln Thr
 65                  70                  75                  80

Arg Ala Thr Phe Met Glu Val Leu Thr Lys Ile Leu Gln Gln Gly Thr
                 85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
```

-continued

```
                180                 185                 190
Cys Phe Lys Val Tyr Gly Ala Thr Tyr Leu Gln Lys Leu Leu Asp Pro
            195                 200                 205
Leu Leu Arg Ile Val Ile Thr Ser Ser Asp Trp Gln His Val Ser Phe
        210                 215                 220
Glu Val Asp Pro Thr Arg Leu Glu Pro Ser Glu Ser Leu Glu Glu Asn
225                 230                 235                 240
Gln Arg Asn Leu Leu Gln Met Thr Glu Lys Phe Phe His Ala Ile Ile
                245                 250                 255
Ser Ser Ser Ser Glu Phe Pro Pro Gln Leu Arg Ser Val Cys His Cys
            260                 265                 270
Leu Tyr Gln Ala Thr Cys His Ser Leu Leu Asn Lys Ala Thr Val Lys
        275                 280                 285
Glu Lys Lys Glu Asn Lys Lys Ser Val Val Ser Gln Arg Phe Pro Gln
        290                 295                 300
Asn Ser Ile Gly Ala Val Gly Ser Ala Met Phe Leu Arg Phe Ile Asn
305                 310                 315                 320
Pro Ala Ile Val Ser Pro Tyr Glu Ala Gly Ile Leu Asp Lys Lys Pro
                325                 330                 335
Pro Pro Arg Ile Glu Arg Gly Leu Lys Leu Met Ser Lys Ile Leu Gln
            340                 345                 350
Ser Ile Ala Asn His Val Leu Phe Thr Lys Glu Glu His Met Arg Pro
        355                 360                 365
Phe Asn Asp Phe Val Lys Ser Asn Phe Asp Ala Ala Arg Arg Phe Phe
        370                 375                 380
Leu Asp Ile Ala Ser Asp Cys Pro Thr Ser Asp Ala Val Asn His Ser
385                 390                 395                 400
Leu Ser Phe Ile Ser Asp Gly Asn Val Leu Ala Leu His Arg Leu Leu
                405                 410                 415
Trp Asn Asn Gln Glu Lys Ile Gly Gln Tyr Leu Ser Ser Asn Arg Asp
            420                 425                 430
His Lys Ala Val Gly Arg Arg Pro Phe Asp Lys Met Ala Thr Leu Leu
        435                 440                 445
Ala Tyr Leu Gly Pro Pro Glu His Lys Pro Val Ala Asp Thr His Trp
        450                 455                 460
Ser Ser Leu Asn Leu Thr Ser Ser Lys Phe Glu Glu Phe Met Thr Arg
465                 470                 475                 480
His Gln Val His Glu Lys Glu Glu Phe Lys Ala Leu Lys Thr Leu Ser
                485                 490                 495
Ile Phe Tyr Gln Ala Gly Thr Ser Lys Ala Gly Asn Pro Ile Phe Tyr
            500                 505                 510
Tyr Val Ala Arg Arg Phe Lys Thr Gly Gln Ile Asn Gly Asp Leu Leu
        515                 520                 525
Ile Tyr His Val Leu Leu Thr Leu Lys Pro Tyr Tyr Ala Lys Pro Tyr
        530                 535                 540
Glu Ile Val Val Asp Leu Thr His Thr Gly Pro Ser Asn Arg Phe Lys
545                 550                 555                 560
Thr Asp Phe Leu Ser Lys Trp Phe Val Val Phe Pro Gly Phe Ala Tyr
                565                 570                 575
Asp Asn Val Ser Ala Val Tyr Ile Tyr Asn Cys Asn Ser Trp Val Arg
            580                 585                 590
Glu Tyr Thr Lys Tyr His Glu Arg Leu Leu Thr Gly Leu Lys Gly Ser
        595                 600                 605
```

Lys Arg Leu Val Phe Ile Asp Cys Pro Gly Lys Leu Ala Glu His Ile
610                 615                 620

Glu His Glu Gln Gln Lys Leu Pro Ala Ala Thr Leu Ala Leu Glu Glu
625                 630                 635                 640

Asp Leu Lys

<210> SEQ ID NO 4
<211> LENGTH: 1929
<212> TYPE: DNA
<213> ORGANISM: Artificial Sequence
<220> FEATURE:
<223> OTHER INFORMATION: Synthetic

<400> SEQUENCE: 4

| | | | | |
|---|---|---|---|---|
| atggaagcca | agagccagct | gtttctgaaa | tactttaccc | tgtttatgaa | tctgctgaac | 60 |
| gactgtagtg | aggtggagga | cgagagtgcc | cagaccggcg | gcaggaagag | aggcatgtct | 120 |
| aggagactgg | ccagcctgag | gcactgcaca | gtgctggcca | tgtccaacct | gctgaacgcc | 180 |
| aatgtggact | ccggcctgat | gcactctatc | ggcctgggct | accacaagga | tctgcagacc | 240 |
| cgcgccacat | tcatggaggt | gctgaccaag | atcctgcagc | agggcaccga | gtttgacaca | 300 |
| ctggccgaga | ccgtgctggc | agataggttc | gagcgcctgg | tggagctggt | gacaatgatg | 360 |
| ggcgaccagg | gagagctgcc | tatcgcaatg | cactggcca | acgtggtgcc | atgcagccag | 420 |
| tgggacgagc | tggccagggt | gctggtgacc | ctgtttgatt | ccagacacct | gctgtaccag | 480 |
| ctgctgtgga | acatgttctc | taaggaggtg | gagctggccg | acagcatgca | gacactgttt | 540 |
| agggggcaatt | ccctggcctc | taagatcatg | accttctgtt | ttaaggtgta | cggcgccaca | 600 |
| tatctgcaga | agctgctgga | tccactgctg | agaatcgtga | tcaccagctc | cgactggcag | 660 |
| cacgtgtcct | tcgaggtgga | tcctacacgg | ctggagccaa | gcgagtccct | ggaggagaac | 720 |
| cagcgcaatc | tgctgcagat | gaccgagaag | ttctttcacg | ccatcatctc | tagctcctct | 780 |
| gagtttcccc | ctcagctgcg | gtccgtgtgc | cactgtctgt | accaggccac | ctgccactct | 840 |
| ctgctgaaca | aggccacagt | gaaggagaag | aaggagaata | gaagagcgt | ggtgtcccag | 900 |
| aggttcccac | agaacagcat | cggagcagtg | ggatccgcca | tgttcctgag | gttcatcaat | 960 |
| cccgccatcg | tgagcccta | tgaggccggc | atcctggaca | gaagccaccc | cctaggatc | 1020 |
| gagagaggcc | tgaagctgat | gagcaagatc | ctgcagtcca | tcgccaacca | cgtgctgttc | 1080 |
| accaaggagg | agcacatgcg | cccccttcaac | gactttgtga | agtctaattt | tgatgccgcc | 1140 |
| cggcgcttct | ttctggacat | cgcctctgat | tgtcctacaa | gcgacgccgt | gaaccactct | 1200 |
| ctgagcttca | tcagcgatgg | caatgtgctg | gccctgcacc | ggctgctgtg | gaacaatcag | 1260 |
| gagaagatcg | ccagtaacct | gagctccaac | agggaccaca | aggcagtggg | caggagacca | 1320 |
| tttgataaga | tggccacact | gctggcctat | ctgggaccac | cagagcacaa | gccagtggca | 1380 |
| gacacacact | ggtctagcct | gaatctgacc | tcctctaagt | tcgaggagtt | tatgacccgg | 1440 |
| caccaggtgc | acgagaagga | ggagtttaag | gccctgaaga | cactgtctat | cttctaccag | 1500 |
| gcaggcacca | gcaaggcagg | aaacccaatc | ttttactatg | tggcccggcg | cttcaagaca | 1560 |
| ggccagatca | atggcgatct | gctgatctac | cacgtgctgc | tgaccctgaa | gcatactat | 1620 |
| gccaagccct | atgagatcgt | ggtggacctg | acccacacag | gcccctccaa | caggtttaag | 1680 |
| accgatttcc | tgtctaagtg | gttcgtggtg | tttcctggct | tcgcctatga | caatgtgagc | 1740 |
| gccgtgtaca | tctataactg | caattcctgg | gtgcgggagt | acacaaagta | tcacgagcgc | 1800 |

```
ctgctgaccg gcctgaaggg atccaagaga ctggtgttca tcgattgtcc cggcaagctg    1860
gccgagcaca ttgaacacga acagcagaaa ctgcccgccg caaccctggc cctggaagag    1920
gacctgaag                                                             1929
```

<210> SEQ ID NO 5
<211> LENGTH: 742
<212> TYPE: PRT
<213> ORGANISM: Artificial Sequence
<220> FEATURE:
<223> OTHER INFORMATION: Synthetic

<400> SEQUENCE: 5

```
Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Leu Ala Ser Leu Arg His
        35                  40                  45

Cys Thr Val Leu Ala Met Ser Asn Leu Leu Asn Ala Asn Val Asp Ser
50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335
```

```
Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
        370                 375             380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
        435                 440                 445

Ala Tyr Leu Gly Pro Pro Glu His Lys Pro Val Ala Asp Thr His Trp
        450                 455             460

Ser Ser Leu Asn Leu Thr Ser Ser Lys Phe Glu Glu Phe Met Thr Arg
465                 470                 475                 480

His Gln Val His Glu Lys Glu Phe Lys Ala Leu Lys Thr Leu Ser
                485                 490                 495

Ile Phe Tyr Gln Ala Gly Thr Ser Lys Ala Gly Asn Pro Ile Phe Tyr
                500                 505                 510

Tyr Val Ala Arg Arg Phe Lys Thr Gly Gln Ile Asn Gly Asp Leu Leu
            515                 520                 525

Ile Tyr His Val Leu Leu Thr Leu Lys Pro Tyr Tyr Ala Lys Pro Tyr
        530                 535                 540

Glu Ile Val Val Asp Leu Thr His Thr Gly Pro Ser Asn Arg Phe Lys
545                 550                 555                 560

Thr Asp Phe Leu Ser Lys Trp Phe Val Val Phe Pro Gly Phe Ala Tyr
                565                 570                 575

Asp Asn Val Ser Ala Val Tyr Ile Tyr Asn Cys Asn Ser Trp Val Arg
            580                 585                 590

Glu Tyr Thr Lys Tyr His Glu Arg Leu Leu Thr Gly Leu Lys Gly Ser
        595                 600                 605

Lys Arg Leu Val Phe Ile Asp Cys Pro Gly Lys Leu Ala Glu His Ile
        610                 615                 620

Glu His Glu Gln Gln Lys Leu Pro Ala Ala Thr Leu Ala Leu Glu Glu
625                 630                 635                 640

Asp Leu Lys Val Phe His Asn Ala Leu Lys Leu Ala His Lys Asp Thr
                645                 650                 655

Lys Val Ser Ile Lys Val Gly Ser Thr Ala Val Gln Val Thr Ser Ala
            660                 665                 670

Glu Arg Thr Lys Val Leu Gly Gln Ser Val Phe Leu Asn Asp Ile Tyr
        675                 680                 685

Tyr Ala Ser Glu Ile Glu Glu Ile Cys Leu Val Asp Glu Asn Gln Phe
        690                 695             700

Thr Leu Thr Ile Ala Asn Gln Gly Thr Pro Leu Thr Phe Met His Gln
705                 710                 715                 720

Glu Cys Glu Ala Ile Val Gln Ser Ile Ile His Ile Arg Thr Arg Trp
                725                 730                 735

Glu Leu Ser Gln Pro Asp
            740
```

<210> SEQ ID NO 6
<211> LENGTH: 2226
<212> TYPE: DNA
<213> ORGANISM: Artificial Sequence
<220> FEATURE:
<223> OTHER INFORMATION: Synthetic

<400> SEQUENCE: 6

| | | | | | |
|---|---|---|---|---|---|
| atggaagcca | agagccagct | gtttctgaaa | tactttaccc | tgtttatgaa | tctgctgaac | 60 |
| gactgtagtg | aggtggagga | cgagagtgcc | cagaccggcg | gcaggaagag | aggcatgtct | 120 |
| aggagactgg | ccagcctgag | gcactgcaca | gtgctggcca | tgtccaacct | gctgaacgcc | 180 |
| aatgtggact | ccggcctgat | gcactctatc | ggcctgggct | accacaagga | tctgcagacc | 240 |
| cgcgccacat | tcatggaggt | gctgaccaag | atcctgcagc | agggcaccga | gtttgacaca | 300 |
| ctggccgaga | ccgtgctggc | agataggttc | gagcgcctgg | tggagctggt | gacaatgatg | 360 |
| ggcgaccagg | gagagctgcc | tatcgcaatg | gcactggcca | acgtggtgcc | atgcagccag | 420 |
| tgggacgagc | tggccagggt | gctggtgacc | ctgtttgatt | ccagacacct | gctgtaccag | 480 |
| ctgctgtgga | acatgttctc | taaggaggtg | gagctggccg | acagcatgca | gacactgttt | 540 |
| agggcaattc | ccctggcctc | taagatcatg | accttctgtt | ttaaggtgta | cggcgccaca | 600 |
| tatctgcaga | agctgctgga | tccactgctg | agaatcgtga | tcaccagctc | cgactggcag | 660 |
| cacgtgtcct | tcgaggtgga | tcctacacgg | ctggagccaa | gcgagtccct | ggaggagaac | 720 |
| cagcgcaatc | tgctgcagat | gaccgagaag | ttctttcacg | ccatcatctc | tagctcctct | 780 |
| gagtttcccc | tcagctgcg | gtccgtgtgc | cactgtctgt | accaggccac | tgccactct | 840 |
| ctgctgaaca | aggccacagt | gaaggagaag | aaggagaata | gaagagcgt | ggtgtcccag | 900 |
| aggttcccac | agaacagcat | cggagcagtg | ggatccgcca | tgttcctgag | gttcatcaat | 960 |
| cccgccatcg | tgagccctta | tgaggccggc | atcctggaca | agaagccacc | ccctaggatc | 1020 |
| gagagaggcc | tgaagctgat | gagcaagatc | ctgcagtcca | tcgccaacca | cgtgctgttc | 1080 |
| accaaggagg | agcacatgcg | ccccttcaac | gactttgtga | agtctaattt | tgatgccgcc | 1140 |
| cggcgcttct | ttctggacat | cgcctctgat | tgtcctacaa | gcgacgccgt | gaaccactct | 1200 |
| ctgagcttca | tcagcgatgg | caatgtgctg | gccctgcacc | ggctgctgtg | gaacaatcag | 1260 |
| gagaagatcg | ccagtacct | gagctccaac | agggaccaca | aggcagtggg | caggagacct | 1320 |
| tttgataaga | tggccaccct | gctggcatat | ctgggaccac | cagagcacaa | gccagtggca | 1380 |
| gacacccact | ggtctagcct | gaatctgaca | tcctctaagt | tcgaggagtt | tatgacccgg | 1440 |
| caccaggtgc | acgagaagga | ggagtttaag | gccctgaaga | ccctgtccat | cttctaccag | 1500 |
| gccggcacat | ctaaggccgg | caaccctatc | ttttactatg | tggcccggcg | cttcaagacc | 1560 |
| ggccagatca | atggcgatct | gctgatctac | cacgtgctgc | tgacactgaa | gccatactat | 1620 |
| gccaagccct | atgagatcgt | ggtggacctg | acccacacag | gcccaagcaa | caggtttaag | 1680 |
| accgatttcc | tgtccaagtg | gttcgtggtg | tttcccggct | tcgcctatga | caacgtgagc | 1740 |
| gccgtgtaca | tctataactg | caatagctgg | gtgcgggagt | acaccaagta | tcacgagcgc | 1800 |
| ctgctgacag | gcctgaaggg | cagcaagaga | ctggtgttca | tcgattgtcc | cggcaagctg | 1860 |
| gccgagcaca | tcgagcacga | gcagcagaag | ctgcctgcag | ccaccctggc | cctggaggag | 1920 |
| gacctgaagg | tgtttcacaa | cgccctgaag | ctggcccaca | aggatacaaa | ggtgtccatc | 1980 |
| aaggtcggct | ctacagccgt | gcaggtgacc | tccgccgaga | gaacaaaggt | gctgggccag | 2040 |
| agcgtgttcc | tgaatgacat | ctactatgcc | agcgagatcg | aggagatctg | cctggtggat | 2100 |

| | | |
|---|---|---|
| gagaaccagt ttaccctgac aatcgccaat cagggcaccc ccctgacatt catgcaccag | 2160 | |
| gagtgtgaag caatcgtcca gagcattatt cacattcgca ctcggtggga actgagccag | 2220 | |
| cctgac | 2226 | |

<210> SEQ ID NO 7
<211> LENGTH: 6521
<212> TYPE: DNA
<213> ORGANISM: Artificial Sequence
<220> FEATURE:
<223> OTHER INFORMATION: Synthetic

<400> SEQUENCE: 7

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccaga tcttcaatat tggccattag ccatattatt | 180 |
| cattggttat atagcataaa tcaatattgg ctattggcca ttgcatacgt tgtatctata | 240 |
| tcataatatg tacatttata ttggctcatg tccaatatga ccgccatgtt ggcattgatt | 300 |
| attgactagt tattaatagt aatcaattac ggggtcatta gttcatagcc catatatgga | 360 |
| gttccgcgtt acataactta cggtaaatgg cccgcctggc tgaccgccca acgacccccg | 420 |
| cccattgacg tcaataatga cgtatgttcc catagtaacg ccaatagggacttccattg | 480 |
| acgtcaatgg gtggagtatt tacggtaaac tgcccacttg gcagtacatc aagtgtatca | 540 |
| tatgccaagt ccgccccta ttgacgtcaa tgacggtaaa tggcccgcct ggcattatgc | 600 |
| ccagtacatg accttacggg actttcctac ttggcagtac atctacgtat tagtcatcgc | 660 |
| tattaccatg gtcgaggtga gccccacgtt ctgcttcact ctccccatct cccccccctc | 720 |
| cccacccca atttgtgtat tatttatttt ttaattattt tgtgcagcga tgggggcggg | 780 |
| gggggggggg gggcgcgcgc caggcggggc ggggcggggc gaggggcggg gcggggcgag | 840 |
| gcggagaggt gcggcggcag ccaatcagag cggcgcgctc cgaaagtttc cttttatggc | 900 |
| gaggcggcgg cggcggcggc cctataaaaa gcgaagcgcg cggcggggcgg gagtcgctgc | 960 |
| gcgctgcctt cgccccgtgc cccgctccgc cgccgcctcg cgccgcccgc cccggctctg | 1020 |
| actgaccgcg ttactcccac aggtgagcgg gcgggacggc ccttctcctc cgggctgtaa | 1080 |
| ttagcgcttg gtttaatgac ggcttgtttc ttttctgtgg ctgcgtgaaa gccttgaggg | 1140 |
| gctccgggag ggccctttgt gcgggggag cggctcgggg ggtgcgtgcg tgtgtgtgtg | 1200 |
| cgtggggagc gccgcgtgcg gctccgcgct gcccggcggc tgtgagcgct gcgggcgcgg | 1260 |
| cgcggggctt tgtgcgctcc gcagtgtgcg cgaggggagc gcggccgggg cggtgccccc | 1320 |
| gcggtgcggg ggggctgcg agggaacaa aggctgcgtg cggggtgtgt gcgtgggggg | 1380 |
| gtgagcaggg ggtgtgggcg cgtcggtcgg gctgcaaccc ccctgcacc ccctccccg | 1440 |
| agttgctgag cacggcccgg cttcgggtgc gggctccgt acggggcgtg gcgcggggct | 1500 |
| cgccgtgccg gcggggggt ggcggcaggt ggggtgccg gcggggcgg ggccgcctcg | 1560 |
| ggccggggag ggctcgggggagggcgcgcg cggcccccgg agcgccggcg gctgtcgagg | 1620 |
| cgcggcgagc cgcagccatt gcctttatg gtaatcgtgc gagagggcgc agggacttcc | 1680 |
| tttgtcccaa atctgtgcgg agccgaaatc tgggaggcgc cgccgcaccc cctctagcgg | 1740 |
| gcgcggggcg aagcggtgcg gcgccggcag gaaggaaatg ggcggggagg gccttcgtgc | 1800 |
| gtcgccgcgc cgccgtcccc ttctccctct ccagcctcgg gctgtccgc gggggacggg | 1860 |
| ctgccttcgg gggggacggg gcagggcggg gttcggcttc tggcgtgtga ccggcggctc | 1920 |

```
tagagcctct gctaaccatg ttcatgcctt cttcttttc ctacagctcc tgggcaacgt      1980
gctggttatt gtgctgtctc atcattttgg caaagaattc gatatcaagc ttgccaccat      2040
ggaagccaag agccagctgt ttctgaaata ctttaccctg tttatgaatc tgctgaacga      2100
ctgtagtgag gtggaggacg agagtgccca gaccggcggc aggaagagag gcatgtctag      2160
gagactggcc agcctgaggc actgcacagt gctggccatg tccaacctgc tgaacgccaa      2220
tgtggactcc ggcctgatgc actctatcgg cctgggctac acaaggatc tgcagacccg       2280
cgccacattc atggaggtgc tgaccaagat cctgcagcag ggcaccgagt tgacacact       2340
ggccgagacc gtgctggcag ataggttcga gcgcctggtg gagctggtga caatgatggg      2400
cgaccaggga gagctgccta tcgcaatggc actggccaac gtggtgccat gcagccagtg      2460
ggacgagctg gccagggtgc tggtgaccct gtttgattcc agacacctgc tgtaccagct      2520
gctgtggaac atgttctcta aggaggtgga gctggccgac agcatgcaga cactgtttag      2580
gggcaattcc ctggcctcta agatcatgac cttctgtttt aaggtgtacg cgccacata      2640
tctgcagaag ctgctggatc cactgctgag aatcgtgatc accagctccg actggcagca      2700
cgtgtccttc gaggtggatc ctacacggct ggagccaagc gagtccctgg aggagaacca      2760
gcgcaatctg ctgcagatga ccgagaagtt cttcacgcc atcatctcta gctcctctga       2820
gtttccccct cagctgcggt ccgtgtgcca ctgtctgtac caggccacct gccactctct      2880
gctgaacaag gccacagtga aggagaagaa ggagaataag aagagcgtgg tgtcccagag      2940
gttcccacag aacagcatcg gagcagtggg atccgccatg ttcctgaggt tcatcaatcc      3000
cgccatcgtg agcccttatg aggccggcat cctggacaag aagccacccc ctaggatcga      3060
gagaggcctg aagctgatga gcaagatcct gcagtccatc gccaaccacg tgctgttcac      3120
caaggaggag cacatgcgcc ccttcaacga ctttgtgaag tctaattttg atgccgcccg      3180
gcgcttcttt ctggacatcg cctctgattg tcctacaagc gacgccgtga ccactctct       3240
gagcttcatc agcgatggca atgtgctggc cctgcaccgg ctgctgtgga caatcagga       3300
gaagatcggc cagtacctga gctccaacag ggaccacaag gcagtgggca ggagaccttt      3360
tgataagatg gccacccctgc tggcatatct gggaccacca gagcacaagc cagtggcaga      3420
cacccactgg tctagcctga atctgacatc ctctaagttc gaggagtta tgacccggca       3480
ccaggtgcac gagaaggagg agtttaaggc cctgaagacc ctggatgact cgagtttttt      3540
tttgcggccg cttcgagcag acatgataag atacattgat gagtttggac aaaccacaac      3600
tagaatgcag tgaaaaaaat gctttatttg tgaaatttgt gatgctattg ctttatttgt      3660
aaccattata agctgcaata aacaagttaa caacaacaat tgcattcatt ttatgtttca      3720
ggttcagggg gagatgtggg aggtttttta agcaagtaa aacctctaca aatgtggtaa       3780
aatcgatagg ccgcaggaac ccctagtgat ggagttggcc actccctctc tgcgcgctcg      3840
ctcgctcact gaggccgggc gaccaaaggt cgcccgacgc ccgggcggcc tcagtgagcg      3900
agcgagcgcg cagctgcctg caggacatgt gagcaaaagg ccagcaaaag gccaggaacc      3960
gtaaaaaggc cgcgttgctg gcgttttcc ataggctccg ccccctgac gagcatcaca        4020
aaaatcgacg ctcaagtcag aggtggcgaa acccgacagg actataaaga taccaggcgt      4080
ttccccctgg aagctccctc gtgcgctctc ctgttccgac cctgccgctt accggatacc      4140
tgtccgcctt tctcccttcg ggaagcgtgg cgctttctca tagctcacgc tgtaggtatc      4200
tcagttcggt gtaggtcgtt cgctccaagc tgggctgtgt gcacgaaccc cccgttcagc      4260
```

```
ccgaccgctg cgccttatcc ggtaactatc gtcttgagtc caacccggta agacacgact    4320
tatcgccact ggcagcagcc actggtaaca ggattagcag agcgaggtat gtaggcggtg    4380
ctacagagtt cttgaagtgg tggcctaact acggctacac tagaagaaca gtatttggta    4440
tctgcgctct gctgaagcca gttaccttcg aaaaagagt tggtagctct tgatccggca     4500
aacaaaccac cgctggtagc ggtggttttt ttgtttgcaa gcagcagatt acgcgcagaa    4560
aaaaaggatc tcaagaagat cctttgatct tttctacggg gtctgacgct cagtggaacg    4620
aaaactcacg ttaagggatt ttggtcatga gattatcaaa aaggatcttc acctagatcc    4680
ttttaaatta aaaatgaagt tttaaatcaa tctaaagtat atatgagtaa acttggtctg    4740
acagttacca atgcttaatc agtgaggcac ctatctcagc gatctgtcta tttcgttcat    4800
ccatagttgc ctgactcccc gtcgtgtaga taactacgat acgggagggc ttaccatctg    4860
gccccagtgc tgcaatgata ccgcgagacc cacgctcacc ggctccagat ttatcagcaa    4920
taaaccagcc agccggaagg gccgagcgca gaagtggtcc tgcaacttta tccgcctcca    4980
tccagtctat taattgttgc cgggaagcta gagtaagtag ttcgccagtt aatagtttgc    5040
gcaacgttgt tgccattgct acaggcatcg tggtgtcacg ctcgtcgttt ggtatggctt    5100
cattcagctc cggttcccaa cgatcaaggc gagttacatg atccccatg ttgtgcaaaa     5160
aagcggttag ctccttcggt cctccgatcg ttgtcagaag taagttggcc gcagtgttat    5220
cactcatggt tatggcagca ctgcataatt ctcttactgt catgccatcc gtaagatgct    5280
tttctgtgac tggtgagtac tcaaccaagt cattctgaga atagtgtatg cggcgaccga    5340
gttgctcttg cccggcgtca atacgggata ataccgcgcc acatagcaga actttaaaag    5400
tgctcatcat tggaaaacgt tcttcggggc gaaaactctc aaggatctta ccgctgttga    5460
gatccagttc gatgtaaccc actcgtgcac ccaactgatc ttcagcatct tttactttca    5520
ccagcgtttc tgggtgagca aaaacaggaa ggcaaaatgc cgcaaaaaag ggaataaggg    5580
cgacacggaa atgttgaata ctcatactct ccttttttca atattattga agcatttatc    5640
agggttattg tctcatgagc ggatacatat ttgaatgtat ttagaaaaat aaacaaatag    5700
gggttccgcg cacatttccc cgaaaagtgc cacctgacgt ctaagaaacc attattatca    5760
tgacattaac ctataaaaat aggcgtatca cgaggccctt tcgtctcgcg cgtttcggtg    5820
atgacggtga aaacctctga cacatgcagc tcccggagac ggtcacagct tgtctgtaag    5880
cggatgccgg gagcagacaa gcccgtcagg gcgcgtcagc gggtgttggc gggtgtcggg    5940
gctggcttaa ctatgcggca tcagagcaga ttgtactgag agtgcaccat aaaattgtaa    6000
acgttaatat tttgttaaaa ttcgcgttaa attttttgtta aatcagctca ttttttaacc    6060
aataggccga atcggcaaa atcccttata aatcaaaaga atagcccgag atagggttga     6120
gtgttgttcc agtttggaac aagagtccac tattaaagaa cgtggactcc aacgtcaaag    6180
ggcgaaaaac cgtctatcag ggcgatggcc cactacgtga accatcaccc aaatcaagtt    6240
ttttggggtc gaggtgccgt aaagcactaa atcggaaccc taaagggagc ccccgattta    6300
gagcttgacg gggaaagccg gcgaacgtgg cgagaaagga agggaagaaa gcgaaaggag    6360
cgggcgctaa ggcgctggca agtgtagcgg tcacgctgcg cgtaaccacc acacccgccg    6420
cgcttaatgc gccgctacag ggcgcgtact atggttgctt tgacgtatgc ggtgtgaaat    6480
accgcacaga tgcgtaagga gaaaataccg catcaggcgc c                        6521

<210> SEQ ID NO 8
<211> LENGTH: 6965
```

```
<212> TYPE: DNA
<213> ORGANISM: Artificial Sequence
<220> FEATURE:
<223> OTHER INFORMATION: Synthetic

<400> SEQUENCE: 8
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccaga tcttcaatat tggccattag ccatattatt    180
cattggttat atagcataaa tcaatattgg ctattggcca ttgcatacgt tgtatctata    240
tcataatatg tacatttata ttggctcatg tccaatatga ccgccatgtt ggcattgatt    300
attgactagt tattaatagt aatcaattac ggggtcatta gttcatagcc catatatgga    360
gttccgcgtt acataactta cggtaaatgg cccgcctggc tgaccgccca acgacccccg    420
cccattgacg tcaataatga cgtatgttcc catagtaacg ccaataggga ctttccattg    480
acgtcaatgg gtggagtatt tacggtaaac tgcccacttg gcagtacatc aagtgtatca    540
tatgccaagt ccgccccta ttgacgtcaa tgacggtaaa tggcccgcct ggcattatgc    600
ccagtacatg accttacggg actttcctac ttggcagtac atctacgtat tagtcatcgc    660
tattaccatg gtcgaggtga gccccacgtt ctgcttcact ctccccatct cccccccctc    720
cccaccccca attttgtatt tatttatttt ttaattattt tgtgcagcga tggggggcggg    780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcggggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gccccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc cccctgcacc cccctccccg   1440
agttgctgag cacggcccgg cttcgggtgc ggggctccgt acggggcgtg gcgcggggct   1500
cgccgtgccg gcgggggggt ggcggcaggt ggggggtgccg ggcggggcgg ggccgcctcg   1560
ggccggggag ggctcggggg aggggcgcgg cggcccccgg agcgccggcg gctgtcgagg   1620
cgcggcgagc cgcagccatt gccttttatg gtaatcgtgc gagagggcgc agggacttcc   1680
tttgtcccaa atctgtgcgg agccgaaatc tgggaggcgc cgccgcaccc cctctagcgg   1740
gcgcggggcg aagcggtgcg cgcgcggcag gaaggaaatg ggcggggagg gccttcgtgc   1800
gtcgccgcgc cgccgtcccc ttctccctct ccagcctcgg ggctgtccgc ggggggacgg   1860
ctgccttcgg gggggacggg gcagggcggg gttcggcttc tggcgtgtga ccggcggctc   1920
tagagcctct gctaaccatg ttcatgcctt cttctttttc ctacagctcc tgggcaacgt   1980
gctggttatt gtgctgtctc atcatttttgg caaagaattc gatatcaagc ttgccaccat   2040
ggaagccaag agccagctgt ttctgaaata ctttacccctg tttatgaatc tgctgaacga   2100
ctgtagtgag gtggaggacg agagtgccca gaccggcggc aggaagagag gcatgtctag   2160
```

| | |
|---|---|
| gagactggcc agcctgaggc actgcacagt gctggccatg tccaacctgc tgaacgccaa | 2220 |
| tgtggactcc ggcctgatgc actctatcgg cctgggctac cacaaggatc tgcagacccg | 2280 |
| cgccacattc atggaggtgc tgaccaagat cctgcagcag ggcaccgagt tgacacact | 2340 |
| ggccgagacc gtgctggcag ataggttcga gcgcctggtg gagctggtga caatgatggg | 2400 |
| cgaccaggga gagctgccta tcgcaatggc actggccaac gtggtgccat gcagccagtg | 2460 |
| ggacgagctg gccagggtgc tggtgaccct gtttgattcc agacacctgc tgtaccagct | 2520 |
| gctgtggaac atgttctcta aggaggtgga gctggccgac agcatgcaga cactgtttag | 2580 |
| gggcaattcc ctggcctcta agatcatgac cttctgtttt aaggtgtacg gcgccacata | 2640 |
| tctgcagaag ctgctggatc cactgctgag aatcgtgatc accagctccg actggcagca | 2700 |
| cgtgtccttc gaggtggatc ctacacggct ggagccaagc gagtccctgg aggaaacca | 2760 |
| gcgcaatctg ctgcagatga ccgagaagtt cttcacgcc atcatctcta gctcctctga | 2820 |
| gtttccccct cagctgcggt ccgtgtgcca ctgtctgtac caggccacct gccactctct | 2880 |
| gctgaacaag gccacagtga aggagaagaa ggagaataag aagagcgtgg tgtcccagag | 2940 |
| gttcccacag aacagcatcg gagcagtggg atccgccatg ttcctgaggt tcatcaatcc | 3000 |
| cgccatcgtg agcccttatg aggccggcat cctggacaag aagccacccc ctaggatcga | 3060 |
| gagaggcctg aagctgatga gcaagatcct gcagtccatc gccaaccacg tgctgttcac | 3120 |
| caaggaggag cacatgcgcc ccttcaacga ctttgtgaag tctaattttg atgccgcccg | 3180 |
| gcgcttcttt ctggacatcg cctctgattg tcctacaagc gacgccgtga ccactctct | 3240 |
| gagcttcatc agcgatggca atgtgctggc cctgcaccgg ctgctgtgga caatcagga | 3300 |
| gaagatcggc cagtacctga gctccaacag ggaccacaag gcagtgggca ggagaccatt | 3360 |
| tgataagatg gccacactgc tggcctatct gggaccacca gagcacaagc cagtggcaga | 3420 |
| cacacactgg tctagcctga atctgacctc ctctaagttc gaggagttta tgacccggca | 3480 |
| ccaggtgcac gagaaggagg agtttaaggc cctgaagaca ctgtctatct tctaccaggc | 3540 |
| aggcaccagc aaggcaggaa acccaatctt ttactatgtg gcccggcgct tcaagacagg | 3600 |
| ccagatcaat ggcgatctgc tgatctacca cgtgctgctg accctgaagc catactatgc | 3660 |
| caagccctat gagatcgtgg tggacctgac ccacacaggc ccctccaaca ggtttaagac | 3720 |
| cgatttcctg tctaagtggt tcgtggtgtt tcctggcttc gcctatgaca atgtgagcgc | 3780 |
| cgtgtacatc tataactgca attcctgggt gcgggagtac acaaagtatc acgagcgcct | 3840 |
| gctgaccggc ctgaagggat ccaagagact ggtgttcatc gattgtcccg gcaagctggc | 3900 |
| cgagcacatt gaacacgaac agcagaaact gcccgccgca accctggccc tggaagagga | 3960 |
| cctgaaggat gactcgagtt ttttttttgcg gccgcttcga gcagacatga taagatacat | 4020 |
| tgatgagttt ggacaaacca caactagaat gcagtgaaaa aaatgcttta tttgtgaaat | 4080 |
| ttgtgatgct attgctttat ttgtaaccat tataagctgc aataaacaag ttaacaacaa | 4140 |
| caattgcatt cattttatgt ttcaggttca gggggagatg tgggaggttt tttaaagcaa | 4200 |
| gtaaaacctc tacaaatgtg gtaaaatcga taggccgcag gaaccccctag tgatggagtt | 4260 |
| ggccactccc tctctgcgcg ctcgctcgct cactgaggcc gggcgaccaa aggtcgcccg | 4320 |
| acgcccgggc ggcctcagtg agcgagcgag cgcgcagctg cctgcaggac atgtgagcaa | 4380 |
| aaggccagca aaaggccagg aaccgtaaaa aggccgcgtt gctggcgttt ttccataggc | 4440 |
| tccgcccccc tgacgagcat cacaaaaatc gacgctcaag tcagaggtgg cgaaacccga | 4500 |
| caggactata agataccag gcgtttcccc ctggaagctc cctcgtgcgc tctcctgttc | 4560 |

```
cgaccctgcc gcttaccgga tacctgtccg cctttctccc ttcgggaagc gtggcgcttt    4620
ctcatagctc acgctgtagg tatctcagtt cggtgtaggt cgttcgctcc aagctgggct    4680
gtgtgcacga accccccgtt cagcccgacc gctgcgcctt atccggtaac tatcgtcttg    4740
agtccaaccc ggtaagacac gacttatcgc cactggcagc agccactggt aacaggatta    4800
gcagagcgag gtatgtaggc ggtgctacag agttcttgaa gtggtggcct aactacggct    4860
acactagaag aacagtattt ggtatctgcg ctctgctgaa gccagttacc ttcggaaaaa    4920
gagttggtag ctcttgatcc ggcaaacaaa ccaccgctgg tagcggtggt ttttttgttt    4980
gcaagcagca gattacgcgc agaaaaaaag gatctcaaga agatcctttg atcttttcta    5040
cggggtctga cgctcagtgg aacgaaaact cacgttaagg gattttggtc atgagattat    5100
caaaaaggat cttcacctag atccttttaa attaaaaatg aagttttaaa tcaatctaaa    5160
gtatatatga gtaaacttgg tctgacagtt accaatgctt aatcagtgag gcacctatct    5220
cagcgatctg tctatttcgt tcatccatag ttgcctgact ccccgtcgtg tagataacta    5280
cgatacggga gggcttacca tctggcccca gtgctgcaat gataccgcga gacccacgct    5340
caccggctcc agatttatca gcaataaacc agccagccgg aagggccgag cgcagaagtg    5400
gtcctgcaac tttatccgcc tccatccagt ctattaattg ttgccgggaa gctagagtaa    5460
gtagttcgcc agttaatagt ttgcgcaacg ttgttgccat tgctacaggc atcgtggtgt    5520
cacgctcgtc gtttggtatg gcttcattca gctccggttc ccaacgatca aggcgagtta    5580
catgatcccc catgttgtgc aaaaaagcgg ttagctcctt cggtcctccg atcgttgtca    5640
gaagtaagtt ggccgcagtg ttatcactca tggttatggc agcactgcat aattctctta    5700
ctgtcatgcc atccgtaaga tgcttttctg tgactggtga gtactcaacc aagtcattct    5760
gagaatagtg tatgcggcga ccgagttgct cttgcccggc gtcaatacgg gataataccg    5820
cgccacatag cagaacttta aaagtgctca tcattggaaa acgttcttcg gggcgaaaac    5880
tctcaaggat cttaccgctg ttgagatcca gttcgatgta acccactcgt gcacccaact    5940
gatcttcagc atcttttact ttcaccagcg tttctgggtg agcaaaaaca ggaaggcaaa    6000
atgccgcaaa aaagggaata agggcgacac ggaaatgttg aatactcata ctcttccttt    6060
ttcaatatta ttgaagcatt tatcagggtt attgtctcat gagcggatac atatttgaat    6120
gtatttagaa aaataaacaa ataggggttc cgcgcacatt tccccgaaaa gtgccacctg    6180
acgtctaaga aaccattatt atcatgacat taacctataa aaataggcgt atcacgaggc    6240
cctttcgtct cgcgcgtttc ggtgatgacg gtgaaaacct ctgacacatg cagctcccgg    6300
agacggtcac agcttgtctg taagcggatg ccgggagcag acaagcccgt cagggcgcgt    6360
cagcgggtgt tggcgggtgt cggggctggc ttaactatgc ggcatcagag cagattgtac    6420
tgagagtgca ccataaaatt gtaaacgtta atattttgtt aaaattcgcg ttaaattttt    6480
gttaaatcag ctcattttt aaccaatagg ccgaaatcgg caaaatccct tataaatcaa    6540
aagaatagcc cgagataggg ttgagtgttg ttccagtttg gaacaagagt ccactattaa    6600
agaacgtgga ctccaacgtc aaagggcgaa aaaccgtcta tcaggcgat ggcccactac    6660 gtgaaccatc acccaaatca agttttttgg ggtcgaggtg ccgtaaagca ctaaatcgga    6720
accctaaagg gagcccccga tttagagctt gacggggaaa gccggcgaac gtggcgagaa    6780
aggaagggaa gaaagcgaaa ggagcgggcg ctaaggcgct ggcaagtgta gcggtcacgc    6840
tgcgcgtaac caccacaccc gccgcgctta atgcgccgct acagggcgcg tactatggtt    6900
```

-continued

| | |
|---|---|
| gctttgacgt atgcggtgtg aaataccgca cagatgcgta aggagaaaat accgcatcag | 6960 |
| gcgcc | 6965 |

<210> SEQ ID NO 9
<211> LENGTH: 7262
<212> TYPE: DNA
<213> ORGANISM: Artificial Sequence
<220> FEATURE:
<223> OTHER INFORMATION: Synthetic

<400> SEQUENCE: 9

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggttcc tgcggccaga tcttcaatat tggccattag ccatattatt | 180 |
| cattggttat atagcataaa tcaatattgg ctattggcca ttgcatacgt tgtatctata | 240 |
| tcataatatg tacatttata ttggctcatg tccaatatga ccgccatgtt ggcattgatt | 300 |
| attgactagt tattaatagt aatcaattac ggggtcatta gttcatagcc catatatgga | 360 |
| gttccgcgtt acataactta cggtaaatgg cccgcctggc tgaccgccca acgaccccg | 420 |
| cccattgacg tcaataatga cgtatgttcc catagtaacg ccaatagggga ctttccattg | 480 |
| acgtcaatgg gtggagtatt tacggtaaac tgcccacttg gcagtacatc aagtgtatca | 540 |
| tatgccaagt ccgcccccta ttgacgtcaa tgacggtaaa tggcccgcct ggcattatgc | 600 |
| ccagtacatg accttacggg actttcctac ttggcagtac atctacgtat tagtcatcgc | 660 |
| tattaccatg gtcgaggtga gccccacgtt ctgcttcact ctccccatct ccccccctc | 720 |
| cccacccca attttgtatt tatttatttt ttaattattt tgtgcagcga tgggggcggg | 780 |
| ggggggggg gggcgcgcgc caggcggggc gggcggggc gaggggcggg gcggggcgag | 840 |
| gcggagaggt gcggcggcag ccaatcagag cggcgcgctc gaaagtttc cttttatggc | 900 |
| gaggcggcgg cggcggcggc cctataaaaa gcgaagcgcg cggcgggcgg gagtcgctgc | 960 |
| gcgctgcctt cgccccgtgc cccgctccgc cgccgcctcg cgccgcccgc cccggctctg | 1020 |
| actgaccgcg ttactcccac aggtgagcgg cgggacggc ccttctcctc cgggctgtaa | 1080 |
| ttagcgcttg gtttaatgac ggcttgtttc ttttctgtgg ctgcgtgaaa gccttgaggg | 1140 |
| gctccgggag ggccctttgt gcgggggag cggctcgggg ggtgcgtgcg tgtgtgtgtg | 1200 |
| cgtggggagc gccgcgtgcg gctccgcgct gcccggcggc tgtgagcgct gcgggcgcgg | 1260 |
| cgcggggctt tgtgcgctcc gcagtgtgcg cgaggggagc gcggccgggg gcggtgcccc | 1320 |
| gcggtgcggg gggggctgcg aggggaacaa aggctgcgtg cggggtgtgt gcgtgggggg | 1380 |
| gtgagcaggg ggtgtgggcg cgtcggtcgg gctgcaaccc cccctgcacc cccctccccg | 1440 |
| agttgctgag cacggcccgg cttcgggtgc ggggctccgt acggggcgtg gcgcggggct | 1500 |
| cgccgtgccg gcggggggt ggcgcaggt ggggtgccg gcggggcgg ggccgcctcg | 1560 |
| ggccggggag ggctcggggg aggggcgcgg cggcccccgg agcgccggcg gctgtcgagg | 1620 |
| cgcggcgagc cgcagccatt gccttttatg gtaatcgtgc gagagggcgc agggacttcc | 1680 |
| tttgtcccaa atctgtgcgg agccgaaatc tgggaggcgc cgccgcaccc cctctagcgg | 1740 |
| gcgcggggcg aagcggtgcg gcgccggcag gaaggaaatg ggcgggagg gccttcgtgc | 1800 |
| gtcgccgcgc cgccgtcccc ttctccctct ccagcctcgg ggctgtccgc ggggggacgg | 1860 |
| ctgccttcgg gggggacggg gcagggcggg gttcggcttc tggcgtgtga ccggcggctc | 1920 |
| tagagcctct gctaaccatg ttcatgcctt cttctttttc ctacagctcc tgggcaacgt | 1980 |

```
gctggttatt gtgctgtctc atcattttgg caaagaattc gatatcaagc ttgccaccat   2040
ggaagccaag agccagctgt ttctgaaata ctttaccctg tttatgaatc tgctgaacga   2100
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
cgccacattc atggaggtgc tgaccaagat cctgcagcag gcaccgagt ttgacacact    2340 ggccgagacc gtgctggcag ataggttcga gcgcctggtg gagctggtga caatgatggg   2400
cgaccaggga gagctgccta tcgcaatggc actggccaac gtggtgccat gcagccagtg   2460
ggacgagctg gccagggtgc tggtgaccct gtttgattcc agacacctgc tgtaccagct   2520
gctgtggaac atgttctcta aggaggtgga gctggccgac agcatgcaga cactgtttag   2580
gggcaattcc ctggcctcta agatcatgac cttctgtttt aaggtgtacg gcgccacata   2640
tctgcagaag ctgctggatc cactgctgag aatcgtgatc accagctccg actggcagca   2700
cgtgtccttc gaggtggatc ctacacggct ggagccaagc gagtccctgg aggagaacca   2760
gcgcaatctg ctgcagatga ccgagaagtt cttcacgcc atcatctcta gctcctctga    2820
gtttccccct cagctgcggt ccgtgtgcca ctgtctgtac caggccacct gccactctct   2880
gctgaacaag gccacagtga aggagaagaa ggagaataag aagagcgtgg tgtcccagag   2940
gttcccacag aacagcatcg gagcagtggg atccgccatg ttcctgaggt tcatcaatcc   3000
cgccatcgtg agcccttatg aggccggcat cctggacaag aagccacccc ctaggatcga   3060
gagaggcctg aagctgatga gcaagatcct gcagtccatc gccaaccacg tgctgttcac   3120
caaggaggag cacatgcgcc ccttcaacga ctttgtgaag tctaattttg atgccgcccg   3180
gcgcttcttt ctggacatcg cctctgattg tcctacaagc gacgccgtga accactctct   3240
gagcttcatc agcgatggca atgtgctggc cctgcaccgg ctgctgtgga caatcagga    3300 gaagatcggc cagtacctga ctccaacag ggaccacaag gcagtgggca ggagaccttt    3360
tgataagatg gccaccctgc tggcatatct gggaccacca gagcacaagc cagtggcaga   3420
cacccactgg tctagcctga atctgacatc ctctaagttc gaggagttta tgacccggca   3480
ccaggtgcac gagaaggagg agtttaaggc cctgaagacc ctgtccatct tctaccaggc   3540
cggcacatct aaggccggca acctatctt ttactatgtg gcccggcgct tcaagaccgg    3600
ccagatcaat ggcgatctgc tgatctacca cgtgctgctg acactgaagc catactatgc   3660
caagccctat gagatcgtgg tggacctgac ccacacaggc caagcaaca ggtttaagac    3720 cgatttcctg tccaagtggt tcgtggtgtt tcccggcttc gcctatgaca acgtgagcgc   3780
cgtgtacatc tataactgca atagctgggt gcgggagtac accaagtatc acgagcgcct   3840
gctgacaggc ctgaagggca gcaagagact ggtgttcatc gattgtcccg gcaagctggc   3900
cgagcacatc gagcacgagc agcagaagct gcctgcagcc accctggccc tggaggagga   3960
cctgaaggtg tttcacaacg ccctgaagct ggcccacaag gatacaaagg tgtccatcaa   4020
ggtcggctct acagccgtgc aggtgacctc cgccgagaga acaaaggtgc tgggccagag   4080
cgtgttcctg aatgacatct actatgccag cgagatcgag gagatctgcc tggtggatga   4140
gaaccagttt accctgacaa tcgccaatca gggcaccccc ctgacattca tgcaccagga   4200
gtgtgaagca atcgtccaga gcattattca cattcgcact cggtgggaac tgagccagcc   4260
tgacgatgac tcgagttttt ttttgcggcc gcttcgagca gacatgataa gatacattga   4320
```

```
tgagtttgga caaaccacaa ctagaatgca gtgaaaaaaa tgctttattt gtgaaatttg    4380
tgatgctatt gctttatttg taaccattat aagctgcaat aaacaagtta acaacaacaa    4440
ttgcattcat tttatgtttc aggttcaggg ggagatgtgg gaggttttt aaagcaagta    4500 aaacctctac aaatgtggta aaatcgatag gccgcaggaa ccctagtga tggagttggc    4560 cactccctct ctgcgcgctc gctcgctcac tgaggccggg cgaccaaagg tcgcccgacg    4620
cccgggcggc ctcagtgagc gagcgagcgc gcagctgcct gcaggacatg tgagcaaaag    4680
gccagcaaaa ggccaggaac cgtaaaaagg ccgcgttgct ggcgtttttc cataggctcc    4740
gcccccctga cgagcatcac aaaaatcgac gctcaagtca gaggtggcga aacccgacag    4800
gactataaag ataccaggcg tttccccctg gaagctccct cgtgcgctct cctgttccga    4860
ccctgccgct taccggatac ctgtccgcct ttctcccttc gggaagcgtg gcgctttctc    4920
atagctcacg ctgtaggtat ctcagttcgg tgtaggtcgt tcgctccaag ctgggctgtg    4980
tgcacgaacc ccccgttcag cccgaccgct gcgccttatc cggtaactat cgtcttgagt    5040
ccaacccggt aagacacgac ttatcgccac tggcagcagc cactggtaac aggattagca    5100
gagcgaggta tgtaggcggt gctacagagt tcttgaagtg gtggcctaac tacggctaca    5160
ctagaagaac agtatttggt atctgcgctc tgctgaagcc agttaccttc ggaaaaagag    5220
ttggtagctc ttgatccggc aaacaaacca ccgctggtag cggtggtttt tttgtttgca    5280
agcagcagat tacgcgcaga aaaaaggat ctcaagaaga tcctttgatc ttttctacgg    5340
ggtctgacgc tcagtggaac gaaaactcac gttaagggat tttggtcatg agattatcaa    5400
aaaggatctt cacctagatc cttttaaatt aaaaatgaag ttttaaatca atctaaagta    5460
tatatgagta aacttggtct gacagttacc aatgcttaat cagtgaggca cctatctcag    5520
cgatctgtct atttcgttca tccatagttg cctgactccc cgtcgtgtag ataactacga    5580
tacgggaggg cttaccatct ggccccagtg ctgcaatgat accgcgagac ccacgctcac    5640
cggctccaga tttatcagca ataaaccagc cagccggaag ggccgagcgc agaagtggtc    5700
ctgcaacttt atccgcctcc atccagtcta ttaattgttg ccgggaagct agagtaagta    5760
gttcgccagt taatagtttg cgcaacgttg ttgccattgc tacaggcatc gtggtgtcac    5820
gctcgtcgtt tggtatggct tcattcagct ccggttccca acgatcaagg cgagttacat    5880 gatccccat gttgtgcaaa aaagcggtta gctccttcgg tcctccgatc gttgtcagaa    5940
gtaagttggc cgcagtgtta tcactcatgg ttatggcagc actgcataat tctcttactg    6000
tcatgccatc cgtaagatgc ttttctgtga ctggtgagta ctcaaccaag tcattctgag    6060
aatagtgtat gcggcgaccg agttgctctt gcccggcgtc aatacgggat aataccgcgc    6120
cacatagcag aactttaaaa gtgctcatca ttggaaaacg ttcttcgggg cgaaaactct    6180
caaggatctt accgctgttg agatccagtt cgatgtaacc cactcgtgca cccaactgat    6240
cttcagcatc ttttactttc accagcgttt ctgggtgagc aaaaacagga aggcaaaatg    6300
ccgcaaaaaa gggaataagg gcgacacgga aatgttgaat actcatactc ttcctttttc    6360
aatattattg aagcatttat cagggttatt gtctcatgag cggatacata tttgaatgta    6420
tttagaaaaa taaacaaata ggggttccgc gcacatttcc ccgaaaagtg ccacctgacg    6480
tctaagaaac cattattatc atgacattaa cctataaaaa taggcgtatc acgaggccct    6540
ttcgtctcgc gcgtttcggt gatgacggtg aaaacctctg acacatgcag ctcccggaga    6600
cggtcacagc ttgtctgtaa gcggatgccg ggagcagaca agcccgtcag ggcgcgtcag    6660
cgggtgttgg cgggtgtcgg ggctggctta actatgcggc atcagagcag attgtactga    6720
```

```
gagtgcacca taaaattgta aacgttaata ttttgttaaa attcgcgtta aattttttgtt    6780 aaatcagctc attttttaac caataggccg aaatcggcaa aatcccttat aaatcaaaag    6840
aatagcccga gatagggttg agtgttgttc cagtttggaa caagagtcca ctattaaaga    6900
acgtggactc caacgtcaaa gggcgaaaaa ccgtctatca gggcgatggc ccactacgtg    6960
aaccatcacc caaatcaagt tttttggggt cgaggtgccg taaagcacta atcggaacc     7020 ctaaagggag cccccgattt agagcttgac ggggaaagcc ggcgaacgtg gcgagaaagg    7080
aagggaagaa agcgaaagga gcgggcgcta aggcgctggc aagtgtagcg gtcacgctgc    7140
gcgtaaccac cacacccgcc gcgcttaatg cgccgctaca gggcgcgtac tatggttgct    7200
ttgacgtatg cggtgtgaaa taccgcacag atgcgtaagg agaaaatacc gcatcaggcg    7260
cc                                                                   7262
```

```
<210> SEQ ID NO 10
<211> LENGTH: 1391
<212> TYPE: PRT
<213> ORGANISM: Artificial Sequence
<220> FEATURE:
<223> OTHER INFORMATION: Synthetic

<400> SEQUENCE: 10
```

Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
            20                  25                  30

Lys Val Ser Thr Glu His Asn Lys Glu Cys Leu Ile Asn Ile Ser Lys
        35                  40                  45

Tyr Lys Phe Ser Leu Val Ile Ser Gly Leu Thr Thr Ile Leu Lys Asn
    50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
        115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205

Gln Leu Ala Val Ile Asn Ser Leu Glu Lys Ala Phe Trp Asn Trp Val
    210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

```
Ala Glu Ser Thr Lys Arg Lys Ala Ala Val Trp Pro Leu Gln Ile Ile
            260                 265                 270

Leu Leu Ile Leu Cys Pro Glu Ile Ile Gln Asp Ile Ser Lys Asp Val
        275                 280                 285

Val Asp Glu Asn Asn Met Asn Lys Lys Leu Phe Leu Asp Ser Leu Arg
    290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
        355                 360                 365

Gln Pro Ala Asp Val Asp Leu Met Ile Asp Cys Leu Val Ser Cys Phe
    370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
        435                 440                 445

Lys Ala Val Gln Gly Cys Gly Ala His Pro Ala Ile Arg Met Ala Pro
    450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
        515                 520                 525

Leu Val Gln Leu Val Pro Gln Ser His Met Pro Glu Ile Ala Gln Glu
    530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
    610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
```

```
            675                 680                 685
Val Ala Leu Tyr Met Phe Leu Trp Asn Pro Asp Thr Glu Ala Val Leu
690                 695                 700

Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
                740                 745                 750

Ala Ala Leu Gln Lys Arg Val Met Ala Leu Leu Arg Arg Ile Glu His
                755                 760                 765

Pro Thr Ala Gly Asn Thr Glu Ala Trp Glu Asp Thr His Ala Lys Trp
770                 775                 780

Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Ser Ile Asp Leu Ser Asp Thr Asp
                820                 825                 830

Ser Leu Gln Glu Trp Ile Asn Met Thr Gly Phe Leu Cys Ala Leu Gly
                835                 840                 845

Gly Val Cys Leu Gln Gln Arg Ser Asn Ser Gly Leu Ala Thr Tyr Ser
850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
                900                 905                 910

Ile Arg Thr Asn Val Lys Asp Leu Val Gly Leu Glu Leu Ser Pro Ala
                915                 920                 925

Leu Tyr Pro Met Leu Phe Asn Lys Leu Lys Asn Thr Ile Ser Lys Phe
            930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
                965                 970                 975

Glu Gly Ser Ser Glu His Leu Gly Gln Ala Ser Ile Glu Thr Met Met
                980                 985                 990

Leu Asn Leu Val Arg Tyr Val Arg  Val Leu Gly Asn Met  Val His Ala
            995                 1000                1005

Ile Gln  Ile Lys Thr Lys Leu  Cys Gln Leu Val Glu  Val Met Met
    1010                1015                1020

Ala Arg  Arg Asp Asp Leu Ser  Phe Cys Gln Glu Met  Lys Phe Arg
    1025                1030                1035

Asn Lys  Met Val Glu Tyr Leu  Thr Asp Trp Val Met  Gly Thr Ser
    1040                1045                1050

Asn Gln  Ala Ala Asp Asp Asp  Val Lys Cys Leu Thr  Arg Asp Leu
    1055                1060                1065

Asp Gln  Ala Ser Met Glu Ala  Val Val Ser Leu Leu  Ala Gly Leu
    1070                1075                1080

Pro Leu  Gln Pro Glu Glu Gly  Asp Gly Val Glu Leu  Met Glu Ala
    1085                1090                1095
```

Lys Ser Gln Leu Phe Leu Lys Tyr Phe Thr Leu Phe Met Asn Leu
1100            1105                1110

Leu Asn Asp Cys Ser Glu Val Glu Asp Glu Ser Ala Gln Thr Gly
1115            1120                1125

Gly Arg Lys Arg Gly Met Ser Arg Arg Leu Ala Ser Leu Arg His
1130            1135                1140

Cys Thr Val Leu Ala Met Ser Asn Leu Leu Asn Ala Asn Val Asp
1145            1150                1155

Ser Gly Leu Met His Ser Ile Gly Leu Gly Tyr His Lys Asp Leu
1160            1165                1170

Gln Thr Arg Ala Thr Phe Met Glu Val Leu Thr Lys Ile Leu Gln
1175            1180                1185

Gln Gly Thr Glu Phe Asp Thr Leu Ala Glu Thr Val Leu Ala Asp
1190            1195                1200

Arg Phe Glu Arg Leu Val Glu Leu Val Thr Met Met Gly Asp Gln
1205            1210                1215

Gly Glu Leu Pro Ile Ala Met Ala Leu Ala Asn Val Val Pro Cys
1220            1225                1230

Ser Gln Trp Asp Glu Leu Ala Arg Val Leu Val Thr Leu Phe Asp
1235            1240                1245

Ser Arg His Leu Leu Tyr Gln Leu Leu Trp Asn Met Phe Ser Lys
1250            1255                1260

Glu Val Glu Leu Ala Asp Ser Met Gln Thr Leu Phe Arg Gly Asn
1265            1270                1275

Ser Leu Ala Ser Lys Ile Met Thr Phe Cys Phe Lys Val Tyr Gly
1280            1285                1290

Ala Thr Tyr Leu Gln Lys Leu Leu Asp Pro Leu Leu Arg Ile Val
1295            1300                1305

Ile Thr Ser Ser Asp Trp Gln His Val Ser Phe Glu Val Asp Pro
1310            1315                1320

Thr Arg Leu Glu Pro Ser Glu Ser Leu Glu Glu Asn Gln Arg Asn
1325            1330                1335

Leu Leu Gln Met Thr Glu Lys Phe Phe His Ala Ile Ile Ser Ser
1340            1345                1350

Ser Ser Glu Phe Pro Pro Gln Leu Arg Ser Val Cys His Cys Leu
1355            1360                1365

Tyr Gln Ala Thr Cys His Ser Leu Leu Asn Lys Ala Thr Val Lys
1370            1375                1380

Glu Lys Lys Glu Asn Lys Lys Ser
1385            1390

<210> SEQ ID NO 11
<211> LENGTH: 4173
<212> TYPE: DNA
<213> ORGANISM: Artificial Sequence
<220> FEATURE:
<223> OTHER INFORMATION: Synthetic

<400> SEQUENCE: 11
atggccgcgc acaggccggt ggaatgggtc caggccgtgg tcagccgctt cgacgagcag     60
cttccaataa aaacaggaca gcagaacaca cataccaaag tcagtactga gcacaacaag    120
gaatgtctaa tcaatatttc caaatacaag ttttctttgg ttataagcgg cctcactact    180
attttaaaga atgttaacaa tatgagaata tttggagaag ctgctgaaaa aaatttatat    240

```
ctctctcagt tgattatatt ggatacactg gaaaaatgtc ttgctgggca accaaaggac      300
acaatgagat tagatgaaac gatgctggtc aaacagttgc tgccagaaat ctgccatttt      360
cttcacacct gtcgtgaagg aaaccagcat gcagctgaac ttcggaattc tgcctctggg      420
gttttatttt ctctcagctg caacaacttc aatgcagtct ttagtcgcat ttctaccagg      480
ttacaggaat taactgtttg ttcagaagac aatgttgatg ttcatgatat agaattgtta      540
cagtatatca atgtggattg tgcaaaatta aaacgactcc tgaaggaaac agcatttaaa      600
tttaaagccc taagaaggt tgcgcagtta gcagttataa atagcctgga aaaggcattt       660
```

```
atgtcttcag agggaaacgc agatacacct gtcagcaaat ttatggatcg gctgttgtcc    2700
ttaatggtgt gtaaccatga gaaagtggga cttcaaatac ggaccaatgt taaggatctg    2760
gtgggtctag aattgagtcc tgctctgtat ccaatgctat ttaacaaatt gaagaatacc    2820
atcagcaagt tttttgactc ccaaggacag gttttattga ctgataccaa tactcaattt    2880
gtagaacaaa ccatagctat aatgaagaac ttgctagata tcatactga aggcagctct     2940 gaacatctag ggcaagctag cattgaaaca atgatgttaa atctggtcag gtatgttcgt    3000
gtgcttggga atatggtcca tgcaattcaa ataaaaacga aactgtgtca attagttgaa    3060
gtaatgatgg caaggagaga tgacctctca ttttgccaag atgaaaatt taggaataag     3120 atggtagaat acctgacaga ctgggttatg ggaacatcaa accaagcagc agatgatgat    3180
gtaaaatgtc ttacaagaga tttggaccag gcaagcatgg aagcagtagt ttcacttcta    3240
gctggtctcc ctctgcagcc tgaagaagga gatggtgtgg aattgatgga agccaaatca    3300
cagttatttc ttaaatactt cacattattt atgaaccttt tgaatgactg cagtgaagtt    3360
gaagatgaaa gtgcgcaaac aggtggcagg aaacgtggca tgtctcggag gctggcatca    3420
ctgaggcact gtacggtcct tgcaatgtca aacttactca atgccaacgt agacagtggt    3480
ctcatgcact ccataggctt aggttaccac aaggatctcc agacaagagc tacatttatg    3540
gaagttctga caaaaatcct tcaacaaggc acagaatttg acacacttgc agaaacagta    3600
ttggctgatc ggtttgagag attggtggaa ctggtcacaa tgatgggtga tcaaggagaa    3660
ctccctatag cgatggctct ggccaatgtg gttccttgtt ctcagtggga tgaactagct    3720
cgagttctgg ttactctgtt tgattctcgg catttactct accaactgct ctggaacatg    3780
ttttctaaag aagtagaatt ggcagactcc atgcagactc tcttccgagg caacagcttg    3840
gccagtaaaa taatgacatt ctgtttcaag gtatatggtg ctacctatct acaaaaactc    3900
ctggatcctt tattacgaat tgtgatcaca tcctctgatt ggcaacatgt tagctttgaa    3960
gtggatccta ccaggttaga accatcagag agccttgagg aaaaccagcg gaacctcctt    4020
cagatgactg aaaagttctt ccatgccatc atcagttcct cctcagaatt cccccctcaa    4080
cttcgaagtg tgtgccactg tttataccag gcaacttgcc actccctact gaataaagct    4140
acagtaaaag aaaaaaagga aaacaaaaaa tca                                 4173
```

<210> SEQ ID NO 12
<211> LENGTH: 7463
<212> TYPE: DNA
<213> ORGANISM: Artificial Sequence
<220> FEATURE:
<223> OTHER INFORMATION: Synthetic

<400> SEQUENCE: 12

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccaga tctgtcgaca attgagggcg tcaccgctaa    180
ggctccgccc cagcctgggc tccacaacca atgaagggta atctcgacaa agagcaaggg    240
gtggggcgcg ggcgcgcagg tgcagcagca cacaggctgg tcgggagggc ggggcgcgac    300
gtctgccgtg cggggtcccg gcatcggttg cgcgcgcgct ccctcctctc ggagagaggg    360
ctgtggtaaa acccgtccgg aaaactagtc caccatggcc cgcgcacagg ccggtggaat    420
gggtccaggc cgtggtcagc cgcttcgacg agcagcttcc aataaaaaca ggacagcaga    480
```

```
acacacatac caaagtcagt actgagcaca caaggaatg tctaatcaat atttccaaat      540
acaagttttc tttggttata agcggcctca ctactatttt aaagaatgtt aacaatatga    600
gaatatttgg agaagctgct gaaaaaaatt tatatctctc tcagttgatt atattggata    660
cactggaaaa atgtcttgct gggcaaccaa aggacacaat gagattagat gaaacgatgc    720
tggtcaaaca gttgctgcca gaaatctgcc attttcttca cacctgtcgt gaaggaaacc    780
agcatgcagc tgaacttcgg aattctgcct ctggggtttt attttctctc agctgcaaca    840
acttcaatgc agtctttagt cgcatttcta ccaggttaca ggaattaact gtttgttcag    900
aagacaatgt tgatgttcat gatatagaat tgttacagta tatcaatgtg gattgtgcaa    960
aattaaaacg actcctgaag gaaacagcat ttaaatttaa agccctaaag aaggttgcgc   1020
agttagcagt tataaatagc ctggaaaagg cattttggaa ctgggtagaa aattatccag   1080
atgaatttac aaaactgtac cagatcccac agactgatat ggctgaatgt gcagaaaagc   1140
tatttgactt ggtggatggt tttgctgaaa gcaccaaacg taaagcagca gtttggccac   1200
tacaaatcat tctccttatc ttgtgcccag aaataatcca ggatatatcc aaagacgtgg   1260
ttgatgaaaa caacatgaat aagaagttat ttctggacag tctacgaaaa gctcttgctg   1320
gccatggagg aagtaggcag ctgacagaaa gtgctgcaat tgcctgtgtc aaactgtgta   1380
aagcaagtac ttcatcaat tgggaagata actctgtcat tttcctactt gttcagtcca    1440
tggtggttga tcttaagaac ctgcttttta atccaagtaa gccattctca agaggcagtc   1500
agcctgcaga tgtggatcta atgattgact gccttgtttc ttgctttcgt ataagccctc   1560
acaacaacca cactttaag atctgcctgg ctcagaattc accttctaca tttcactatg    1620
tgctggtaaa ttcactccat cgaatcatca ccaattccgc attggattgg tggcctaaga   1680
ttgatgctgt gtattgtcac tcggttgaac ttcgaaatat gtttggtgaa acacttcata   1740
aagcagtgca aggttgtgga gcacacccag caatacgaat ggcaccgagt cttacattta   1800
aagaaaaagt aacaagcctt aaatttaaag aaaaacctac agacctggag acaagaagct   1860
ataagtatct tctcttgtcc atggtgaaac taattcatgc agatccaaag ctcttgctttt  1920 gtaatccaag aaaacagggg cccgaaaccc aaggcagtac agcagaatta attacagggc   1980
tcgtccaact ggtccctcag tcacacatgc cagagattgc tcaggaagca atggaggctc   2040
tgctggttct tcatcagtta gatagcattg atttgtggaa tcctgatgct cctgtagaaa   2100
cattttggga gattagctca caaatgcttt tttacatctg caagaaatta actagtcatc   2160
aaatgcttag tagcacagaa attctcaagt ggttgcggga atattgatc tgcaggaata    2220 aatttcttct taaaaataag caggcagata gaagttcctg tcactttctc cttttttacg   2280
gggtaggatg tgatattcct tctagtggaa ataccagtca aatgtccatg gatcatgaag   2340
aattactacg tactcctgga gcctctctcc ggaagggaaa agggaactcc tctatggata   2400
gtgcagcagg atgcagcgga acccccccaa tttgccgaca agcccagacc aaactagaag   2460
tggccctgta catgtttctg tggaaccctg acactgaagc tgttctggtt gccatgtcct   2520
gtttccgcca cctctgtgag gaagcagata tccggtgtgg ggtggatgaa gtgtcagtgc   2580
ataacctctt gcccaactat aacacattca tggagtttgc ctctgtcagc aatatgatgt   2640
caacaggaag agcagcactt cagaaaagag tgatggcact gctgaggcgc attgagcatc   2700
ccactgcagg aaacactgag gcttgggaag atacacatgc aaaatgggaa caagcaacaa   2760
agctaatcct taactatcca aaagccaaaa tggaagatgg ccaggctgct gaaagccttc   2820
acaagaccat tgttaagagg cgaatgtccc atgtgagtgg aggaggatcc atagatttgt   2880
```

```
ctgacacaga ctccctacag gaatggatca acatgactgg cttcctttgt gcccttgggg   2940
gagtgtgcct ccagcagaga agcaattctg gcctggcaac ctatagccca cccatgggtc   3000
cagtcagtga acgtaagggt tctatgattt cagtgatgtc ttcagaggga aacgcagata   3060
cacctgtcag caaatttatg gatcggctgt tgtccttaat ggtgtgtaac catgagaaag   3120
tgggacttca aatacggacc aatgttaagg atctggtggg tctagaattg agtcctgctc   3180
tgtatccaat gctatttaac aaattgaaga ataccatcag caagtttttt gactcccaag   3240
gacaggtttt attgactgat accaatactc aatttgtaga acaaaccata gctataatga   3300
agaacttgct agataatcat actgaaggca gctctgaaca tctagggcaa gctagcattg   3360
aaacaatgat gttaaatctg gtcaggtatg ttcgtgtgct tgggaatatg gtccatgcaa   3420
ttcaaataaa aacgaaactg tgtcaattag ttgaagtaat gatggcaagg agagatgacc   3480
tctcattttg ccaagagatg aaatttagga ataagatggt agaatacctg acagactggg   3540
ttatgggaac atcaaaccaa gcagcagatg atgatgtaaa atgtcttaca agagatttgg   3600
accaggcaag catggaagca gtagtttcac ttctagctgg tctccctctg cagcctgaag   3660
aaggagatgt tgtggaattg atggaagcca aatcacagtt atttcttaaa tacttcacat   3720
tatttatgaa cctttttgaat gactgcagtg aagttgaaga tgaaagtgcg caaacaggtg   3780
gcaggaaacg tggcatgtct cggaggctgg catcactgag gcactgtacg gtccttgcaa   3840
tgtcaaactt actcaatgcc aacgtagaca gtggtctcat gcactccata ggcttaggtt   3900
accacaagga tctccagaca agagctacat ttatggaagt tctgacaaaa atccttcaac   3960
aaggcacaga atttgacaca cttgcagaaa cagtattggc tgatcggttt gagagattgg   4020
tggaactggt cacaatgatg ggtgatcaag gagaactccc tatagcgatg gctctggcca   4080
atgtggttcc ttgttctcag tgggatgaac tagctcgagt tctggttact ctgtttgatt   4140
ctcggcattt actctaccaa ctgctctgga acatgttttc taaagaagta gaattggcag   4200
actccatgca gactctcttc cgaggcaaca gcttggccag taaaataatg acattctgtt   4260
tcaaggtata tggtgctacc tatctacaaa aactcctgga tcctttatta cgaattgtga   4320
tcacatcctc tgattggcaa catgttagct ttgaagtgga tcctaccagg ttagaaccat   4380
cagagagcct tgaggaaaac cagcggaacc tccttcagat gactgaaaag ttcttccatg   4440
ccatcatcag ttcctcctca gaattcccc ctcaacttcg aagtgtgtgc cactgtttat   4500
accaggcaac ttgccactcc ctactgaata aagctacagt aaaagaaaaa aaggaaaaca   4560
aaaaatcagt gggcagcatg tggaacctgg cgagccccat ccccggcaag ctctcaagcc   4620
atgctggtgg ggacgactga atgccagggc ccttcactgg gctatttcac ccagggacgc   4680
ttcttgaagg caccccccac tccaagctca attgaactcg agaatcgata ggccgcagga   4740
acccctagtg atggagttgg ccactccctc tctgcgcgct cgctcgctca ctgaggccgg   4800
gcgaccaaag gtcgcccgac gcccgggcgg cctcagtgag cgagcgagcg cgcagctgcc   4860
tgcaggacat gtgagcaaaa ggccagcaaa aggccaggaa ccgtaaaaag gccgcgttgc   4920
tggcgttttt ccataggctc cgcccccctg acgagcatca aaaaatcga cgctcaagtc   4980 agaggtggcg aaacccgaca ggactataaa gataccaggc gtttccccct ggaagctccc   5040
tcgtgcgctc tcctgttccg accctgccgc ttaccggata cctgtccgcc tttctccctt   5100
cgggaagcgt ggcgctttct catagctcac gctgtaggta tctcagttcg gtgtaggtcg   5160
ttcgctccaa gctgggctgt gtgcacgaac cccccgttca gcccgaccgc tgcgccttat   5220
```

```
ccggtaacta tcgtcttgag tccaacccgg taagacacga cttatcgcca ctggcagcag    5280
ccactggtaa caggattagc agagcgaggt atgtaggcgg tgctacagag ttcttgaagt    5340
ggtggcctaa ctacggctac actagaagaa cagtatttgg tatctgcgct ctgctgaagc    5400
cagttacctt cggaaaaaga gttggtagct cttgatccgg caaacaaacc accgctggta    5460
gcggtggttt ttttgtttgc aagcagcaga ttacgcgcag aaaaaaagga tctcaagaag    5520
atcctttgat cttttctacg gggtctgacg ctcagtggaa cgaaaactca cgttaaggga    5580
ttttggtcat gagattatca aaaggatctt cacctagat  cctttttaaat taaaaatgaa    5640 gttttaaatc aatctaaagt atatatgagt aaacttggtc tgacagttac caatgcttaa    5700
tcagtgaggc acctatctca gcgatctgtc tatttcgttc atccatagtt gcctgactcc    5760
ccgtcgtgta gataactacg atacgggagg gcttaccatc tggccccagt gctgcaatga    5820
taccgcgaga cccacgctca ccggctccag atttatcagc aataaaccag ccagccggaa    5880
gggccgagcg cagaagtggt cctgcaactt tatccgcctc catccagtct attaattgtt    5940
gccgggaagc tagagtaagt agttcgccag ttaatagttt gcgcaacgtt gttgccattg    6000
ctacaggcat cgtggtgtca cgctcgtcgt ttggtatggc ttcattcagc tccggttccc    6060
aacgatcaag gcgagttaca tgatccccca tgttgtgcaa aaaagcggtt agctccttcg    6120
gtcctccgat cgttgtcaga agtaagttgg ccgcagtgtt atcactcatg gttatggcag    6180
cactgcataa ttctcttact gtcatgccat ccgtaagatg cttttctgtg actggtgagt    6240
actcaaccaa gtcattctga gaatagtgta tgcggcgacc gagttgctct tgcccggcgt    6300
caatacggga taataccgcg ccacatagca gaactttaaa agtgctcatc attggaaaac    6360
gttcttcggg gcgaaaactc tcaaggatct taccgctgtt gagatccagt tcgatgtaac    6420
ccactcgtgc acccaactga tcttcagcat cttttacttt caccagcgtt tctgggtgag    6480
caaaaacagg aaggcaaaat gccgcaaaaa agggaataag ggcgacacgg aaatgttgaa    6540
tactcatact cttccttttt caatattatt gaagcattta tcagggttat tgtctcatga    6600
gcggatacat atttgaatgt atttagaaaa ataaacaaat aggggttccg cgcacatttc    6660
cccgaaaagt gccacctgac gtctaagaaa ccattattat catgacatta acctataaaa    6720
ataggcgtat cacgaggccc tttcgtctcg cgcgtttcgg tgatgacggt gaaaacctct    6780
gacacatgca gctcccggag acggtcacag cttgtctgta agcggatgcc gggagcagac    6840
aagcccgtca gggcgcgtca gcgggtgttg gcgggtgtcg ggctggctt aactatgcgg    6900 catcagagca gattgtactg agagtgcacc ataaaattgt aaacgttaat attttgttaa    6960
aattcgcgtt aaatttttgt taaatcagct catttttta ccaataggcc gaaatcggca    7020
aaatccctta taaatcaaaa gaatagcccg agataggtt gagtgttgtt ccagtttgga    7080
acaagagtcc actattaaag aacgtggact ccaacgtcaa agggcgaaaa accgtctatc    7140
agggcgatgg cccactacgt gaaccatcac ccaaatcaag ttttttgggg tcgaggtgcc    7200
gtaaagcact aaatcggaac cctaaaggga gcccccgatt tagagcttga cggggaaagc    7260
cggcgaacgt ggcgagaaag gaagggaaga agcgaaagg agcgggcgct aaggcgctgg    7320
caagtgtagc ggtcacgctg cgcgtaacca ccacacccgc cgcgcttaat gcgccgctac    7380
agggcgcgta ctatggttgc tttgacgtat gcggtgtgaa ataccgcaca gatgcgtaag    7440
gagaaaatac cgcatcaggc gcc                                            7463
```

<210> SEQ ID NO 13
<211> LENGTH: 1448

<212> TYPE: PRT
<213> ORGANISM: Artificial Sequence
<220> FEATURE:
<223> OTHER INFORMATION: Synthetic

<400> SEQUENCE: 13

Met Val Ser Gln Arg Phe Pro Gln Asn Ser Ile Gly Ala Val Gly Ser
1               5                   10                  15

Ala Met Phe Leu Arg Phe Ile Asn Pro Ala Ile Val Ser Pro Tyr Glu
            20                  25                  30

Ala Gly Ile Leu Asp Lys Lys Pro Pro Arg Ile Glu Arg Gly Leu
        35                  40                  45

Lys Leu Met Ser Lys Ile Leu Gln Ser Ile Ala Asn His Val Leu Phe
    50                  55                  60

Thr Lys Glu Glu His Met Arg Pro Phe Asn Asp Phe Val Lys Ser Asn
65                  70                  75                  80

Phe Asp Ala Ala Arg Arg Phe Phe Leu Asp Ile Ala Ser Asp Cys Pro
                85                  90                  95

Thr Ser Asp Ala Val Asn His Ser Leu Ser Phe Ile Ser Asp Gly Asn
            100                 105                 110

Val Leu Ala Leu His Arg Leu Leu Trp Asn Asn Gln Glu Lys Ile Gly
        115                 120                 125

Gln Tyr Leu Ser Ser Asn Arg Asp His Lys Ala Val Gly Arg Arg Pro
    130                 135                 140

Phe Asp Lys Met Ala Thr Leu Leu Ala Tyr Leu Gly Pro Pro Glu His
145                 150                 155                 160

Lys Pro Val Ala Asp Thr His Trp Ser Ser Leu Asn Leu Thr Ser Ser
                165                 170                 175

Lys Phe Glu Glu Phe Met Thr Arg His Gln Val His Glu Lys Glu Glu
            180                 185                 190

Phe Lys Ala Leu Lys Thr Leu Ser Ile Phe Tyr Gln Ala Gly Thr Ser
        195                 200                 205

Lys Ala Gly Asn Pro Ile Phe Tyr Tyr Val Ala Arg Arg Phe Lys Thr
    210                 215                 220

Gly Gln Ile Asn Gly Asp Leu Leu Ile Tyr His Val Leu Leu Thr Leu
225                 230                 235                 240

Lys Pro Tyr Tyr Ala Lys Pro Tyr Glu Ile Val Val Asp Leu Thr His
                245                 250                 255

Thr Gly Pro Ser Asn Arg Phe Lys Thr Asp Phe Leu Ser Lys Trp Phe
            260                 265                 270

Val Val Phe Pro Gly Phe Ala Tyr Asp Asn Val Ser Met Val Tyr Ile
        275                 280                 285

Tyr Asn Cys Asn Ser Trp Val Arg Glu Tyr Thr Lys Tyr His Glu Arg
    290                 295                 300

Leu Leu Thr Gly Leu Lys Gly Ser Lys Arg Leu Val Phe Ile Asp Cys
305                 310                 315                 320

Pro Gly Lys Leu Ala Glu His Ile Glu His Glu Gln Gln Lys Leu Pro
                325                 330                 335

Ala Ala Thr Leu Ala Leu Glu Glu Asp Leu Lys Val Phe His Asn Ala
            340                 345                 350

Leu Lys Leu Ala His Lys Asp Thr Lys Val Ser Ile Lys Val Gly Ser
        355                 360                 365

Thr Ala Val Gln Val Thr Ser Ala Glu Arg Thr Lys Val Leu Gly Gln
    370                 375                 380

```
Ser Val Phe Leu Asn Asp Ile Tyr Tyr Ala Ser Glu Ile Glu Glu Ile
385                 390                 395                 400

Cys Leu Val Asp Glu Asn Gln Phe Thr Leu Thr Ile Ala Asn Gln Gly
                405                 410                 415

Thr Pro Leu Thr Phe Met His Gln Glu Cys Glu Ala Ile Val Gln Ser
            420                 425                 430

Ile Ile His Ile Arg Thr Arg Trp Glu Leu Ser Gln Pro Asp Ser Ile
        435                 440                 445

Pro Gln His Thr Lys Ile Arg Pro Lys Asp Val Pro Gly Thr Leu Leu
    450                 455                 460

Asn Ile Ala Leu Leu Asn Leu Gly Ser Ser Asp Pro Ser Leu Arg Ser
465                 470                 475                 480

Ala Ala Tyr Asn Leu Leu Cys Ala Leu Thr Cys Thr Phe Asn Leu Lys
                485                 490                 495

Ile Glu Gly Gln Leu Leu Glu Thr Ser Gly Leu Cys Ile Pro Ala Asn
            500                 505                 510

Asn Thr Leu Phe Ile Val Ser Ile Ser Lys Thr Leu Ala Ala Asn Glu
        515                 520                 525

Pro His Leu Thr Leu Glu Phe Leu Glu Glu Cys Ile Ser Gly Phe Ser
    530                 535                 540

Lys Ser Ser Ile Glu Leu Lys His Leu Cys Leu Glu Tyr Met Thr Pro
545                 550                 555                 560

Trp Leu Ser Asn Leu Val Arg Phe Cys Lys His Asn Asp Asp Ala Lys
                565                 570                 575

Arg Gln Arg Val Thr Ala Ile Leu Asp Lys Leu Ile Thr Met Thr Ile
            580                 585                 590

Asn Glu Lys Gln Met Tyr Pro Ser Ile Gln Ala Lys Ile Trp Gly Ser
        595                 600                 605

Leu Gly Gln Ile Thr Asp Leu Leu Asp Val Val Leu Asp Ser Phe Ile
    610                 615                 620

Lys Thr Ser Ala Thr Gly Gly Leu Gly Ser Ile Lys Ala Glu Val Met
625                 630                 635                 640

Ala Asp Thr Ala Val Ala Leu Ala Ser Gly Asn Val Lys Leu Val Ser
                645                 650                 655

Ser Lys Val Ile Gly Arg Met Cys Lys Ile Ile Asp Lys Thr Cys Leu
            660                 665                 670

Ser Pro Thr Pro Thr Leu Glu Gln His Leu Met Trp Asp Asp Ile Ala
        675                 680                 685

Ile Leu Ala Arg Tyr Met Leu Met Leu Ser Phe Asn Asn Ser Leu Asp
    690                 695                 700

Val Ala Ala His Leu Pro Tyr Leu Phe His Val Val Thr Phe Leu Val
705                 710                 715                 720

Ala Thr Gly Pro Leu Ser Leu Arg Ala Ser Thr His Gly Leu Val Ile
                725                 730                 735

Asn Ile Ile His Ser Leu Cys Thr Cys Ser Gln Leu His Phe Ser Glu
            740                 745                 750

Glu Thr Lys Gln Val Leu Arg Leu Ser Leu Thr Glu Phe Ser Leu Pro
        755                 760                 765

Lys Phe Tyr Leu Leu Phe Gly Ile Ser Lys Val Lys Ser Ala Ala Val
    770                 775                 780

Ile Ala Phe Arg Ser Ser Tyr Arg Asp Arg Ser Phe Ser Pro Gly Ser
785                 790                 795                 800

Tyr Glu Arg Glu Thr Phe Ala Leu Thr Ser Leu Glu Thr Val Thr Glu
```

```
                805                 810                 815
Ala Leu Glu Ile Met Glu Ala Cys Met Arg Asp Ile Pro Thr Cys
            820                 825                 830

Lys Trp Leu Asp Gln Trp Thr Glu Leu Ala Gln Arg Phe Ala Phe Gln
            835                 840                 845

Tyr Asn Pro Ser Leu Gln Pro Arg Ala Leu Val Val Phe Gly Cys Ile
            850                 855                 860

Ser Lys Arg Val Ser His Gly Gln Ile Lys Gln Ile Ile Arg Ile Leu
865                 870                 875                 880

Ser Lys Ala Leu Glu Ser Cys Leu Lys Gly Pro Asp Thr Tyr Asn Ser
            885                 890                 895

Gln Val Leu Ile Glu Ala Thr Val Ile Ala Leu Thr Lys Leu Gln Pro
            900                 905                 910

Leu Leu Asn Lys Asp Ser Pro Leu His Lys Ala Leu Phe Trp Val Ala
            915                 920                 925

Val Ala Val Leu Gln Leu Asp Glu Val Asn Leu Tyr Ser Ala Gly Thr
            930                 935                 940

Ala Leu Leu Glu Gln Asn Leu His Thr Leu Asp Ser Leu Arg Ile Phe
945                 950                 955                 960

Asn Asp Lys Ser Pro Glu Glu Val Phe Met Ala Ile Arg Asn Pro Leu
            965                 970                 975

Glu Trp His Cys Lys Gln Met Asp His Phe Val Gly Leu Asn Phe Asn
            980                 985                 990

Ser Asn Phe Asn Phe Ala Leu Val Gly His Leu Leu Lys Gly Tyr Arg
            995                 1000                1005

His Pro Ser Pro Ala Ile Val Ala Arg Thr Val Arg Ile Leu His
    1010                1015                1020

Thr Leu Leu Thr Leu Val Asn Lys His Arg Asn Cys Asp Lys Phe
    1025                1030                1035

Glu Val Asn Thr Gln Ser Val Ala Tyr Leu Ala Ala Leu Leu Thr
    1040                1045                1050

Val Ser Glu Glu Val Arg Ser Arg Cys Ser Leu Lys His Arg Lys
    1055                1060                1065

Ser Leu Leu Leu Thr Asp Ile Ser Met Glu Asn Val Pro Met Asp
    1070                1075                1080

Thr Tyr Pro Ile His His Gly Asp Pro Ser Tyr Arg Thr Leu Lys
    1085                1090                1095

Glu Thr Gln Pro Trp Ser Ser Pro Lys Gly Ser Glu Gly Tyr Leu
    1100                1105                1110

Ala Ala Thr Tyr Pro Thr Val Gly Gln Thr Ser Pro Arg Ala Arg
    1115                1120                1125

Lys Ser Met Ser Leu Asp Met Gly Gln Pro Ser Gln Ala Asn Thr
    1130                1135                1140

Lys Lys Leu Leu Gly Thr Arg Lys Ser Phe Asp His Leu Ile Ser
    1145                1150                1155

Asp Thr Lys Ala Pro Lys Arg Gln Glu Met Glu Ser Gly Ile Thr
    1160                1165                1170

Thr Pro Pro Lys Met Arg Arg Val Ala Glu Thr Asp Tyr Glu Met
    1175                1180                1185

Glu Thr Gln Arg Ile Ser Ser Ser Gln Gln His Pro His Leu Arg
    1190                1195                1200

Lys Val Ser Val Ser Glu Ser Asn Val Leu Leu Asp Glu Glu Val
    1205                1210                1215
```

```
Leu Thr Asp Pro Lys Ile Gln Ala Leu Leu Thr Val Leu Ala
    1220            1225                1230

Thr Leu Val Lys Tyr Thr Thr Asp Glu Phe Asp Gln Arg Ile Leu
    1235                1240                1245

Tyr Glu Tyr Leu Ala Glu Ala Ser Val Val Phe Pro Lys Val Phe
    1250                1255                1260

Pro Val Val His Asn Leu Leu Asp Ser Lys Ile Asn Thr Leu Leu
    1265                1270                1275

Ser Leu Cys Gln Asp Pro Asn Leu Leu Asn Pro Ile His Gly Ile
    1280                1285                1290

Val Gln Ser Val Val Tyr His Glu Glu Ser Pro Pro Gln Tyr Gln
    1295                1300                1305

Thr Ser Tyr Leu Gln Ser Phe Gly Phe Asn Gly Leu Trp Arg Phe
    1310                1315                1320

Ala Gly Pro Phe Ser Lys Gln Thr Gln Ile Pro Asp Tyr Ala Glu
    1325                1330                1335

Leu Ile Val Lys Phe Leu Asp Ala Leu Ile Asp Thr Tyr Leu Pro
    1340                1345                1350

Gly Ile Asp Glu Glu Thr Ser Glu Glu Ser Leu Leu Thr Pro Thr
    1355                1360                1365

Ser Pro Tyr Pro Pro Ala Leu Gln Ser Gln Leu Ser Ile Thr Ala
    1370                1375                1380

Asn Leu Asn Leu Ser Asn Ser Met Thr Ser Leu Ala Thr Ser Gln
    1385                1390                1395

His Ser Pro Gly Ile Asp Lys Glu Asn Val Glu Leu Ser Pro Thr
    1400                1405                1410

Thr Gly His Cys Asn Ser Gly Arg Thr Arg His Gly Ser Ala Ser
    1415                1420                1425

Gln Val Gln Lys Gln Arg Ser Ala Gly Ser Phe Lys Arg Asn Ser
    1430                1435                1440

Ile Lys Lys Ile Val
    1445

<210> SEQ ID NO 14
<211> LENGTH: 4344
<212> TYPE: DNA
<213> ORGANISM: Artificial Sequence
<220> FEATURE:
<223> OTHER INFORMATION: Synthetic

<400> SEQUENCE: 14
gtggttagcc agcgtttccc tcagaacagc atcggtgcag taggaagtgc catgttcctc      60
agatttatca atcctgccat tgtctcaccg tatgaagcag ggattttaga taaaaagcca     120
ccacctagaa tcgaaagggg cttgaagtta atgtcaaaga tacttcagag tattgccaat     180
catgttctct tcacaaaaga agaacatatg cggccttttca atgattttgt gaaaagcaac     240
tttgatgcag cacgcaggtt tttccttgat atagcatctg attgtcctac aagtgatgca     300
gtaaatcata gtcttttcctt cataagtgac ggcaatgtgc ttgctttaca tcgtctactc     360
tggaacaatc aggagaaaat tgggcagtat ctttccagca acagggatca taaagctgtt     420
ggaagacgac ttttgataaa gatggcaaca cttcttgcat acctgggtcc tccagagcac     480
aaacctgtgg cagatacaca ctggtccagc cttaacctta ccagttcaaa gtttgaggaa     540
tttatgacta ggcatcaggt acatgaaaaa gaagaattca aggctttgaa aacgttaagt     600
```

```
attttctacc aagctgggac ttccaaagct gggaatccta ttttttatta tgttgcacgg    660
aggttcaaaa ctggtcaaat caatggtgat ttgctgatat accatgtctt actgacttta    720
aagccatatt atgcaaagcc atatgaaatt gtagtggacc ttacccatac cgggcctagc    780
aatcgcttta aaacagactt tctctctaag tggtttgttg ttttcctgg  ctttgcttac    840
gacaacgtct ccgcagtcta tatctataac tgtaactcct gggtcaggga gtacaccaag    900
tatcatgagc ggctgctgac tggcctcaaa ggtagcaaaa ggcttgtttt catagactgt    960
cctgggaaac tggctgagca catagagcat gaacaacaga aactacctgc tgccaccttg   1020
gctttagaag aggacctgaa ggtattccac aatgctctca agctagctca caaagacacc   1080
aaagtttcta ttaaagttgg ttctactgct gtccaagtaa cttcagcaga gcgaacaaaa   1140
gtcctagggc aatcagtctt tctaaatgac atttattatg cttcggaaat tgaagaaatc   1200
tgcctagtag atgagaacca gttcacctta accattgcaa accagggcac gccgctcacc   1260
ttcatgcacc aggagtgtga agccattgtc cagtctatca ttcatatccg gacccgctgg   1320
gaactgtcac agcccgactc tatcccccaa cacaccaaga ttcggccaaa agatgtccct   1380
gggacactgc tcaatatcgc attacttaat ttaggcagtt ctgacccgag tttacggtca   1440
gctgcctata atcttctgtg tgccttaact tgtaccttta atttaaaaat cgagggccag   1500
ttactagaga catcaggttt atgtatccct gccaacaaca ccctctttat tgtctctatt   1560
agtaagcaca tggcagccaa tgagccacac ctcacgttag aattttgga  agagtgtatt   1620
tctggattta gcaaatctag tattgaattg aaacacctt  gtttggaata catgactcca   1680
tggctgtcaa atctagttcg ttttgcaag  cataatgatg atgccaaacg acaaagagtt   1740
actgctattc ttgacaagct gataacaatg accatcaatg aaaaacagat gtacccatct   1800
attcaagcaa aaatatgggg aagccttggg cagattacag atctgcttga tgttgtacta   1860
gacagtttca tcaaaaccag tgcaacaggt ggcttgggat caataaaagc tgaggtgatg   1920
gcagatactg ctgtagcttt ggcttctgga aatgtgaaat tggtttcaag caaggttatt   1980
ggaaggatgt gcaaaataat tgacaagaca tgcttatctc caactcctac tttagaacaa   2040
catcttatgt gggatgatat tgctatttta gcacgctaca tgctgatgct gtccttcaac   2100
aattcccttg atgtggcagc tcatcttccc tacctcttcc acgttgttac tttcttagta   2160
gccacaggtc cgctctccct tagagcttcc acacatggac tggtcattaa tatcattcac   2220
tctctgtgta cttgttcaca gcttcatttt agtgaagaga ccaagcaagt tttgagactc   2280
agtctgacag agttctcatt acccaaattt tacttgctgt ttggcattag caaagtcaag   2340
tcagctgctg tcattgcctt ccgttccagt taccgggaca ggtcattctc tcctggctcc   2400
tatgagagag agacttttgc tttgacatcc ttggaaacag tcacagaagc tttgttggag   2460
atcatggagg catgcatgag agatattcca acgtgcaagt ggctggacca gtggacagaa   2520
ctagctcaaa gatttgcatt ccaatataat ccatccctgc aaccaagagc tcttgttgtc   2580
tttgggtgta ttagcaaacg agtgtctcat ggcagataa  agcagataat ccgtattctt   2640
agcaaggcac ttgagagttg cttaaaagga cctgacactt acaacagtca agttctgata   2700
gaagctacag taatagcact aaccaaatta cagccacttc ttaataagga ctcgcctctg   2760
cacaaagccc tcttttgggt agctgtggct gtgctgcagc ttgatgaggt caacttgtat   2820
tcagcaggta ccgcacttct tgaacaaaac ctgcatactt tagatagtct ccgtatattc   2880
aatgacaaga gtccagagga agtatttatg gcaatccgga atcctctgga gtggcactgc   2940
aagcaaatgg atcattttgt tggactcaat ttcaactcta actttaactt tgcattggtt   3000
```

```
ggacaccttt taaaagggta caggcatcct tcacctgcta ttgttgcaag aacagtcaga    3060
attttacata cactactaac tctggttaac aaacacagaa attgtgacaa atttgaagtg    3120
aatacacaga gcgtggccta cttagcagct ttacttacag tgtctgaaga agttcgaagt    3180
cgctgcagcc taaaacatag aaagtcactt cttcttactg atatttcaat ggaaaatgtt    3240
cctatggata catatcccat tcatcatggt gacccttcct ataggacact aaaggagact    3300
cagccatggt cctctcccaa aggttctgaa ggatacctttg cagccaccta tccaactgtc    3360
ggccagacca gtccccgagc caggaaatcc atgagcctgg acatggggca accttctcag    3420
gccaacacta gaagttgct tggaacaagg aaaagttttg atcacttgat atcagacaca    3480
aaggctccta aaaggcaaga atggaatca gggatcacaa cacccccaa aatgaggaga     3540 gtagcagaaa ctgattatga aatggaaact cagaggattt cctcatcaca acagcaccca    3600
catttacgta aagtttcagt gtctgaatca aatgttctct tggatgaaga agtacttact    3660
gatccgaaga tccaggcgct gcttcttact gttctagcta cactggtaaa atataccaca    3720
gatgagtttg atcaacgaat tctttatgaa tacttagcag aggccagtgt tgtgtttccc    3780
aaagtctttc ctgttgtgca taatttgttg gactctaaga tcaacaccct gttatcattg    3840
tgccaagatc caaatttgtt aaatccaatc catggaattg tgcagagtgt ggtgtaccat    3900
gaagaatccc caccacaata ccaaacatct tacctgcaaa gttttggttt taatggcttg    3960
tggcggtttg caggaccgtt ttcaaagcaa acacaaattc cagactatgc tgagcttatt    4020 gttaagttc ttgatgcctt gattgacacg tacctgcctg gaattgatga agaaaccagt    4080
gaagaatccc tcctgactcc cacatctcct taccctcctg cactgcagag ccagcttagt    4140
atcactgcca accttaacct ttctaattcc atgacctcac ttgcaacttc ccagcattcc    4200
ccaggaatcg acaaggagaa cgttgaactc tcccctacca ctggccactg taacagtgga    4260
cgaactcgcc acggatccgc aagccaagtg cagaagcaaa gaagcgctgg cagtttcaaa    4320
cgtaatagca ttaagaagat cgtg                                          4344
```

<210> SEQ ID NO 15
<211> LENGTH: 7601
<212> TYPE: DNA
<213> ORGANISM: Artificial Sequence
<220> FEATURE:
<223> OTHER INFORMATION: Synthetic

<400> SEQUENCE: 15

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccaga tctgcaaatt aggaccgaga gtcagtggcc     180
gctcaagagt ctgtgaccat gccccaaatt cagagatggt cccaggagag atgggggaa      240 ctgccaagca atgagtgacc ggttccccct ccccaggtg gttagccagc gtttccctca      300
gaacagcatc ggtgcagtag aagtgccat gttcctcaga tttatcaatc ctgccattgt      360
ctcaccgtat gaagcaggga ttttagataa aaagccacca cctagaatcg aaaggggctt      420
gaagttaatg tcaaagatac ttcagagtat tgccaatcat gttctcttca caaaagaaga     480
acatatgcgg cctttcaatg attttgtgaa aagcaacttt gatgcagcac gcaggttttt      540
ccttgatata gcatctgatt gtcctacaag tgatgcagta atcatagtc tttccttcat      600 aagtgacggc aatgtgcttg ctttacatcg tctactctgg aacaatcagg agaaaattgg      660
```

```
gcagtatctt tccagcaaca gggatcataa agctgttgga agacgacctt tgataagat     720 ggcaacactt cttgcatacc tgggtcctcc agagcacaaa cctgtggcag atacacactg    780
gtccagcctt aaccttacca gttcaaagtt tgaggaattt atgactaggc atcaggtaca    840
tgaaaaagaa gaattcaagg ctttgaaaac gttaagtatt ttctaccaag ctgggacttc    900
caaagctggg aatcctattt tttattatgt tgcacggagg ttcaaaactg gtcaaatcaa    960
tggtgatttg ctgatatacc atgtcttact gactttaaag ccatattatg caaagccata   1020
tgaaattgta gtggacctta cccataccgg gcctagcaat cgctttaaaa cagactttct   1080
ctctaagtgg tttgttgttt ttcctggctt tgcttacgac aacgtctccg cagtctatat   1140
ctataactgt aactcctggg tcagggagta caccaagtat catgagcggc tgctgactgg   1200
cctcaaaggt agcaaaaggc ttgttttcat agactgtcct gggaaactgg ctgagcacat   1260
agagcatgaa caacagaaac tacctgctgc caccttggct tagaagagg acctgaaggt    1320 attccacaat gctctcaagc tagctcacaa agacaccaaa gtttctatta aagttggttc   1380
tactgctgtc caagtaactt cagcagagcg aacaaaagtc ctagggcaat cagtctttct   1440
aaatgacatt tattatgctt cggaaattga agaaatctgc ctagtagatg agaaccagtt   1500
caccttaacc attgcaaacc agggcacgcc gctcaccttc atgcaccagg agtgtgaagc   1560
cattgtccag tctatcattc atatccggac ccgctgggaa ctgtcacagc ccgactctat   1620
cccccaacac accaagattc ggccaaaaga tgtccctggg acactgctca atatcgcatt   1680
acttaattta ggcagttctg acccgagttt acggtcagct gcctataatc ttctgtgtgc   1740
cttaacttgt acctttaatt taaaaatcga gggccagtta ctagagacat caggtttatg   1800
tatccctgcc aacaacaccc tctttattgt ctctattagt aagacactgg cagccaatga   1860
gccacacctc acgttagaat ttttggaaga gtgtatttct ggatttagca aatctagtat   1920
tgaattgaaa cacctttgtt tggaatacat gactccatgg ctgtcaaatc tagttcgttt   1980
ttgcaagcat aatgatgatg ccaaacgaca aagagttact gctattcttg acaagctgat   2040
aacaatgacc atcaatgaaa acagatgta cccatctatt caagcaaaaa tatggggaag    2100
ccttgggcag attacagatc tgcttgatgt tgtactagac agtttcatca aaaccagtgc   2160
aacaggtggc ttgggatcaa taaaagctga ggtgatggca gatactgctg tagctttggc   2220
ttctggaaat gtgaaattgg tttcaagcaa ggttattgga aggatgtgca aaataattga   2280
caagacatgc ttatctccaa ctcctacttt agaacaacat cttatgtggg atgatattgc   2340
tattttagca cgctacatgc tgatgctgtc cttcaacaat tcccttgatg tggcagctca   2400
tcttccctac ctcttccacg ttgttacttt cttagtagcc acaggtccgc tctcccttag   2460
agcttccaca catggactgg tcattaatat cattcactct ctgtgtactt gttcacagct   2520 tcatttagt gaagagacca agcaagtttt gagactcagt ctgacagagt tctcattacc   2580
caaattttac ttgctgtttg gcattagcaa agtcaagtca gctgctgtca ttgccttccg   2640
ttccagttac cgggacaggt cattctctcc tggctcctat gagagagaga cttttgcttt   2700
gacatccttg gaaacagtca cagaagcttt gttggagatc atggaggcat gcatgagaga   2760
tattccaacg tgcaagtggc tggaccagtg gacagaacta gctcaaagat tgcattcca   2820 atataatcca tccctgcaac caagagctct tgttgtcttt gggtgtatta gcaaacgagt   2880
gtctcatggg cagataaagc agataatccg tattcttagc aaggcacttg agagttgctt   2940
aaaaggacct gacacttaca acagtcaagt tctgatagaa gctacagtaa tagcactaac   3000
caaattacag ccacttctta ataaggactc gcctctgcac aaagccctct tttgggtagc   3060
```

```
tgtggctgtg ctgcagcttg atgaggtcaa cttgtattca gcaggtaccg cacttcttga    3120
acaaaacctg catactttag atagtctccg tatattcaat gacaagagtc cagaggaagt    3180
atttatggca atccggaatc ctctggagtg gcactgcaag caaatggatc attttgttgg    3240
actcaatttc aactctaact ttaactttgc attggttgga cacctttta  aagggtacag    3300 gcatccttca cctgctattg ttgcaagaac agtcagaatt ttacatacac tactaactct    3360
ggttaacaaa cacagaaatt gtgacaaatt tgaagtgaat acacagagcg tggcctactt    3420
agcagcttta cttacagtgt ctgaagaagt tcgaagtcgc tgcagcctaa aacatagaaa    3480
gtcacttctt cttactgata tttcaatgga aaatgttcct atggatacat atcccattca    3540
tcatggtgac ccttcctata ggacactaaa ggagactcag ccatggtcct ctcccaaagg    3600
ttctgaagga taccttgcag ccacctatcc aactgtcggc cagaccagtc cccgagccag    3660
gaaatccatg agcctggaca tgggcaacc  ttctcaggcc aacactaaga agttgcttgg    3720
aacaaggaaa agttttgatc acttgatatc agacacaaag gctcctaaaa ggcaagaaat    3780
ggaatcaggg atcacaacac cccccaaaat gaggagagta gcagaaactg attatgaaat    3840
ggaaactcag aggatttcct catcacaaca gcacccacat ttacgtaaag tttcagtgtc    3900
tgaatcaaat gttctcttgg atgaagaagt acttactgat ccgaagatcc aggcgctgct    3960
tcttactgtt ctagctacac tggtaaaata taccacagat gagtttgatc aacgaattct    4020
ttatgaatac ttagcagagg ccagtgttgt gtttcccaaa gtctttcctg ttgtgcataa    4080
tttgttggac tctaagatca acaccctgtt atcattgtgc caagatccaa atttgttaaa    4140
tccaatccat ggaattgtgc agagtgtggt gtaccatgaa gaatccccac cacaatacca    4200
aacatcttac ctgcaaagtt ttggttttaa tggcttgtgg cggtttgcag accgttttc     4260 aaagcaaaca caaattccag actatgctga gcttattgtt aagtttcttg atgccttgat    4320
tgacacgtac ctgcctggaa ttgatgaaga accagtgaa  gaatccctcc tgactcccac    4380
atctccttac cctcctgcac tgcagagcca gcttagtatc actgccaacc ttaacctttc    4440
taattccatg acctcacttg caacttccca gcattcccca ggaatcgaca aggagaacgt    4500
tgaactctcc cctaccactg gccactgtaa cagtggacga actcgccacg gatccgcaag    4560
ccaagtgcag aagcaaagaa gcgctggcag tttcaaacgt aatagcatta agaagatcgt    4620
ggagcggccg cttcgagcag acatgataag atacattgat gagtttggac aaaccacaac    4680
tagaatgcag tgaaaaaaat gctttatttg tgaaatttgt gatgctattg ctttatttgt    4740
aaccattata agctgcaata aacaagttaa caacaacaat tgcattcatt ttatgtttca    4800
ggttcagggg gagatgtggg aggttttta  aagcaagtaa aacctctaca aatgtggtaa    4860
aatcgatagg ccgcaggaac ccctagtgat ggagttggcc actccctctc tgcgcgctcg    4920
ctcgctcact gaggccgggc gaccaaaggt cgcccgacgc ccgggcggcc tcagtgagcg    4980
agcgagcgcg cagctgcctg caggacatgt gagcaaaagg ccagcaaaag gccaggaacc    5040
gtaaaaaggc cgcgttgctg gcgtttttcc ataggctccg ccccctgac  gagcatcaca    5100 aaaatcgacg ctcaagtcag aggtggcgaa acccgacagg actataaaga taccaggcgt    5160
ttccccctgg aagctccctc gtgcgctctc ctgttccgac cctgccgctt accggatacc    5220
tgtccgcctt tctcccttcg ggaagcgtgg cgctttctca tagctcacgc tgtaggtatc    5280
tcagttcggt gtaggtcgtt cgctccaagc tgggctgtgt gcacgaaccc ccgttcagc    5340 ccgaccgctg cgccttatcc ggtaactatc gtcttgagtc aacccggta  agacacgact    5400
```

```
tatcgccact ggcagcagcc actggtaaca ggattagcag agcgaggtat gtaggcggtg      5460
ctacagagtt cttgaagtgg tggcctaact acggctacac tagaagaaca gtatttggta      5520
tctgcgctct gctgaagcca gttaccttcg aaaaagagt tggtagctct tgatccggca      5580
aacaaaccac cgctggtagc ggtggttttt tgtttgcaa gcagcagatt acgcgcagaa      5640
aaaaaggatc tcaagaagat cctttgatct tttctacggg gtctgacgct cagtggaacg      5700
aaaactcacg ttaagggatt ttggtcatga gattatcaaa aaggatcttc acctagatcc      5760
ttttaaatta aaaatgaagt tttaaatcaa tctaaagtat atatgagtaa acttggtctg      5820
acagttacca atgcttaatc agtgaggcac ctatctcagc gatctgtcta tttcgttcat      5880
ccatagttgc ctgactcccc gtcgtgtaga taactacgat acgggagggc ttaccatctg      5940
gccccagtgc tgcaatgata ccgcgagacc cacgctcacc ggctccagat ttatcagcaa      6000
taaaccagcc agccggaagg gccgagcgca gaagtggtcc tgcaacttta tccgcctcca      6060
tccagtctat taattgttgc cgggaagcta gagtaagtag ttcgccagtt aatagtttgc      6120
gcaacgttgt tgccattgct acaggcatcg tggtgtcacg ctcgtcgttt ggtatggctt      6180
cattcagctc cggttcccaa cgatcaaggc gagttacatg atcccccatg ttgtgcaaaa      6240
aagcggttag ctccttcggt cctccgatcg ttgtcagaag taagttggcc gcagtgttat      6300
cactcatggt tatggcagca ctgcataatt ctcttactgt catgccatcc gtaagatgct      6360
tttctgtgac tggtgagtac tcaaccaagt cattctgaga atagtgtatg cggcgaccga      6420
gttgctcttg cccggcgtca atacgggata ataccgcgcc acatagcaga actttaaaag      6480
tgctcatcat tggaaaacgt tcttcggggc gaaaactctc aaggatctta ccgctgttga      6540
gatccagttc gatgtaaccc actcgtgcac ccaactgatc ttcagcatct tttactttca      6600
ccagcgtttc tgggtgagca aaaacaggaa ggcaaaatgc cgcaaaaaag ggaataaggg      6660
cgacacggaa atgttgaata ctcatactct tcctttttca atattattga agcatttatc      6720
agggttattg tctcatgagc ggatacatat ttgaatgtat ttagaaaaat aaacaaatag      6780
gggttccgcg cacatttccc cgaaaagtgc cacctgacgt ctaagaaacc attattatca      6840
tgacattaac ctataaaaat aggcgtatca cgaggccctt tcgtctcgcg cgtttcggtg      6900
atgacggtga aaacctctga cacatgcagc tcccggagac ggtcacagct tgtctgtaag      6960
cggatgccgg gagcagacaa gcccgtcagg gcgcgtcagc gggtgttggc gggtgtcggg      7020
gctggcttaa ctatgcggca tcagagcaga ttgtactgag agtgcaccat aaaattgtaa      7080
acgttaatat tttgttaaaa ttcgcgttaa attttgtta aatcagctca ttttttaacc      7140
aataggccga atcggcaaa atcccttata aatcaaaaga atagcccgag atagggttga      7200
gtgttgttcc agtttggaac aagagtccac tattaaagaa cgtggactcc aacgtcaaag      7260
ggcgaaaaac cgtctatcag ggcgatggcc cactacgtga accatcaccc aaatcaagtt      7320
ttttggggtc gaggtgccgt aaagcactaa atcggaaccc taagggagc ccccgattta      7380
gagcttgacg gggaaagccg gcgaacgtgg cgagaaagga agggaagaaa gcgaaaggag      7440
cgggcgctaa ggcgctggca agtgtagcgg tcacgctgcg cgtaaccacc acacccgccg      7500
cgcttaatgc gccgctacag ggcgcgtact atggttgctt tgacgtatgc ggtgtgaaat      7560
accgcacaga tgcgtaagga gaaaataccg catcaggcgc c                          7601

<210> SEQ ID NO 16
<211> LENGTH: 12373
<212> TYPE: DNA
<213> ORGANISM: Homo Sapiense
```

<400> SEQUENCE: 16

```
acttccggtg gggtgtcatg gcggcgtctc ggactgtgat ggctgtgggg agacggcgct    60
agtggggaga gcgaccaaga ggccccctcc cctcccgggg tccccttccc ctatccccct   120
cccccagcc tccttgccaa cgccccctttt ccctctcccc ctcccgctcg gcgctgaccc   180
cccatcccca cccccgtggg aacactggga gcctgcactc cacagaccct ctccttgcct   240
cttccctcac ctcagcctcc gctccccgcc ctcttcccgg cccagggcgc cggcccaccc   300
ttccctccgc cgccccccgg ccgcggggag gacatggccg cgcacaggcc ggtggaatgg   360
gtccaggccg tggtcagccg cttcgacgag cagcttccaa taaaaacagg acagcagaac   420
acacatacca aagtcagtac tgagcacaac aaggaatgtc taatcaatat ttccaaatac   480
aagtttttctt tggttataag cggcctcact actattttaa agaatgttaa caatatgaga   540
atatttggag aagctgctga aaaaaattta tatctctctc agttgattat attggataca   600
ctggaaaaat gtcttgctgg gcaaccaaag gacacaatga gattagatga aacgatgctg   660
gtcaaacagt tgctgccaga atctgccat tttcttcaca cctgtcgtga aggaaaccag   720
catgcagctg aacttcggaa ttctgcctct ggggttttat tttctctcag ctgcaacaac   780
ttcaatgcag tctttagtcg catttctacc aggttacagg aattaactgt tgttcagaa    840
gacaatgttg atgttcatga tatagaattg ttacagtata tcaatgtgga ttgtgcaaaa   900
ttaaaacgac tcctgaagga acagcattt aaatttaaag ccctaaagaa ggttgcgcag   960
ttagcagtta taaatagcct ggaaaaggca ttttggaact gggtagaaaa ttatccagat  1020
gaatttacaa aactgtacca gatcccacag actgatatgg ctgaatgtgc agaaaagcta  1080
tttgacttgg tggatggttt tgctgaaagc accaaacgta agcagcagt ttggccacta   1140
caaatcattc tccttatctt gtgtccagaa ataatccagg atatatccaa agacgtggtt  1200
gatgaaaaca acatgaataa gaagttattt ctggacagtc tacgaaaagc tcttgctggc  1260
catggaggaa gtaggcagct gacagaaagt gctgcaattg cctgtgtcaa actgtgtaaa  1320
gcaagtactt acatcaattg ggaagataac tctgtcattt tcctacttgt tcagtccatg  1380
gtggttgatc ttaagaacct gctttttaat ccaagtaagc cattctcaag aggcagtcag  1440
cctgcagatg tggatctaat gattgactgc cttgtttctt gctttcgtat aagccctcac  1500
aacaaccaac actttaagat ctgcctggct cagaattcac cttctacatt tcactatgtg  1560
ctggtaaatt cactccatcg aatcatcacc aattccgcat tggattggtg gcctaagatt  1620
gatgctgtgt attgtcactc ggttgaactt cgaaatatgt ttggtgaaac acttcataaa  1680
gcagtgcaag gttgtggagc acacccagca atacgaatgg caccgagtct tacatttaaa  1740
gaaaaagtaa caagccttaa atttaaagaa aaacctacag acctggagac aagaagctat  1800
aagtatcttc tcttgtccat ggtgaaacta attcatgcag atccaaagct cttgctttgt  1860
aatccaagaa aacaggggcc cgaaacccaa ggcagtacag cagaattaat tacagggctc  1920
gtccaactgg tccctcagtc acacatgcca gagattgctc aggaagcaat ggaggctctg  1980
ctggttcttc atcagttaga tagcattgat ttgtggaatc ctgatgctcc tgtagaaaca  2040
ttttgggaga ttagctcaca aatgcttttt tacatctgca agaaattaac tagtcatcaa  2100
atgcttagta gcacagaaat tctcaagtgg ttgcgggaaa tattgatctg caggaataaa  2160
ttcttctta aaaataagca ggcagataga agttcctgtc actttctcct tttttacggg  2220
gtaggatgtg atattccttc tagtggaaat accagtcaaa tgtccatgga tcatgaagaa  2280
```

-continued

| | |
|---|---|
| ttactacgta ctcctggagc ctctctccgg aagggaaaag ggaactcctc tatggatagt | 2340 |
| gcagcaggat gcagcggaac ccccccgatt tgccgacaag cccagaccaa actagaagtg | 2400 |
| gccctgtaca tgtttctgtg gaaccctgac actgaagctg ttctggttgc catgtcctgt | 2460 |
| ttccgccacc tctgtgagga agcagatatc cggtgtgggg tggatgaagt gtcagtgcat | 2520 |
| aacctcttgc ccaactataa cacattcatg gagtttgcct ctgtcagcaa tatgatgtca | 2580 |
| acaggaagag cagcacttca gaaaagagtg atggcactgc tgaggcgcat tgagcatccc | 2640 |
| actgcaggaa acactgaggc ttgggaagat acacatgcaa aatgggaaca agcaacaaag | 2700 |
| ctaatcctta actatccaaa agccaaaatg gaagatggcc aggctgctga aagccttcac | 2760 |
| aagaccattg ttaagaggcg aatgtcccat gtgagtggag gaggatccat agatttgtct | 2820 |
| gacacagact ccctcaggga atggatcaac atgactggct tcctttgtgc ccttggggga | 2880 |
| gtgtgcctcc agcagagaag caattctggc ctggcaacct atagcccacc catgggtcca | 2940 |
| gtcagtgaac gtaagggttc tatgatttca gtgatgtctt cagagggaaa cgcagataca | 3000 |
| cctgtcagca aatttatgga tcggctgttg tccttaatgg tgtgtaacca tgagaaagtg | 3060 |
| ggacttcaaa tacggaccaa tgttaaggat ctggtgggtc tagaattgag tcctgctctg | 3120 |
| tatccaatgc tatttaacaa attgaagaat accatcagca agtttttga ctcccaagga | 3180 |
| caggttttat tgactgatac caatactcaa tttgtagaac aaaccatagc tataatgaag | 3240 |
| aacttgctag ataatcatac tgaaggcagc tctgaacatc tagggcaagc tagcattgaa | 3300 |
| acaatgatgt taaatctggt caggtatgtt cgtgtgcttg ggaatatggt ccatgcaatt | 3360 |
| caaataaaaa cgaaactgtg tcaattagtt gaagtaatga tggcaaggag agatgacctc | 3420 |
| tcatttttgcc aagagatgaa atttaggaat aagatggtag aatacctgac agactgggtt | 3480 |
| atgggaacat caaaccaagc agcagatgat gatgtaaaat gtcttacaag agatttggac | 3540 |
| caggcaagca tggaagcagt agtttcactt ctagctggtc tccctctgca gcctgaagaa | 3600 |
| ggagatggtg tggaattgat ggaagccaaa tcacagttat ttcttaaata cttcacatta | 3660 |
| tttatgaacc ttttgaatga ctgcagtgaa gttgaagatg aaagtgcgca aacaggtggc | 3720 |
| aggaaacgtg gcatgtctcg gaggctggca tcactgaggc actgtacggt ccttgcaatg | 3780 |
| tcaaacttac tcaatgccaa cgtagacagt ggtctcatgc actccatagg cttaggttac | 3840 |
| cacaaggatc tccagacaag agctacattt atggaagttc tgacaaaaat ccttcaacaa | 3900 |
| ggcacagaat ttgacacact tgcagaaaca gtattggctg atcggtttga gagattggtg | 3960 |
| gaactggtca aatgatggg tgatcaagga gaactcccta tagcgatggc tctggccaat | 4020 |
| gtggttcctt gttctcagtg ggatgaacta gctcgagttc tggttactct gtttgattct | 4080 |
| cggcatttac tctaccaact gctctggaac atgttttcta agaagtagaa attggcagac | 4140 |
| tccatgcaga ctctcttccg aggcaacagc ttggccagta aaataatgac attctgtttc | 4200 |
| aaggtatatg gtgctaccta tctacaaaaa ctccctggatc ctttattacg aattgtgatc | 4260 |
| acatcctctg attggcaaca tgttagcttt gaagtggatc ctaccaggtt agaaccatca | 4320 |
| gagagccttg aggaaaacca gcggaacctc cttcagatga ctgaaaagtt cttccatgcc | 4380 |
| atcatcagtt cctcctcaga attcccccct caacttcgaa gtgtgtgcca ctgtttatac | 4440 |
| caggcaactt gccactccct actgaataaa gctacagtaa agaaaaaaa ggaaaacaaa | 4500 |
| aaatcagtgg ttagccagcg tttccctcag aacagcatcg gtgcagtagg aagtgccatg | 4560 |
| ttcctcagat ttatcaatcc tgccattgtc tcaccgtatg aagcagggat tttagataaa | 4620 |
| aagccaccac ctagaatcga aaggggcttg aagttaatgt caaagatact tcagagtatt | 4680 |

```
gccaatcatg ttctcttcac aaaagaagaa catatgcggc ctttcaatga ttttgtgaaa    4740
agcaactttg atgcagcacg caggtttttc cttgatatag catctgattg tcctacaagt    4800
gatgcagtaa atcatagtct ttccttcata agtgacggca atgtgcttgc tttacatcgt    4860
ctactctgga acaatcagga gaaaattggg cagtatcttt ccagcaacag ggatcataaa    4920
gctgttggaa gacgaccttt tgataagatg gcaacacttc ttgcatacct gggtcctcca    4980
gagcacaaac ctgtggcaga tacacactgg tccagcctta accttaccag ttcaaagttt    5040
gaggaattta tgactaggca tcaggtacat gaaaagaag  aattcaaggc tttgaaaacg    5100
ttaagtattt tctaccaagc tgggacttcc aaagctggga tcctattttt ttattatgtt    5160
gcacggaggt tcaaaactgg tcaaatcaat ggtgatttgc tgatatacca tgtcttactg    5220
actttaaagc catattatgc aaagccatat gaaattgtag tggaccttac ccataccggg    5280
cctagcaatc gctttaaaac agactttctc tctaagtggt ttgttgtttt tcctggcttt    5340
gcttacgaca acgtctccgc agtctatatc tataactgta actcctgggt cagggagtac    5400
accaagtatc atgagcggct gctgactggc ctcaaaggta gcaaaaggct tgttttcata    5460
gactgtcctg ggaaactggc tgagcacata gagcatgaac aacagaaact acctgctgcc    5520
accttggctt tagaagagga cctgaaggta ttccacaatg ctctcaagct agctcacaaa    5580
gacaccaaag tttctattaa agttggttct actgctgtcc aagtaacttc agcagagcga    5640
acaaaagtcc tagggcaatc agtctttcta aatgacattt attatgcttc ggaaattgaa    5700
gaaatctgcc tagtagatga gaaccagttc accttaacca ttgcaaacca gggcacgccg    5760
ctcaccttca tgcaccagga gtgtgaagcc attgtccagt ctatcattca tatccggacc    5820
cgctgggaac tgtcacagcc cgactctatc ccccaacaca ccaagattcg gccaaaagat    5880
gtccctggga cactgctcaa tatcgcatta cttaatttag gcagttctga cccgagttta    5940
cggtcagctg cctataatct tctgtgtgcc ttaacttgta cctttaattt aaaaatcgag    6000
ggccagttac tagagacatc aggtttatgt atccctgcca acaacaccct ctttattgtc    6060
tctattagta agacactggc agccaatgag ccacacctca cgttagaatt tttggaagag    6120
tgtatttctg gatttagcaa atctagtatt gaattgaaac cctttgttt  ggaatacatg    6180 actccatggc tgtcaaatct agttcgtttt tgcaagcata atgatgatgc caaacgacaa    6240
agagttactg ctattcttga caagctgata acaatgacca tcaatgaaaa acagatgtac    6300
ccatctattc aagcaaaaat atggggaagc cttgggcaga ttacagatct gcttgatgtt    6360
gtactagaca gtttcatcaa aaccagtgca acaggtggct tgggatcaat aaaagctgag    6420
gtgatggcag atactgctgt agctttggct tctggaaatg tgaaattggt ttcaagcaag    6480
gttattggaa ggatgtgcaa aataattgac aagacatgct tatctccaac tcctacttta    6540
gaacaacatc ttatgtggga tgatattgct attttagcac gctacatgct gatgctgtcc    6600
ttcaacaatt cccttgatgt ggcagctcat cttccctacc tcttccacgt tgttactttc    6660
ttagtagcca caggtccgct ctcccttaga gcttccacac atggactggt cattaatatc    6720
attcactctc tgtgtacttg ttcacagctt cattttagtg aagagaccaa gcaagttttg    6780
agactcagtc tgacagagtt ctcattaccc aaattttact tgctgtttgg cattagcaaa    6840
gtcaagtcag ctgctgtcat tgccttccgt tccagttacc gggacaggtc attctctcct    6900
ggctcctatg agagagagac ttttgctttg acatccttgg aaacagtcac agaagctttg    6960
ttggagatca tggaggcatg catgagagat attccaacgt gcaagtggct ggaccagtgg    7020
```

```
acagaactag ctcaaagatt tgcattccaa tataatccat ccctgcaacc aagagctctt    7080
gttgtctttg ggtgtattag caaacgagtg tctcatgggc agataaagca gataatccgt    7140
attcttagca aggcacttga gagttgctta aaaggacctg acacttacaa cagtcaagtt    7200
ctgatagaag ctacagtaat agcactaacc aaattacagc cacttcttaa taaggactcg    7260
cctctgcaca aagccctctt ttgggtagct gtggctgtgc tgcagcttga tgaggtcaac    7320
ttgtattcag caggtaccgc acttcttgaa caaaacctgc atactttaga tagtctccgt    7380
atattcaatg acaagagtcc agaggaagta tttatggcaa tccggaatcc tctggagtgg    7440
cactgcaagc aaatggatca ttttgttgga ctcaatttca actctaactt taactttgca    7500
ttggttggac accttttaaa agggtacagg catccttcac ctgctattgt tgcaagaaca    7560
gtcagaattt tacatacact actaactctg gttaacaaac acagaaattg tgacaaattt    7620
gaagtgaata cacagagcgt ggcctactta gcagctttac ttacagtgtc tgaagaagtt    7680
cgaagtcgct gcagcctaaa acatagaaag tcacttcttc ttactgatat ttcaatggaa    7740
aatgttccta tggatacata tcccattcat catggtgacc cttcctatag gacactaaag    7800
gagactcagc catggtcctc tcccaaaggt tctgaaggat accttgcagc cacctatcca    7860
actgtcggcc agaccagtcc ccgagccagg aaatccatga gcctggacat ggggcaacct    7920
tctcaggcca cactaagaa gttgcttgga acaaggaaaa gttttgatca cttgatatca    7980
gacacaaagg ctcctaaaag gcaagaaatg gaatcaggga tcacaacacc ccccaaaatg    8040
aggagagtag cagaaactga ttatgaaatg gaaactcaga ggatttcctc atcacaacag    8100
cacccacatt tacgtaaagt ttcagtgtct gaatcaaatg ttctcttgga tgaagaagta    8160
cttactgatc cgaagatcca ggcgctgctt cttactgttc tagctacact ggtaaaatat    8220
accacagatg agtttgatca acgaattctt tatgaatact tagcagaggc cagtgttgtg    8280
tttcccaaag tctttcctgt tgtgcataat ttgttggact ctaagatcaa cccctgtta    8340 tcattgtgcc aagatccaaa tttgttaaat ccaatccatg gaattgtgca gagtgtggtg    8400
taccatgaag aatccccacc acaataccaa acatcttacc tgcaaagttt tggtttaat    8460 ggcttgtggc ggtttgcagg accgttttca aagcaaacac aaattccaga ctatgctgag    8520
cttattgtta agtttcttga tgccttgatt gacacgtacc tgcctggaat tgatgaagaa    8580
accagtgaag aatccctcct gactcccaca tctccttacc ctcctgcact gcagagccag    8640
cttagtatca ctgccaacct taacctttct aattccatga cctcacttgc aacttcccag    8700
cattccccag gaatcgacaa ggagaacgtt gaactctccc ctaccactgg ccactgtaac    8760
agtggacgaa ctcgccacgg atccgcaagc caagtgcaga agcaaagaag cgctggcagt    8820
ttcaaacgta atagcattaa gagatcgtg tgaagcttgc ttgctttctt ttttaaaatc    8880
aacttaacat gggctcttca ctagtgaccc cttccctgtc cttgcccttt cccccatgt    8940 tgtaatgctg cacttcctgt tttataatga cccatccgg tttgccatgt tgccagatga    9000
tcaactcttc gaagccttgc ctaaatttaa tgctgccttt tctttaactt ttttttcttct    9060 acttttggcg tgtatctggt atatgtaagt gttcagaaca actgcaaaga aagtgggagg    9120
tcaggaaact tttaactgag aaatctcaat tgtaagagag gatgaattct tgaatactgc    9180
tactactggc cagtgatgaa agccatttgc acagagctct gccttctgtg gttttccctt    9240
cttcatccta cagagtaaag tgttagtcct atttatacat ttttcaagat acaagtttat    9300
gagagaaata gtattataac cccagtatgt ttaatctttt agctgtggac tttttttta    9360 accgtacaaa actgaaagaa ccatagaggt caagcctcag tgacttgaca ccataaagcc    9420
```

```
acagacaagg tacttggggg ggagggcagg gaaatttcat attttatagt ggattcttaa    9480
gaaatactaa cacttgagta ttagcaataa ttacaggaaa ataagtgcga ccacatatat    9540
cttaacatta ctgaattaaa actatggctt ctaagtcctt atccaaactc agtcatccaa    9600
actagtttat tttttctcc agttgattat cttttaattt ttaattttgc taaaggtggt    9660
tttttgtgt tttgttttt gtaaaccaaa actatactaa gtatagtaat tatatatata    9720
tatatatttt ttcccctccc cctcttcttt cctaactaat tctgagcagg gtaatcagtg    9780
aacaaagtgt tgaaaattgt tcccagaagg taattttcat agatgtttgc attagctcca    9840
tagcaaaatg gaatggtacg tgacatttag ggtagctgat attttatttt tgttaaataa    9900
tttccaagaa tagagtatgg tgtatattat aaatttcttt gataagatgt attttgaatg    9960
tcttttaatc ttcctcctcc tctccaaaaa aatcagaaac ctctttaaga aaacatgtag    10020
gttatatatg ctagaattgc atttaatcac tgtgaaaaga ctggtcagcc tgcattagta    10080
tgacagtagg ggggctgtta gaattgctgc tatactggtg gtatggatta tcatggcatt    10140
ggaattttca tagtaatgca gatccaattt ctttgtggta cctgcagttt acaaaataat    10200
ttgacttcag tgagcatatt ggtatctgga tgttccaatt tagaactaaa ccatatttat    10260
tacaaaaaga tattaatccc tctactccca ggttcccttt atatgttaag atataatggc    10320
tttgagggg gaaaaaataa acctagggga gaggggagtt tcctgtagtg ctgtttcatt    10380
agaggatttc agtaaattaa attccacagc taattcaata aataatggta catttaagtg    10440
ttctgatttt aataatatat ttcacattta tccacacagt aacaatgtaa tatgttaatg    10500
taaataaaat tggttttgat actcagaaat aacaagaatt taattttta aatttgttta    10560
cagtcctggg aaaagtaaga attatttgcc aaaataagag gaaagaaaac cttagtatta    10620
ttaatgagtt taccatagaa ttgttggaaa tactgaagac aggtgcaatt tactaaactt    10680
ttgttttaa actattgtag aggctgcatt agaagaaaat gtttataatg acagagcaac    10740
tatgactata taaaaaagct gaaattagaa ctgtgtttag aaatagatca gtaacccagt    10800
gccaaggatg ccaagctgcc accatggtct tggctctccc acaacccagt gtttctgggg    10860
taagtttcac agtttctagg ccctggaata gcaggcagtg taagcctttg ataacttag    10920
ttcgatgttt ttcttgtttt tgtttgttgg tttggtgcat atgatagtgg gtgttatgct    10980
attttgctct tcccatcaaa ataaagaaac ttccagaggt ttactgttaa aaatactgat    11040
atttccataa acgggtttac caagggtgta gtatttcata ccgcctgaaa tgatcagcat    11100
tggcacaaat caaaattcag ccgcctttga aatgcaaaaa tacctttgac tagtaagtac    11160
atcctaggag tttgaaaact taactaaggt ttaaaattta ccttgtttaa agaacttctg    11220
acttttgagg aaaatctagc tttccaagta actaaaatgt acatgagata aacctctcac    11280
cactatgtgt cccttgagaa atgcaacact ttttagtct tcatacttgt aatctataaa    11340
agaaattctg aagtttagac caagttgccc atttctgcgt aattgacata agttctgtta    11400
aaaatattat aagtaattcg tttcggtttg tagatgtttc ccctgacttg ttaaagagga    11460
aaccaggaac tcagtcatgt ttttgtcctg gataatctac ctgttatgcc agtactccca    11520
tccgagggc atgcccttag ttgcccagat ggagatgcag ttcagtagat ttggggcaaa    11580
gtggctacag ctctgtcttc cattcactca acacctgttc atgactgagc caggtgccca    11640
ggacacatcc taaacagtca gcttctatcc tgtgtcctag ttggggagac agagtgccag    11700
ccagcaaccc tcccaggttt gtaggtttta ggggttttca gttttgtttg ggttttttgt    11760
```

```
ttttttgtttt tgtttctaca tccttccccg actcccaggc ataatgaggc atgtcttact   11820
caatgttatg caatggattt aggcaaaaat tcattcttag tgtcagccac acaattttt    11880 ttaatgcagt atattcacct gtaaatagtt tgtgtaaaat ttgacaaaaa aagtatattt   11940
actatactgt aaatatatgt gatgatatat tgtattattt tgcttttttg taaagcagtt   12000
agttgctgca catggataac aacaaaaatt tgattattct cgtgttagta ttgttaactt   12060 cttttttgcga ctgcgttaca tcatttaaag aaaatgctgt gtattgtaaa cttaaattgt   12120
atatgataac ttactgtcct ttccatccgg gcctaaactt tggcagttcc tttgtctaca   12180
accttgttaa tactgtaaac agttgtacgc cagcaggaaa aatactgccc aacagacaaa   12240
atcgatcatt gtaggggaaa atcatagaaa tccatttcag atctttattg ttcctcaccc   12300
cattttcctc cttgtgtatg tacttccccc accccccttt ttttaagtaa aatgtaaatt   12360
caatctgctc taa                                                      12373

<210> SEQ ID NO 17
<211> LENGTH: 2839
<212> TYPE: PRT
<213> ORGANISM: Homo Sapiens

<400> SEQUENCE: 17

Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
                20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
        50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
        115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205

Gln Leu Ala Val Ile Asn Ser Leu Glu Lys Ala Phe Trp Asn Trp Val
    210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
```

-continued

```
                260                 265                 270
Leu Leu Ile Leu Cys Pro Glu Ile Ile Gln Asp Ile Ser Lys Asp Val
            275                 280                 285

Val Asp Glu Asn Asn Met Asn Lys Lys Leu Phe Leu Asp Ser Leu Arg
        290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
        355                 360                 365

Gln Pro Ala Asp Val Asp Leu Met Ile Asp Cys Leu Val Ser Cys Phe
370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
        435                 440                 445

Lys Ala Val Gln Gly Cys Gly Ala His Pro Ala Ile Arg Met Ala Pro
450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
        515                 520                 525

Leu Val Gln Leu Val Pro Gln Ser His Met Pro Glu Ile Ala Gln Glu
530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
        675                 680                 685
```

```
Val Ala Leu Tyr Met Phe Leu Trp Asn Pro Asp Thr Glu Ala Val Leu
        690             695             700
Val Ala Met Ser Cys Phe Arg His Leu Cys Glu Glu Ala Asp Ile Arg
705             710             715             720
Cys Gly Val Asp Glu Val Ser Val His Asn Leu Leu Pro Asn Tyr Asn
            725             730             735
Thr Phe Met Glu Phe Ala Ser Val Ser Asn Met Met Ser Thr Gly Arg
            740             745             750
Ala Ala Leu Gln Lys Arg Val Met Ala Leu Leu Arg Arg Ile Glu His
        755             760             765
Pro Thr Ala Gly Asn Thr Glu Ala Trp Glu Asp Thr His Ala Lys Trp
770             775             780
Glu Gln Ala Thr Lys Leu Ile Leu Asn Tyr Pro Lys Ala Lys Met Glu
785             790             795             800
Asp Gly Gln Ala Ala Glu Ser Leu His Lys Thr Ile Val Lys Arg Arg
            805             810             815
Met Ser His Val Ser Gly Gly Ser Ile Asp Leu Ser Asp Thr Asp
                820             825             830
Ser Leu Gln Glu Trp Ile Asn Met Thr Gly Phe Leu Cys Ala Leu Gly
        835             840             845
Gly Val Cys Leu Gln Gln Arg Ser Asn Ser Gly Leu Ala Thr Tyr Ser
850             855             860
Pro Pro Met Gly Pro Val Ser Glu Arg Lys Gly Ser Met Ile Ser Val
865             870             875             880
Met Ser Ser Glu Gly Asn Ala Asp Thr Pro Val Ser Lys Phe Met Asp
            885             890             895
Arg Leu Leu Ser Leu Met Val Cys Asn His Glu Lys Val Gly Leu Gln
            900             905             910
Ile Arg Thr Asn Val Lys Asp Leu Val Gly Leu Glu Leu Ser Pro Ala
        915             920             925
Leu Tyr Pro Met Leu Phe Asn Lys Leu Lys Asn Thr Ile Ser Lys Phe
930             935             940
Phe Asp Ser Gln Gly Gln Val Leu Leu Thr Asp Thr Asn Thr Gln Phe
945             950             955             960
Val Glu Gln Thr Ile Ala Ile Met Lys Asn Leu Leu Asp Asn His Thr
            965             970             975
Glu Gly Ser Ser Glu His Leu Gly Gln Ala Ser Ile Glu Thr Met Met
            980             985             990
Leu Asn Leu Val Arg Tyr Val Arg  Val Leu Gly Asn Met  Val His Ala
        995             1000             1005
Ile Gln  Ile Lys Thr Lys Leu  Cys Gln Leu Val Glu  Val Met Met
    1010             1015             1020
Ala Arg  Arg Asp Asp Leu Ser  Phe Cys Gln Glu Met  Lys Phe Arg
    1025             1030             1035
Asn Lys  Met Val Glu Tyr Leu  Thr Asp Trp Val Met  Gly Thr Ser
    1040             1045             1050
Asn Gln  Ala Ala Asp Asp Asp  Val Lys Cys Leu Thr  Arg Asp Leu
    1055             1060             1065
Asp Gln  Ala Ser Met Glu Ala  Val Val Ser Leu Leu  Ala Gly Leu
    1070             1075             1080
Pro Leu  Gln Pro Glu Glu Gly  Asp Gly Val Glu Leu  Met Glu Ala
    1085             1090             1095
```

-continued

```
Lys Ser Gln Leu Phe Leu Lys Tyr Phe Thr Leu Phe Met Asn Leu
    1100                1105                1110

Leu Asn Asp Cys Ser Glu Val Glu Asp Glu Ser Ala Gln Thr Gly
    1115                1120                1125

Gly Arg Lys Arg Gly Met Ser Arg Arg Leu Ala Ser Leu Arg His
    1130                1135                1140

Cys Thr Val Leu Ala Met Ser Asn Leu Leu Asn Ala Asn Val Asp
    1145                1150                1155

Ser Gly Leu Met His Ser Ile Gly Leu Gly Tyr His Lys Asp Leu
    1160                1165                1170

Gln Thr Arg Ala Thr Phe Met Glu Val Leu Thr Lys Ile Leu Gln
    1175                1180                1185

Gln Gly Thr Glu Phe Asp Thr Leu Ala Glu Thr Val Leu Ala Asp
    1190                1195                1200

Arg Phe Glu Arg Leu Val Glu Leu Val Thr Met Met Gly Asp Gln
    1205                1210                1215

Gly Glu Leu Pro Ile Ala Met Ala Leu Ala Asn Val Val Pro Cys
    1220                1225                1230

Ser Gln Trp Asp Glu Leu Ala Arg Val Leu Val Thr Leu Phe Asp
    1235                1240                1245

Ser Arg His Leu Leu Tyr Gln Leu Leu Trp Asn Met Phe Ser Lys
    1250                1255                1260

Glu Val Glu Leu Ala Asp Ser Met Gln Thr Leu Phe Arg Gly Asn
    1265                1270                1275

Ser Leu Ala Ser Lys Ile Met Thr Phe Cys Phe Lys Val Tyr Gly
    1280                1285                1290

Ala Thr Tyr Leu Gln Lys Leu Leu Asp Pro Leu Leu Arg Ile Val
    1295                1300                1305

Ile Thr Ser Ser Asp Trp Gln His Val Ser Phe Glu Val Asp Pro
    1310                1315                1320

Thr Arg Leu Glu Pro Ser Glu Ser Leu Glu Glu Asn Gln Arg Asn
    1325                1330                1335

Leu Leu Gln Met Thr Glu Lys Phe Phe His Ala Ile Ile Ser Ser
    1340                1345                1350

Ser Ser Glu Phe Pro Pro Gln Leu Arg Ser Val Cys His Cys Leu
    1355                1360                1365

Tyr Gln Ala Thr Cys His Ser Leu Leu Asn Lys Ala Thr Val Lys
    1370                1375                1380

Glu Lys Lys Glu Asn Lys Lys Ser Val Val Ser Gln Arg Phe Pro
    1385                1390                1395

Gln Asn Ser Ile Gly Ala Val Gly Ser Ala Met Phe Leu Arg Phe
    1400                1405                1410

Ile Asn Pro Ala Ile Val Ser Pro Tyr Glu Ala Gly Ile Leu Asp
    1415                1420                1425

Lys Lys Pro Pro Pro Arg Ile Glu Arg Gly Leu Lys Leu Met Ser
    1430                1435                1440

Lys Ile Leu Gln Ser Ile Ala Asn His Val Leu Phe Thr Lys Glu
    1445                1450                1455

Glu His Met Arg Pro Phe Asn Asp Phe Val Lys Ser Asn Phe Asp
    1460                1465                1470

Ala Ala Arg Arg Phe Phe Leu Asp Ile Ala Ser Asp Cys Pro Thr
    1475                1480                1485

Ser Asp Ala Val Asn His Ser Leu Ser Phe Ile Ser Asp Gly Asn
```

```
            1490                1495                1500

Val Leu Ala Leu His Arg Leu Leu Trp Asn Asn Gln Glu Lys Ile
    1505                1510                1515

Gly Gln Tyr Leu Ser Ser Asn Arg Asp His Lys Ala Val Gly Arg
    1520                1525                1530

Arg Pro Phe Asp Lys Met Ala Thr Leu Leu Ala Tyr Leu Gly Pro
    1535                1540                1545

Pro Glu His Lys Pro Val Ala Asp Thr His Trp Ser Ser Leu Asn
    1550                1555                1560

Leu Thr Ser Ser Lys Phe Glu Glu Phe Met Thr Arg His Gln Val
    1565                1570                1575

His Glu Lys Glu Phe Lys Ala Leu Lys Thr Leu Ser Ile Phe
    1580                1585                1590

Tyr Gln Ala Gly Thr Ser Lys Ala Gly Asn Pro Ile Phe Tyr Tyr
    1595                1600                1605

Val Ala Arg Arg Phe Lys Thr Gly Gln Ile Asn Gly Asp Leu Leu
    1610                1615                1620

Ile Tyr His Val Leu Leu Thr Leu Lys Pro Tyr Ala Lys Pro
    1625                1630                1635

Tyr Glu Ile Val Val Asp Leu Thr His Thr Gly Pro Ser Asn Arg
    1640                1645                1650

Phe Lys Thr Asp Phe Leu Ser Lys Trp Phe Val Val Phe Pro Gly
    1655                1660                1665

Phe Ala Tyr Asp Asn Val Ser Ala Val Tyr Ile Tyr Asn Cys Asn
    1670                1675                1680

Ser Trp Val Arg Glu Tyr Thr Lys Tyr His Glu Arg Leu Leu Thr
    1685                1690                1695

Gly Leu Lys Gly Ser Lys Arg Leu Val Phe Ile Asp Cys Pro Gly
    1700                1705                1710

Lys Leu Ala Glu His Ile Glu His Glu Gln Gln Lys Leu Pro Ala
    1715                1720                1725

Ala Thr Leu Ala Leu Glu Glu Asp Leu Lys Val Phe His Asn Ala
    1730                1735                1740

Leu Lys Leu Ala His Lys Asp Thr Lys Val Ser Ile Lys Val Gly
    1745                1750                1755

Ser Thr Ala Val Gln Val Thr Ser Ala Glu Arg Thr Lys Val Leu
    1760                1765                1770

Gly Gln Ser Val Phe Leu Asn Asp Ile Tyr Tyr Ala Ser Glu Ile
    1775                1780                1785

Glu Glu Ile Cys Leu Val Asp Glu Asn Gln Phe Thr Leu Thr Ile
    1790                1795                1800

Ala Asn Gln Gly Thr Pro Leu Thr Phe Met His Gln Glu Cys Glu
    1805                1810                1815

Ala Ile Val Gln Ser Ile Ile His Ile Arg Thr Arg Trp Glu Leu
    1820                1825                1830

Ser Gln Pro Asp Ser Ile Pro Gln His Thr Lys Ile Arg Pro Lys
    1835                1840                1845

Asp Val Pro Gly Thr Leu Leu Asn Ile Ala Leu Leu Asn Leu Gly
    1850                1855                1860

Ser Ser Asp Pro Ser Leu Arg Ser Ala Ala Tyr Asn Leu Leu Cys
    1865                1870                1875

Ala Leu Thr Cys Thr Phe Asn Leu Lys Ile Glu Gly Gln Leu Leu
    1880                1885                1890
```

```
Glu Thr Ser Gly Leu Cys Ile Pro Ala Asn Asn Thr Leu Phe Ile
    1895                1900                1905

Val Ser Ile Ser Lys Thr Leu Ala Ala Asn Glu Pro His Leu Thr
    1910                1915                1920

Leu Glu Phe Leu Glu Glu Cys Ile Ser Gly Phe Ser Lys Ser Ser
    1925                1930                1935

Ile Glu Leu Lys His Leu Cys Leu Glu Tyr Met Thr Pro Trp Leu
    1940                1945                1950

Ser Asn Leu Val Arg Phe Cys Lys His Asn Asp Asp Ala Lys Arg
    1955                1960                1965

Gln Arg Val Thr Ala Ile Leu Asp Lys Leu Ile Thr Met Thr Ile
    1970                1975                1980

Asn Glu Lys Gln Met Tyr Pro Ser Ile Gln Ala Lys Ile Trp Gly
    1985                1990                1995

Ser Leu Gly Gln Ile Thr Asp Leu Leu Asp Val Val Leu Asp Ser
    2000                2005                2010

Phe Ile Lys Thr Ser Ala Thr Gly Gly Leu Gly Ser Ile Lys Ala
    2015                2020                2025

Glu Val Met Ala Asp Thr Ala Val Ala Leu Ala Ser Gly Asn Val
    2030                2035                2040

Lys Leu Val Ser Ser Lys Val Ile Gly Arg Met Cys Lys Ile Ile
    2045                2050                2055

Asp Lys Thr Cys Leu Ser Pro Thr Pro Thr Leu Glu Gln His Leu
    2060                2065                2070

Met Trp Asp Asp Ile Ala Ile Leu Ala Arg Tyr Met Leu Met Leu
    2075                2080                2085

Ser Phe Asn Asn Ser Leu Asp Val Ala Ala His Leu Pro Tyr Leu
    2090                2095                2100

Phe His Val Val Thr Phe Leu Val Ala Thr Gly Pro Leu Ser Leu
    2105                2110                2115

Arg Ala Ser Thr His Gly Leu Val Ile Asn Ile Ile His Ser Leu
    2120                2125                2130

Cys Thr Cys Ser Gln Leu His Phe Ser Glu Glu Thr Lys Gln Val
    2135                2140                2145

Leu Arg Leu Ser Leu Thr Glu Phe Ser Leu Pro Lys Phe Tyr Leu
    2150                2155                2160

Leu Phe Gly Ile Ser Lys Val Lys Ser Ala Ala Val Ile Ala Phe
    2165                2170                2175

Arg Ser Ser Tyr Arg Asp Arg Ser Phe Ser Pro Gly Ser Tyr Glu
    2180                2185                2190

Arg Glu Thr Phe Ala Leu Thr Ser Leu Glu Thr Val Thr Glu Ala
    2195                2200                2205

Leu Leu Glu Ile Met Glu Ala Cys Met Arg Asp Ile Pro Thr Cys
    2210                2215                2220

Lys Trp Leu Asp Gln Trp Thr Glu Leu Ala Gln Arg Phe Ala Phe
    2225                2230                2235

Gln Tyr Asn Pro Ser Leu Gln Pro Arg Ala Leu Val Val Phe Gly
    2240                2245                2250

Cys Ile Ser Lys Arg Val Ser His Gly Gln Ile Lys Gln Ile Ile
    2255                2260                2265

Arg Ile Leu Ser Lys Ala Leu Glu Ser Cys Leu Lys Gly Pro Asp
    2270                2275                2280
```

```
Thr Tyr Asn Ser Gln Val Leu Ile Glu Ala Thr Val Ile Ala Leu
2285                2290                2295

Thr Lys Leu Gln Pro Leu Leu Asn Lys Asp Ser Pro Leu His Lys
2300                2305                2310

Ala Leu Phe Trp Val Ala Val Ala Val Leu Gln Leu Asp Glu Val
2315                2320                2325

Asn Leu Tyr Ser Ala Gly Thr Ala Leu Leu Glu Gln Asn Leu His
2330                2335                2340

Thr Leu Asp Ser Leu Arg Ile Phe Asn Asp Lys Ser Pro Glu Glu
2345                2350                2355

Val Phe Met Ala Ile Arg Asn Pro Leu Glu Trp His Cys Lys Gln
2360                2365                2370

Met Asp His Phe Val Gly Leu Asn Phe Asn Ser Asn Phe Asn Phe
2375                2380                2385

Ala Leu Val Gly His Leu Leu Lys Gly Tyr Arg His Pro Ser Pro
2390                2395                2400

Ala Ile Val Ala Arg Thr Val Arg Ile Leu His Thr Leu Leu Thr
2405                2410                2415

Leu Val Asn Lys His Arg Asn Cys Asp Lys Phe Glu Val Asn Thr
2420                2425                2430

Gln Ser Val Ala Tyr Leu Ala Ala Leu Leu Thr Val Ser Glu Glu
2435                2440                2445

Val Arg Ser Arg Cys Ser Leu Lys His Arg Lys Ser Leu Leu Leu
2450                2455                2460

Thr Asp Ile Ser Met Glu Asn Val Pro Met Asp Thr Tyr Pro Ile
2465                2470                2475

His His Gly Asp Pro Ser Tyr Arg Thr Leu Lys Glu Thr Gln Pro
2480                2485                2490

Trp Ser Ser Pro Lys Gly Ser Glu Gly Tyr Leu Ala Ala Thr Tyr
2495                2500                2505

Pro Thr Val Gly Gln Thr Ser Pro Arg Ala Arg Lys Ser Met Ser
2510                2515                2520

Leu Asp Met Gly Gln Pro Ser Gln Ala Asn Thr Lys Lys Leu Leu
2525                2530                2535

Gly Thr Arg Lys Ser Phe Asp His Leu Ile Ser Asp Thr Lys Ala
2540                2545                2550

Pro Lys Arg Gln Glu Met Glu Ser Gly Ile Thr Thr Pro Pro Lys
2555                2560                2565

Met Arg Arg Val Ala Glu Thr Asp Tyr Glu Met Glu Thr Gln Arg
2570                2575                2580

Ile Ser Ser Ser Gln Gln His Pro His Leu Arg Lys Val Ser Val
2585                2590                2595

Ser Glu Ser Asn Val Leu Leu Asp Glu Glu Val Leu Thr Asp Pro
2600                2605                2610

Lys Ile Gln Ala Leu Leu Leu Thr Val Leu Ala Thr Leu Val Lys
2615                2620                2625

Tyr Thr Thr Asp Glu Phe Asp Gln Arg Ile Leu Tyr Glu Tyr Leu
2630                2635                2640

Ala Glu Ala Ser Val Val Phe Pro Lys Val Phe Pro Val Val His
2645                2650                2655

Asn Leu Leu Asp Ser Lys Ile Asn Thr Leu Leu Ser Leu Cys Gln
2660                2665                2670

Asp Pro Asn Leu Leu Asn Pro Ile His Gly Ile Val Gln Ser Val
```

```
                  2675                2680                2685

Val Tyr His Glu Glu Ser Pro Pro Gln Tyr Gln Thr Ser Tyr Leu
     2690                2695                2700

Gln Ser Phe Gly Phe Asn Gly Leu Trp Arg Phe Ala Gly Pro Phe
     2705                2710                2715

Ser Lys Gln Thr Gln Ile Pro Asp Tyr Ala Glu Leu Ile Val Lys
     2720                2725                2730

Phe Leu Asp Ala Leu Ile Asp Thr Tyr Leu Pro Gly Ile Asp Glu
     2735                2740                2745

Glu Thr Ser Glu Glu Ser Leu Leu Thr Pro Thr Ser Pro Tyr Pro
     2750                2755                2760

Pro Ala Leu Gln Ser Gln Leu Ser Ile Thr Ala Asn Leu Asn Leu
     2765                2770                2775

Ser Asn Ser Met Thr Ser Leu Ala Thr Ser Gln His Ser Pro Gly
     2780                2785                2790

Ile Asp Lys Glu Asn Val Glu Leu Ser Pro Thr Gly His Cys
     2795                2800                2805

Asn Ser Gly Arg Thr Arg His Gly Ser Ala Ser Gln Val Gln Lys
     2810                2815                2820

Gln Arg Ser Ala Gly Ser Phe Lys Arg Asn Ser Ile Lys Lys Ile
     2825                2830                2835

Val

<210> SEQ ID NO 18
<211> LENGTH: 148
<212> TYPE: DNA
<213> ORGANISM: Artificial Sequence
<220> FEATURE:
<223> OTHER INFORMATION: Synthetic

<400> SEQUENCE: 18
gtgggcagca tgtggaacct ggcgagcccc atccccggca agctctcaag ccatgctggt    60
ggggacgact gaatgccagg gcccttcact gggctatttc acccagggac gcttcttgaa   120 ggcaccccc actccaagct caattgaa                                       148

<210> SEQ ID NO 19
<211> LENGTH: 124
<212> TYPE: DNA
<213> ORGANISM: Artificial Sequence
<220> FEATURE:
<223> OTHER INFORMATION: Synthetic

<400> SEQUENCE: 19
gcaaattagg accgagagtc agtggccgct caagagtctg tgaccatgcc ccaaattcag    60
agatggtccc aggagagatg gggggaactg ccaagcaatg agtgaccggt tccccctccc   120
ccag                                                                124

<210> SEQ ID NO 20
<211> LENGTH: 504
<212> TYPE: PRT
<213> ORGANISM: Artificial Sequence
<220> FEATURE:
<223> OTHER INFORMATION: Synthetic

<400> SEQUENCE: 20

Met Glu Ala Lys Ser Gln Leu Phe Leu Lys Tyr Phe Thr Leu Phe Met
1               5                   10                  15
```

Asn Leu Leu Asn Asp Cys Ser Glu Val Asp Glu Ser Ala Gln Thr
            20                  25                  30

Gly Gly Arg Lys Arg Gly Met Ser Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu

```
                 435                 440                 445
Ala Tyr Leu Gly Pro Pro Glu His Lys Pro Val Ala Asp Thr His Trp
        450                 455                 460

Ser Ser Leu Asn Leu Thr Ser Ser Lys Phe Glu Glu Phe Met Thr Arg
465                 470                 475                 480

His Gln Val His Glu Lys Glu Phe Lys Ala Leu Lys Thr Leu Tyr
                485                 490                 495

Pro Tyr Asp Val Pro Asp Tyr Ala
        500

<210> SEQ ID NO 21
<211> LENGTH: 1512
<212> TYPE: DNA
<213> ORGANISM: Artificial Sequence
<220> FEATURE:
<223> OTHER INFORMATION: Synthetic

<400> SEQUENCE: 21
atggaagcca agagccagct gtttctgaaa tactttaccc tgtttatgaa tctgctgaac      60
gactgtagtg aggtggagga cgagagtgcc cagaccggcg gcaggaagag aggcatgtct     120
aggagactgg ccagcctgag gcactgcaca gtgctggcca tgtccaacct gctgaacgcc     180
aatgtggact ccggcctgat gcactctatc ggcctgggct accacaagga tctgcagacc     240
cgcgccacat tcatggaggt gctgaccaag atcctgcagc agggcaccga gtttgacaca     300
ctggccgaga ccgtgctggc agataggttc gagcgcctgg tggagctggt gacaatgatg     360
ggcgaccagg gagagctgcc tatcgcaatg gcactggcca acgtggtgcc atgcagccag     420
tgggacgagc tggccagggt gctggtgacc ctgtttgatt ccagacacct gctgtaccag     480
ctgctgtgga acatgttctc taaggaggtg agctggccg acagcatgca gacactgttt     540
aggggcaatt ccctggcctc taagatcatg accttctgtt ttaaggtgta cggcgccaca     600
tatctgcaga gctgctgga tccactgctg agaatcgtga tcaccagctc cgactggcag     660
cacgtgtcct tcgaggtgga tcctacacgg ctggagccaa gcgagtccct ggaggagaac     720
cagcgcaatc tgctgcagat gaccgagaag ttctttcacg ccatcatctc tagctcctct     780
gagtttcccc ctcagctgcg gtccgtgtgc cactgtctgt accaggccac ctgccactct     840
ctgctgaaca aggccacagt gaaggagaag aaggagaata agaagagcgt ggtgtcccag     900
aggttcccac agaacagcat cggagcagtg ggatccgcca tgttcctgag gttcatcaat     960
cccgccatcg tgagccctta tgaggccggc atcctggaca gaagccaccc cctaggatc    1020 gagagaggcc tgaagctgat gagcaagatc ctgcagtcca tcgccaacca cgtgctgttc    1080
accaaggagg agcacatgcg cccccttcaac gactttgtga agtctaattt tgatgccgcc    1140
cggcgcttct ttctggacat cgcctctgat tgtcctacaa gcgacgccgt gaaccactct    1200
ctgagcttca tcagcgatgg caatgtgctg ccctgcacc ggctgctgtg gaacaatcag    1260
gagaagatcg gccagtacct gagctccaac agggaccaca aggcagtggg caggagacct    1320
tttgataaga tggccaccct gctggcatat ctgggaccac cagagcacaa gccagtggca    1380
gacacccact ggtctagcct gaatctgaca tcctctaagt tcgaggagtt tatgacccgg    1440
caccaggtgc acgagaagga ggagtttaag gccctgaaga ccctgtatcc gtatgatgtg    1500
ccggattatg cg                                                        1512

<210> SEQ ID NO 22
<211> LENGTH: 652
```

```
<212> TYPE: PRT
<213> ORGANISM: Artificial Sequence
<220> FEATURE:
<223> OTHER INFORMATION: Synthetic

<400> SEQUENCE: 22

Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
370                 375                 380
```

```
Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
            405                 410                 415

Trp Asn Asn Gln Glu Lys Ile Gly Gln Tyr Leu Ser Ser Asn Arg Asp
        420                 425                 430

His Lys Ala Val Gly Arg Arg Pro Phe Asp Lys Met Ala Thr Leu Leu
    435                 440                 445

Ala Tyr Leu Gly Pro Pro Glu His Lys Pro Val Ala Asp Thr His Trp
450                 455                 460

Ser Ser Leu Asn Leu Thr Ser Ser Lys Phe Glu Glu Phe Met Thr Arg
465                 470                 475                 480

His Gln Val His Glu Lys Glu Phe Lys Ala Leu Lys Thr Leu Ser
                485                 490                 495

Ile Phe Tyr Gln Ala Gly Thr Ser Lys Ala Gly Asn Pro Ile Phe Tyr
            500                 505                 510

Tyr Val Ala Arg Arg Phe Lys Thr Gly Gln Ile Asn Gly Asp Leu Leu
            515                 520                 525

Ile Tyr His Val Leu Leu Thr Leu Lys Pro Tyr Tyr Ala Lys Pro Tyr
        530                 535                 540

Glu Ile Val Val Asp Leu Thr His Thr Gly Pro Ser Asn Arg Phe Lys
545                 550                 555                 560

Thr Asp Phe Leu Ser Lys Trp Phe Val Phe Pro Gly Phe Ala Tyr
                565                 570                 575

Asp Asn Val Ser Ala Val Tyr Ile Tyr Asn Cys Asn Ser Trp Val Arg
            580                 585                 590

Glu Tyr Thr Lys Tyr His Glu Arg Leu Leu Thr Gly Leu Lys Gly Ser
        595                 600                 605

Lys Arg Leu Val Phe Ile Asp Cys Pro Gly Lys Leu Ala Glu His Ile
        610                 615                 620

Glu His Glu Gln Gln Lys Leu Pro Ala Ala Thr Leu Ala Leu Glu Glu
625                 630                 635                 640

Asp Leu Lys Tyr Pro Tyr Asp Val Pro Asp Tyr Ala
                645                 650
```

<210> SEQ ID NO 23
<211> LENGTH: 1956
<212> TYPE: DNA
<213> ORGANISM: Artificial Sequence
<220> FEATURE:
<223> OTHER INFORMATION: Synthetic

<400> SEQUENCE: 23

```
atggaagcca agagccagct gtttctgaaa tactttaccc tgtttatgaa tctgctgaac    60
gactgtagtg aggtggagga cgagagtgcc cagaccggcg gcaggaagag aggcatgtct   120
aggagactgg ccagcctgag gcactgcaca gtgctggcca tgtccaacct gctgaacgcc   180
aatgtggact ccggcctgat gcactctatc ggcctgggct accacaagga tctgcagacc   240
cgcgccacat tcatggaggt gctgaccaag atcctgcagc agggcaccga gtttgacaca   300
ctggccgaga ccgtgctggc agataggttc gagcgcctgg tggagctggt gacaatgatg   360
ggcgaccagg gagagctgcc tatcgcaatg gcactggcca acgtggtgcc atgcagccag   420
tgggacgagc tggccagggt gctggtgacc ctgtttgatt ccagacacct gctgtaccag   480
ctgctgtgga acatgttctc taaggaggtg gagctggccg acagcatgca gacactgttt   540
```

| | |
|---|---|
| aggggcaatt ccctggcctc taagatcatg accttctgtt ttaaggtgta cggcgccaca | 600 |
| tatctgcaga agctgctgga tccactgctg agaatcgtga tcaccagctc cgactggcag | 660 |
| cacgtgtcct tcgaggtgga tcctacacgg ctggagccaa gcgagtccct ggaggagaac | 720 |
| cagcgcaatc tgctgcagat gaccgagaag ttctttcacg ccatcatctc tagctcctct | 780 |
| gagtttcccc ctcagctgcg gtccgtgtgc cactgtctgt accaggccac ctgccactct | 840 |
| ctgctgaaca aggccacagt gaaggagaag aaggagaata agaagagcgt ggtgtcccag | 900 |
| aggttcccac agaacagcat cggagcagtg ggatccgcca tgttcctgag gttcatcaat | 960 |
| cccgccatcg tgagcccta tgaggccggc atcctggaca agaagccacc ccctaggatc | 1020 |
| gagagaggcc tgaagctgat gagcaagatc ctgcagtcca tcgccaacca cgtgctgttc | 1080 |
| accaaggagg agcacatgcg ccccttcaac gactttgtga agtctaattt tgatgccgcc | 1140 |
| cggcgcttct ttctggacat cgcctctgat tgtcctacaa gcgacgccgt gaaccactct | 1200 |
| ctgagcttca tcagcgatgg caatgtgctg gccctgcacc ggctgctgtg gaacaatcag | 1260 |
| gagaagatcg gccagtacct gagctccaac agggaccaca aggcagtggg caggagacca | 1320 |
| tttgataaga tggccacact gctggcctat ctgggaccac cagagcacaa gccagtggca | 1380 |
| gacacacact ggtctagcct gaatctgacc tcctctaagt tcgaggagtt tatgacccgg | 1440 |
| caccaggtgc acgagaagga ggagtttaag gccctgaaga cactgtctat cttctaccag | 1500 |
| gcaggcacca gcaaggcagg aaacccaatc ttttactatg tggcccggcg cttcaagaca | 1560 |
| ggccagatca atggcgatct gctgatctac cacgtgctgc tgaccctgaa gccatactat | 1620 |
| gccaagccct atgagatcgt ggtggacctg acccacacag gcccctccaa caggtttaag | 1680 |
| accgatttcc tgtctaagtg gttcgtggtg tttcctggct tcgcctatga caatgtgagc | 1740 |
| gccgtgtaca tctataactg caattcctgg gtgcgggagt acacaaagta tcacgagcgc | 1800 |
| ctgctgaccg gcctgaaggg atccaagaga ctggtgttca tcgattgtcc cggcaagctg | 1860 |
| gccgagcaca ttgaacacga acagcagaaa ctgcccgccg caaccctggc cctggaagag | 1920 |
| gacctgaagt atccgtatga tgtgccggat tatgcg | 1956 |

<210> SEQ ID NO 24
<211> LENGTH: 750
<212> TYPE: PRT
<213> ORGANISM: Artificial Sequence
<220> FEATURE:
<223> OTHER INFORMATION: Synthetic

<400> SEQUENCE: 24

```
Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Val Leu Ala Asp Arg Phe Glu Arg
                100                 105                 110
```

```
Leu Val Glu Leu Val Thr Met Met Gly Asp Gln Gly Glu Leu Pro Ile
            115                 120                 125
Ala Met Ala Leu Ala Asn Val Val Pro Cys Ser Gln Trp Asp Glu Leu
130                 135                 140
Ala Arg Val Leu Val Thr Leu Phe Asp Ser Arg His Leu Leu Tyr Gln
145                 150                 155                 160
Leu Leu Trp Asn Met Phe Ser Lys Glu Val Glu Leu Ala Asp Ser Met
                165                 170                 175
Gln Thr Leu Phe Arg Gly Asn Ser Leu Ala Ser Lys Ile Met Thr Phe
                180                 185                 190
Cys Phe Lys Val Tyr Gly Ala Thr Tyr Leu Gln Lys Leu Leu Asp Pro
                195                 200                 205
Leu Leu Arg Ile Val Ile Thr Ser Ser Asp Trp Gln His Val Ser Phe
            210                 215                 220
Glu Val Asp Pro Thr Arg Leu Glu Pro Ser Glu Ser Leu Glu Glu Asn
225                 230                 235                 240
Gln Arg Asn Leu Leu Gln Met Thr Glu Lys Phe Phe His Ala Ile Ile
                245                 250                 255
Ser Ser Ser Ser Glu Phe Pro Pro Gln Leu Arg Ser Val Cys His Cys
                260                 265                 270
Leu Tyr Gln Ala Thr Cys His Ser Leu Leu Asn Lys Ala Thr Val Lys
            275                 280                 285
Glu Lys Lys Glu Asn Lys Lys Ser Val Val Ser Gln Arg Phe Pro Gln
            290                 295                 300
Asn Ser Ile Gly Ala Val Gly Ser Ala Met Phe Leu Arg Phe Ile Asn
305                 310                 315                 320
Pro Ala Ile Val Ser Pro Tyr Glu Ala Gly Ile Leu Asp Lys Lys Pro
                325                 330                 335
Pro Pro Arg Ile Glu Arg Gly Leu Lys Leu Met Ser Lys Ile Leu Gln
                340                 345                 350
Ser Ile Ala Asn His Val Leu Phe Thr Lys Glu Glu His Met Arg Pro
            355                 360                 365
Phe Asn Asp Phe Val Lys Ser Asn Phe Asp Ala Ala Arg Arg Phe Phe
            370                 375                 380
Leu Asp Ile Ala Ser Asp Cys Pro Thr Ser Asp Ala Val Asn His Ser
385                 390                 395                 400
Leu Ser Phe Ile Ser Asp Gly Asn Val Leu Ala Leu His Arg Leu Leu
                405                 410                 415
Trp Asn Asn Gln Glu Lys Ile Gly Gln Tyr Leu Ser Ser Asn Arg Asp
                420                 425                 430
His Lys Ala Val Gly Arg Arg Pro Phe Asp Lys Met Ala Thr Leu Leu
            435                 440                 445
Ala Tyr Leu Gly Pro Pro Glu His Lys Pro Val Ala Asp Thr His Trp
            450                 455                 460
Ser Ser Leu Asn Leu Thr Ser Ser Lys Phe Glu Glu Phe Met Thr Arg
465                 470                 475                 480
His Gln Val His Glu Lys Glu Glu Phe Lys Ala Leu Lys Thr Leu Ser
                485                 490                 495
Ile Phe Tyr Gln Ala Gly Thr Ser Lys Ala Gly Asn Pro Ile Phe Tyr
                500                 505                 510
Tyr Val Ala Arg Arg Phe Lys Thr Gly Gln Ile Asn Gly Asp Leu Leu
            515                 520                 525
Ile Tyr His Val Leu Leu Thr Leu Lys Pro Tyr Tyr Ala Lys Pro Tyr
```

```
                530              535              540
Glu Ile Val Val Asp Leu Thr His Thr Gly Pro Ser Asn Arg Phe Lys
545                  550              555                  560

Thr Asp Phe Leu Ser Lys Trp Phe Val Val Phe Pro Gly Phe Ala Tyr
                565              570              575

Asp Asn Val Ser Ala Val Tyr Ile Tyr Asn Cys Asn Ser Trp Val Arg
            580              585              590

Glu Tyr Thr Lys Tyr His Glu Arg Leu Leu Thr Gly Leu Lys Gly Ser
        595              600              605

Lys Arg Leu Val Phe Ile Asp Cys Pro Gly Lys Leu Ala Glu His Ile
    610              615              620

Glu His Glu Gln Gln Lys Leu Pro Ala Ala Thr Leu Ala Leu Glu Glu
625              630              635              640

Asp Leu Lys Val Phe His Asn Ala Leu Lys Leu Ala His Lys Asp Thr
                645              650              655

Lys Val Ser Ile Lys Val Gly Ser Thr Ala Val Gln Val Thr Ser Ala
            660              665              670

Glu Arg Thr Lys Val Leu Gly Gln Ser Val Phe Leu Asn Asp Ile Tyr
        675              680              685

Tyr Ala Ser Glu Ile Glu Ile Cys Leu Val Asp Glu Asn Gln Phe
    690              695              700

Thr Leu Thr Ile Ala Asn Gln Gly Thr Pro Leu Thr Phe Met His Gln
705              710              715              720

Glu Cys Glu Ala Ile Val Gln Ser Ile Ile His Ile Arg Thr Arg Trp
                725              730              735

Glu Leu Ser Gln Pro Asp Tyr Pro Tyr Asp Val Pro Asp Tyr
            740              745              750
```

<210> SEQ ID NO 25
<211> LENGTH: 2252
<212> TYPE: DNA
<213> ORGANISM: Artificial Sequence
<220> FEATURE:
<223> OTHER INFORMATION: Synthetic

<400> SEQUENCE: 25

```
atggaagcca agagccagct gtttctgaaa tactttaccc tgtttatgaa tctgctgaac      60
gactgtagtg aggtggagga cgagagtgcc cagaccggcg gcaggaagag aggcatgtct     120
aggagactgg ccagcctgag gcactgcaca gtgctggcca tgtccaacct gctgaacgcc     180
aatgtggact ccggcctgat gcactctatc ggcctgggct accacaagga tctgcagacc     240
cgcgccacat tcatggaggt gctgaccaag atcctgcagc agggcaccga gtttgacaca     300
ctggccgaga ccgtgctggc agataggttc gagcgcctgg tggagctggt gacaatgatg     360
ggcgaccagg gagagctgcc tatcgcaatg gcactggcca acgtggtgcc atgcagccag     420
tgggacgagc tggccagggt gctggtgacc ctgtttgatt ccagacacct gctgtaccag     480
ctgctgtgga acatgttctc taaggaggtg gagctggccg acagcatgca gacactgttt     540
agggcaattc cctggcctc taagatcatg accttctgtt ttaaggtgta cggcgccaca     600
tatctgcaga agctgctgga tccactgctg agaatcgtga tcaccagctc cgactggcag     660
cacgtgtcct tcgaggtgga tcctacacgg ctggagccaa gcgagtccct ggaggagaac     720
cagcgcaatc tgctgcagat gaccgagaag ttctttcacg ccatcatctc tagctccctc     780
gagtttcccc ctcagctgcg gtccgtgtgc cactgtctgt accaggccac tgccactctc     840
```

```
ctgctgaaca aggccacagt gaaggagaag aaggagaata agaagagcgt ggtgtcccag    900
aggttcccac agaacagcat cggagcagtg ggatccgcca tgttcctgag gttcatcaat    960
cccgccatcg tgagcccttac tgaggccggc atcctggaca agaagccacc ccctaggatc   1020
gagagaggcc tgaagctgat gagcaagatc ctgcagtcca tcgccaacca cgtgctgttc   1080
accaaggagg agcacatgcg ccccttcaac gactttgtga agtctaattt tgatgccgcc   1140
cggcgcttct ttctggacat cgcctctgat tgtcctacaa gcgacgccgt gaaccactct   1200
ctgagcttca tcagcgatgg caatgtgctg ccctgcacc ggctgctgtg aacaatcag     1260
gagaagatcg ccagtacct gagctccaac agggaccaca aggcagtggg caggagacct    1320
tttgataaga tggccaccct gctggcatat ctgggaccac cagagcacaa gccagtggca   1380
gacacccact ggtctagcct gaatctgaca tcctctaagt tcgaggagtt tatgacccgg   1440
caccaggtgc acgagaagga ggagtttaag gccctgaaga ccctgtccat cttctaccag   1500
gccggcacat ctaaggccgg caaccctatc ttttactatg tggcccggcg cttcaagacc   1560
ggccagatca atggcgatct gctgatctac cacgtgctgc tgacactgaa gccatactat   1620
gccaagccct atgagatcgt ggtggacctg acccacacag gcccaagcaa caggtttaag   1680
accgatttcc tgtccaagtg gttcgtggtg tttcccggct tcgcctatga caacgtgagc   1740
gccgtgtaca tctataactg caatagctgg gtgcgggagt acaccaagta tcacgagcgc   1800
ctgctgacag gctgaaggg cagcaagaga ctggtgttca tcgattgtcc cggcaagctg   1860
gccgagcaca tcgagcacga gcagcagaag ctgcctgcag ccaccctggc cctggaggag   1920
gacctgaagg tgtttcacaa cgccctgaag ctggcccaca aggatacaaa ggtgtccatc   1980
aaggtcggct ctacagccgt gcaggtgacc tccgccgaga aacaaaggt gctgggccag   2040
agcgtgttcc tgaatgacat ctactatgcc agcgagatcg aggagatctg cctggtggat   2100
gagaaccagt ttaccctgac aatcgccaat cagggcaccc ccctgacatt catgcaccag   2160
gagtgtgaag caatcgtcca gagcattatt cacattcgca ctcggtggga actgagccag   2220
cctgactatc cgtatgatgt gccggattat gc                                  2252
```

<210> SEQ ID NO 26
<211> LENGTH: 1457
<212> TYPE: PRT
<213> ORGANISM: Artificial Sequence
<220> FEATURE:
<223> OTHER INFORMATION: Synthetic

<400> SEQUENCE: 26

```
Met Val Ser Gln Arg Phe Pro Gln Asn Ser Ile Gly Ala Val Gly Ser
1               5                   10                  15

Ala Met Phe Leu Arg Phe Ile Asn Pro Ala Ile Val Ser Pro Tyr Glu
            20                  25                  30

Ala Gly Ile Leu Asp Lys Lys Pro Pro Arg Ile Glu Arg Gly Leu
        35                  40                  45

Lys Leu Met Ser Lys Ile Leu Gln Ser Ile Ala Asn His Val Leu Phe
    50                  55                  60

Thr Lys Glu Glu His Met Arg Pro Phe Asn Asp Phe Val Lys Ser Asn
65                  70                  75                  80

Phe Asp Ala Ala Arg Arg Phe Phe Leu Asp Ile Ala Ser Asp Cys Pro
                85                  90                  95

Thr Ser Asp Ala Val Asn His Ser Leu Ser Phe Ile Ser Asp Gly Asn
            100                 105                 110
```

```
Val Leu Ala Leu His Arg Leu Leu Trp Asn Asn Gln Glu Lys Ile Gly
            115                 120                 125

Gln Tyr Leu Ser Ser Asn Arg Asp His Lys Ala Val Gly Arg Arg Pro
    130                 135                 140

Phe Asp Lys Met Ala Thr Leu Leu Ala Tyr Leu Gly Pro Pro Glu His
145                 150                 155                 160

Lys Pro Val Ala Asp Thr His Trp Ser Ser Leu Asn Leu Thr Ser Ser
                165                 170                 175

Lys Phe Glu Glu Phe Met Thr Arg His Gln Val His Glu Lys Glu Glu
            180                 185                 190

Phe Lys Ala Leu Lys Thr Leu Ser Ile Phe Tyr Gln Ala Gly Thr Ser
    195                 200                 205

Lys Ala Gly Asn Pro Ile Phe Tyr Tyr Val Ala Arg Arg Phe Lys Thr
210                 215                 220

Gly Gln Ile Asn Gly Asp Leu Leu Ile Tyr His Val Leu Leu Thr Leu
225                 230                 235                 240

Lys Pro Tyr Tyr Ala Lys Pro Tyr Glu Ile Val Val Asp Leu Thr His
                245                 250                 255

Thr Gly Pro Ser Asn Arg Phe Lys Thr Asp Phe Leu Ser Lys Trp Phe
            260                 265                 270

Val Val Phe Pro Gly Phe Ala Tyr Asp Asn Val Ser Met Val Tyr Ile
    275                 280                 285

Tyr Asn Cys Asn Ser Trp Val Arg Glu Tyr Thr Lys Tyr His Glu Arg
290                 295                 300

Leu Leu Thr Gly Leu Lys Gly Ser Lys Arg Leu Val Phe Ile Asp Cys
305                 310                 315                 320

Pro Gly Lys Leu Ala Glu His Ile Glu His Glu Gln Gln Lys Leu Pro
                325                 330                 335

Ala Ala Thr Leu Ala Leu Glu Glu Asp Leu Lys Val Phe His Asn Ala
            340                 345                 350

Leu Lys Leu Ala His Lys Asp Thr Lys Val Ser Ile Lys Val Gly Ser
    355                 360                 365

Thr Ala Val Gln Val Thr Ser Ala Glu Arg Thr Lys Val Leu Gly Gln
370                 375                 380

Ser Val Phe Leu Asn Asp Ile Tyr Tyr Ala Ser Glu Ile Glu Glu Ile
385                 390                 395                 400

Cys Leu Val Asp Glu Asn Gln Phe Thr Leu Thr Ile Ala Asn Gln Gly
                405                 410                 415

Thr Pro Leu Thr Phe Met His Gln Glu Cys Glu Ala Ile Val Gln Ser
            420                 425                 430

Ile Ile His Ile Arg Thr Arg Trp Glu Leu Ser Gln Pro Asp Ser Ile
    435                 440                 445

Pro Gln His Thr Lys Ile Arg Pro Lys Asp Val Pro Gly Thr Leu Leu
450                 455                 460

Asn Ile Ala Leu Leu Asn Leu Gly Ser Ser Asp Pro Ser Leu Arg Ser
465                 470                 475                 480

Ala Ala Tyr Asn Leu Leu Cys Ala Leu Thr Cys Thr Phe Asn Leu Lys
                485                 490                 495

Ile Glu Gly Gln Leu Leu Glu Thr Ser Gly Leu Cys Ile Pro Ala Asn
            500                 505                 510

Asn Thr Leu Phe Ile Val Ser Ile Ser Lys Thr Leu Ala Ala Asn Glu
    515                 520                 525

Pro His Leu Thr Leu Glu Phe Leu Glu Glu Cys Ile Ser Gly Phe Ser
```

```
            530                 535                 540
Lys Ser Ser Ile Glu Leu Lys His Leu Cys Leu Glu Tyr Met Thr Pro
545                 550                 555                 560

Trp Leu Ser Asn Leu Val Arg Phe Cys Lys His Asn Asp Asp Ala Lys
                    565                 570                 575

Arg Gln Arg Val Thr Ala Ile Leu Asp Lys Leu Ile Thr Met Thr Ile
                580                 585                 590

Asn Glu Lys Gln Met Tyr Pro Ser Ile Gln Ala Lys Ile Trp Gly Ser
            595                 600                 605

Leu Gly Gln Ile Thr Asp Leu Leu Asp Val Val Leu Asp Ser Phe Ile
        610                 615                 620

Lys Thr Ser Ala Thr Gly Gly Leu Gly Ser Ile Lys Ala Glu Val Met
625                 630                 635                 640

Ala Asp Thr Ala Val Ala Leu Ala Ser Gly Asn Val Lys Leu Val Ser
                645                 650                 655

Ser Lys Val Ile Gly Arg Met Cys Lys Ile Ile Asp Lys Thr Cys Leu
                660                 665                 670

Ser Pro Thr Pro Thr Leu Glu Gln His Leu Met Trp Asp Asp Ile Ala
            675                 680                 685

Ile Leu Ala Arg Tyr Met Leu Met Leu Ser Phe Asn Asn Ser Leu Asp
        690                 695                 700

Val Ala Ala His Leu Pro Tyr Leu Phe His Val Val Thr Phe Leu Val
705                 710                 715                 720

Ala Thr Gly Pro Leu Ser Leu Arg Ala Ser Thr His Gly Leu Val Ile
                725                 730                 735

Asn Ile Ile His Ser Leu Cys Thr Cys Ser Gln Leu His Phe Ser Glu
                740                 745                 750

Glu Thr Lys Gln Val Leu Arg Leu Ser Leu Thr Glu Phe Ser Leu Pro
            755                 760                 765

Lys Phe Tyr Leu Leu Phe Gly Ile Ser Lys Val Lys Ser Ala Ala Val
        770                 775                 780

Ile Ala Phe Arg Ser Ser Tyr Arg Asp Arg Ser Phe Ser Pro Gly Ser
785                 790                 795                 800

Tyr Glu Arg Glu Thr Phe Ala Leu Thr Ser Leu Glu Thr Val Thr Glu
                805                 810                 815

Ala Leu Leu Glu Ile Met Glu Ala Cys Met Arg Asp Ile Pro Thr Cys
                820                 825                 830

Lys Trp Leu Asp Gln Trp Thr Glu Leu Ala Gln Arg Phe Ala Phe Gln
            835                 840                 845

Tyr Asn Pro Ser Leu Gln Pro Arg Ala Leu Val Val Phe Gly Cys Ile
        850                 855                 860

Ser Lys Arg Val Ser His Gly Gln Ile Lys Gln Ile Ile Arg Ile Leu
865                 870                 875                 880

Ser Lys Ala Leu Glu Ser Cys Leu Lys Gly Pro Asp Thr Tyr Asn Ser
                885                 890                 895

Gln Val Leu Ile Glu Ala Thr Val Ile Ala Leu Thr Lys Leu Gln Pro
                900                 905                 910

Leu Leu Asn Lys Asp Ser Pro Leu His Lys Ala Leu Phe Trp Val Ala
            915                 920                 925

Val Ala Val Leu Gln Leu Asp Glu Val Asn Leu Tyr Ser Ala Gly Thr
        930                 935                 940

Ala Leu Leu Glu Gln Asn Leu His Thr Leu Asp Ser Leu Arg Ile Phe
945                 950                 955                 960
```

```
Asn Asp Lys Ser Pro Glu Glu Val Phe Met Ala Ile Arg Asn Pro Leu
            965                 970                 975
Glu Trp His Cys Lys Gln Met Asp His Phe Val Gly Leu Asn Phe Asn
            980                 985                 990
Ser Asn Phe Asn Phe Ala Leu Val Gly His Leu Leu Lys Gly Tyr Arg
            995                1000                1005
His Pro Ser Pro Ala Ile Val Ala Arg Thr Val Arg Ile Leu His
    1010                1015                1020
Thr Leu Leu Thr Leu Val Asn Lys His Arg Asn Cys Asp Lys Phe
    1025                1030                1035
Glu Val Asn Thr Gln Ser Val Ala Tyr Leu Ala Ala Leu Leu Thr
    1040                1045                1050
Val Ser Glu Glu Val Arg Ser Arg Cys Ser Leu Lys His Arg Lys
    1055                1060                1065
Ser Leu Leu Leu Thr Asp Ile Ser Met Glu Asn Val Pro Met Asp
    1070                1075                1080
Thr Tyr Pro Ile His His Gly Asp Pro Ser Tyr Arg Thr Leu Lys
    1085                1090                1095
Glu Thr Gln Pro Trp Ser Ser Pro Lys Gly Ser Glu Gly Tyr Leu
    1100                1105                1110
Ala Ala Thr Tyr Pro Thr Val Gly Gln Thr Ser Pro Arg Ala Arg
    1115                1120                1125
Lys Ser Met Ser Leu Asp Met Gly Gln Pro Ser Gln Ala Asn Thr
    1130                1135                1140
Lys Lys Leu Leu Gly Thr Arg Lys Ser Phe Asp His Leu Ile Ser
    1145                1150                1155
Asp Thr Lys Ala Pro Lys Arg Gln Glu Met Glu Ser Gly Ile Thr
    1160                1165                1170
Thr Pro Pro Lys Met Arg Arg Val Ala Glu Thr Asp Tyr Glu Met
    1175                1180                1185
Glu Thr Gln Arg Ile Ser Ser Ser Gln His Pro His Leu Arg
    1190                1195                1200
Lys Val Ser Val Ser Glu Ser Asn Val Leu Leu Asp Glu Glu Val
    1205                1210                1215
Leu Thr Asp Pro Lys Ile Gln Ala Leu Leu Leu Thr Val Leu Ala
    1220                1225                1230
Thr Leu Val Lys Tyr Thr Thr Asp Glu Phe Asp Gln Arg Ile Leu
    1235                1240                1245
Tyr Glu Tyr Leu Ala Glu Ala Ser Val Val Phe Pro Lys Val Phe
    1250                1255                1260
Pro Val Val His Asn Leu Leu Asp Ser Lys Ile Asn Thr Leu Leu
    1265                1270                1275
Ser Leu Cys Gln Asp Pro Asn Leu Leu Asn Pro Ile His Gly Ile
    1280                1285                1290
Val Gln Ser Val Val Tyr His Glu Glu Ser Pro Pro Gln Tyr Gln
    1295                1300                1305
Thr Ser Tyr Leu Gln Ser Phe Gly Phe Asn Gly Leu Trp Arg Phe
    1310                1315                1320
Ala Gly Pro Phe Ser Lys Gln Thr Gln Ile Pro Asp Tyr Ala Glu
    1325                1330                1335
Leu Ile Val Lys Phe Leu Asp Ala Leu Ile Asp Thr Tyr Leu Pro
    1340                1345                1350
```

| | | | | | | | | | | | |
|---|---|---|---|---|---|---|---|---|---|---|---|
| Gly | Ile | Asp | Glu | Glu | Thr | Ser | Glu | Glu | Ser | Leu | Leu | Thr | Pro | Thr |
| | | 1355 | | | | 1360 | | | | 1365 | |

Gly Ile Asp Glu Glu Thr Ser Glu Glu Ser Leu Leu Thr Pro Thr
          1355                 1360                1365

Ser Pro Tyr Pro Pro Ala Leu Gln Ser Gln Leu Ser Ile Thr Ala
        1370                 1375                1380

Asn Leu Asn Leu Ser Asn Ser Met Thr Ser Leu Ala Thr Ser Gln
        1385                 1390                1395

His Ser Pro Gly Ile Asp Lys Glu Asn Val Glu Leu Ser Pro Thr
        1400                 1405                1410

Thr Gly His Cys Asn Ser Gly Arg Thr Arg His Gly Ser Ala Ser
        1415                 1420                1425

Gln Val Gln Lys Gln Arg Ser Ala Gly Ser Phe Lys Arg Asn Ser
        1430                 1435                1440

Ile Lys Lys Ile Val Tyr Pro Tyr Asp Val Pro Asp Tyr Ala
        1445                 1450                1455

<210> SEQ ID NO 27
<211> LENGTH: 4372
<212> TYPE: DNA
<213> ORGANISM: Artificial Sequence
<220> FEATURE:
<223> OTHER INFORMATION: Synthetic

<400> SEQUENCE: 27

```
gtggttagcc agcgtttccc tcagaacagc atcggtgcag taggaagtgc catgttcctc    60
agatttatca atcctgccat tgtctcaccg tatgaagcag ggattttaga taaaaagcca   120
ccacctagaa tcgaaggggg cttgaagtta atgtcaaaga tacttcagag tattgccaat   180
catgttctct tcacaaaaga agaacatatg cggcctttca atgattttgt gaaaagcaac   240
tttgatgcag cacgcaggtt tttccttgat atagcatctg attgtcctac aagtgatgca   300
gtaaatcata gtcttttcctt cataagtgac ggcaatgtgc ttgctttaca tcgtctactc   360
tggaacaatc aggagaaaat tgggcagtat ctttccagca acagggatca taaagctgtt   420
ggaagacgac cttttgataa gatggcaaca cttcttgcat acctgggtcc tccagagcac   480
aaacctgtgg cagatacaca ctggtccagc cttaacctta ccagttcaaa gtttgaggaa   540
tttatgacta ggcatcaggt acatgaaaaa gaagaattca aggctttgaa acgttaagt   600
attttctacc aagctgggac ttccaaagct gggaatccta ttttttatta tgttgcacgg   660
aggttcaaaa ctggtcaaat caatggtgat ttgctgatat accatgtctt actgacttta   720
aagccatatt atgcaaagcc atatgaaatt gtagtggacc ttacccatac cgggcctagc   780
aatcgcttta aaacagactt tctctctaag tggtttgttg ttttttcctgg ctttgcttac   840
gacaacgtct ccgcagtcta tatctataac tgtaactcct gggtcaggga gtacaccaag   900
tatcatgagc ggctgctgac tggcctcaaa ggtagcaaaa ggcttgtttt catagactgt   960
cctgggaaac tggctgagca catagagcat gaacaacaga actacctgc tgccaccttg  1020
gctttagaag aggacctgaa ggtattccac aatgctctca gctagctca caaagacacc  1080
aaagtttcta ttaaagttgg ttctactgct gtccaagtaa cttcagcaga gcgaacaaaa  1140
gtcctagggc aatcagtctt tctaaatgac atttattatg cttcggaaat tgaagaaatc  1200
tgcctagtag atgagaacca gttcaccctta accattgcaa accagggcac gccgctcacc  1260
ttcatgcacc aggagtgtga agccattgtc cagtctatca ttcatatccg gacccgctgg  1320
gaactgtcac agcccgactc tatccccaa cacaccaaga ttcggccaaa agatgtccct  1380
gggacactgc tcaatatcgc attacttaat ttaggcagtt ctgacccgag tttacggtca  1440
```

-continued

```
gctgcctata atcttctgtg tgccttaact tgtacccttta atttaaaaat cgagggccag    1500
ttactagaga catcaggttt atgtatccct gccaacaaca ccctctttat tgtctctatt    1560
agtaagacac tggcagccaa tgagccacac ctcacgttag aattttttgga agagtgtatt    1620 tctggattta gcaaatctag tattgaattg aaacacctttt gtttggaata catgactcca    1680
tggctgtcaa atctagttcg tttttgcaag cataatgatg atgccaaacg acaaagagtt    1740
actgctattc ttgacaagct gataacaatg accatcaatg aaaaacagat gtacccatct    1800
attcaagcaa aaatatgggg aagccttggg cagattacag atctgcttga tgttgtacta    1860
gacagtttca tcaaaaccag tgcaacaggt ggcttgggat caataaaagc tgaggtgatg    1920
gcagatactg ctgtagcttt ggcttctgga aatgtgaaat tggtttcaag caaggttatt    1980
ggaaggatgt gcaaaataat tgacaagaca tgcttatctc caactcctac tttagaacaa    2040
catcttatgt gggatgatat tgctatttta gcacgctaca tgctgatgct gtccttcaac    2100
aattcccttg atgtggcagc tcatcttccc tacctcttcc acgttgttac tttcttagta    2160
gccacaggtc cgctctccct tagagcttcc acacatggac tggtcattaa tatcattcac    2220
tctctgtgta cttgttcaca gcttcatttt agtgaagaga ccaagcaagt tttgagactc    2280
agtctgacag agttctcatt acccaaattt tacttgctgt ttggcattag caaagtcaag    2340
tcagctgctg tcattgcctt ccgttccagt taccgggaca ggtcattctc tcctggctcc    2400
tatgagagag agacttttgc tttgacatcc ttggaaacag tcacagaagc tttgttggag    2460
atcatggagg catgcatgag agatattcca acgtgcaagt ggctggacca gtggacagaa    2520
ctagctcaaa gatttgcatt ccaatataat ccatccctgc aaccaagagc tcttgttgtc    2580
tttgggtgta ttagcaaacg agtgtctcat gggcagataa agcagataat ccgtattctt    2640
agcaaggcac ttgagagttg cttaaaagga cctgacactt acaacagtca agttctgata    2700
gaagctacag taatagcact aaccaaatta cagccacttc ttaataagga ctcgcctctg    2760
cacaaagccc tcttttgggt agctgtggct gtgctgcagc ttgatgaggt caacttgtat    2820
tcagcaggta ccgcacttct tgaacaaaac ctgcatactt tagatagtct ccgtatattc    2880
aatgacaaga gtccagagga agtatttatg gcaatccgga atcctctgga gtggcactgc    2940
aagcaaatgg atcattttgt tggactcaat ttcaactcta actttaactt tgcattggtt    3000
ggacaccttt taaagggta caggcatcct tcacctgcta ttgttgcaag aacagtcaga    3060
attttacata cactactaac tctggttaac aaaacacagaa attgtgacaa atttgaagtg    3120
aatacacaga gcgtggccta cttagcagct ttacttacag tgtctgaaga agttcgaagt    3180
cgctgcagcc taaaacatag aaagtcactt cttcttactg atatttcaat ggaaaatgtt    3240
cctatggata catatcccat tcatcatggt gacccttcct ataggacact aaaggagact    3300
cagccatggt cctctcccaa aggttctgaa ggatacccttg cagccaccta tccaactgtc    3360
ggccagacca gtccccgagc caggaaatcc atgagcctgg acatgggggca accttctcag    3420 gccaacacta agaagttgct tggaacaagg aaaagttttg atcacttgat atcagacaca    3480
aaggctccta aaggcaaga atggaatca gggatcacaa caccccccaa aatgaggaga    3540
gtagcagaaa ctgattatga aatggaaact cagaggattt cctcatcaca acagcaccca    3600
catttacgta aagtttcagt gtctgaatca aatgttctct tggatgaaga agtacttact    3660
gatccgaaga tccaggcgct gcttcttact gttctagcta cactggtaaa atataccaca    3720
gatgagtttg atcaacgaat tctttatgaa tacttagcag aggccagtgt tgtgtttccc    3780
aaagtctttc ctgttgtgca taatttgttg gactctaaga tcaacaccct gttatcattg    3840
```

```
tgccaagatc caaatttgtt aaatccaatc catggaattg tgcagagtgt ggtgtaccat    3900
gaagaatccc caccacaata ccaaacatct tacctgcaaa gttttggttt taatggcttg    3960
tggcggtttg caggaccgtt ttcaaagcaa acacaaattc cagactatgc tgagcttatt    4020
gttaagtttc ttgatgcctt gattgacacg tacctgcctg gaattgatga agaaaccagt    4080
gaagaatccc tcctgactcc cacatctcct taccctcctg cactgcagag ccagcttagt    4140
atcactgcca accttaacct ttctaattcc atgacctcac ttgcaacttc ccagcattcc    4200
ccaggaatcg acaaggagaa cgttgaactc tcccctacca ctggccactg taacagtgga    4260
cgaactcgcc acggatccgc aagccaagtg cagaagcaaa gaagcgctgg cagtttcaaa    4320
cgtaatagca ttaagaagat cgtgtatccg tatgatgtgc cggattatgc gt            4372
```

<210> SEQ ID NO 28
<211> LENGTH: 6549
<212> TYPE: DNA
<213> ORGANISM: Artificial Sequence
<220> FEATURE:
<223> OTHER INFORMATION: Synthetic

<400> SEQUENCE: 28

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccaga tcttcaatat tggccattag ccatattatt     180
cattggttat atagcataaa tcaatattgg ctattggcca ttgcatacgt tgtatctata     240
tcataatatg tacatttata ttggctcatg tccaatatga ccgccatgtt ggcattgatt     300
attgactagt tattaatagt aatcaattac ggggtcatta gttcatagcc catatatgga     360
gttccgcgtt acataactta cggtaaatgg cccgcctggc tgaccgccca acgacccccg     420
cccattgacg tcaataatga cgtatgttcc catagtaacg ccaataggga ctttccattg     480
acgtcaatgg gtggagtatt tacggtaaac tgcccacttg gcagtacatc aagtgtatca     540
tatgccaagt ccgcccccta ttgacgtcaa tgacggtaaa tggcccgcct ggcattatgc     600
ccagtacatg accttacggg actttcctac ttggcagtac atctacgtat tagtcatcgc     660
tattaccatg gtcgaggtga gccccacgtt ctgcttcact ctccccatct cccccccctc     720
cccaccccca attttgtatt tatttatttt ttaattattt tgtgcagcga tggggcggg     780 gggggggggg gggcgcgcgc caggcggggc ggggcggggc gaggggcggg gcggggcgag     840
gcggagaggt gcggcggcag ccaatcagag cggcgcgctc cgaaagtttc cttttatggc     900
gaggcggcgg cggcggcggc cctataaaaa gcgaagcgcg cggcgggcgg gagtcgctgc     960
gcgctgcctt cgccccgtgc cccgctccgc cgccgcctcg cgccgcccgc cccggctctg    1020
actgaccgcg ttactcccac aggtgagcgg gcgggacggc ccttctcctc cgggctgtaa    1080
ttagcgcttg gtttaatgac ggcttgtttc ttttctgtgg ctgcgtgaaa gccttgaggg    1140
gctccgggag ggccctttgt gcgggggagt cggctcgggg ggtgcgtgcg tgtgtgtgtg    1200
cgtggggagc gccgcgtgcg gctccgcgct gcccggcggc tgtgagcgct gcgggcgcgg    1260
cgcggggctt tgtgcgctcc gcagtgtgcg cgaggggagc gcggccgggg gcggtgcccc    1320
gcggtgcggg gggggctgcg aggggaacaa aggctgcgtg cggggtgtgt gcgtgggggg    1380
gtgagcaggg ggtgtgggcg cgtcggtcgg gctgcaaccc cccctgcacc ccctccccg    1440 agttgctgag cacggcccgg cttcgggtgc ggggctccgt acggggcgtg gcgcggggct    1500
```

```
cgccgtgccg ggcgggggt  ggcggcaggt ggggtgccg  ggcggggcgg ggccgcctcg  1560
ggccggggag ggctcggggg aggggcgcgg cggcccccgg agcgccggcg gctgtcgagg  1620
cgcggcgagc cgcagccatt gccttttatg gtaatcgtgc gagagggcgc agggacttcc  1680
tttgtcccaa atctgtgcgg agccgaaatc tgggaggcgc cgccgcaccc cctctagcgg  1740
gcgcggggcg aagcggtgcg gcgccggcag gaaggaaatg ggcggggagg gccttcgtgc  1800
gtcgccgcgc cgccgtcccc ttctccctct ccagcctcgg ggctgtccgc gggggacgg   1860
ctgccttcgg ggggacggg  gcagggcggg gttcggcttc tggcgtgtga ccggcggctc  1920
tagagcctct gctaaccatg ttcatgcctt cttcttttc  ctacagctcc tgggcaacgt  1980
gctggttatt gtgctgtctc atcattttgg caaagaattc gatatcaagc ttgccaccat  2040
ggaagccaag agccagctgt ttctgaaata ctttaccctg tttatgaatc tgctgaacga  2100
ctgtagtgag gtggaggacg agagtgccca gaccggcggc aggaagagag gcatgtctag  2160
gagactggcc agcctgaggc actgcacagt gctggccatg tccaacctgc tgaacgccaa  2220
tgtggactcc ggcctgatgc actctatcgg cctgggctac acaaggatc  tgcagacccg  2280
cgccacattc atggaggtgc tgaccaagat cctgcagcag ggcaccgagt ttgacacact  2340
ggccgagacc gtgctggcag ataggttcga gcgcctggtg gagctggtga caatgatggg  2400
cgaccaggga gagctgccta tcgcaatggc actggccaac gtggtgccat gcagccagtg  2460
ggacgagctg ccagggtgc  tggtgaccct gtttgattcc agacacctgc tgtaccagct  2520
gctgtggaac atgttctcta aggaggtgga gctggccgac agcatgcaga cactgtttag  2580
gggcaattcc ctgcctcta  agatcatgac cttctgtttt aaggtgtacg cgccacata   2640
tctgcagaag ctgctggatc cactgctgag aatcgtgatc accagctccg actggcagca  2700
cgtgtccttc gaggtggatc ctacacggct ggagccaagc gagtccctgg aggagaacca  2760
gcgcaatctg ctgcagatga ccgagaagtt cttcacgcc  atcatctcta gctcctctga  2820
gtttccccct cagctgcggt ccgtgtgcca ctgtctgtac caggccacct gccactctct  2880
gctgaacaag gccacagtga aggagaagaa ggagaataag aagagcgtgg tgtcccagag  2940
gttcccacag aacagcatcg gagcagtggg atccgccatg ttcctgaggt tcatcaatcc  3000
cgccatcgtg agcccttatg aggccggcat cctggacaag aagccacccc ctaggatcga  3060
gagaggcctg aagctgatga gcaagatcct gcagtccatc gccaaccacg tgctgttcac  3120
caaggaggag cacatgcgcc ccttcaacga ctttgtgaag tctaattttg atgccgcccg  3180
gcgcttcttt ctggacatcg cctctgattg tcctacaagc gacgccgtga ccactctct   3240
gagcttcatc agcgatggca atgtgctggc cctgcaccgg ctgctgtgga caatcagga   3300
gaagatcggc cagtacctga gctccaacag ggaccacaag gcagtgggca ggagaccttt  3360
tgataagatg gccacccctgc tggcatatct gggaccacca gagcacaagc cagtggcaga  3420
cacccactgg tctagcctga atctgacatc ctctaagttc gaggagttta tgacccggca  3480
ccaggtgcac gagaaggagg agtttaaggc cctgaagacc ctgtatccgt atgatgtgcc  3540
ggattatgcg tgatgactcg agtttttttt tgcggccgct tcgagcagac atgataagat  3600
acattgatga gtttggacaa accacaacta gaatgcagtg aaaaaaatgc tttatttgtg  3660
aaatttgtga tgctattgct ttatttgtaa ccattataag ctgcaataaa caagttaaca  3720
acaacaattg cattcatttt atgtttcagg ttcagggga  gatgtgggag gttttttaaa  3780
gcaagtaaaa cctctacaaa tgtggtaaaa tcgataggcc gcaggaaccc ctagtgatgg  3840
agttggccac tccctctctg cgcgctcgct cgctcactga ggccgggcga ccaaaggtcg  3900
```

```
cccgacgccc gggcggcctc agtgagcgag cgagcgcgca gctgcctgca ggacatgtga    3960
gcaaaaggcc agcaaaaggc caggaaccgt aaaaaggccg cgttgctggc gttttttccat   4020
aggctccgcc cccctgacga gcatcacaaa aatcgacgct caagtcagag gtggcgaaac    4080
ccgacaggac tataaagata ccaggcgttt ccccctggaa gctccctcgt gcgctctcct    4140
gttccgaccc tgccgcttac cggatacctg tccgcctttc tcccttcggg aagcgtggcg    4200
ctttctcata gctcacgctg taggtatctc agttcggtgt aggtcgttcg ctccaagctg    4260
ggctgtgtgc acgaaccccc cgttcagccc gaccgctgcg ccttatccgg taactatcgt    4320
cttgagtcca acccggtaag acacgactta tcgccactgg cagcagccac tggtaacagg    4380
attagcagag cgaggtatgt aggcggtgct acagagttct tgaagtggtg cctaactac     4440
ggctacacta gaagaacagt atttggtatc tgcgctctgc tgaagccagt taccttcgga    4500
aaaagagttg gtagctcttg atccggcaaa caaaccaccg ctggtagcgg tggttttttt    4560
gtttgcaagc agcagattac gcgcagaaaa aaaggatctc aagaagatcc tttgatcttt    4620
tctacggggt ctgacgctca gtggaacgaa aactcacgtt aagggatttt ggtcatgaga    4680
ttatcaaaaa ggatcttcac ctagatcctt taaattaaa aatgaagttt taaatcaatc     4740
taaagtatat atgagtaaac ttggtctgac agttaccaat gcttaatcag tgaggcacct    4800
atctcagcga tctgtctatt tcgttcatcc atagttgcct gactccccgt cgtgtagata    4860
actacgatac gggagggctt accatctggc cccagtgctg caatgatacc gcgagaccca    4920
cgctcaccgg ctccagattt atcagcaata aaccagccag ccggaagggc cgagcgcaga    4980
agtggtcctg caactttatc cgcctccatc cagtctatta attgttgccg ggaagctaga    5040
gtaagtagtt cgccagttaa tagtttgcgc aacgttgttg ccattgctac aggcatcgtg    5100
gtgtcacgct cgtcgtttgg tatggcttca ttcagctccg gttcccaacg atcaaggcga    5160
gttacatgat cccccatgtt gtgcaaaaaa gcggttagct ccttcggtcc tccgatcgtt    5220
gtcagaagta agttggccgc agtgttatca ctcatggtta tggcagcact gcataattct    5280
cttactgtca tgccatccgt aagatgcttt tctgtgactg gtgagtactc aaccaagtca    5340
ttctgagaat agtgtatgcg gcgaccgagt tgctcttgcc cggcgtcaat acgggataat    5400
accgcgccac atagcagaac tttaaaagtg ctcatcattg gaaaacgttc ttcggggcga    5460
aaactctcaa ggatcttacc gctgttgaga tccagttcga tgtaacccac tcgtgcaccc    5520
aactgatctt cagcatcttt tactttcacc agcgtttctg ggtgagcaaa acaggaagg    5580
caaaatgccg caaaaaaggg aataagggcg acacggaaat gttgaatact catactcttc    5640
cttttcaat attattgaag catttatcag ggttattgtc tcatgagcgg atacatattt     5700
gaatgtattt agaaaaataa acaaataggg gttccgcgca catttccccg aaaagtgcca    5760
cctgacgtct aagaaaccat tattatcatg acattaacct ataaaaatag gcgtatcacg    5820
aggccctttc gtctcgcgcg tttcggtgat gacggtgaaa acctctgaca catgcagctc    5880
ccggagacgg tcacagcttg tctgtaagcg gatgccggga gcagacaagc ccgtcagggc    5940
gcgtcagcgg gtgttggcgg gtgtcggggc tggcttaact atgcggcatc agagcagatt   6000
gtactgagag tgcaccataa aattgtaaac gttaatattt tgttaaaatt cgcgttaaat    6060
ttttgttaaa tcagctcatt ttttaaccaa taggccgaaa tcggcaaaat cccttataaa    6120
tcaaaagaat agcccgagat agggttgagt gttgttccag tttggaacaa gagtccacta    6180
ttaaagaacg tggactccaa cgtcaagggg cgaaaaaccg tctatcaggg cgatggccca    6240
```

| | |
|---|---:|
| ctacgtgaac catcacccaa atcaagtttt ttggggtcga ggtgccgtaa agcactaaat | 6300 |
| cggaacccta aagggagccc ccgatttaga gcttgacggg gaaagccggc gaacgtggcg | 6360 |
| agaaaggaag ggaagaaagc gaaaggagcg ggcgctaagg cgctggcaag tgtagcggtc | 6420 |
| acgctgcgcg taaccaccac acccgccgcg cttaatgcgc cgctacaggg cgcgtactat | 6480 |
| ggttgctttg acgtatgcgg tgtgaaatac cgcacagatg cgtaaggaga aaataccgca | 6540 |
| tcaggcgcc | 6549 |

<210> SEQ ID NO 29
<211> LENGTH: 6993
<212> TYPE: DNA
<213> ORGANISM: Artificial Sequence
<220> FEATURE:
<223> OTHER INFORMATION: Synthetic

<400> SEQUENCE: 29

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccaga tcttcaatat tggccattag ccatattatt | 180 |
| cattggttat atagcataaa tcaatattgg ctattggcca ttgcatacgt tgtatctata | 240 |
| tcataatatg tacatttata ttggctcatg tccaatatga ccgccatgtt ggcattgatt | 300 |
| attgactagt tattaatagt aatcaattac ggggtcatta gttcatagcc catatatgga | 360 |
| gttccgcgtt acataactta cggtaaatgg cccgcctggc tgaccgccca acgacccccg | 420 |
| cccattgacg tcaataatga cgtatgttcc catagtaacg ccaataggga ctttccattg | 480 |
| acgtcaatgg gtggagtatt tacggtaaac tgcccacttg gcagtacatc aagtgtatca | 540 |
| tatgccaagt ccgcccccta ttgacgtcaa tgacggtaaa tggcccgcct ggcattatgc | 600 |
| ccagtacatg accttacggg actttcctac ttggcagtac atctacgtat tagtcatcgc | 660 |
| tattaccatg gtcgaggtga gccccacgtt ctgcttcact ctccccatct cccccccctc | 720 |
| cccaccccca attttgtatt tatttatttt ttaattattt tgtgcagcga tgggggcggg | 780 |
| gggggggggg gggcgcgcgc caggcggggc gggcggggc gaggggcggg gcggggcgag | 840 |
| gcggagaggt gcggcggcag ccaatcagag cggcgcgctc cgaaagtttc cttttatggc | 900 |
| gaggcggcgg cggcggcggc cctataaaaa gcgaagcgcg cggcgggcgg gagtcgctgc | 960 |
| gcgctgcctt cgccccgtgc cccgctccgc cgccgcctcg cgccgcccgc cccggctctg | 1020 |
| actgaccgcg ttactcccac aggtgagcgg cgggacggc ccttctcctc cgggctgtaa | 1080 |
| ttagcgcttg gtttaatgac ggcttgtttc ttttctgtgg ctgcgtgaaa gccttgaggg | 1140 |
| gctccgggag ggccctttgt gcgggggag cggctcgggg ggtgcgtgcg tgtgtgtgtg | 1200 |
| cgtggggagc gccgcgtgcg gctccgcgct gcccggcggc tgtgagcgct gcgggcgcgg | 1260 |
| cgcggggctt tgtgcgctcc gcagtgtgcg cgaggggagc gcggccgggg cggtgcccc | 1320 |
| gcggtgcggg ggggctgcg agggaacaa aggctgcgtg cggggtgtgt gcgtgggggg | 1380 |
| gtgagcaggg ggtgtgggcg cgtcggtcgg gctgcaaccc ccctgcacc ccctccccg | 1440 |
| agttgctgag cacggcccgg cttcgggtgc ggggctccgt acggggcgtg gcgcggggct | 1500 |
| cgccgtgccg gcgggggt ggcggcaggt ggggtgcc ggcggggcgg ggccgcctcg | 1560 |
| ggccggggag ggctcgggg agggggcgcgg cggcccccgg agcgccggcg gctgtcgagg | 1620 |
| cgcggcgagc cgcagccatt gcctttatg gtaatcgtgc gagagggcgc agggacttcc | 1680 |
| tttgtcccaa atctgtgcgg agccgaaatc tgggaggcgc cgccgcaccc cctctagcgg | 1740 |

```
gcgcggggcg aagcggtgcg gcgccggcag gaaggaaatg ggcggggagg gccttcgtgc    1800
gtcgccgcgc cgccgtcccc ttctccctct ccagcctcgg ggctgtccgc gggggggacgg    1860 ctgccttcgg gggggacggg gcagggcggg gttcggcttc tggcgtgtga ccggcggctc    1920
tagagcctct gctaaccatg ttcatgcctt cttcttttc ctacagctcc tgggcaacgt    1980
gctggttatt gtgctgtctc atcattttgg caaagaattc gatatcaagc ttgccaccat    2040
ggaagccaag agccagctgt ttctgaaata ctttaccctg tttatgaatc tgctgaacga    2100
ctgtagtgag gtggaggacg agagtgccca gaccggcggc aggaagagag gcatgtctag    2160
gagactggcc agcctgaggc actgcacagt gctggccatg tccaacctgc tgaacgccaa    2220
tgtggactcc ggcctgatgc actctatcgg cctgggctac cacaaggatc tgcagacccg    2280
cgccacattc atggaggtgc tgaccaagat cctgcagcag gcaccgagt ttgacacact    2340 ggccgagacc gtgctggcag ataggttcga gcgcctggtg gagctggtga caatgatggg    2400
cgaccaggga gagctgccta tcgcaatggc actggccaac gtggtgccat gcagccagtg    2460
ggacgagctg gccagggtgc tggtgacccct gtttgattcc agacacctgc tgtaccagct    2520
gctgtggaac atgttctcta aggaggtgga gctggccgac agcatgcaga cactgtttag    2580
gggcaattcc ctggcctcta agatcatgac cttctgtttt aaggtgtacg cgccacata    2640 tctgcagaag ctgctggatc cactgctgag aatcgtgatc accagctccg actggcagca    2700
cgtgtccttc gaggtggatc ctacacggct ggagccaagc gagtccctgg aggagaacca    2760
gcgcaatctg ctgcagatga ccgagaagtt ctttcacgcc atcatctcta gctcctctga    2820
gtttccccct cagctgcggt ccgtgtgcca ctgtctgtac caggccacct gccactctct    2880
gctgaacaag gccacagtga aggagaagaa ggagaataag aagagcgtgg tgtcccagag    2940
gttcccacag aacagcatcg gagcagtggg atccgccatg ttcctgaggt tcatcaatcc    3000
cgccatcgtg agcccttatg aggccggcat cctggacaag aagccacccc ctaggatcga    3060
gagaggcctg aagctgatga gcaagatcct gcagtccatc gccaaccacg tgctgttcac    3120
caaggaggag cacatgcgcc ccttcaacga ctttgtgaag tctaattttg atgccgcccg    3180
gcgcttcttt ctggacatcg cctctgattg tcctacaagc gacgccgtga ccactctct    3240 gagcttcatc agcgatggca atgtgctggc cctgcaccgg ctgctgtgga caatcagga    3300 gaagatcggc cagtacctga gctccaacag ggaccacaag gcagtgggca ggagaccatt    3360
tgataagatg gccacactgc tggcctatct gggaccacca gagcacaagc cagtggcaga    3420
cacacactgg tctagcctga atctgacctc ctctaagttc gaggagttta tgacccggca    3480
ccaggtgcac gagaaggagg agtttaaggc cctgaagaca ctgtctatct tctaccaggc    3540
aggcaccagc aaggcaggaa acccaatctt ttactatgtg gcccggcgct tcaagacagg    3600
ccagatcaat ggcgatctgc tgatctacca cgtgctgctg accctgaagc catactatgc    3660
caagccctat gagatcgtgg tggacctgac ccacacaggc ccctccaaca ggtttaagac    3720
cgatttcctg tctaagtggt tcgtggtgtt tcctggcttc gcctatgaca atgtgagcgc    3780
cgtgtacatc tataactgca attcctgggt gcgggagtac acaaagtatc acgagcgcct    3840
gctgaccggc ctgaagggat ccaagagact ggtgttcatc gattgtccg gcaagctggc    3900 cgagcacatt gaacacgaac agcagaaact gcccgccgca accctggccc tggaagagga    3960
cctgaagtat ccgtatgatg tgccggatta tgcgtgatga ctcgagtttt tttttgcggc    4020
cgcttcgagc agacatgata agatacattg atgagtttgg acaaaccaca actagaatgc    4080
```

```
agtgaaaaaa atgctttatt tgtgaaattt gtgatgctat tgctttattt gtaaccatta    4140
taagctgcaa taaacaagtt aacaacaaca attgcattca ttttatgttt caggttcagg    4200
gggagatgtg ggaggttttt taaagcaagt aaaacctcta caaatgtggt aaaatcgata    4260
ggccgcagga acccctagtg atggagttgg ccactccctc tctgcgcgct cgctcgctca    4320
ctgaggccgg gcgaccaaag gtcgcccgac gcccgggcgg cctcagtgag cgagcgagcg    4380
cgcagctgcc tgcaggacat gtgagcaaaa ggccagcaaa aggccaggaa ccgtaaaaag    4440
gccgcgttgc tggcgttttt ccataggctc cgcccccctg acgagcatca caaaaatcga    4500
cgctcaagtc agaggtggcg aaacccgaca ggactataaa gataccaggc gtttccccct    4560
ggaagctccc tcgtgcgctc tcctgttccg accctgccgc ttaccggata cctgtccgcc    4620
tttctccctt cgggaagcgt ggcgctttct catagctcac gctgtaggta tctcagttcg    4680
gtgtaggtcg ttcgctccaa gctgggctgt gtgcacgaac cccccgttca gcccgaccgc    4740
tgcgccttat ccggtaacta tcgtcttgag tccaacccgg taagacacga cttatcgcca    4800
ctggcagcag ccactggtaa caggattagc agagcgaggt atgtaggcgg tgctacagag    4860
ttcttgaagt ggtggcctaa ctacggctac actagaagaa cagtatttgg tatctgcgct    4920
ctgctgaagc cagttacctt cggaaaaaga gttggtagct cttgatccgg caaacaaacc    4980
accgctggta gcggtggttt ttttgtttgc aagcagcaga ttacgcgcag aaaaaaagga    5040
tctcaagaag atcctttgat cttttctacg ggtctgacg ctcagtggaa cgaaaactca    5100
cgttaaggga ttttggtcat gagattatca aaaaggatct tcacctagat ccttttaaat    5160
taaaaatgaa gttttaaatc aatctaaagt atatatgagt aaacttggtc tgacagttac    5220
caatgcttaa tcagtgaggc acctatctca gcgatctgtc tatttcgttc atccatagtt    5280
gcctgactcc ccgtcgtgta gataactacg atacgggagg gcttaccatc tggccccagt    5340
gctgcaatga taccgcgaga cccacgctca ccggctccag atttatcagc aataaaccag    5400
ccagccggaa gggccgagcg cagaagtggt cctgcaactt tatccgcctc catccagtct    5460
attaattgtt gccgggaagc tagagtaagt agttcgccag ttaatagttt cgcaacgtt    5520
gttgccattg ctacaggcat cgtggtgtca cgctcgtcgt ttggtatggc ttcattcagc    5580
tccggttccc aacgatcaag gcgagttaca tgatccccca tgttgtgcaa aaaagcggtt    5640
agctccttcg gtcctccgat cgttgtcaga agtaagttgg ccgcagtgtt atcactcatg    5700
gttatggcag cactgcataa ttctcttact gtcatgccat ccgtaagatg cttttctgtg    5760
actggtgagt actcaaccaa gtcattctga gaatagtgta tgcggcgacc gagttgctct    5820
tgcccggcgt caatacggga taataccgcg ccacatagca gaactttaaa agtgctcatc    5880
attggaaaac gttcttcggg gcgaaaactc tcaaggatct taccgctgtt gagatccagt    5940
tcgatgtaac ccactcgtgc acccaactga tcttcagcat cttttacttt caccagcgtt    6000
tctgggtgag caaaaacagg aaggcaaaat gccgcaaaaa agggaataag ggcgacacgg    6060
aaatgttgaa tactcatact cttcctttt caatattatt gaagcattta tcagggttat    6120
tgtctcatga gcggatacat atttgaatgt atttagaaaa ataaacaaat aggggttccg    6180
cgcacatttc cccgaaaagt gccacctgac gtctaagaaa ccattattat catgacatta    6240
acctataaaa ataggcgtat cacgaggccc tttcgtctcg cgcgtttcgg tgatgacggt    6300
gaaaacctct gacacatgca gctcccggag acggtcacag cttgtctgta agcggatgcc    6360
gggagcagac aagcccgtca gggcgcgtca gcgggtgttg gcgggtgtcg ggctggctt    6420
aactatgcgg catcagagca gattgtactg agagtgcacc ataaaattgt aaacgttaat    6480
```

-continued

```
attttgttaa aattcgcgtt aaattttgt taaatcagct cattttttaa ccaataggcc      6540
gaaatcggca aaatcccta taaatcaaaa gaatagcccg agatagggtt gagtgttgtt      6600
ccagtttgga acaagagtcc actattaaag aacgtggact ccaacgtcaa agggcgaaaa     6660
accgtctatc agggcgatgg cccactacgt gaaccatcac ccaaatcaag ttttttgggg    6720
tcgaggtgcc gtaaagcact aaatcggaac cctaaaggga gccccgatt tagagcttga     6780 cggggaaagc cggcgaacgt ggcgagaaag gaagggaaga aagcgaaagg agcgggcgct    6840
aaggcgctgg caagtgtagc ggtcacgctg cgcgtaacca ccacacccgc cgcgcttaat    6900
gcgccgctac agggcgcgta ctatggttgc tttgacgtat gcggtgtgaa ataccgcaca    6960
gatgcgtaag gagaaaatac cgcatcaggc gcc                                 6993
```

<210> SEQ ID NO 30
<211> LENGTH: 7290
<212> TYPE: DNA
<213> ORGANISM: Artificial Sequence
<220> FEATURE:
<223> OTHER INFORMATION: Synthetic

<400> SEQUENCE: 30

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac tagggttcc tgcggccaga tcttcaatat tggccattag ccatattatt    180
cattggttat atagcataaa tcaatattgg ctattggcca ttgcatacgt tgtatctata    240
tcataatatg tacatttata ttggctcatg tccaatatga ccgccatgtt ggcattgatt    300
attgactagt tattaatagt aatcaattac ggggtcatta gttcatagcc catatatgga    360
gttccgcgtt acataactta cggtaaatgg cccgcctggc tgaccgccca acgaccccg     420 cccattgacg tcaataatga cgtatgttcc catagtaacg ccaatagggg actttccattg    480 acgtcaatgg gtggagtatt tacggtaaac tgcccacttg gcagtacatc aagtgtatca    540
tatgccaagt ccgccccta ttgacgtcaa tgacggtaaa tggcccgcct ggcattatgc     600
ccagtacatg accttacggg actttcctac ttggcagtac atctacgtat tagtcatcgc    660
tattaccatg gtcgaggtga gccccacgtt ctgcttcact ctccccatct ccccccctc     720 cccaccccca ttttgtatt tatttattt ttaattattt tgtgcagcga tgggggcggg      780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcgggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gcccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc ccctgcacc cccctccccg    1440 agttgctgag cacggcccgg cttcgggtgc ggggctccgt acggggcgtg gcgcggggct   1500
```

```
cgccgtgccg ggcgggggt  ggcggcaggt ggggtgccg  ggcggggcgg ggccgcctcg    1560
ggccggggag ggctcggggg aggggcgcgg cggcccccgg agcgccggcg gctgtcgagg    1620
cgcggcgagc cgcagccatt gccttttatg gtaatcgtgc gagagggcgc agggacttcc    1680
tttgtcccaa atctgtgcgg agccgaaatc tgggaggcgc cgccgcaccc cctctagcgg    1740
gcgcggggcg aagcggtgcg gcgccggcag gaaggaaatg ggcggggagg gccttcgtgc    1800
gtcgccgcgc cgccgtcccc ttctccctct ccagcctcgg ggctgtccgc gggggacgg    1860 ctgccttcgg gggggacggg gcagggcggg gttcggcttc tggcgtgtga ccggcggctc    1920
tagagcctct gctaaccatg ttcatgcctt cttcttttc  ctacagctcc tgggcaacgt    1980
gctggttatt gtgctgtctc atcattttgg caaagaattc gatatcaagc ttgccaccat    2040
ggaagccaag agccagctgt ttctgaaata ctttaccctg tttatgaatc tgctgaacga    2100
ctgtagtgag gtggaggacg agagtgccca gaccggcggc aggaagagag gcatgtctag    2160
gagactggcc agcctgaggc actgcacagt gctggccatg tccaacctgc tgaacgccaa    2220
tgtggactcc ggcctgatgc actctatcgg cctgggctac cacaaggatc tgcagacccg    2280
cgccacattc atggaggtgc tgaccaagat cctgcagcag ggcaccgagt ttgacacact    2340
ggccgagacc gtgctggcag ataggttcga gcgcctggtg gagctggtga caatgatggg    2400
cgaccaggga gagctgccta tcgcaatggc actggccaac gtggtgccat gcagccagtg    2460
ggacgagctg ccagggtgc  tggtgaccct gtttgattcc agacacctgc tgtaccagct    2520
gctgtggaac atgttctcta aggaggtgga gctggccgac agcatgcaga cactgtttag    2580
gggcaattcc ctgcctctca agatcatgac cttctgtttt aaggtgtacg cgccacata    2640 tctgcagaag ctgctggatc cactgctgag aatcgtgatc accagctccg actggcagca    2700
cgtgtccttc gaggtggatc ctacacggct ggagccaagc gagtccctgg aggagaacca    2760
gcgcaatctg ctgcagatga ccgagaagtt cttcacgcc  atcatctcta gctcctctga    2820
gtttccccct cagctgcggt ccgtgtgcca ctgtctgtac caggccacct gccactctct    2880
gctgaacaag gccacagtga aggagaagaa ggagaataag aagagcgtgg tgtcccagag    2940
gttcccacag aacagcatcg gagcagtggg atccgccatg ttcctgaggt tcatcaatcc    3000
cgccatcgtg agcccttatg aggccggcat cctggacaag aagccacccc ctaggatcga    3060
gagaggcctg aagctgatga gcaagatcct gcagtccatc gccaaccacg tgctgttcac    3120
caaggaggag cacatgcgcc ccttcaacga ctttgtgaag tctaattttg atgccgcccg    3180
gcgcttcttt ctggacatcg cctctgattg tcctacaagc gacgccgtga ccactctct    3240 gagcttcatc agcgatggca atgtgctggc cctgcaccgg ctgctgtgga caatcagga    3300 gaagatcggc cagtacctga gctccaacag ggaccacaag gcagtgggca ggagacctt    3360 tgataagatg gccacctgc  tggcatatct gggaccacca gagcacaagc cagtggcaga    3420
cacccactgg tctagcctga atctgacatc ctctaagttc gaggagttta tgacccggca    3480
ccaggtgcac gagaaggagg agtttaaggc cctgaagacc ctgtccatct tctaccaggc    3540
cggcacatct aaggccggca accctatctt ttactatgtg gcccggcgct tcaagaccgg    3600
ccagatcaat ggcgatctgc tgatctacca cgtgctgctg acactgaagc catactatgc    3660
caagccctat gagatcgtgg tggacctgac ccacacaggc caagcaaca ggtttaagac    3720 cgatttcctg tccaagtggt tcgtggtgtt tcccggcttc gcctatgaca acgtgagcgc    3780
cgtgtacatc tataactgca atagctgggt gcggagtac accaagtatc acgagcgcct    3840
gctgacaggc ctgaagggca gcaagagact ggtgttcatc gattgtcccg gcaagctggc    3900
```

```
cgagcacatc gagcacgagc agcagaagct gcctgcagcc accctggccc tggaggagga   3960
cctgaaggtg tttcacaacg ccctgaagct ggcccacaag gatacaaagg tgtccatcaa   4020
ggtcggctct acagccgtgc aggtgacctc cgccgagaga acaaaggtgc tgggccagag   4080
cgtgttcctg aatgacatct actatgccag cgagatcgag gagatctgcc tggtggatga   4140
gaaccagttt accctgacaa tcgccaatca gggcaccccc ctgacattca tgcaccagga   4200
gtgtgaagca atcgtccaga gcattattca cattcgcact cggtgggaac tgagccagcc   4260
tgactatccg tatgatgtgc cggattatgc gtgatgactc gagttttttt ttgcggccgc   4320
ttcgagcaga catgataaga tacattgatg agtttggaca aaccacaact agaatgcagt   4380
gaaaaaaatg ctttatttgt gaaatttgtg atgctattgc tttatttgta accattataa   4440
gctgcaataa acaagttaac aacaacaatt gcattcattt tatgtttcag gttcaggggg   4500
agatgtggga ggttttttaa agcaagtaaa acctctacaa atgtggtaaa atcgataggc   4560
cgcaggaacc cctagtgatg gagttggcca ctccctctct cgcgctcgc tcgctcactg   4620 aggccgggcg accaaaggtc gcccgacgcc cgggcggcct cagtgagcga gcgagcgcgc   4680
agctgcctgc aggacatgtg agcaaaaggc cagcaaaagg ccaggaaccg taaaaaggcc   4740
gcgttgctgg cgttttttcca taggctccgc ccccctgacg agcatcacaa aaatcgacgc   4800
tcaagtcaga ggtggcgaaa cccgacagga ctataaagat accaggcgtt ccccctggaa   4860
agctccctcg tgcgctctcc tgttccgacc ctgccgctta ccggatacct gtccgccttt   4920
ctcccttcgg gaagcgtggc gctttctcat agctcacgct gtaggtatct cagttcggtg   4980
taggtcgttc gctccaagct gggctgtgtg cacgaacccc ccgttcagcc cgaccgctgc   5040
gccttatccg gtaactatcg tcttgagtcc aacccggtaa gacacgactt atcgccactg   5100
gcagcagcca ctggtaacag gattagcaga gcgaggtatg taggcggtgc tacagagttc   5160
ttgaagtggt ggcctaacta cggctacact agaagaacag tatttggtat ctgcgctctg   5220
ctgaagccag ttaccttcgg aaaaagagtt ggtagctctt gatccggcaa acaaaccacc   5280
gctggtagcg gtggtttttt tgtttgcaag cagcagatta cgcgcagaaa aaaggatct   5340 caagaagatc ctttgatctt ttctacgggg tctgacgctc agtggaacga aaactcacgt   5400
taagggattt tggtcatgag attatcaaaa aggatcttca cctagatcct tttaaattaa   5460
aaatgaagtt ttaaatcaat ctaaagtata tatgagtaaa cttggtctga cagttaccaa   5520
tgcttaatca gtgaggcacc tatctcagcg atctgtctat ttcgttcatc catagttgcc   5580
tgactccccg tcgtgtagat aactacgata cgggagggct taccatctgg ccccagtgct   5640
gcaatgatac cgcgagaccc acgctcaccg gctccagatt tatcagcaat aaaccagcca   5700
gccgaagggg ccgagcgcag aagtggtcct gcaactttat ccgcctccat ccagtctatt   5760
aattgttgcc gggaagctag agtaagtagt tcgccagtta atagtttgcg caacgttgtt   5820
gccattgcta caggcatcgt ggtgtcacgc tcgtcgtttg gtatggcttc attcagctcc   5880
ggttcccaac gatcaaggcg agttacatga tcccccatgt tgtgcaaaaa agcggttagc   5940
tccttcggtc ctccgatcgt tgtcagaagt aagttggccg cagtgttatc actcatggtt   6000
atggcagcac tgcataattc tcttactgtc atgccatccg taagatgctt ttctgtgact   6060
ggtgagtact caaccaagtc attctgagaa tagtgtatgc ggcgaccgag ttgctcttgc   6120
ccggcgtcaa tacgggataa taccgcgcca catagcagaa ctttaaaagt gctcatcatt   6180
ggaaaacgtt cttcggggcg aaaactctca aggatcttac cgctgttgag atccagttcg   6240
```

| | |
|---|---|
| atgtaaccca ctcgtgcacc caactgatct tcagcatctt ttactttcac cagcgtttct | 6300 |
| gggtgagcaa aaacaggaag gcaaaatgcc gcaaaaaagg gaataagggc gacacggaaa | 6360 |
| tgttgaatac tcatactctt cctttttcaa tattattgaa gcatttatca gggttattgt | 6420 |
| ctcatgagcg gatacatatt tgaatgtatt tagaaaaata aacaaatagg ggttccgcgc | 6480 |
| acatttcccc gaaaagtgcc acctgacgtc taagaaacca ttattatcat gacattaacc | 6540 |
| tataaaaata ggcgtatcac gaggccctt cgtctcgcgc gtttcggtga tgacggtgaa | 6600 |
| aacctctgac acatgcagct cccggagacg gtcacagctt gtctgtaagc ggatgccggg | 6660 |
| agcagacaag cccgtcaggg cgcgtcagcg ggtgttggcg ggtgtcgggg ctggcttaac | 6720 |
| tatgcggcat cagagcagat tgtactgaga gtgcaccata aaattgtaaa cgttaatatt | 6780 |
| ttgttaaaat tcgcgttaaa ttttgttaa atcagctcat tttttaacca ataggccgaa | 6840 |
| atcggcaaaa tcccttataa atcaaaagaa tagcccgaga taggttgag tgttgttcca | 6900 |
| gtttggaaca agagtccact attaaagaac gtggactcca acgtcaaagg gcgaaaaacc | 6960 |
| gtctatcagg gcgatggccc actacgtgaa ccatcaccca aatcaagttt ttgggtcg | 7020 |
| aggtgccgta agcactaaa tcggaaccct aaagggagcc cccgatttag agcttgacgg | 7080 |
| ggaaagccgg cgaacgtggc gagaaaggaa gggaagaaag cgaaaggagc gggcgctaag | 7140 |
| gcgctggcaa gtgtagcggt cacgctgcgc gtaaccacca cacccgccgc gcttaatgcg | 7200 |
| ccgctacagg gcgcgtacta tggttgcttt gacgtatgcg gtgtgaaata ccgcacagat | 7260 |
| gcgtaaggag aaaataccgc atcaggcgcc | 7290 |

<210> SEQ ID NO 31
<211> LENGTH: 7629
<212> TYPE: DNA
<213> ORGANISM: Artificial Sequence
<220> FEATURE:
<223> OTHER INFORMATION: Synthetic

<400> SEQUENCE: 31

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccaga tctgcaaatt aggaccgaga gtcagtggcc | 180 |
| gctcaagagt ctgtgaccat gccccaaatt cagagatggt cccaggagag atgggggaa | 240 |
| ctgccaagca atgagtgacc ggttcccct cccccaggtg gttagccagc gtttccctca | 300 |
| gaacagcatc ggtgcagtag gaagtgccat gttcctcaga tttatcaatc ctgccattgt | 360 |
| ctcaccgtat gaagcaggga ttttagataa aaagccacca cctagaatcg aaaggggctt | 420 |
| gaagttaatg tcaaagatac ttcagagtat tgccaatcat gttctcttca caaaagaaga | 480 |
| acatatgcgg cctttcaatg attttgtgaa aagcaacttt gatgcagcac gcaggttttt | 540 |
| ccttgatata gcatctgatt gtcctacaag tgatgcagta aatcatagtc tttccttcat | 600 |
| aagtgacggc aatgtgcttg ctttacatcg tctactctgg aacaatcagg agaaaattgg | 660 |
| gcagtatctt tccagcaaca gggatcataa agctgttgga agacgacctt tgataagat | 720 |
| ggcaacactt cttgcatacc tgggtcctcc agagcacaaa cctgtggcag atacacactg | 780 |
| gtccagcctt aaccttacca gttcaaagtt tgaggaattt atgactaggc atcaggtaca | 840 |
| tgaaaaagaa gaattcaagg ctttgaaaac gttaagtatt ttctaccaag ctgggacttc | 900 |
| caaagctggg aatcctattt tttattatgt tgcacggagg ttcaaaactg gtcaaatcaa | 960 |
| tggtgatttg ctgatatacc atgtcttact gactttaaag ccatattatg caaagccata | 1020 |

-continued

```
tgaaattgta gtggacctta cccataccgg gcctagcaat cgctttaaaa cagactttct   1080
ctctaagtgg tttgttgttt ttcctggctt tgcttacgac aacgtctccg cagtctatat   1140
ctataactgt aactcctggg tcagggagta caccaagtat catgagcggc tgctgactgg   1200
cctcaaaggt agcaaaaggc ttgttttcat agactgtcct gggaaactgg ctgagcacat   1260
agagcatgaa caacagaaac tacctgctgc caccttggct ttagaagagg acctgaaggt   1320
attccacaat gctctcaagc tagctcacaa agacaccaaa gtttctatta agttggttc    1380
tactgctgtc caagtaactt cagcagagcg aacaaaagtc ctagggcaat cagtctttct   1440
aaatgacatt tattatgctt cggaaattga agaaatctgc ctagtagatg agaaccagtt   1500
caccttaacc attgcaaacc agggcacgcc gctcaccttc atgcaccagg agtgtgaagc   1560
cattgtccag tctatcattc atatccggac ccgctgggaa ctgtcacagc ccgactctat   1620
cccccaacac accaagattc ggccaaaaga tgtccctggg acactgctca atatcgcatt   1680
acttaattta ggcagttctg acccgagttt acggtcagct gcctataatc ttctgtgtgc   1740
cttaacttgt acctttaatt taaaaatcga gggccagtta ctagagacat caggtttatg   1800
tatccctgcc aacaacaccc tctttattgt ctctattagt aagacactgg cagccaatga   1860
gccacacctc acgttagaat ttttggaaga gtgtatttct ggatttagca aatctagtat   1920
tgaattgaaa cacctttgtt tggaatacat gactccatgg ctgtcaaatc tagttcgttt   1980
ttgcaagcat aatgatgatg ccaaacgaca aagagttact gctattcttg acaagctgat   2040
aacaatgacc atcaatgaaa acagatgta  cccatctatt caagcaaaaa tatggggaag   2100
ccttgggcag attacagatc tgcttgatgt tgtactagac agtttcatca aaccagtgc    2160
aacaggtggc ttgggatcaa taaaagctga ggtgatggca gatactgctg tagctttggc   2220
ttctggaaat gtgaaattgg tttcaagcaa ggttattgga aggatgtgca aaataattga   2280
caagacatgc ttatctccaa ctcctacttt agaacaacat cttatgtggg atgatattgc   2340
tattttagca cgctacatgc tgatgctgtc cttcaacaat tcccttgatg tggcagctca   2400
tcttccctac ctcttccacg ttgttacttt cttagtagcc acaggtccgc tctcccttag   2460
agcttccaca catggactgg tcattaatat cattcactct ctgtgtactt gttcacagct   2520
tcattttagt gaagagacca agcaagtttt gagactcagt ctgacagagt tctcattacc   2580
caaattttac ttgctgtttg gcattagcaa agtcaagtca gctgctgtca ttgccttccg   2640
ttccagttac cgggacaggt cattctctcc tggctcctat gagagagaga cttttgcttt   2700
gacatccttg gaaacagtca cagaagcttt gttggagatc atggaggcat gcatgagaga   2760
tattccaacg tgcaagtggc tggaccagtg gacagaacta gctcaaagat tgcattcca    2820
atataatcca tccctgcaac caagagctct tgttgtcttt gggtgtatta gcaaacgagt   2880
gtctcatggg cagataaagc agataatccg tattcttagc aaggcacttg agagttgctt   2940
aaaaggacct gacacttaca acagtcaagt tctgatagaa gctacagtaa tagcactaac   3000
caaattacag ccacttctta taaggactcc gcctctgcac aaagccctct tttgggtagc   3060
tgtggctgtg ctgcagcttg atgaggtcaa cttgtattca gcaggtaccg cacttcttga   3120
acaaaacctg catactttag atagtctccg tatattcaat gacaagagtc cagaggaagt   3180
atttatggca atccggaatc tctggagtg gcactgcaag caaatggatc attttgttgg    3240
actcaatttc aactctaact ttaactttgc attggttgga cacctttaa  aagggtacag   3300
gcatccttca cctgctattg ttgcaagaac agtcagaatt ttacatacac tactaactct   3360
```

```
ggttaacaaa cacagaaatt gtgacaaatt tgaagtgaat acacagagcg tggcctactt    3420
agcagcttta cttacagtgt ctgaagaagt tcgaagtcgc tgcagcctaa aacatagaaa    3480
gtcacttctt cttactgata tttcaatgga aaatgttcct atggatacat atcccattca    3540
tcatggtgac ccttcctata ggacactaaa ggagactcag ccatggtcct ctcccaaagg    3600
ttctgaagga taccttgcag ccacctatcc aactgtcggc cagaccagtc cccgagccag    3660
gaaatccatg agcctggaca tggggcaacc ttctcaggcc aacactaaga agttgcttgg    3720
aacaaggaaa agttttgatc acttgatatc agacacaaag gctcctaaaa ggcaagaaat    3780
ggaatcaggg atcacaacac cccccaaaat gaggagagta gcagaaactg attatgaaat    3840
ggaaactcag aggatttcct catcacaaca gcacccacat ttacgtaaag tttcagtgtc    3900
tgaatcaaat gttctcttgg atgaagaagt acttactgat ccgaagatcc aggcgctgct    3960
tcttactgtt ctagctacac tggtaaaata taccacagat gagtttgatc aacgaattct    4020
ttatgaatac ttagcagagg ccagtgttgt gtttcccaaa gtcttcctg ttgtgcataa     4080
tttgttggac tctaagatca cacccctgtt atcattgtgc caagatccaa atttgttaaa    4140
tccaatccat ggaattgtgc agagtgtggt gtaccatgaa gaatccccac cacaatacca    4200
aacatcttac ctgcaaagtt ttggttttaa tggcttgtgg cggtttgcag gaccgttttc    4260
aaagcaaaca caaattccag actatgctga gcttattgtt aagtttcttg atgccttgat    4320
tgacacgtac ctgcctggaa ttgatgaaga aaccagtgaa gaatccctcc tgactcccac    4380
atctccttac cctcctgcac tgcagagcca gcttagtatc actgccaacc ttaacctttc    4440
taattccatg acctcacttg caacttccca gcattcccca ggaatcgaca aggagaacgt    4500
tgaactctcc cctaccactg gccactgtaa cagtggacga actcgccacg gatccgcaag    4560
ccaagtgcag aagcaaagaa gcgctggcag tttcaaacgt aatagcatta agaagatcgt    4620
gtatccgtat gatgtgccgg attatgcgtg agcggccgct tcgagcagac atgataagat    4680
acattgatga gtttggacaa accacaacta gaatgcagtg aaaaaaatgc tttatttgtg    4740
aaatttgtga tgctattgct ttatttgtaa ccattataag ctgcaataaa caagttaaca    4800
acaacaattg cattcatttt atgtttcagg ttcaggggga gatgtgggag gttttttaaa    4860
gcaagtaaaa cctctacaaa tgtggtaaaa tcgataggcc gcaggaaccc ctagtgatgg    4920
agttggccac tccctctctg cgcgctcgct cgctcactga ggccgggcga ccaaaggtcg    4980
cccgacgccc gggcggcctc agtgagcgag cgagcgcgca gctgcctgca ggacatgtga    5040
gcaaaaggcc agcaaaaggc caggaaccgt aaaaaggccg cgttgctggc gttttttccat   5100
aggctccgcc ccctgacga gcatcacaaa aatcgacgct caagtcagag gtggcgaaac     5160
ccgacaggac tataaagata ccaggcgttt cccctggaa gctccctcgt gcgctctcct     5220
gttccgaccc tgccgcttac cggatacctg tccgcctttc tcccttcggg aagcgtggcg    5280
ctttctcata gctcacgctg taggtatctc agttcggtgt aggtcgttcg ctccaagctg    5340
ggctgtgtgc acgaaccccc cgttcagccc gaccgctgcg ccttatccgg taactatcgt    5400
cttgagtcca acccggtaag acacgactta tcgccactgg cagcagccac tggtaacagg    5460
attagcagag cgaggtatgt aggcggtgct acagagttct tgaagtggtg gcctaactac    5520
ggctacacta agaacagt atttggtatc tgcgctctgc tgaagccagt taccttcgga     5580
aaaagagttg gtagctcttg atccggcaaa caaaccaccg ctggtagcgg tggtttttt     5640
gtttgcaagc agcagattac gcgcagaaaa aaaggatctc aagaagatcc tttgatcttt    5700
tctacggggt ctgacgctca gtggaacgaa aactcacgtt aagggatttt ggtcatgaga    5760
```

```
ttatcaaaaa ggatcttcac ctagatcctt ttaaattaaa aatgaagttt taaatcaatc    5820
taaagtatat atgagtaaac ttggtctgac agttaccaat gcttaatcag tgaggcacct    5880
atctcagcga tctgtctatt tcgttcatcc atagttgcct gactcccgt cgtgtagata     5940 actacgatac gggagggctt accatctggc cccagtgctg caatgatacc gcagaccca     6000 cgctcaccgg ctccagattt atcagcaata aaccagccag ccggaagggc cgagcgcaga    6060
agtggtcctg caactttatc cgcctccatc cagtctatta attgttgccg ggaagctaga    6120
gtaagtagtt cgccagttaa tagtttgcgc aacgttgttg ccattgctac aggcatcgtg    6180
gtgtcacgct cgtcgtttgg tatggcttca ttcagctccg gttcccaacg atcaaggcga    6240
gttacatgat cccccatgtt gtgcaaaaaa gcggttagct ccttcggtcc tccgatcgtt    6300
gtcagaagta agttggccgc agtgttatca ctcatggtta tggcagcact gcataattct    6360
cttactgtca tgccatccgt aagatgcttt tctgtgactg gtgagtactc aaccaagtca    6420
ttctgagaat agtgtatgcg cgaccgagt tgctcttgcc cggcgtcaat acgggataat     6480
accgcgccac atagcagaac tttaaaagtg ctcatcattg gaaaacgttc ttcggggcga    6540
aaactctcaa ggatcttacc gctgttgaga tccagttcga tgtaacccac tcgtgcaccc    6600
aactgatctt cagcatcttt tactttcacc agcgtttctg ggtgagcaaa aacaggaagg    6660
caaaatgccg caaaaaaggg aataagggcg cacggaaat gttgaatact catactcttc     6720 cttttttcaat attattgaag catttatcag ggttattgtc tcatgagcgg atacatattt    6780
gaatgtattt agaaaaataa acaaataggg gttccgcgca catttcccg aaaagtgcca     6840 cctgacgtct aagaaaccat tattatcatg acattaacct ataaaaatag gcgtatcacg    6900 aggcccttc gtctcgcgcg tttcggtgat gacggtgaaa acctctgaca catgcagctc     6960
ccggagacgg tcacagcttg tctgtaagcg gatgccggga gcagacaagc ccgtcagggc    7020
gcgtcagcgg gtgttggcgg gtgtcggggc tggcttaact atgcggcatc agagcagatt    7080
gtactgagag tgcaccataa aattgtaaac gttaatattt tgttaaaatt cgcgttaaat    7140
ttttgttaaa tcagctcatt ttttaaccaa taggccgaaa tcggcaaaat cccttataaa    7200
tcaaaagaat agcccgagat agggttgagt gttgttccag tttggaacaa gagtccacta    7260
ttaaagaacg tggactccaa cgtcaaaggg cgaaaaaccg tctatcaggg cgatggccca    7320
ctacgtgaac catcacccaa atcaagtttt tggggtcga ggtgccgtaa agcactaaat     7380
cggaacccta aagggagccc ccgatttaga gcttgacggg gaaagccggc gaacgtggcg    7440
agaaaggaag ggaagaaagc gaaaggagcg ggcgctaagg cgctggcaag tgtagcggtc    7500
acgctgcgcg taaccaccac acccgccgcg cttaatgcgc cgctacaggg cgcgtactat    7560
ggttgctttg acgtatgcgg tgtgaaatac cgcacagatg cgtaaggaga aaataccgca    7620
tcaggcgcc                                                           7629
```

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gly Cys Met Ser Cys Lys Cys Val Leu Ser
1               5                   10